US011203788B2

(12) United States Patent
Viguie et al.

(10) Patent No.: US 11,203,788 B2
(45) **Date of Patent: *Dec. 21, 2021**

(54) TET2 AS A DIAGNOSTIC AND PRONOSTIC MARKER IN HEMATOPOIETIC NEOPLASMS

(71) Applicants: INSTITUT NATIONAL DE LA SANTE ET DE LA RECHERCHE MEDICALE (INSERM), Paris (FR); INSTITUT GUSTAVE-ROUSSY, Villejuif (FR); Assistance Publique—Hopitaux de Paris, Paris (FR); Centre Henri Becquerel, Rouen (FR); Universite Paris Descartes, Paris (FR); Universite Pierre et Marie Curie, Paris (FR); Universite Paris—SUD, Orsay (FR)

(72) Inventors: Franck Viguie, Deuil la Barre (FR); Olivier Bernard, Vanves (FR); Michaela Fontenay, Paris (FR); Christian Bastard, Ardouval (FR); Francois Delhommeau, Antony (FR); William Vainchenker, Paris (FR)

(73) Assignees: INSTITUT NATIONAL DE LA SANTE ET DE LA RECHERCHE MEDICALE (INSERM), Paris (FR); INSTITUT GUSTAVE-ROUSSY, Villejuif (FR); ASSISTANCE PUBLIQUE-HOPITAUX DE PARIS, Paris (FR); CENTRE HENRI BECQUEREL, Rouen (FR); UNIVERSITE PIERRE ET MARIE CURIE, Paris (FR); UNIVERSITE PARIS-SUD, Orsay (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/843,507

(22) Filed: Apr. 8, 2020

(65) Prior Publication Data

US 2020/0255912 A1 Aug. 13, 2020

Related U.S. Application Data

(63) Continuation of application No. 15/177,055, filed on Jun. 8, 2016, now Pat. No. 10,662,482, which is a (Continued)

(30) Foreign Application Priority Data

Jun. 12, 2008 (EP) .................................... 08305255
Mar. 13, 2009 (EP) .................................... 09155169

(51) Int. Cl.
*C12Q 1/6886* (2018.01)
*G01N 33/574* (2006.01)
*A61K 31/7068* (2006.01)

(52) U.S. Cl.
CPC ........ *C12Q 1/6886* (2013.01); *A61K 31/7068* (2013.01); *G01N 33/57426* (2013.01); (Continued)

(58) Field of Classification Search
CPC ........................ C12Q 1/6886; C12Q 2600/156
See application file for complete search history.

(56) References Cited

U.S. PATENT DOCUMENTS 4,683,202 A 7/1987 Mullis
5,854,033 A 12/1998 Lizardi
(Continued)

OTHER PUBLICATIONS

International Search Report issued in application No. PCT/EP2009/057295 dated Oct. 5, 2009.
(Continued)

*Primary Examiner* — Diana B Johannsen
(74) *Attorney, Agent, or Firm* — Rouget F. Henschel; Potomac Law Group, PLLC

(57) ABSTRACT

The present invention concerns an in vitro method for diagnosing a myeloid tumour or a lymphoid tumour in a subject, which comprises the step of analyzing a biological
(Continued)

sample from said subject by (i) detecting the presence of a mutation in the Ten Eleven Translocation protein family member 2 gene (TET2) coding for the polypeptide having the sequence SEQ ID NO: 2, and/or (ii) analyzing the expression of the TET2 gene; wherein the detection of such a TET2 mutation, of the absence of expression of TET2 or of the expression of a truncated TET2 is indicative of a subject developing or predisposed to develop a myeloid tumour or a lymphoid tumour.

3 Claims, 10 Drawing Sheets

Specification includes a Sequence Listing.

Related U.S. Application Data continuation of application No. 12/997,203, filed as application No. PCT/EP2009/057295 on Jun. 12, 2009, now Pat. No. 9,389,233.

(52) U.S. Cl.
CPC .. *C12Q 2600/106* (2013.01); *C12Q 2600/118* (2013.01); *C12Q 2600/154* (2013.01); *C12Q 2600/156* (2013.01); *C12Q 2600/158* (2013.01); *C12Q 2600/16* (2013.01)

(56) References Cited

U.S. PATENT DOCUMENTS

| | | | |
|---|---|---|---|
| 9,389,233 B2 | 7/2016 | Viguie et al. | |
| 10,662,482 B2 * | 5/2020 | Viguie | G01N 33/57426 |
| 2007/0059717 A1 | 3/2007 | Pascual et al. | |
| 2012/0302517 A1 | 11/2012 | Viguie et al. | |

OTHER PUBLICATIONS

Barany, Genetic disease detection and DNA amplification using cloned thermostable ligase, Proc. Natl. Acad. Sci. USA, Jan. 1991, vol. 88, pp. 189-193.
Baxter et al., "Acquired mutation of the tyrosine kinase JAK2 in human myeloproliferative disorders" Lancet, Mar. 2005, vol. 365, pp. 1054-1061.
Bellanné-Chantelot et al., "Genetic and clinical implications of the Val617Phe JAK2 mutation in 72 families with myeloproliferative disorders," Blood, 2006, vol. 108, No. 1, pp. 346-352.
Braun et al., "NF-kB constitutes a potential therapeutic target in high-risk myelodysplastic syndrome," Blood, 2006, vol. 107(3), pp. 1156-1165.
Campbell et al., "The Myeloproliferactive Disorders," N. Engl. J. Med., 2006, vol. 355(23), pp. 2452-2466.
Chaligné et al., "New mutations of MPL in primitive myelofibrosis: only the MPL W515 mutations promote a $G_1$/S-phase transition," Leukemia, 2008, vol. 22, pp. 1557-1566.
Charbonnier et al., "Detection of Exon Deletions and Duplications of the Mismatch Repair Genes in Hereditary Nonpolyposis Colorectal Cancer Families Using Multiplex Polymerase Chain Reaction of Short Fluorescent Fragments," Cancer Res., Jun. 2000, vol. 60, pp. 2760-2763.
Claessens et al., "In vitro proliferation and differentiation of erythroid progenitors from patients with myelodysplastic syndromes: evidence for Fas-dependent apoptosis," Blood, Mar. 2002, vol. 99, No. 5, pp. 1594-1601.
Clasessens et al., "Rescue of early-stage myelodysplastic syndrome-deriving erythroid precursors by the ectopic expression of a dominant-negative form of FADD," *Blood*, May 2005, vol. 105, No. 10, pp. 4035-4042.
Cole et al., "The EBV-Hybridoma Technique and its Application to Human Lung Cancer," Monoclonal Antibodies and Cancer Therapy, Alan R. Liss, Inc., 1985, pp. 77-96.
Daser A, et al., "The versatile mixed lineage leukaemia gene MLL and its many associations in leukaemogenesis". Seminars Cancer Biol., 2005, vol. 15(3), pp. 175-188.
Database Genbank [Online], Apr. 2, 1996, XP002502623 (2 pages).
Database Uniprot [online], Jun. 10, 2008 (Jun. 10, 2008), XP002502624, Database Accession No. Q6N021, http://www.uniprot.org:uniprot.q6n021.txt? (4 pages).
Database Uniprot [online], Jun. 10, 2008 (Jun. 10, 2008), XP002502625, Database Accession No. Q8NFU7, http://www.uniprot.org:uniprot.q8nfu7.txt? (3 pages).
Database UniProt [Online], Jun. 10, 2008, XP002502625, Database Accession No. Q8NFU7 <URL: http://www.uniprot.org:uniprot.Q8NFU7.txt?> (3 pages).
Delhommeau et al., "LBA-3 TET2 is Novel Tumor Suppressor Gene Inactivated in Myeloproliferative Neoplasm: Identification of a Pre-JAK2 V617F event", Annu Meet Abstr, 2008 (2 pages).
Delhommeau et al., "Oncogenic mechanisms in myeloproliferative disorders," Cell Mol. Life Sci., 2006, vol. 63(24), pp. 2939-2953.
Dupont et al., "The JAK2 617V>F mutation triggers erythropoietin hypersensitivity and terminal erythroid amplification in primary cells from patients with polycythemia vera," Blood, Aug. 2007, vol. 110(3), pp. 1013-1021.
Ebert et al., "Identification of RPS14 as a $5q^-$syndrome gene by RNA interference screen," Nature, Jan. 2008, vol. 451, No. 17, pp. 335-339.
Fenaux et al., "A multicenter phase 2 study of the famsyltransferase inhibitor tipifarnib in intermediate- to high-risk myelodysplastic syndrome," Blood, May 2007, vol. 109, No. 10, pp. 4158-4163.
Finazzi et al., "Essential Thrombocythemia," Semin. Hematol., 2005, vol. 42, pp. 230-238.
Gilbert H.S., "Familial Myeloproliferative disease," *Baillieres Clin. Haematol.*, Dec. 1998, vol. 11, No. 4, pp. 849-858.
Guatelli et al., "Isothermal, in vitro amplification of nucleic acids by a multienzyme reaction modeled after retroviral replication," Proc. Natl. Acad. Sei. USA, Mar. 1990, vol. 87, pp. 1874-1878.
Haase D., "Cytogenetic features in myelodysplastic syndromes," Annals of Hematology, 2008, vol. 87, No. 7, pp. 515-526.
Harper, et al., "Chromosomal Rearrangements Leading to MLL Gene Fusions: Clinical and Biological Aspects," Cancer Res, Dec. 2008, vol. 68(24), pp. 10024-10027.
Itzykson et al., "Optimal sequencing of treatments for patients with myelodysplastic syndromes," Current Opinion in Hematology, 2009, vol. 16, pp. 77-83.
Jabbour et al., "Evolution of Decitabine Development: Accomplishments, Ongoing Investigations, and Future Strategies," Cancer, Jun. 2008, vol. 112, No. 11, pp. 2341-2351.
James et al., "The hematopoietic stem cell compartment of JAK2V617F-positive myeloproliferative disorders is a reflection of disease heterogeneity," Blood, Sep. 2008, vol. 112, No. 6, pp. 2429-2438.
James et al., "A unique clonal JAK2 mutation leading io constitutive signalling causes polycythaemia vera," Nature, Apr. 2005, vol. 434, pp. 1144-1148.
Kiladjian et al., "Pegylated interferon-alfa-2a induces complete hematologic and molecular responses with low toxicity in polycythemia vera," Blood, Oct. 2008, vol. 112, No. 8, pp. 3065-3072.
Köhler et al., "Continuous cultures of fused ceils secreting antibody of predefined specificity," Nature, Aug. 1975, vol. 256, pp. 495-497.
Kojima et al., "FLJ10849, a septin family gene, fuses MLL in a novel leukemia cell line CNLBC1 derived from chronic neutrophilic leukemia in transformation with 1(4;11)(q21;q23)," Leukemia, 2004, vol. 18, No. 5, pp. 998-1005.
Kozbor et al., "The production of monoclonal antibodies from human lymphocytes," Immunol. Today, 1983, vol. 4, No. 3, pp. 72-79.
Kralovics et al., "A Gain-of-Function Mutation of JAK2 in Myeloproliferative Disorders," N. Engl. J. Med., Apr. 2005, vol. 352, pp. 1779-1790.

(56) References Cited

OTHER PUBLICATIONS

Kralovics et al., "Clonal hematopoiesis in familial polycythemia vera suggests the involvement of multiple mutational events in the early pathogenesis of the disease," Blood, Nov. 2003, vol. 102, No. 10, pp. 3793-3796.
Kuendgen et al., "Current status of epigenetic treatment in myelodysplastic syndromes," Ann. Hematol., vol. 87, pp. 601-611, 2008.
Kwoh et al., "Transcription-based amplification system and detection of amplified human immunodeficiency virus type 1 with a bead-based sandwich hybridization format," Proc. Natl. Acad. Sci. USA, Feb. 1989, vol. 86, pp. 1173-1177.
Levine et al., "The JAK2V617F activating mutation occurs in chronic myelomonocytic leukemia and acute myeloid leukemia, but not in acute lymphoblastic leukemia or chronic lymphocytic leukemia," Blood, Nov. 2005, vol. 106, No. 10, pp. 3377-3379.
Lizardi et al., "Exponential Amplification of Recombinant-RNA Hybridization Probes," Bio/Technology, Oct. 1988, vol. 6, pp. 1197-1202.
Lorsbach et al., "TET1, a Member of a Novel Protein Family, is Fused to MLL in Acute Myeloid Leukemia Containing the t(10;11) (q22;q23)," Leukemia, 2003, vol. 17(3), pp. 637-641.
Morgan et al., "A Role for JAK2 Mutations in Myeloproliferactive Diseases," Annu. Rev. Med., 2008, vol. 59, pp. 213-222.
Ono et al., "LCX, Leukemia-associated Protein with a CXXC Domain, Is Fused to MLL in Acute Myeloid Leukemia with Trilineage Dysplasia Having t(10;11)(022;q23)," Cancer Research, Jul. 2002, vol. 62(14), pp. 4075-4080.
Passamonti et al., "A dynamic prognostic model to predict survival in post-polycythemia vera myelofibrosis," Blood, Apr. 2008, vol. 111, No. 7, pp. 3383-3387.
Passamonti et al., "Prognostic factors for thrombosis, myelofibrosis, and leukemia in essential thrombocythemia: a study of 605 patients," Haematologica, 2008, vol. 93, No. 11, pp. 1645-1651.
Pikman et al., "MPLW515L Is a Novel Somatic Activating Mutation in Myelofibrosis with Myeloid Metaplasia," PLoS Med, Jul. 2006, vol. 3, No. 7 (e270), pp. 1140-1151.
Robert-Richard et al., "Human cell engraftment after busulfan or irradiation conditioning of NOD/SCID mice," Haematologica, The Hematology Journal, 2006, vol. 91(10), pp. 1384-1387.
Rumi et al., "JAK2 (V617F) As an Acquired Somatic Mutation and a Secondary Genetic Event Associated With Disease Progression in Familial Myeloproliferative Disorders," Cancer, Nov. 2006, vol. 107, No. 9, pp. 2206-2211.
Sheils et al., "Nucleic acid microarray: an overview," Current Diagnostic Pathology, 2003, vol. 9, pp. 155-158.
Tahiliani et al., "Conversion of 5-Methylcytosine to 5-Hydroxymethylcytosine in Mammalian DNA by MLL Partner TET1," NIH Public Access Author Manuscript, Science, available in PMC Jul. 2009, pp. 1-11.
Tefferi et al., "Classification and diagnosis of myeloproliferative neoplasms: The 2008 World Health Organization criteria and point-of-care diagnostic algorithms," Leukemia, 2008, vol. 22, pp. 14-22.
Tiu et al., "Clonality of the stem cell compartment during evolution of myelodysplastic syndromes and other bone marrow failure syndromes," *Leukemia*, 2007, vol. 21, pp. 1648-1657.
"Diagnosis"—The Leukemia & Lymphoma Society, www.lls.org, Jun. 24, 2014, 2 pgs.
"Signs and Symptoms" (acute AML), Someday is today—The Leukemia & Lymphoma Society, www.lls.org, Jun. 24, 2014, 1 pg.
"Signs and Symptoms" (early sign of non-Hodgkin lymphoma)—The Leukemia & Lymphoma Society, (Jun. 24, 2014) 1 pg.
"Signs and Symptoms" (no MDS symptoms)—Someday is today—The Leukemia & Lymphoma Society (Jun. 24, 2014), 1 pg.
Acute Myeloid Leukemia—NCCN Clinical Practice Guidelines in Oncology (NCCN Guidelines ), Version 2.2014, (Mar. 28, 2014), 89 pages.
Acute Myeloid Leukemia, Practice Guidelines in Oncology—v1.1. 2008 (Dec. 30, 2007), National Comprehensive Cancer Network, Inc., 36 pages.
Buckstein, et al. "Myelodysplastic Syndromes (MDS)",(May 2008), 20 pgs.
Fabre, et al. "Treatment of AML with Azacytidine (AZA): Current Results of the French ATU Program", Blood (ASH Annual Meeting Abstracts) (2007), vol. 110, Abstract 1849 (printed online Jun. 24, 2014), 1 pg.
Fenaux, et al. "Azacitidine prolongs overall survival and reduces infections and hospitalizations in patients with WHO-defined acute myeloid leukaemia compared with conventional care regimens: an update", ecancermedicalscience (2008), vol. 2, No. 121, pp. 1-3.
Garcia-Manero, "Demethylating Agents in Myeloid Malignancies", Curr Opin Oncol. (Nov. 2008), vol. 20, No. 6, pp. 1-11.
Is Lymphoma on Your Radar?, Leukaemia Foundation, downloaded on Jun. 13, 2014, 2 pgs.
Itzykson, et ai. "Optimal sequencing of treatments for patients with myelodysplastic syndromes", Current Opinion in Hematology (2009), vol. 16, pp. 77-83.
Leone, et al. "DNA methylation and demethylating drugs in myelodysplastic syndromes and secondary leukemias", Haematologica (2002), vol. 87, pp. 1324-1341.
Myelodysplastic Syndromes—NCCN Clinical Practice Guidelines in Oncology (NCCN Guidelines), Version 2.2014 (May 21, 2013), 65 pages.
NCBI dbSNP entry for submission ss81446742 of cluster rs949681. Build 129, Apr. 2008 (9 pages).
Langemeijer, et al., "Acquired mutations in TET2 are common in myelodysplastic syndromes," Nature Genetics 41(7):pp. 838-843 (Jul. 2009; published online May 31, 2009).
Tefferi, et al., "TET2 mutations and their clinical correlates in polycythemia vera, essential thrombocythema and myelofibrosis," Leukemia 23: pp. 905-911 (Mar. 5, 2009).
Tefferi, et al., Detection of mutant TET2 in myeloid malignancies other than myeloproliferative neoplasms: CMML, MDS, MDS/MPN and AML, Leukemia 23: pp. 1343-1345 (Mar. 19, 2009).
Thomas, et al., "The rationale and use of hypomethylation agents in adult acute myeloid leukemia," Expert Opin. Drug Discov. 4(2): pp. 195-205 (Feb. 2009).
Gaiger et al., "Increase of BCR-ABL Chimeric mRNA Expression in Tumor Cells of Patients with Chronic Myeloid Leukemia Precedes Disease Progression," Blood, vol. 86, No. 6, pp. 2371-2378, Sep. 1995.

* cited by examiner

MEQDRTNHVEGNRLSPFLIPSPPICQTEPLATKLQNGSPLPERAHPEVNGDTKWHSFKSYYGIPCM
KGSQNSRVSPDFTQESRGYSKCLQNGGIKRTVSEPSLSGLLQIKKLKQDQKANGERRNFGVSQERN
PGESSQPNVSDLSDKKESVSSVAQENAVKDFTSFSTHNCSGPENPELQILNEQEGKSANYHDKNIV
LLKNKAVLMPNGATVSASSVEHTHGELLEKTLSQYYPDCVSIAVQKTTSHINAINSQATNELSCEI
THPSHTSGQINSAQTSNSELPPKPAAVVSEACDADDADNASKLAAMLNTCSFQKPEQLQQQKSVFE
ICPSPAENNIQGTTKLASGEEFCSGSSSNLQAPGGSSERYLKQNEMNGAYFKQSSVFTKDSFSATT
TPPPPSQLLLSPPPPLPQVPQLPSEGKSTLNGGVLEEHHHYPNQSNTTLLREVKIEGKPEAPPSQS
PNPSTHVCSPSPMLSERPQNNCVNRNDIQTAGTMTVPLCSEKTRPMSEHLKHNPPIFGSSGELQDN
CQQLMRNKEQEILKGRDKEQTRDLVPPTQHYLKPGWIELKAPRFHQAESHLKRNEASLPSILQYQP
NLSNQMTSKQYTGNSNMPGGLPRQAYTQKTTQLEHKSQMYQVEMNQGQSQGTVDQHLQFQKPSHQV
HFSKTDHLPKAHVQSLCGTRFHFQQRADSQTEKLMSPVLKQHLNQQASETEPFSNSHLLQHKPHKQ
AAQTQPSQSSHLPQNQQQQQKLQIKNKEEILQTFPHPQSNNDQQREGSFFGQTKVEECFHGENQYS
KSSEFETHNVQMGLEEVQNINRRNSPYSQTMKSSACKIQVSCSNNTHLVSENKEQTTHPELFAGNK
TQNLHHMQYFPNNVIPKQDLLHRCFQEQEQKSQQASVLQGYKNRNQDMSGQQAAQLAQQRYLIHNH
ANVFPVPDQGGSHTQTPPQKDTQKHAALRWHLLQKQEQQQTQQPQTESCHSQMHRPIKVEPGCKPH
ACMHTAPPENKTWKKVTKQENPPASCDNVQQKSIIETMEQHLKQFHAKSLFDHKALTLKSQKQVKV
EMSGPVTVLTRQTTAAELDSHTPALEQQTTSSEKTPTKRTAASVLNNFIESPSKLLDTPIKNLLDT
PVKTQYDFPSCRCVEQIIEKDEGPFYTHLGAGPNVAAIREIMEERFGQKGKAIRIERVIYTGKEGK
SSQGCPIAKWVVRRSSSEEKLLCLVRERAGHTCEAAVIVILILVWEGIPLSLADKLYSELTETLRK
YGTLTNRRCALNEERTCACQGLDPETCGASFSFGCSWSMYYNGCKFARSKIPRKFKLLGDDPKEEE
KLESHLQNLSTLMAPTYKKLAPDAYNNQIEYEHRAPECRLGLKEGRPFSGVTACLDFCAHAHRDLH
NMQNGSTLVCTLTREDNREFGGKPEDEQLHVLPLYKVSDVDEFGSVEAQEEKKRSGAIQVLSSFRR
KVRMLAEPVKTCRQRKLEAKKAAAEKLSSLENSSNKNEKEKSAPSRTKQTENASQAKQLAELLRLS
GPVMQQSQQPQPLQKQPPQPQQQQRPQQQQPHHPQTESVNSYSASGSTNPYMRRPNPVSPYPNSSH
TSDIYGSTSPMNFYSTSSQAAGSYLNSSNPMNPYPGLLNQNTQYPSYQCNGNLSVDNCSPYLGSYS
PQSQPMDLYRYPSQDPLSKLSLPPIHTLYQPRFGNSQSFTSKYLGYGNQNMQGDGFSSCTIRPNVH
HVGKLPPYPTHEMDGHFMGATSRLPPNLSNPNMDYKNGEHHSPSHIIHNYSAAPGMFNSSLHALHL
QNKENDMLSHTANGLSKMLPALNHDRTACVQGGLHKLSDANGQEKQPLALVQGVASGAEDNDEVWS
DSEQSFLDPDIGGVAVAPTHGSILIECAKRELHATTPLKNPNRNHPTRISLVFYQHKSMNEPKHGL
ALWEAKMAEKAREKEEECEKYGPDYVPQKSHGKKVKREPAEPHETSEPTYLRFIKSLAERTMSVTT
DSTVTTSPYAFTRVTGPYNRYI-2002

Figure 1

FIG. 3A
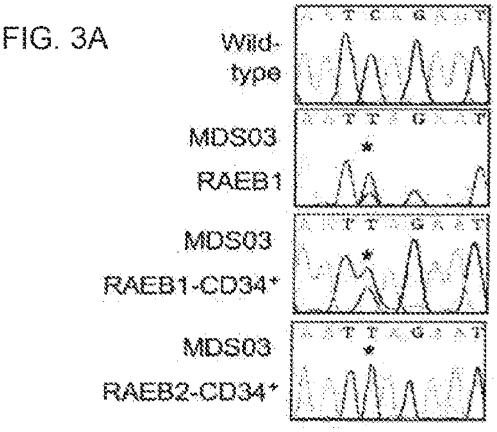
FIG. 3B
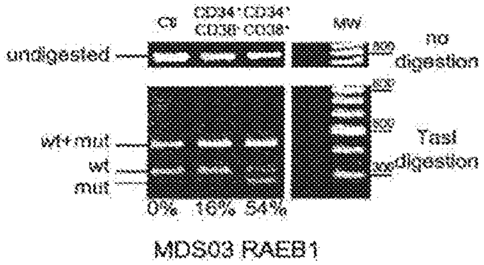
FIG. 3C
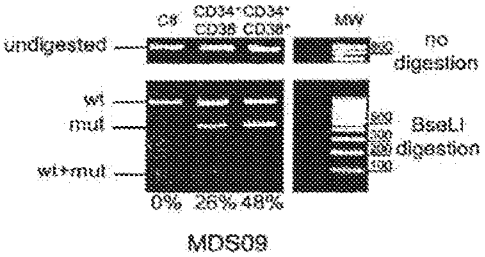
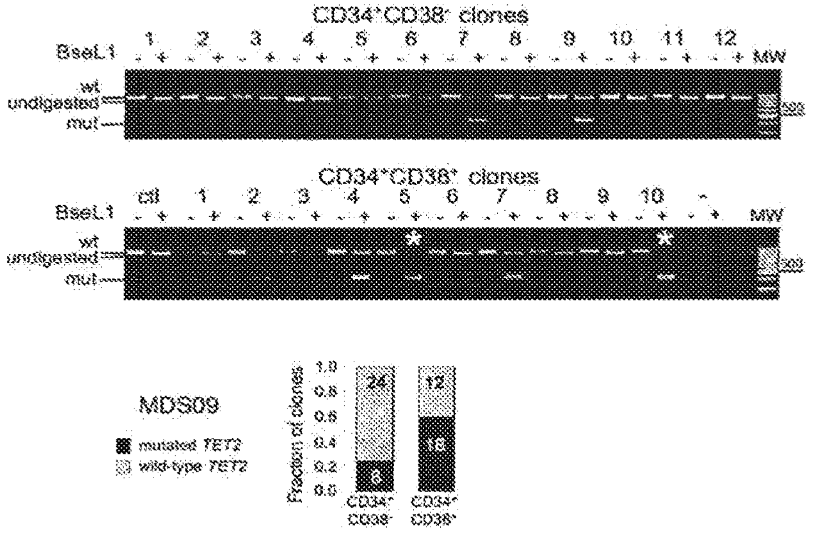
FIG. 3D

SEQUENCE LISTING

```
<160> NUMBER OF SEQ ID NOS: 39

<210> SEQ ID NO 1
<211> LENGTH: 132428
<212> TYPE: DNA
<213> ORGANISM: Homo sapiens
<220> FEATURE:
<221> NAME/KEY: Intron
<222> LOCATION: (1)..(100)
<220> FEATURE:
<221> NAME/KEY: exon
<222> LOCATION: (101)..(787)
<220> FEATURE:
<221> NAME/KEY: Intron
<222> LOCATION: (788)..(44167)
<220> FEATURE:
```

-continued

<221> NAME/KEY: exon
<222> LOCATION: (44168)..(44294)
<220> FEATURE:
<221> NAME/KEY: Intron
<222> LOCATION: (44295)..(87704)
<220> FEATURE:
<221> NAME/KEY: exon
<222> LOCATION: (87705)..(91159)
<220> FEATURE:
<221> NAME/KEY: Intron
<222> LOCATION: (91160)..(95146)
<220> FEATURE:
<221> NAME/KEY: exon
<222> LOCATION: (95147)..(95237)
<220> FEATURE:
<221> NAME/KEY: Intron
<222> LOCATION: (95238)..(96641)
<220> FEATURE:
<221> NAME/KEY: exon
<222> LOCATION: (96642)..(96735)
<220> FEATURE:
<221> NAME/KEY: Intron
<222> LOCATION: (96736)..(97377)
<220> FEATURE:
<221> NAME/KEY: exon
<222> LOCATION: (97378)..(97586)
<220> FEATURE:
<221> NAME/KEY: Intron
<222> LOCATION: (97587)..(113426)
<220> FEATURE:
<221> NAME/KEY: exon
<222> LOCATION: (113427)..(113577)
<220> FEATURE:
<221> NAME/KEY: Intron
<222> LOCATION: (113578)..(115566)
<220> FEATURE:
<221> NAME/KEY: exon
<222> LOCATION: (115567)..(115656)
<220> FEATURE:
<221> NAME/KEY: Intron
<222> LOCATION: (115657)..(123417)
<220> FEATURE:
<221> NAME/KEY: exon
<222> LOCATION: (123418)..(123555)
<220> FEATURE:
<221> NAME/KEY: Intron
<222> LOCATION: (123556)..(126371)
<220> FEATURE:
<221> NAME/KEY: exon
<222> LOCATION: (126372)..(126726)
<220> FEATURE:
<221> NAME/KEY: Intron
<222> LOCATION: (126727)..(128855)
<220> FEATURE:
<221> NAME/KEY: exon
<222> LOCATION: (128856)..(132328)
<220> FEATURE:
<221> NAME/KEY: Intron
<222> LOCATION: (132329)..(132428)

<400> SEQUENCE: 1
gcgcgggggc gtgtgcgcgg gacctcgaag tggtggtgga gtgcagacca gcaaaaagtt 60
tcaaagggaa atcttagatg tcacgtcttt gtccaggcac ccgtgccatc ccaacctccc 120
acctcgcccc caaccttcgc gcttgctctg cttcttctcc caggggtgga gacccgccga 180
ggtccccggg gttcccgagg gctgcaccct tccccgcgct cgccagccct ggcccctact 240
ccgcgctggt ccgggcgcac cactcccccc gcgccactgc acggcgtgag ggcagcccag 300
gtctccactg cgcgccccgc tgtacggccc caggtgccgc cggcctttgt gctggacgcc 360
cggtgcgggg ggctaattcc ctgggagccg gggctgaggg ccccagggcg gcggcgcagg 420
ccggggcgga gcgggaggag gccggggcgg agcaggagga ggcccgggcg gaggaggaga 480
gccggcggta gcggcagtgg cagcggcgag agcttgggcg gccgccgccg cctcctcgcg 540
agcgccgcgc gcccgggtcc cgctcgcatg caagtcacgt ccgccccctc ggcgcggccg 600
ccccgagacg ccggccccgc tgagtgatga gaacagacgt caaactgcct tatgaatatt 660
gatgcggagg ctaggctgct ttcgtagaga agcagaagga agcaagatgg ctgcccttta 720
ggatttgtta gaaaggagac ccgactgcaa ctgctggatt gctgcaaggc tgagggacga 780
gaacgaggtc agagcgcttc tcttatgccg cgaaactctc cctttcttct ccccttcgct 840
ttttctcggg cttccaggga ctggggagca aaccctgtag tgtcacccac aaataccaag 900
agggaagagg gaagcttcac aaattactgg agcctcttca acatggctga caaatatagt 960
tttaattccc tctacccctt ttaaacctgt agttctgtgt tctcttctct cctcctaatg 1020
ctcgtcccct catctcccag aaaacttacc tttgtgcctc cgacgagccg gtttcccggc 1080
ctttttaat cctcagaaaa gtgattttta aatttgcttt cctttctaaa atagttcagc 1140
tttgggggca ctacttttcc ctttaatcct cttcccctgt ttctttcgtg taagtgaaac 1200
gagtctcccg tttatcctga acaacctcag agagaacact gatagggtgt ttttcgaccc 1260
ttttatcagc tgtagggtct gggtctgggt ttgtgtctgc ctcctcctac cttcttatcc 1320
ccctttaggg ggctgtacga agtgaatgtc acagggagtg gaattggagt acactgagtg 1380
ggtttttttt ttccttaagt ccgcgcgttt tgttagcggc gctgagtgaa agaggaaaga 1440
atagtttctc tggttcccca aacaagacca gaactcactt ttctcaaggt acataagtca 1500
gcgctgggct gagccttcca gcctggggaa tgtatgtaag agaatttatg gacaaatctg 1560
tgtcccggct ttgtgcttct cccgaatcag cttcgtttgg ttccttggta agtgacaggc 1620
agacacaaag gcaggcgcag gcccggggag ggggcgggag ggggtgggga gcgcagcgtt 1680
ggagttgcaa gactgcaagg tcaggggcgc ctaaagaaat gaaacccaat cccagcaaag 1740
aagtgaagag cagatttata acagtcccat ccaaatttct ctttggcttc tctctttggt 1800
ctttcatctc tctgcctttc tctctgtgtc tcctctctac tctttcttct ctctctctca 1860
tacacataca cacacacaca cacacacaca cctcactcgc atcttgctga atcttttcac 1920
tgggactgct tgtctagttt tattaagcta atagggtttg tatggagagt tttctaccta 1980
tgacataatg aagtgtggcc tggatagact cctggaaagg ccgaaaatga aatataagtg 2040
ttatttgctg gttattcccc tcatgatata cttttaatta cattgaggga gttctccctt 2100
cttcatctaa tgtttaagaa ttgagaaaag gcttattttc cagcggtaaa atttagtgca 2160
taaaatttag tgaaatattt atatatttac gtgtctaggg agtggaatac attcatgaat 2220
ttaatatctc aaatcacaca ttgtgctttt tccccttcag tcagggatta taatgggaaa 2280
cccaaattca aagatattca tcaacaaatg atccatcata ggaataagat tgtatcttaa 2340
gggaagttgg gattcacaga gaaaagacat tggtttggtt tggtgtgata ctgtgggtat 2400
tgttgcctgg ctaatgaaat cattacattt gcattttaat ggaaagttga aatactaagg 2460
ggagttatgt tcttttacat gtttgtatgt gtgcttaata atgtttggaa tagaatataa 2520
atttaaacac aataaatatt gattttttta aatgttaata agcagagaac ggttaatgaa 2580
gtgttggata atcaaactga agtttagaag acaatttata ggattaaaaa atggatagaa 2640
ggaaaaacac aataatagat atttctccat aagtcgaatt tccaaaacta tttgtcctcg 2700
atagttcact ttgtaacttt ctattttgat ctttgttaat ttaatgtagt ttgctttaat 2760
cattgatacg tggggttctt tcacatgatt acaagggaga agcattactc atctctgtgg 2820
aatagaaacg gttcattggt tagttcttat ttgccctaaa attaaaacaa aaattaggat 2880

```
tttaccatta atgctgttca tggtaaacta tcgagaaaac tatggttaat tattccagca   2940
attcagaatt aaaaacaatt ccttttgcta acaaactaat atttactttt tggggacaac   3000
ttttcaaatg ttgtggtata tactgtcttc aggctactca actaataata gatacaacat   3060
tttccactca ataaataaga ataactacat tggttaataa ttttgaatac aactatgaag   3120
gcttgttttt tcctgtcatc aaatttagat tcttgttatt ttgtgcatcc tacttttata   3180
ctgaaaatag ctgctaatta atactgtata aagtatttca gtgattataa ggaagagatg   3240
tgtatgttag tcactttatc ctttgttgga aaagagaaat tattttaata agtatggggt   3300
agtttacaat aaaagacata acctcagttc tttctttacc atatatgtga tcatactacc   3360
taggtgctcc aaaaattcca taggactgtc ttgggttatt gaattttagg aacatgataa   3420
tggacaataa caagatagat agcttttctt aactatgaca ttgttttgct tattttctta   3480
ttgaactaat catcaatgag aaattaagtt gcagtgagag aaatcccttg ctttgtttaa   3540
attgtcatat ttgccaaact cttcttaagg ctttaattag gtctgatgtg ccagtttatg   3600
ccagaagccg gaggaattga tatgattttg aggcagtggc acatggtcct actagacatt   3660
ggcaagtgaa tatcacttcc agaacaagtg aagtgcacct gccaaggagt tgttatgaaa   3720
gaattccaaa gtccttattg ggcactggtc ttgtattagg taacaacaac tggagttaat   3780
gttttagttt cacttgttga agttaaaagt tccctatcaa ttcttctaag actccacccc   3840
caaacaatgt tgtaagtcaa atgtcactat tgaaatgtat ttccttaatt actgacctca   3900
ttaagaagcc cttcttatga ttcataggca cacctcacag aaactctatt ttccatcctg   3960
cccaaagtct gagtaggtaa attcttatga attcttatga aattaccttg aaataaaata   4020
tcttcaaaag ttacggatgc tagacattgt ataatgtcaa tattttagaa tatctaatat   4080
ttagaaaatc ttagatctac tttttatgct ttaattgctt ctaatgcaag ttaaattgtt   4140
tttgttgtta ttgttttaat agaatttcat agtcttatct agcaatttca aatcgctgga   4200
aagagtcatc tttgttatat aaataaccat gtagactgtt ttaatgttat tgtttcctac   4260
cttgggaaca ggctaaaact ttggaccagc tgtcagtatt tgttcatcag aataacactt   4320
tgtcaatgat tattctacca ttgcacagta gttcttaagg atagtaatgg taccaaagcc   4380
agcagcaata gaatatctcc caagccaact ttacaattgg agccttcact gtgggaaaga   4440
ccagttgcca agtagagctg gtggttatct gggaaactgt gctgaagaac acaaccacaa   4500
atgattttgc caaatataca gtatttactt ggtctagatc tccaatttct atttctactc   4560
actgccaaaa ctgagtgaat actgtgacat tattgaagga ggttatgcag tacatctgtt   4620
ggtttggtat atagtaggag agaagggttc caggagggaa aggggaaagt cagagcatgt   4680
gaatcactgt gactacaatc caaaaagaat tatgtatgtc tgctatttcc agcattattt   4740
ttgtcctata ttgtacattg cagagacttg ctgacttaaa atagatatat aatctttttc   4800
tcaaaagaat agatatttgg ttgtccattc caaataacaa attttggatg ggcgtggtga   4860
ctcatgcctg taatcctagc actttgggag gccaaggtga gagatcactt gaggccagga   4920
gtttgaaacc accctgggca acacagtcag gccccagtct ctacaaaaaa tttaaaaagt   4980
tagtggggca tggtggtaca ttcctgtagt cccagctact caggagactg agataggagg   5040
atggattgag ctcaagtgtt ctaacttata gtgagctctg atcacaccac tgcgctccag   5100
cccaggcaag agggagagac cctatctcaa acagcgacaa caacaaaacc aaacaaacaa   5160
aaaagcacat tctatcagct ttgatttatg ttttcttcat ttgtaatgac atgtagttaa   5220
atgtgtcata cttcaaaaag aagaaacaga tagtaggtgg attttcaata taatatatat   5280
```

-continued

```
tagatataga taatatatat tttcaatata taatatatgt aaaaataaat tcagtgataa   5340
tatcatccta cctgcagttt taagaattca gaactcaggc caggtgtggt ggctcattct   5400
gggaggggaa ggcaggagga tcacttgagg ccagaagttc tagaccagcc tgggcaacat   5460
agtgagatac ctgtctctat tcaataaaaa taaaaataaa aataattcag aactcaatgc   5520
tttatactca ctgaaagttg ttcctctaaa ctgacttgaa atcatgttcc aaataaactg   5580
agaattaaag taagagacga ggccggttgt ggtggctcat gcctgtaatc ccagcacttt   5640
gggacgacaa ggcaggtgga tgacctgagg tcaggagttt gagaccagcc tggccaacat   5700
ggtgaaaccc tgtctctact aaaaatacaa aaattagccg ggcatggtgg cacacaccag   5760
taatcccagc tactcaggag gctgaggccc gagaatcact tgagcctggg catggtggct   5820
catacctata atcccagcac tttgggaggc cgaggcaggt ggatcacctg acgtcaggaa   5880
ttcgagacca gtctggccaa catggtgaaa ccccatctcc actaaacata caaaattagc   5940
tgggtgtggt ggcacatgcc tgtagtctca gctattctgg aggctgatac aggagaattg   6000
cttgaaccct cccgggaggc agaggctgcg gtgagccgag atggctctgc tgcactccag   6060
cctgggcgag gcagagagac tctgcctcaa aaaaagaaaa ataataataa taaataggag   6120
atgaataaat tgggataaag tgtttttgaa ggacagtcta ggatataaaa tgaactggtt   6180
gtttgactaa aaatactaca aatgtttctt tcaaattaca tttctttttt gtctattgga   6240
aggtaggcac tgatttctat gtctttctat tccctaatag aacctactgt tgacctctca   6300
gtcaatattt aatggatgat atagaactag tgaaaaacca tgcaatttaa ctagaaaaaa   6360
aaagtataat ctattttctt ttccttttc tttctttctt tctttctttt tttttttttt   6420
tttgagacgg tatcttgctc tgtcacctag gctggagtgc agtggtgtga tctcggctca   6480
ctgcaacctc tgccttccag gttcaagtga ttctctttct cagcccccag agtagctggg   6540
actaggagcg tgccccacca cacctggcta atttttctat ttttattaga gacagggttt   6600
caccatgttg gccaggctga tctcgtactc ctggtctcag gtgatctgcc tgcccgggtc   6660
tcccaaagtg ctgggattac aggcatgagc cactgcacct ggtctaatct attttcaatg   6720
tataagagaa aaatagtgtt aagtgtcttg gtgatggtga tgatggtagg agtaatggtg   6780
tgttttcctt acatttaatt tctacaggct atggcaattg ccctataaaa gccacccatt   6840
ttaagcacaa aagtgaatgg tttttagtaa acttatatgg gatcatatat ttttaattga   6900
aatatttttt gagttaatta tagattcata tgccattgta tgaaataata cagagagatt   6960
ccacgtatac ttgctcaatt tcccccagtg gcaacacttt gcaaaactat aatatcatat   7020
cacatcacat gcaaaactat aatatcatat cacaaccatg atactgacat tgatgtggcc   7080
tactaatctt attcagatgt cctcagttta acttgtactc atttgtgtgt gttttgtttt   7140
ataccattta gtcacatgat cacatatttt taaacctttt tttctcaaaa cagagaagtt   7200
tagcacaaaa gtttagcaat ttatcaatct tgtgattgtg ctgttatgcc atattaaaat   7260
gtgtgtcaga atgtaagttt ttgttttctt aaaagtcctt tttttgatag aatggccttt   7320
atgttaaaaa tattttaagt tgttttgtga cagtgtaagt cgatgtcatt taattctcat   7380
cacaacccta gagataggta ttattcttat ccctatttat gagtgaggaa actgaagccc   7440
agtgaggtta aataacttcc ttaagttcat acagcctata catggcttag gcttagccag   7500
catttgagtt aagcagtctg tctctagtgc caaatctttt aatcactata ttatacttca   7560
tcattatcat tgatagctgt aaaagtgtat aatgtggact atgtagagaa agtcataaaa   7620
```

-continued

```
ggagatttaa aatgcataca gttgttcaca tgaaaacttg tagccaaatg ttcattacag   7680
cattattaat aatggtaaaa aatggaaaca acccagatgt ctatcatgtc atgagtgaat   7740
aaacaaattg tggtatatcc atacagtgaa atattattaa gtagtataaa ggaatggatt   7800
attgataaat gctgtcacat aggtgaatct gagaggcaca agaaaggcca catatgatat   7860
gctttcaatt ttaagtaacg tccagaatag gcaaatctaa ggagacagaa agttggctag   7920
ttattactag gggctaggga tgggagggag gtgactccta ataagtatga gatttctttt   7980
ggtgatgatg aaaatgttct ataattagat agtaatgatt gcccaactct ttgaatatgc   8040
tgaaacccac tgaattatat gctttaaaag gatgaattta ttgtatgtga attatatttc   8100
aaaaagctgt tgttataaaa atgaatgtag ttgagttatt tggtttattt tatgtcagaa   8160
aatgtcttac atctcatgca aaagaaatgc aggaactatt tggattgaat gaggctaagc   8220
atatctttct aggaagatgg catcaaggag ttttattatg cctgtaatcc tggcactttg   8280
ggaggccaag gcgggagacc agaagtttga gattagtctg ggcaacatcc tcttatagat   8340
gagaaggata cttaatcact caaaagttgg cattgtgttt tgtgataaca atagccttta   8400
gagctcatat gggaagattc aatagatagt gataggttat atgacttggt aaagagggct   8460
taatgtatag gtgcaagaaa ctttctcaga tgtctttagt tacctagcca ttcagttcag   8520
gagatgtaac ccaagtgtta aaaggaatgt gactgggtgc ggtggctcac acctgtaatc   8580
ccagcacttt gcgaggcgga agtgggtggg tctcttgagc tcaggagttg gagacaagcc   8640
tgggcaacat ggcaaaaccc catccctaca aaaaatgcac aaattagctg ggtgtggtgg   8700
cacatccctg tagttccagg tacttgtggg gctgaggcgg gaggatggct cgagcctggg   8760
aagttgaggc tgcagtgagc catgttggtg cccccacact tcagcctggg tgacaaaatg   8820
agaccctctc tctcaaaaaa aaactataaa aattgctgtt cttgtttaaa ttactacaaa   8880
gtgcagttta atctagaaat aataacaaat tactagattt ggggggttat taatgtctta   8940
tctatgtgaa aacagaaggg caatgcaggg cagagaataa acttcaaaac tttgagtttg   9000
ttaactgttt atatctccac ttgtcatgtt tcagatttta aagttaaaat gacaaagtat   9060
ctcatagggt ttaaacaagt gactcttttc ctgttaactg atactgtggc atgttgaaga   9120
tgtaaaataa ggttgaaaag gaaattgctt tgcagcagtc ttcataatgc caggacaaag   9180
tgagaaacag ggtcagaatg atgatggctc tccatctttg ctacacatgg ctgcaagtat   9240
ttacaaatac cagcagaact tctacaaacc acttacaggt aaaatgagtg cagattttta   9300
acactagtcc ctatggaact atgacttgta gttttggaca cacagggtga attacttggg   9360
gttgattgta tttgaatttc taaccttatg taattctaga taccagacat tcttgttgtg   9420
caatgcttct ctccctttt attctcatga gaatgctggg ttgcagccgg ttggatccca   9480
taccttggga ccatgactga taactggagt ggagaaaatt cactgatctg gaaaggttga   9540
gctttagggt tcagagactt atttaaggta cacatgtgat tgtacccaat aaggaagtat   9600
attggcttta tataattgtt atgatcactt gttcaatgag taactataga attttacttt   9660
ttaagagtat gatcatagca tctacttgta ggtttgttga gtatgtttga caagcccaag   9720
atagatgctc atgttagacc cattaagaag ttggtgtagt gatggttatg gaaagcagta   9780
agatagaatt taggttctgt tctccttact ggagaaatga ctagcttact tgtcttcact   9840
ctctcttgtt tctctcaaaa ctttgtgaac cacctcagct gactataaat ttttgtacta   9900
gtatctccat aattttaaaa aagttgttca caagtttgag tgtagtactt catctttgct   9960
ttttaatgca cttccaaaaa atgtaaatct gttctcgcat attaggaaca ttttgatttg  10020
```

-continued

```
ttgtttattt ttagctttgc tttttataag taatttatac agaaggtaca ccatattcaa  10080
aagaagaaaa atgggctgtg aatttttgct gatgtactac tctcttcaaa gggaattgcc  10140
tatgttcagg catagaaatg caggcagtct gacatttagg tatgccatac agagtattga  10200
tatttttaat ttgctacttt taacattttg agatttgtca cagtttgttc tgtgggtggg  10260
taaaagtaat ggtaatttta attacagttg tcgtgcctca ttagccattg ctaaaacctg  10320
ccttaccaaa tcacttattt tcttgatgca gtgttaaatc tagcttctat gtccaggtta  10380
tacattaatg agaacattca cccatctctc aaatgggtta ttatagtatt ttctcctgaa  10440
atagatgatg cataaaaaaa agtaaaaaag cttcaatagg gataatgaaa gccagataac  10500
atagcatggt atatgagtta ttcctcccgt ttttcttacc tgtctgcact aagaagggca  10560
cccattaaat accataatta ttagttgtgc tgcctctgaa gtagagcacc agaatgtgag  10620
agtaatacaa tgagaccaca cccagattct atccataaca tactgtcctg gtcttattaa  10680
ttttttaac ctgtttgttc ttttagcact tttcctgctt ttgtttgaag tctcttgctt  10740
tgaagttata gaatttttat atttgccatt ggctgtaaag ttatctcagc tcttttataa  10800
cttttcatta tatttgcatt aaaaggatca ctttgagcac cctgtaatta attcagatga  10860
ttattagctt ttttgtttgt tctactgtgc actctcctat atacattata acagaagaaa  10920
aaaccatttc tacaaataca gtgtctgata gttcatcaaa tcagaatgag catcttaaaa  10980
agtgaattat taaaatatta attcatttac attcctattt taatgtacca aatgtaactg  11040
atgaaaagaa gaataccata aatgggtacc tttcaaaaat gaaggaaaaa aaaatctcac  11100
aactaaagat tcttaccata taaattattt attttagtaa ataattattt tagtacaaac  11160
agatacattt tagcaggaaa aaacacactt taaaccttgt tttatagatt ttatctttct  11220
tccaatctag ccactgaaat ggttttttct ccagtgaagt tatattatct acataagttg  11280
aatttaaaac aaggttgtat tttaattttg cagttgtctg ccacattacg cttgtggaaa  11340
aacactggca gaaagcaaag ctaatagaca ttttgctgtt ggctcacctt attaatggct  11400
aagatttaat tatgtatttc tactgaaaag caaacttgaa aaagacgttt ggttactaac  11460
tgtgggaact aaaaattttt atttattttt attttttatt ttttggtaga gtctcactct  11520
cttgcccagg ctggagtgca gtggcatgat cttggctcac tgcagcctcc tccttctggg  11580
ttcaagcgat tctcctgtct cagcctcccg agtagctggg attataggca ccagccacca  11640
tgcctggcta atttttgcat ttttagtaga aacagcgttt cgccatgtag gctaggctgg  11700
tctcgaactc ctgacctcta gtgatccacc cccttctgct tcctaaagtg ctgggattac  11760
aggcatgagc catcggcctg gccaacttat ttactgttac aacttactta ctttgaaaca  11820
acttatttac tgttaaaaaa tgtggttctt atttcaaata agattttatg gacatcaact  11880
aatttttttaa acatatattg taattttaaa acatttttac caacattttt caagagcatg  11940
ggaaatctag ggtatggcat tttaaagtga ctttaaagac acttcttggg ttttgttgaa  12000
gtcagaatat ttttaaaaat acaatgagtt taatttacta ctgacagatt ttctttaatt  12060
tttttgcat tgttataatt agtcatgcct taatcctcgg ggtttttggg aaactatatt  12120
taggggttaa aaacttagtt attgacattg taatttttct cagtattggt aagaattcag  12180
gtgtttaagg aatggagttt acttgttttc tgttcacaaa cccattgtaa aagatataat  12240
gaatgtagat gaaggtgaaa tccgagatag gaagagaggt aaaatgctac ttttttttcc  12300
ttcacccaag gaaagccatt gaatactgaa tgggtcatgt tgtaatttaa ttgggtgtaa  12360
```

attataactt tgtaaatcat ttgcctactt agtgtatatc tctggttttt atgtaattca 12420
tctcccataa tatctcagtt tacactgaag taaataagca agcaggaata agtcctgcaa 12480
atagaggaag tagaaagtgc attcagaatg cattgctgaa attgtaaaac tgatcctaaa 12540
ttgaattagg tagagcagtt aatttagatt acaagaaatg caacaggaaa aaaatattac 12600
agttcttcct cttttttgga aaaaaaaaaa gaaagaaaag acaaataaat cacccttagt 12660
tagtgataat tccttgacat ctgtatgctc atttttaggg ccaaaaaata gtaggcttct 12720
ctttggaaat tgtagacgct ttctctcctt ccagttacac gcggtcacat caacatttga 12780
cacgtgggta ccgtgcacgt ggcagcagta tttacaaaca ccatcctagg attccagaga 12840
ctcttatgta acagtggaga gagtaagctt tgagtgtctg tgggcggagg aatcaacaca 12900
gtttaattca ttgtccggga gcccttgtct ggctctgata gggtcatgaa ccaaagatca 12960
aggtgtttag gtcaggatat tccctaacgc atggttttcc taccaaagcc tcaaaagctg 13020
tgcctaaata caagattaat ctttttcttt ctttctttct tttttttttt ttttttgag 13080 acggagtttc gctcttgctg ccaaggttgg agtgcagtgg cgccgcgatc tcggctcact 13140
gcaacctccg cctcaccggt tcaagcgatt ctccagcctc agacacccaa gtagctggga 13200
ttataggcat gcgccaccac gcccggctaa ttttgtattt ttagtacaga cggggtttct 13260
ccatgttggt cagcctggtg ttgaactccc gacttaaggt gatccgcttg cttcggcccc 13320
ccaaagtgct gggattacag gcttgagcca ccgcgcccag ctaagattaa tctttttatg 13380
ccctgcagca aacaactagt catgccaaac catttttgtg atttggggaa acatgagcag 13440
atgatgcttt ggatctgatt ataattcaca gtgctcttgt aatttacgtg agatttgcat 13500
acctgcctcc cagcctcaca aaatgccttt aaaaaattac atcttggcca ggatggctca 13560
cgcctgtaat cccggcattt tgggaggcca aggcgggtgg caagagatcg agatcatcct 13620
ggccaacacg gtgaaaaccc gtctctgcta aaaatacaaa aattagctgg gcgtggtggc 13680
gggcgcctgt aatcccagct acttgggaga ctgtggcagg agaatcgctt gaccccggga 13740
ggcggaggtt gcagtgagcc gagatcgcgc cactgcactc cagcctggcg acagaacgag 13800
actccgtctc agaaaaaaaa aaaatcttga tatttgtatg catcttaaaa agcaagagaa 13860
ttcatgattg acttcccaaa ctaaacggtc tgaccagaaa acactcaaga aaactcttgg 13920
ttaatcatgc tccttagtat accattatac ctgcctctcc cctttcccca tcctctgtaa 13980
attctctcaa ccttctctca tttttaattt cataccaaga cctagagcta aaacaacaac 14040
aacaaagctt taagtctcta tatttaggga atgtgcctcc tatcccaaat tgatttttag 14100
agcttttcat ttatttttat caatacaaag caagttgaaa taaaaaaaaa ggcatcaaaa 14160
atttaaatgt ctaaccacgt atatttggta tatgtatact ggtgctatgt attagctgta 14220
agcagactgg tttgaatatt taaaatatga acagaatttg agttcttttt gtattgcatc 14280
taaggatcat ttgagatgga tgtcatcatt tatcatccaa aatagaagcc ttcttgccta 14340
acaaagaatt gtaattagat catcaaagat gaaatttata gtaattgaaa agttagctca 14400
tttgactgct tctttcatag actgtgtttt tgtaattaca ctacctttct aaagatagga 14460
aaaatcagag tctctgaaat gtaatactat aagtgaaata tgtatttttt aaaataaagg 14520
atcttttccc aagagctaaa ccaagcacca aatctgtttt ttgggggttt tttggtttgt 14580
tggtttgttt gtttgtttgt ttttgacaga gtctccctct gtcgcccagg ctggagtgaa 14640
gcggagcgat ctgggctcac cgcaacctcc gcctcctggg ttccagcaat tctctgcctc 14700
aggcttcgga gtagctggga ttacaggcac tcgccaccac gcccggctaa tttttgtatt 14760

```
tttagtagag gcggggtttt accatcttgg tcaggctggt tttgaactcc tgacctggtg  14820
atccactcgc ctcagcctcc caaagtgctg ggattacagg tgtttttctt taagtaatac  14880
ttggtataag agaactttat atctggaata atttaaatat tatctgaccg aatctattat  14940
tcacatatag aaactcaggt tttagccatt taacatctaa agctgttctc atttagagga  15000
aattaccaaa agagtgactt atttaactaa caataaaatc taaggataga tattttttca  15060
ttctgttgca gagcaaaagc agccttctgg atatgaaaag atattacttc tttagtgttt  15120
attacttata atttattgta catttctgat acactgaatt aagatgcgat gagagtaggt  15180
tgtagatttt taaaagttct tatttgcgtg atttatctac ttgctttttt agtgtcggac  15240
tataaatgat gtatttctct caattatcct cggcctaaat agtaaaagct tgggtgaaat  15300
tacttatgag tatacttttc ctgcacagag cagagccatt actgaacact ctcgagcttt  15360
aacaaaaatc atcctatctt atattagaat attaatattt tccctctttc tcggaccttt  15420
gtttcacagt aaatcatata tggatataag ctgcaagtgc tcagaatttg attaaggcta  15480
taagttaatt tctactaaaa aagggattca aatagaactt tcatttggct gtactgtagt  15540
ttcacttgaa ggggcaagca tgcaataaac attgacttat tcaatgcata ggctgtcttc  15600
ataaagatga gactgagtga cagttgtctg tgtattataa aatatcagaa tggtagattg  15660
aatctgatgc ataccaagga gcaatgtgga aattttaggc tgttcgtctt ttttcagtta  15720
ctactaagtg tgtgtatgtg gtgtgtatgt gttttgaact tttcatattt aagctgaatc  15780
ctctttggta gaaatggtta aatagactat agtaaaagtt tctgtctata aatataaaat  15840
gaaaaaatac tgatatcttg cattttccct aatatgttga aagtgcacag aatccttggg  15900
gtcttttgta taaactgttt ttatatggtt cctgtagaag acagctgagg caccaaacac  15960
acacacaaaa caaacagctt gcttggtgat gataacattc gtgcaaggga gttctctctt  16020
gcataggagt cccaggttac cctaatgcct tcccacatgg tcaaacacat ggagctttca  16080
tatttacaca cagctccaga attctgaagc ctgcagttgt ttatcagtgg gatacaggga  16140
gaaagagtgg tgtctatctt actaactgtt taatgacctg gatcatgaat actgatacag  16200
aataagaaag cactggcctg actgcagggg aaacatggta gatgcctaaa ggaggctttt  16260
ccctgcccca cactgtttat tttaaactat cattatcacc tgaaaggagc ttttcacttt  16320
gaacttaaaa tagtagcttt taaccctgac aagcaagtag gcactttagt attcaagaac  16380
tgaaggtgac aagccctgag gagtgttact ctctttcata accaagctga ctcaaactct  16440
tttagaagct agtgtagtaa cttaaccatc tctaataatg ttgctgcatg ccttcataga  16500
aacagttgga gcaagagctg cattttcttt tttttaagtg tttattattt acattttatt  16560
tttgaaaaca tgccattcct attacatata gaaatacttc ccaaaatcac tgtttgtata  16620
gaactatttt gcttaacatt aggattctat tgaagagcct atatctgcaa taatacgggg  16680
agaaaatccc cttttgtgtg atagattaat gataaagaga aagaaaaggt gagaagtaat  16740
tttgggaaat atgcaatgat aaactagtgg tatttattga actaaacacc agcagctgtg  16800
cttagcatgg ataattgcct aaaaggatga gaaaaaaaag taaaaatcag gagactataa  16860
atttttcagt gaagaataaa ttttctgtca caaattatga acattttaaa tatgtatttt  16920
aaactttttc ctacttgtaa caaattatca gactttttaa tctacctttt ttgagctttt  16980
catctttttc cctgaattat agatttaatt ctgtgtatgt atgtgtgtgt ttgaatatat  17040
ttttatattt tagatctaga tttgtaaact agagctgttt ctaactgctt ataagacatt  17100
```

-continued

```
gccacctgga ttgccaccac tttcactcca gtatttcaat aaacacttca tcaaaaacat  17160
agtttatttt caaacataga atcatggatt gctacaagct gaaaggactt tagagactca  17220
gtaaccccat tccttgcatt tacagatgag aaaatggagg catgggaaag taaagtcagt  17280
tgcctcaaat agcgtaacaa gctatgtata tttctaataa tagctactat tgattaagtt  17340
cttatgttgg gttaagtacc atgctaagca ctttccaaag attatctaat tcttatgtca  17400
tctatatttt tgttggtgct attactctcc tcactttact aaggaagaaa ccaagacatg  17460
gggttaaata acttccctat aaattttgaa ttatctttgg catcatctcc ctatttgcaa  17520
atctccattg tctctttgtt cgtaatcaat gtaaatcaac tcttaaacag ttggatgcca  17580
acaagcagtc tggtgtttgg agctcgaaag tttcgagaga gagagagaga gagagagaga  17640
gagagagaga gagagagaga gagtgtgtgt gtgtgtgtgt gtgtgtgtgt gtgtgttcca  17700
gctttgttga ggtataattg acaagtaaac agtccacaaa actgtacaca tttaagagat  17760
acagtgtgat gttttaatat acattgtgaa gtgattatta ctatcaggct aattcacatg  17820
tccatcacct ctcagtcatt ttttgtgttt acggtgagaa cacttaagag ctactcaaat  17880
gtagtcaagg ataccataca gtactaactg tagtcaccat gctgtacatt agatctccag  17940
aatgtattaa atattcatct ggcataactg aaactgtgta tcctttgaca aacctatttc  18000
ccctactacc cagcccatgg caaccaccat gttactctct gcgtttatga gttcgacttc  18060
tttagattcc acatataagt gagatcatgc aataggaaga tctaatttag catcctgact  18120
ttccttttta ttagctgtgt atgtcatatt caggttgcct tagcatttgt gaatctgctt  18180
ctctacctgt aaaatgagaa caactaataa ttcttatctc atggattact gagaggatca  18240
gatgaagtaa cataaataaa acatccagca tgttacttgg caaaattgta gtgattgaat  18300
aaatatttgt ttattcttca agcatgtgtt gagcatctat gtatcaggca agaagagagc  18360
catcatcttt acccttctgg aatatacagg ctcataggaa ataatcaatg ctttgatctt  18420
tttttaaagc ataatgagat gaaaattata ggactcatag actggtcagt tgaggaattt  18480
cccaggatgc ttccagcctc tgctcaaaag gtgtgaattc ccagttgcct gaataggcgc  18540
cagagttggc atagctttct cagtattggg acctgacagg gagattgcac aagtgtaaca  18600
gcacagcctc tgaagattgg ctcaaggggg aagagatgaa ggattacttc catccctttt  18660
attgtttcaa tcaagatata tattatgagc tcatagtacc atcctttcat gatcatcctt  18720
tattgtcttt attagataca atgaaaagat acaaatttgt ccatagaaat attaaatgat  18780
agcaggcatg atttaaaaag tactaaggac tatagatatt actgtttttc ctctattttg  18840
tatcatattt tcaggaagaa gagacaacat tttggcatac cttgcttaaa gatagatgat  18900
agccgggtgt ggtggctcag acctgtaatt ccagcacttt gggaggccga ggcgggcaga  18960
tcacctgagg tcaggagttt gaaaccaacc tggccaacgt agagaaaccc cgtctgtacc  19020
aaaaaataca aaaattagcc aggcgtggtg gtgggcgcct gtaattccag ccactcagga  19080
gactgaggca cgagaatcac ttgaacccag gaggcagagg ttgcagtgag ctgagatcgt  19140
gccattgcac tccagcctgg gtgacagagg gagacttcgt ctcccaaaaa ataaaaataa  19200
aaaataattg tcttggtgtg ctaatcagga gcttcctgtg agagtggaaa ttccttacat  19260
ggcagtgtca tgaaatttta ggcccatgtg aaagatgttt ttgagtgtct caaaatagtt  19320
aacggtttaa aaatacatta tttatgtgtc agaaactgct ttcattgaaa ttgaagtttc  19380
tttgagaact aggatcatat catgtatatc tattgaattt cccacaacaa ttatcacgca  19440
agcaaatgaa tagcagaccc tcaataacac ttactgatga ttattgccat gtataagttg  19500
```

ggatactctt gagtaccttt ctaagtctgc atttagggaa atacagaaca caaaatgaaa 19560
tgtttgattg gttgcttagt ttccacagtg acttttcaaa atgtatagga gcatggtaac 19620
aaaactattt taaatactac aatcttaagt atgcctttat tattcttacc cacaataatg 19680
cattgcttta aaaaattgtt tatcagtgtc agaccatacc tttctgagtc tctactatgt 19740
aagatgtgaa agttaatatt cttcaattcc agctactttt cttttcctgc cttctgtcaa 19800
ctcctgtatt ccatatcatt acttcttatt gctaaattta taatatttat attctggttt 19860
gcatctatag ttaattctct tgtgcttcat ttctcagtgc taattgaaaa agaaaacaca 19920
tcacttacaa tgccatgatt gtaataaata aaattcactg taacacctag cagtatggtt 19980
gaacatgtag aaaaggaaaa agtgatcctg tgacactaaa atttagcttg ttctaaggat 20040
gctactttaa gcattagggt aaaatggatt ccccttttgct aaattctttc agttcctcaa 20100
aattatgcca catttttgtt tctttcacat ttggacttag attttcctgt aagcattcaa 20160
tttttcttga aaattttaat tgcatttttt tattcttgtt gacagaagaa acattttcat 20220
catatcacaa ttttttttca gatttcttaa ttataccatt tgatgaatga aatacacttt 20280
cttcttgaag tctgattttt ctgttctaat ttagagtttc ttctcatttt tctcctggct 20340
atgtctatta ttgctttagt ctcatgtctt tgtatttgat tattattttt ctttttacta 20400
ctgtttttct tcttacagaa aaaaaaagaa aaaaaaacag gggtttttac aaatattgtg 20460
ctgagtcttt acatgtccaa aatgccttat atttttcctt atagtacatt cataaattat 20520
tgtgattaga accataaatt caaagtaatt ttctctcaga gcttgggaaa cattggtacg 20580
ttgttaccct tcatctagga ttgcttatga gatagatatc tgatgccagt ctgattctgt 20640
ctttttttaga taactttttt ccctattcat atgtttatta ggatctttat cttttcactt 20700
ctgaaattcc tccagatatg gctctgttaa aatgtattct tctcagcact tgatgattct 20760
gtacaatctg gaaacaactg cctttattta gcttaaggta cttttcttcc attgtacctt 20820
tgattatttc ttccttcttt ttttcaccct atctttatga aactcatgtt aatggtgcat 20880
tagaacttgt gaactgattt ttcttattta ttaaattcca tcacatattt ttcatctgtt 20940
tatctctgta tattttattt tctcaacttt tgatattttt gttaattgaa atttaatttc 21000
caagaagtcc attttctatt ctctgattga ttctttttaa tggtagccta tttcgtggct 21060
caaatcatat aaaatgtatt aaattttgtg ggaaaattag gcaaacaaag aaaattaaat 21120
tttacctaac tatatctaaa aacaatacaa ctaaacttaa gaaaagtgcg tatatgtgta 21180
cacatataca tatgcgtgta tatgtgtaca catatgctac atatacatgt atatgtagta 21240
tatgtacatg tagtatatgt gtgtatgtat gtatatacac atgtagtata tctatataca 21300
tgtatatgta caaagaaaaa atatgtatat aatagtttca ctgtacttta tttgctcccc 21360
ttttaaaaat aacagtgcta gagttcatga ctgactaatt ttcagaactt ggtgtgtatg 21420
gttgtttatt aagccctcaa taataatgct ttagtattac agtgcccagg catagtcagt 21480
gactgtgcta atagtcctag cagtagcagt tcatcctgta cagatctaag gtgtaactat 21540
tttcatttct gggcccttgg agattctttg gttgtcttca tatcttttac ctatcttgct 21600
gttcaataac aggtaataga aaaggagata aaacttaaat gtcatcattt cccactgctt 21660
aacagtcttt aaaaataaat gtgaaacccg taaggacgta atcttgccta gctttaagga 21720
atgaaggaaa cactagaaac aacagagaga aaaggaataa ctgatcctcc aacatgttct 21780
gttgactcta cctgtaaagt atattcagga tctgactact tcacaccatt tcaccaattt 21840

-continued

```
ccatctccat tcaaaccacc ttcatgtgtt actttgaaaa gtgcagtttc cctgtcatgg  21900
gtttccctgt ttctagcttt gctccccctt cttacctcac cgtgggtttt tacccaaaca  21960
aaaattcaag tgatcattta aaaattaagt caggtcatgc ctctcctctg cttaaaacca  22020
ttaatgggtc tctgtttcac tcagaatata agccaaagcc cttttcatga cccaccagtc  22080
ctcaagtgaa ttggctgcta tttgtgtttc tgattccatt tcttgccact attctccctc  22140
attctattct aatttccttg gtttttcttgc tgtcctggca acaagaagag catccttttt  22200
cctccaggcc tttgcacttg ctgttccctc ttcctggagc acccttcctt cagagagcca  22260
caggtattgt ttctatcttt ccttctaatc tctccttgag tgttactttt tcagagataa  22320
attccctaac cattctatct aacagaactc tgactattga ccttgcttta ttttctctct  22380
ttttttttaa aattttattt ttttattccc ataggttatt ggggaacagg tggtatttgg  22440
ttacatgggt aagttcttta gtggtgattt gtgagatctt ggtgcaccta tcacccgagc  22500
agtatacact tcaccctatt cgtagtcttt tattcctcac ccccttccca cccttttccc  22560
ctgagtccct agagtccatt gtgtcattct tatgcctttg catcctcata gcgtagctcc  22620
cacttatgag tgagaacata tgatgtttgg ttttccatcc ctgagttact tcacttagaa  22680
taatagtctc cagtcttatc caggtcactg caaatgccat taattcattc ctttttatgg  22740
ctgagtagta ttccatctta taaatatacc acagtttctt taactactca ccgattgacg  22800
agcatttggg ttggttccac atttttgcaa ttgcaaattg tgctgctata aatgtgtgtg  22860
caagtatctt tttcatataa tgactttttt cctctgggta gatacccagt agtgggattg  22920
ctggatcaaa tggtagttgt acttttagtt atttaaggaa tctccacact gttttccata  22980
gtggctgtac tagtttacat tcccaccagc agtgtagaag tgttctctgt tcaccatatc  23040
catgccaacg tctactattt tttgattttt tattgccgtt cttgcaggag taaagtattg  23100
cattgtggtt ttgatttgca tttccctgat cattagtgat attgaacatt ttctcatatg  23160
tttgttggtc atttgtatat cttcttttta aaattgtcta ttcatgtcct tagcccactt  23220
tttgatagga ttgtttgttt ttttccttgc taatttgttg gagttccttg tagattctag  23280
atattagtcc tttgccggat gcatagattg tgaagatttt ctcccactct gtgggttgtc  23340
tgtttacgct gctgactgtt cctattgctg tgcagaggct cttttgttta attaagtctc  23400
acctatttat ctttgttttt gttgcatttg cttttgggtt cttggtcatg aagtctttac  23460
ctaagccaat gtctagaagg gtttttctga tgttatcttc tagaattttt atagtttcag  23520
cacgtagatt taagttttttg atccatcttg agttgatttt tatataaggt gagagatgag  23580
gatctagttt cattcttcta tatgtggctt accagctatc ccagcaccat ttgttgaata  23640
gggtgtcctt tacctactaa tttatgtttt tgtttgcttt gtcaaaggtc agttggctgt  23700
aagtatgtgg gtttctttct tggttctcta tccccccatt ggtctctgta cctattttta  23760
taccagtacc atgctgtttt ggtgtctatg gccttctagt ataaagtcag gtaatgtgat  23820
tctgcccaat ttgttctttg tgcttagttt tgctttggct ctgtgggttc tttttttgttt  23880
tcatatgaat tttaaaattg tttttcctaa ttctgtgaag aatgatggtg gtattttgat  23940
gggaattgca tagtttatca acccttggca aagtgtttct gcttttctta aacaattttt  24000
attgtctgct ttctccagta gatgtgagtt ctatgagatg aggaacattg tttgggtcac  24060
tgacatgtat tgtcagcata ccaaacagtg gctagcacat ggtgagcact caataaatat  24120
ttggtgaaag ttgcagtgaa tgaaaatggt ttctaaaatg gcaatgacta tagtcccagc  24180
tactctgaag gctgaggcag gaagattgcc tgagtctcaa aagtttgggg ttgtagtgca  24240
```

ctatgattgt gcctgtgaat agctgctgca ttgtagcctg gtcaacacag tgagaaccca 24300
tctctttaaa aaaatggcaa tgaaataatc ttatttttac tgcttttctc tttaaggctg 24360
ccagtgttgt cttttctctg ctgatttatc ctcattggaa attgaagata gataaaatat 24420
ccattgatta tttataggtg aaattaggct tttggatcca tgaggaatag ctgagacaat 24480
cttccaggag cttctggagc cgaggaaaca ttggtcacta aaataccatt tatattggca 24540
actgtactct tttccgatgc tagtgtttca attacattgt gcatttaaaa ggctgttgcg 24600
gctacctcaa aatataaaca tgatgtgcga cactacttgt tagttttgaa caactgattt 24660
ataaatagac ttagggtgct caagcctcct gcaagatgag cactgcctgt gttcttcctt 24720
ctgcttcctt tatttcagct gtgtgtctac caacttcctc ctccttctac actaggagaa 24780
attgcactgt ttccaatatc tttaacatct gctatcatga tgagaaaata tcttttctgg 24840
atttgaaata ccttcttcat tctttttttt taaatggcgg aaataaattc atagtgtttt 24900
gagtgcagtt ttcttcctgc tgttattgct ggctcaaaat ccaggagcat ttcagtgtta 24960
tttctgagct ccatgatggg agttccattt ctgttttatt caaagtgtta tctccagtgt 25020
ctagcacagt gcctggcaca ttataagcct ataatgttta tctagtggat gtagaccaat 25080
actattaaag aattatcatt gcaaagattt agtggcatga aaaaatgata atgattaatg 25140
ctctactcca tgctaaggaa atgaagtgca aatcgttctt tatttttctt ccaagtatag 25200
agaactttct gaaattaaag aagcattgat taataagttt taatatatgt tattgatcat 25260
aataatatgt aatcatataa ccaaataaga taacacaggc catcttttgt tctttaaaaa 25320
atgacaggaa gattagaata agagaaaaaa ttagaggtca aaacagtttt cttcaaacca 25380
gtagtgtaac ttactgagat atcttctgta atccttaaat tctgtattga tgctaccaag 25440
atgcaactct tgagctacaa ctgcctcttg ataaaggatg ctggtccctg ctgccagtgt 25500
aatgtttgct catttacagt ggaatgtaca atatagtacc tgggatggtg aagaaggtga 25560
agcaacaaat ttaaaatagc tgtgggtaaa cctacagaaa cagactattc tctttcttcc 25620
agattgcatt attcattttc atatgcctgc ctttatctgc tttggaagcc tatttcctaa 25680
tcttccaaga tttatcatca ccttcatatg tccatagcat gcatttctca gacaggtaag 25740
atagaattgg tatatatttg gtatagcaaa aagtcaaggt tgtctttaga ttatatcctt 25800
ggtttttcat gtggtactgg ggagaaagcc tactgtttct tcatctataa aatgaaggac 25860
ctgggcaaga taacattctg tgaaatttca ctgaactttg agctcagcaa agtagggatg 25920
cgtgtgtgtg tgtctatttg caatgcatca cagaccttaa ataaatacag ttgacccttg 25980
aataacatgg aggttaagag caccaacccc ctgcactgtc aaaaatccac atgtaatttt 26040
tgactcccca aaaacttaac tactaatagc ctgctgttgt ctggaggccc tgctgataac 26100
acacacagtt gactaacaca tattttctat gatatgtatt gtgtactata ttcttacaat 26160
aaactaagct agagaaaaga aactgttatt aagaaaatcg taaggtaaag aaaatatatt 26220
tactatttat taaatggaag tagatcatca taaagatctt catcctttgt tgtcttcacc 26280
ttgagtatgc tgaagaagag gaggaaaagg atgggttggt cttgctgttc caggggtggc 26340
agaagtggaa gaaaattcac atataagcag tccatgcagt tcaaacctgt attttaaggt 26400
caacggtatt tgttacattg cattttgtaa gtgaccttgt taattttttt caatgaaaaa 26460
aatagtgttc cattcaaatg cctgtatgtt tatgagaaac atttcagaac tatgaaagtt 26520
gaattcaagg tttcttgcag attgtttgta tactttctgt aatgtttgtc atataatgag 26580

-continued

```
aatactaatg gtcttacaac ttgaaactga ttaactgatt aactctttaa gcaacttaaa  26640
aagaaaatct ttcagtgagg aaagagtatt catcagaagt attctagtag atgacatatt  26700
tttggtaatg aaattgatat gggcaattaa cagcttttc caagttggct atgctgctac  26760
tctcttatta tacaatgata ctatttttca gagcagaaag caaattagtt ttatttttat  26820
aaaccaaatt ttaaatatcc ctttagagaa tagaaaatat gaaaaagtat ttgcttctca  26880
gacctctcaa caatataaat tttcttctta agaggaaatt tattcttgca tgccaacaca  26940
aaggataaaa agtttaccta tccttagttt ctaagaggaa aatgtgcata aaatttccat  27000
ctgctgtgtg ccagttacca aaacgataag ttccaactca atcttggttg ggtgtggtgg  27060
ctcacgcctg tgatcccggc actttgggag gccgaggtgg gcagatcacg agctcaggag  27120
tttgagacca gcctggccaa tatggtgaaa acccgtctct actaaaaata caaaaaaaaa  27180
aaaaaacaaa actagcccgg catggtggtg tgctcccgta gtcccagcta cttgggaggc  27240
tgaggcagga gaatcgattg aacccaggag gtggaggttg cagtgagcca agattgcacc  27300
actgcactcc agcctgggca aaagagggag actctctctc aaacaaacaa aaaagactca  27360
atcttactaa aaaactgcag agaagaatga gtcattttag tcaataaagg aaataaagaa  27420
attctagttt tgaaaatgac ataatttgct acaagaatgc aaaggtgatg acatgaggaa  27480
aaaaggggtt tgctgatttg ttttctctac tactcagcaa atgcaggcca ggaacccatt  27540
tattcaaata tttattacat ggtaaattaa aacatttata aaattaggct catattctta  27600
gaattcctgt taacaaagtg acatataaac aagattataa tctaatggag attaatattg  27660
gttgagaaaa atcttgagac ttctttaaga cttcagttta ataaaatatt gacttaggta  27720
gatatatgtg aggaaatata tattttaccc atgcatgcaa aaatgatgta tgtatttctt  27780
aaaagagtag gtagcaatga cttcaaagga ccatagctgt ccctatcaac atatatatta  27840
acaaaacaat tagaaacatg agcttagtat gctaattata tttctaccca aagcctcaat  27900
ttgttctata gctatactgt tcatatataa gtaaaatttt aggggtatca gagagagtta  27960
gaaaagagca aatacatgta tgaatttgat aagcctatcc cttaatttga tagatcttaa  28020
aagatatttt atcactgcat tcttctaaag aaatgtattt gtacattgca aaacaaccct  28080
ttttgagaag tagactatga tcacagattt tcttgccact agtatttcct aagatttatt  28140
tggaatagaa gatcgatatt tttctgggat gacatatggt taaaaagtaa aaaacaaaac  28200
aaaacaaaaa actctttaaa aacacaacaa gtaaaaagct gaatgaattg gaaaattaac  28260
gaatcttctt agatctgtca gaaaaatgag attatagggc aaaccactgc atcaaatatt  28320
agagaagcag acaggtagat agaaagaatc acaacttagt ggggcaaaaa cctacaagga  28380
aaatttttgt gggaaccggt gccaggtagg aaaacatgaa ctgtaattga aaaattgttc  28440
agtgtgggcg gttgttcagt gtggcaagtc tgagggttaa aaactccagg aggactcact  28500
tacggaaggg cctgtacttt tgtgagttta acctccagga gtgttcacag tgactactgg  28560
agaaaattcc ctaaggggag aagaaaagga accatcttga aatatgtcag agcattttgt  28620
tggactcaag cctgctctca agtgaaacta ttttaccaga gcctaaactt ttgggatttt  28680
ataagagtgt aacctcccaa agggaaggga aatacctaag ttcagccccc ttttagcttt  28740
ccacataggg aaaggaaaat atataactct ggacaactca aaccatcctg tccacgttag  28800
ggggcctagg ggaactgaga aaactggtga agttcatagt ccatgggtac agtttcacca  28860
aagagggaga ccaaattata aggctacaga atgcttccct ttcccacacc ttttactatc  28920
atattactaa aagcctattt gcagcagttt cttttactga gtatatcatg tctgtcattc  28980
```

-continued

```
aaccaaaaaa ttataaggca tgctaaaagg caggaaatgc agtttgaaga cactgaataa  29040
gcatcagaag cagagtcaaa tatggcagtg acattggaat tatcagacca gaaactttat  29100
aaaaaactat ggttaatatg gtgagggatt aaaaaaatga catacaagaa cagatggata  29160
atgtaaatat agagacggaa attttaggaa agaaccaaag agaaatgcca agtatcaagc  29220
atagtgtaca gaaatgatta aaatgtcttt gataggctca taagtagatt gaacatagcc  29280
gaggaaaaaa tctttgaagt taaggatatg ataataggaa cttcaaaact aaaatgcaaa  29340
gagaaaaaag actgtgaaaa aaacagaaga gattattcaa gaactgcagg agaactacaa  29400
aaggtataat gtacgtgcaa tgggcatact agaaaaagaa agaaaggatt agatgcaata  29460
tttgaagaaa tagtgtgtga aaatctcccc caattaatgt cagacaccaa actacttctc  29520
cagagagctc aaagaacacc aagcaggata aatgtcccaa aactactcat gggcatatta  29580
tattcaaact tcagaaaatc aaagattaaa aaaatatcga aagaatccag aaggaaaaaa  29640
cacctataga ggagcaaaaa taataaattt tatctgacat atcctcataa accatacaaa  29700
taagagagta gagtgagaca tttaagatgt tgaaagaaaa atccggcagt gtacgattct  29760
ggaccttgca aaattgtcct tcagaagtta agaaataaag tctgtcttaa agaaacaaaa  29820
atttcaggaa tttgttgcca gtggaccacc cttgcaaaaa atgtttaaag ttctttagag  29880
agaggtaaaa tgatacaggt tagaaactca gatccacata aggaaaataa aattagggat  29940
atagtagtat tccccaactt gataaagaaa atacacaaaa aacctacagt ttacatcata  30000
cttaattttt agaaactcaa agctttcctg ctaagatcaa gaacaagaca aaggtgtctc  30060
ctcttaccac tttgtttcct actggaagtg ctacctaatg caataagaca aaggaaagaa  30120
aatgaaaagc atacagattc cggaggaaga aatcaaactg tctttgttca cggatgacag  30180
ttgtttatat ggaatatcca aaggatcaga aaaaagaaaa ctggaactaa taaatgatta  30240
ttgtaaggtt acagaataca aacttaatat aaagaaagcc aatcactttc ctgtatacca  30300
gcaataaaca agtgtaattt gaattaaaaa cacattacca tttacattag caccccaaga  30360
aatgaaatac ttttgtataa atctaacaga atatgtacat gatctatatg aagaaaacta  30420
caaaagtgta atgaaaaata ccagtgaact aaataatgaa gagatgttac atgttcattg  30480
tcaagatgtc agttcttccc aacttgatct atagattcag tgcaatgcca ttaaaaaaca  30540
cagcacgata ttttatggat atcaacaaaa ggattctaaa gtttatatgg agaggcaaaa  30600
gagcagaata gccaactcag tatttgagga gaacaacaaa gtcagaggac tgacactacc  30660
tggctttaaa gcttactata aagctcagat aatcaatgta gtgggtactg gtgaaagaat  30720
attcaaatag accaatggaa tagaataaag agcccaaaca aacccatgta aatataatca  30780
aatgatcttt gacaagggag caaaggcaat acaatggagc aaagatggtc ttttcaacaa  30840
ataatgctgg aaaaactaca cattaacata caacaacaaa aattttttaa atccaaattg  30900
agtgtaaaca cagatcttat accctttgca aaaattaact tgaatcatag acctaaatgt  30960
aaaatgcaga actataaaac tcccagaaga taacacagga aaaatcctag atgactttgg  31020
tatggcagtg gcattttttta gatacagctc caaaggcacg atacatgaag gaaatgattg  31080
acaagctgga cttaactaaa atttaaaact tctgctctgt gaaagacaat attaagagaa  31140
tgagaagaca agccacagat ggaaaaatta tttgcaaaag atacttctca taaaggacta  31200
ttgttcacaa tgtgcaaaca actcttacaa ctcaacagtt tgaaaatgaa caactcaact  31260
taaaaaatga gcaaaaaacc tgaacagaca actcaccaaa gaagatacac aagtgtcaag  31320
```

-continued

```
aaagcatagg aaaagatgtt aaacatcata gtcattaggg tattgaaaat taaaacaaca  31380
atgagatacc gctacatacc tgttagaatg gctgaagtca gaacactgat gaaaccaagt  31440
gctggtgaga atgtggagca acaggaacct tcattcattg ctggtaagaa ttcaaaatgg  31500
catagtcact ttggaagaca gtttggcagt ttcttacaaa ataaacatac tcttcccata  31560
tgattcagca atagcgctcc ttggtatgga cttgaaaact tatgtcctgg ccgggcacag  31620
tagctcacgc ctgtaattgc agcactttgg gaggcccagg caggtggatc atttgaggtc  31680
aggagttcaa gaccagcctg gtgaaatccc atggtgaaac cccagctcta ctaaagatac  31740
aaaaaagtag ctgggtgtgg cagtgtgcgc ctgtaatctc agctactagg gaggctgagg  31800
caggagaatc acttgagccc aggaggcgga ggttgcagtg agctgagatc atgccattgc  31860
actccagcct gagtgacaga gcaaaactcc atctcaaaaa aaaaagcaaa aacaaaaaca  31920
aacaaacaaa acttatctcc acataaaaac ctgcacacat tgtttaacag ctttacataa  31980
ttgccaaaac ttgggtgcaa tcaagatatc ctttaatatt tgagtggata aactgtggta  32040
catccagatg taagaatatt attcagcact aagaaatgag ctatcacatc ataaaacgac  32100
atggatgaaa cttaaatgca tattataaag tgaaagaagc taatccgaaa aggctaaata  32160
ctgtatgatt ccaactatat gacattccgg aaaagccaaa attatggaga cagtaaaaag  32220
agcagtgttt tccagaggga ggaatgtata ggcaaatttt tagtgcagtg aaatgaatct  32280
atgtaatact atagtggtgg atccatgtca ttatacattt gtccaaacac gtaggatgta  32340
accaccaata gtgaacccta atgtaaacta tggggtttgg gtatcaaaat gcatcaatgt  32400
aggtttatca gttgtaacaa atataccact ctggtatggg atgttgataa tggggaaggt  32460
tgtgggtctg tggggacagg ggtatatggg aactttctac tgttttactg tgaatcaatt  32520
ttactgtaaa gtttattaat gttaaaaaat ttaatgcaca tgtaccctaa aacttaaagt  32580
ataataataa taaaataaat ttaggcaatc tgaaaaaatg ttaataaaaa agaaaataaa  32640
ctagttgaat gtatcagttc attttcatac tgctataaag tactgcctga gactgagtaa  32700
tttataaagg aaagagattt aattgactca cagtttagca tggctgggga ggtctcagga  32760
aacttaacag tcatggcagg tgacttcaca aagtggcagg aaggagaaat gaacgcagaa  32820
gcaactacca aacacttata aaaccatcag atctcatgag aactcactcc ctatgatgag  32880
aacagcatgg gggcaactgc ccccatgatc caattacttc cacctggtct ctgccttgac  32940
acatgggtat tatggagatt atggggatta taattcaaga tgagatttgg gtggggacac  33000
aaagcctaac catatcagtg ataaaactat gtcttttctt ttatggggtg ctatagtgtt  33060
tcatttcaag ttgtcttttt gacctccatt ttccaatttc tggttaggaa aaataacttt  33120
gtctcctcct taattgaccc acaaccttgt ttgcaatgaa gaatcaacac aaatctttca  33180
ttaaaagaaa taggggaggt gatgggggat atccatgagt gtccatgggc ataattcagt  33240
tgccttcatt caatgccaat gatactgcaa agcctacaag gcaaattcat gtacctacag  33300
acagactcca tcctttttct caaactattc aagataaaaa atcttgtttc attttatgtg  33360
aggatttttt tcaccatcta tcctcaaaaa atgaaaaata tcctcttcat ttgggaaatg  33420
agtgcttata atagaaagta atttgtagtc agctgttaca cttagatgat ttgtgtcacc  33480
tctgacctgc tttctgataa tgcatgactt cattcatggc tctctaggtg acctgtgtac  33540
cctgacctgg cataaaccac tagagtatta agtcatttca gtggcacatg tttgagggaa  33600
gattgacatc ccactggaag actatctaca gtgagatcct ctaaagcagc tgcattccta  33660
gtgaggcatg attaagttta tcccactatt aggttctgga gtattacttg tcatgcccaa  33720
```

gaggaaagtt tttctagcat gcagagtatc tggtttttaa tggctactga gctgaaataa 33780
aatgtgccta ctaagggttg ttcatttgtc tgtctccctt ctttcactgt tttttttctt 33840
ggaggttaca gtagttatgc ctttctggtc agctggctgt tgacctatca tagaaatgac 33900
actttcacat cttcaagtgt aaggaattag atgttccagc cttcactttg tttctcatcc 33960
aaaatcaatg acaaaacttt cagtattgat ttctcatggc ctatgaacct gagtcaactt 34020
ggcataaagg acttttcaga caagcttctc taaatgcaga gtcagtggct tctttttgcc 34080
aaactccact ttgctcagtg ataacattaa aatggtgatt tgattcattc ctagtctaaa 34140
aatacttcct catattccaa aatctcagtc attaatacat ggaggaaaat acaaattatt 34200
acatgcctgt gcttctcggc tgttgtagat agataaaata tatacaattg tgttctataa 34260
ttattgagtt cttttaagtt ttatcttttt ttgttttacc aggaagcaaa attatgttta 34320
tttcagagct tatttactgc atttagaatc tcatgacact taaaaaacct ttctaaaacg 34380
taaatattct ccatgatctc catggtcaca aacagtattt cacgttctaa ttgatattgc 34440
cattttatca tttttttttt tttcttggag acagtctcac tctgttgccc aggctgggat 34500
gcagaagcac gatcttgcct cactgcaacc tccacctcct gagttcaagc gattctcctg 34560
cctcagcctg ccgggtagct agaattacag gcatgtgcca ccacacctgg ctaattctgt 34620
atttttagta gagacagggt ttcacgatgt tggccagact ggtcttgaac tcctgacctc 34680
aggtgatcca cccaccgcag cctcccaaag tgctggaatt acaggcgtga ggcactgcat 34740
ctggcccttt tatctttctt ttaactcaaa tcctcaaata tatccctcca tgtgaagttg 34800
ccttccctaa ttatgtactg tcctagttta atcttcattc cttgtttgcc tctataaaac 34860
caagtttaaa aatagtctct gattctgtaa atcatcactc ttatgctcat ttatatttct 34920
atctagaata ttttaaatcc tttgtaacaa agtttctact atgcagtcta cctttctcag 34980
ctacgatcta tatactcctt ggccatgtct tttgttattg tgtgtgtttg tctttgtgtg 35040
tgtctgtata gtagtggttt gtaaattctc catttagtca caatatgctt tttgaggatt 35100
ttccttttcc tgggaatttc ttgatgattt ttattttgtc atgtgatgaa gaatgtatgt 35160
caaagcacca ctgcagaaat agtgcttttc tatttacttg cactcttcca tcttagaaga 35220
gctggtgata gacaaccgac tcttctttta tcttggtttc tacaacacag aggttgctaa 35280
gcgactttaa tcccttttaa cacaggacaa tcaacaacaa attccttctt tctttagatt 35340
cagatatttc acttagaaaa tctagcaaat aaaaaatggt ttaaaacttc tttaaaatgt 35400
gtaattctgt acaatctcct acatctgtaa cccctgcccc aaatattttt tacttatgct 35460
atttcttgag cattatgata tgcttattca taggcaatca acttgtaagt agcaatagtg 35520
tagccccttc taggaaatcg aagatgtgaa aatccagttt aatgtgataa tgagttactt 35580
tgatgaaaaa tactatgtca caatttgtta taaaaatact catttggatt tctgattcac 35640
ttatattacc ctccaacctt aagtatgatt gaatttatag ctttttatac tactttcttt 35700
atttagggag gagtgtattt aaattctgtt atctcggtta ttacttgaaa gttcaacctc 35760
atactttcat ttttatataa ttttaatatt atgaaaatat tttatgtaat tttatgtata 35820
attcgaaaac atttttaaat attgcatctt taaattttta tttcttttat caaattttcc 35880
ctatcatttg ttctctggct acaaccaaag ttaatagtta cattttttttc cagtgacaaa 35940
tggtaatttg caaagacttg taacagttgc ttaatacttt tttatccctt atttaagaat 36000
catgcaaaca accagagctg ataggcagca ggtgcacatg agtgtggctg tgctgatggt 36060

```
tactgaaaga tttccaaggt agctagtaat tctgctaccc taagccacta tagctccttc  36120
cccattactc cctgggtcta cccaccatcc tgcagctaga ataataaatg gcatgtaggt  36180
tcctctagga tcctcctcca gcactatgtc tcatgcctgg acatatgagc tgttaaatat  36240
tttgattatc actcctgtgt ggtaagggag acgtctactt gtcgtaactt gatgtttact  36300
aaactacttt taagattacc ttatgataaa agtagacact tgcaattttg cagaatgcat  36360
agtttgtttt taacaaacca ggtaaacata actgcagagt tttcctatac gttttgaaat  36420
ctttaaaaaa gtatttttta tttgcctttc tattagaaat agattagata aaaatttcct  36480
tgtttcaatt tttagaatga acattagaga atattgttac tgaaggaatt tttttaaaaa  36540
tagtgactga tcaaatgtca gcagctttat actatagtgt aaaattttat tttgtagttt  36600
gccatcccat taagcattag aatttttata attgatcctt tgatgtttat attcatgata  36660
ttaatgtaat gtctttaaac cttagctcat ataggtcata tgacttaaag catccttaga  36720
tgaagatatt tgggctataa ataatttatg acataagtga tttaaaaatt cattctttcc  36780
atccattttg aagaaattgt aaggtagggt tcatgtatac ctaatactta tccccccaaa  36840
atacgaaaaa taaaatcatt tttaaaatat ctgggttaat gctatagatt ggaagcagtt  36900
tttaaaaagc acttaaagtc taccagttta ttgatcctca atctgtggct gttttaaatg  36960
gatgcaatta gcagttcagt ctaagagaac catggtagta gactcattac tccccagaaa  37020
ccattacatc attttgtaat attaaattac taaatataag gaatagaata tatattgtaa  37080
aaattgcttt ggaatcaata ataagtattg tggctatcaa ttatagttat atattacaat  37140
gtaagggata tccttttata aacttaatat cacacaagta gacttagaat aattccatta  37200
atataatttt gcttgtgttt ttatacctat tcatttcaat aactcttttt cctatatata  37260
ttttttatct caaattcgat agtatctaaa tcatggaatc ataaaacctt aaagctgggt  37320
tggaacagaa ataatacaat ttaacatctt ataggctctc tagtcctcag tttccctaag  37380
tgatcggctc aagatcatga atttatggag gattagagtc agaattagaa cccaagatta  37440
atttatactt tgttatctct tctacagcct accccttag tttgcctgtg ggtttatgga  37500
agttacagga gagacattct gagattcagc taaaaaccta gctcccaata gaattattgc  37560
cctgtagtca gccgcgcaaa tacaatcaca aatacctgaa gttccttgtg tgaagaaaaa  37620
gaaaatgact attaaagcat caaaatcaat gcaagttacc tttctttgcc cctttcttcc  37680
cctttcactc ctttcttctc ctatactact tgaaatttct agcggggatc tctaaaatgc  37740
ctggatgtta ggaatggtaa gtctattgta gagaattata ttttctattt tagtggatga  37800
aaaataaacc atacccttaa gaggcttttc aaagttaaga ttttgagcac atccttcatt  37860
ggcccagtct ctgaccagtg aggtcaagta ttagccagtg tcagaatgtc gtgaaaagtt  37920
tgtgtttcag atgcagaatt ttttttgca ttttctgtgt gatgtttata gggtattttc  37980
ttctgaaatg ttttccatct tggtttttaa aaatatctat tattttaaaa aatattccct  38040
cataacttct ttttatttc ggaaactata taaattgatc tgataatcta tacacaatgc  38100
cttgtgaatt tatacctgta cctctcatgt tccagtgttt ggttcttaaa taatcacttt  38160
gtataatgga aatactatgt taaattgttt ataactggtg gttgatattt cagccttgtt  38220
tggctatcgt agttatataa agactgttaa ttagaaacaa cctcatatgg tgtatgcttg  38280
tttttatctt catggaattt gttctgcaaa cactgagttc tttactggga gtcaccactt  38340
tgtctatgtt aggaggagca ggaagtgaat acatttaagg tctttaattt tcttcttaaa  38400
actttgacta ctgtagtggt tttttaaagc attaacagga gaatagccat cactgccaag  38460
```

tagctgacat tctgaaatag cacttccctt taggcactgt acagttggaa tcatttactt 38520
gcagagaggt gtgtgtgtgt gtgtgtgtat ttatgtgtgt actcatgtgt ataagaatag 38580
gagaaacact ttgtgggcat atcctgctga ggtgagtaac gtgctgatta gtgaactcca 38640
gtctcatccc atttaaacct ggaggagaac cacatcaagc acagaagcag ccaaagcagc 38700
atttcaacag gaaggaaaca tctattactg gggctttgaa gaaacatgcc atgaaggtgt 38760
actaatatca caaagggaag ggaaggacta aattcagcat gataaacaaa gtcccttttt 38820
tgtaacggaa gtgtttgatg atgtttgatc aatggtggat ctatctcttg aaaggaaaat 38880
gcatttaaac cccaaatgga ggattcttat ataaggtgcc tagcttgtaa tgatatattc 38940
atgtttatag gtagagtgac tggtttttag agaagaggtt ttttttttc cttcattttt 39000 gaacgaaaac ttgtctgtct ctaggctttg aaatgtagaa ttatttacct ttccccaaaa 39060
tgaaatgttt cactgaatct cctacaagct tgtggaggcc atgaagcatg ttgaataaga 39120
gcacaggctc tggaggccct gccacccaca aagggtgtgc taaggtaaac aactgatagt 39180
attttgaaaa ttagatgact tagaatccat tcaataaatt ttagctattt ttattgtctt 39240 tttttctaa atctatttgg aaaatattgc agataaagta gataatacct ttctaaaaca 39300
cagtgagacc aggcgcagtg gctcatgcct gtaatcccag cactttcgga ggccgaggta 39360
tgcggatcac gaggtcagga gatcgagacc atcctggcta acacggtgaa atcccgtctc 39420
tactaaaaat acaaaaatta gccaggcgtg gggcatgcg cctgtaatcc cagctactca 39480
ggaggctgag gcaggagaat ggcgtgaacc ggggaggcgg agcttgcagt gagccaagat 39540
cgcaccactg cactccagcc tggctacag agcaagactc tgtctctaaa aaataaaaaa 39600
taaaaataga acagtgaata gtttataaag ataaaataga ataggcttca atttagggaa 39660
caaaggaaaa tatgtttagg aatgatatta tgctcaaaat gattgcaact ttgatggtga 39720
agtgtatttt attcaattaa aaatgtagat atggctgggc gtggtggctc acacctgtaa 39780
tcccagcact ttggaaggtt gacgcaggtg gatcacttga ggttaggagt ttgagacctg 39840
cctgggcaac atagtgagac ctcatctcta caaaaaataa acaaaaaatg tgctgggtgt 39900
ggtggtacat gcctgtagtc ctagccactt gggagactga gatggaagga tagcttgagt 39960
ctgggaggtc agtgctgcag tgagccgaga tcgtgccact gcacttgagc ctgggtgaca 40020
gagcaagacc ctgtctcaag aaaacaaaca aaaaaacaaa aacaacagta gatatgtgtg 40080
tgggaatgag aacatttaaa tgtgctcatc ggcttagatt tttctttaac cccctcatg 40140 gcccttatct taacctctgt cttcagcact acccttcata tgtttgttcc gttttatctt 40200
ctaagtgatt tttttataac tctcaatgta tcatggcaga aggaaaactc agtgtataag 40260
ctgactgtat tttgcatttt cttttttttt tttttttttt tgagatggag tctcactctg 40320
tcacccaggc tggagtgcag tggtgcgatc tcagcttatt gcaacctccg cctcctggag 40380
gcgattctcc cgcctcagcc tccccagtag ctgggactac aggcttgcac caccatgcct 40440
ggataatttt tatattttta gtagagacgg ggtttcatca tgttgtctag gcaggtctca 40500
aactcctgac ctcaagtgat ccacccacct tggcctccca aagtgctggg attgcaggca 40560
tgagccaccg cggcctggct tcatgatcca aaatagcatc attaagcttc tctttcaaaa 40620
catgtatata agcctgtgag tcatcactgt atttatcaga atattatcat attggagact 40680
ttgcaaagct gaacaaagcc agaattattg gctactgagg aactatattc tagcaagaga 40740
ctattctatt tgttggggat cacctctttt tactaaaggg gactgttttg ggcatataaa 40800

-continued

```
actagaattc atggtttctc cttgatagtt tgccagcttg attcccagtc aaccagataa  40860
ctgctggtag tgacactcat gtcctccagg actcccaatc ttgtgccagc tcagagaggg  40920
aaatccccct agaactgctc acaccattcc aagaaccaca agcaccacct tggtatagtt  40980
aaaaatgtga taccaactca aattctgata aaaacaagtt ctataaagct taataaagtt  41040
atatttttta ctttttaagt tttgttttac tattttaaac agaaaacaga aggtaaaaac  41100
tcctctgcct tcctcagtat ttggtttgtc agttgctgaa ctcagattta agagtctaat  41160
catatacagg caataaccct cttctaatct taataatgtt tctttgatca tttctttaaa  41220
aagaaaaatg aaatagccta ttgactccaa ccctgacctc ctgtacttca cctgcctgat  41280
gaatatttat ttggaataca taagtttttt caaatgcatc atgtcaagaa tttgtcattt  41340
cagattcctt tctagaatta tctatttatc tcattagtag catcattctt tcagacaacc  41400
aaactcaaaa gctttatcac tataattgaa tttctttttt cttcttacat ttaaaatgtt  41460
actaaatgcc attcatttct ttatcagtaa tatttctgtt tgatcatttt atttcattta  41520
ttctgccacc ctctcattcc aactattgct tatacttgag tactgcaata agccaatatc  41580
ttgcatatga ttatttataa cacctaaatc ttctaccact tcacactcac tgggatggat  41640
ataattttta aaacatacaa taacaggtgt tagtgcggat atggaaaaat tggaaccctg  41700
acacattgct agtggaatgt aaaaaggtgc agccactttg caaaacagtt tggcagttca  41760
tcaaaagatt aagcatggaa ctaccataag acccagtagt ttcgctctta gggattccac  41820
tctcaagaga attgaaaaca tatgcccata caaaaactta taaacattgt atatccatgt  41880
ttgttgcagc attattcaca atagcctaaa ggtagaagca acccaaatgc ctacagatgg  41940
atgaatggat aaacagaatg tggtatagac atacaatgga ctattattca accttaaaga  42000
ggaagaaaat tctgacacat gctagaaaat aaatggatct tgtatacatt ctactaagtg  42060
gaataagcca atcacacaaa gaaaaatatt atgattccac ttacatgagg tacttagaat  42120
agtcaaatta atagaggcat acagtagaat aatgattgcc aggggctggg aggaggagca  42180
aatgggaagt tattgtttaa tgagtataga atttctgttt aggaagatga aaaagttctg  42240
gagatgggtg gcagtgatgg ttgcacagca atgtgaatgt acttaatgcc acagaatagt  42300
atacttaaat atggtttgaa tggcaaactt tgttacatac attttatcac aattaaaaag  42360
tttgaaatga atatccaaag aagcattatt tatgaggcta aaagtggaag taacccaaaa  42420
gttcatcatt gatagctaaa ggaaacatgg catatcaaaa cagtagaata ttagtcatac  42480
aaaggaataa agtacagaca catgctgcaa tacagatgca ccttaaaaac attacactaa  42540
gtgaaagaaa ccagacgtaa aaggccaaat tttgtatggt tttatatata taaagtcgtt  42600
caaaatagga aaacccataa agactgaaag ttgattagtg gtcaccaagg cccgggggag  42660
gaatgaatga aaactggctc ctaatgggta ctgggttttt tggggcgagg gggacagagt  42720
gatgaaaata ttgtagaatt tgatagtaat gataggtgag agtggcataa ttttttttaa  42780
tatactaaaa cccactgact catatacttt acaaggatgt attttatggt atgtgaatta  42840
tatctcaaaa caccccttaa attttaacgt atggctttta tgatgccatg tttctaaaga  42900
agcaacgtgt cccagtctca gcttactatt tctaggcatg tgactttgag aaaaaattaa  42960
gagacctccc ttcttactct gtaaaatggg aataataata atgatgataa tgataataat  43020
aatgatctta ccagattttt ttgagtgtta aatgaggtaa catatgtagt gcatctagca  43080
tagtgtctgg catttaccaa gaaccccggg aacctgagct tcaactgctt ctgatactat  43140
tccagatact atttcaggat attccaatac tgtttccata tattcaggac aatggaccaa  43200
```

ctcctttagc cattttatca aaactcttta gattctgttt caaatcggtc tttccaaagt 43260
cttcttgtgc tcctttgtag acactcttca gtcagagaga gctttttaat ctcctccaat 43320
ttgctgcagc tgtatctgtg cctcaaaaca acgctttctc cccattcctc ttttctctct 43380
gcccttggaa ctctgtggac ttctctcatg tttttaacct actccctttt atcagtgcat 43440
gtcatctcca cttatttgta gcacccaata tttttactac atctttgacc aattaagtct 43500
tacttgggtt atgtttttaa agtaggtatc ttattaggtg gtccttttaa agtatatgtc 43560
cagtctctcc agctaaatta aaacccttga gcacagagac cacatgttat aatgttttac 43620
cttttccata gcacttagca tgttaccttg acatggcata tactgaatga atgcttgcta 43680
tttatgagtt tagttagtgc cacatctcat gaagtacagg gacttaatga ttctcaatcc 43740
tgacttcatc ttacagtcac ctggagaata aagtttcctc ttagctcaac aagtcagaat 43800
ctctgagcaa aatcctcaac ttcttaccta ggtgatactc ttgtaagcca cactgtgaac 43860
cactggattc aacagatgaa gtaatataag ccactggctc ttaagcctca ttgattattg 43920
cggtgaagat gtgaagacta aagatgcttt gggcatggca aagtgttcta cagatattag 43980
aattgttatt atggtacatt tgagagtgtc attgctttga gaaagattct ctaagttttt 44040
taacagccac actgtaatgg aaatatccaa ttataggtat ccaaaacctt ttaaactctt 44100
tatatcaggt gtatataccc tgttcctttt tgctaactta aaaatgttca aactctgtct 44160
tctctaggct ggcaaacatt cagcagcaca ccctctcaag attgtttact tgcctttgct 44220
cctgttgagt tacaacgctt ggaagcagga gatgggctca gcagcagcca ataggacatg 44280
atccaggaag agcagtaagg gactgagctg ctggtaagac agtggagaca gttgacactt 44340
gtttgtcaag tatgaattta ttcctaatgt aatggtaatc tctctcccaa acttcaactt 44400
caagttaccc tgcaccctct caaatacttt tctttattgt ctatgcttag gacacatgga 44460
ttagattgtt aagatttgtg aatttactaa agttgtgtac tgacttatgt atagctgtat 44520
ttttctggag aaagatagat ttttatcaat tctcaatgtc tatggagttt ttaaaaagag 44580
gtaaggatta ttcaaatgta actataaaca taagaaaatg tgatatctat aaccagttgt 44640
tagagtattt atcgcctcca ttttgcttca cttgtagcca cttcgtctca atcttgttaa 44700
ggaccaaata aatggtattt gtggttactt gctgatctga aaagtgagta cctcctgcac 44760
ctggctagtc agtcttgtga caatttggtg ccatagaact agcagagaac taaattatgg 44820
aatggcagat ctcaggagca gctatgtgat tttacatacg gtttgttttt aatggataga 44880
gacagagtct ggctatgttg cccaggctgc tctgaaactc ctgggttcaa gccatcatcc 44940
tgccttagcc tcttaaggag ctgggattac aggtgcatgc ccccaggccc agttcatatg 45000
attttctgaa aatacaaaag aaagagggag atacaaaata ctttttttaat catgttctta 45060
taattatctt aataaaaatc aatttgctct gaatgccatg acctgctgag tgtcccaacc 45120
taagggttgt cagaccattt tctcatatat gcatgtatag aagtagggaa ctaatatatt 45180
tttgtctaaa atgtttaaga tgaagatgag aatgaattct acaatatata attttgcctg 45240
aactatataa gacagttaaa attatagaga cattgcagga gagactctgg attagataga 45300
aaaaaggaag aattaggctt tttttttgtc tataatcctt ttagtaggta attcagcttc 45360
agtttcacta aatcttgttt atgcattcag cataacaaat cttctaataa gcctgtatag 45420
ctctaatctc tgccttactg cagacacctg aggatataag tatccactct gccacttgat 45480
acttctcaga gactgttctg gtgctgagaa atcctttcca gtgtgtcctc agttgaactc 45540

-continued

```
ccatgattcc tggatgttgc cattttcaag acacagggca agcgcatctg tctagattac  45600
ctctctacct tgggaatttt aagtcactct gtgagggaaa gagaactcag tatagtagta  45660
actctcagaa tgaaaatttt cccttgcat gttaatattt ttagagtaat cattgtcact  45720
gaaaatagac ttcctctttc ccctctcatg ctggaaaatc ttaggtaatt atgaataaag  45780
cattctttac ttttcccctc ctcccttgat gattgcttta cctcactctg tgagaactgt  45840
gactactcat tctgctcttg tcttttacat gagaactgag agcgcatttt taagatggaa  45900
ttttcctcct taatgaagtc ataacattag tcagaagatt ttctcttctt gaacgttaag  45960
cctgggtaag gaataaagtg cagaagttta tggaaaatta taagataact taaaaaaaaa  46020
acgaagacaa caaattaaaa tattagccat tgagggaaaa ggttttacag gtagctctct  46080
gaggagttct tccctcatat ctcctcaaaa atcttgtttt gcatttaatt ttttacagtt  46140
ggataagctc agcccttgac atattttcaa tagcaaataa gcctagagtt tatttttagt  46200
acatttatta ggaatgtgtt cttgggaaaa ttatttaacc tctgtaagcc ctgctttaaa  46260
tggcaaagaa gaaagtaggt aataatagat aataacagga ttattttatg cattacctgt  46320
acattgccca acatatagta agttctcaat tttatattgg tatttgtttt attattaacc  46380
acttttatta atgttgcttt tagtttttga aatatgaatt cattcaaaaa tatttcttga  46440
gcacctgcca aataccaggc actcttctag gaactagagt ggcattaatg agtaagaggc  46500
aaaaatctct tcccttgttg agcttagaat ccattagagt aagagacaga cacatacaaa  46560
ataaaatgta taatatagta aataccaaga agtgctaagt tttaaaaatg taaagcagaa  46620
aaaggaaatt gagtggcagg gttaggtagt aattgaagat atagtagtca agtaaggcag  46680
cttcaagaga agattatgtc ttaaataaaa atctgataaa gatataaaaa caagccatga  46740
agttatctga aggaattgca ggtagtggag aacagccaaa agacctggag tagtaaaagg  46800
ttttatgcag agtgatttaa aaagaatcac agtatcttat acatcagtaa atatttacac  46860
atacacttaa gtaagtgata tggacaagaa ctttggaagt tgaatagcaa ggtccatctg  46920
gactataaca gaggaggctt cacaaaggaa ggtgacaggg catggcctgg atcctgaagg  46980
acaggaagaa ttgggatcga taacaaagaa tgacatccca gtggagagaa gtggagggga  47040
aacagcatga aatggagtga aataagaatg ttggccttta gggcaggaat gggccaggca  47100
gagggcaagt gggaagcagg aaaaaggcga ccttgtataa agttcatgtt ggcaaataga  47160
gagaagatgg gaaagcaggg taaggccaaa tttagtaaaa tcctaaagtc aagctaaaga  47220
ttattgcatg ctatcctgaa aatattgggg aataattaga gcagatgagt agaaaggtga  47280
attcttgtat ttagctatat cattattttt acaaatttaa acaaataagg aaatggaggc  47340
agtagttgga gtaatttagg agataaattg aaaatggatt ttgttaagag agaagggaag  47400
atagatttta tatattttaa ggaaaaatca tgaggattta tttgctgact gcacgtaaga  47460
gataaaagag aggagtcaaa gatttctcta aaattttcaa aatgattaat tacgtgttgg  47520
tattaaaaga aatagggaag ttgggacata tgagtttgaa ttcagcatga gtcagttaag  47580
acaatcagat gcagatattc ttaaggcaac taaagttcat ttgatatttg tcatataggc  47640
tgaattaagt ttctaagagc tgtttttact atgcattaaa tccgtgtaat actaacatag  47700
tacaaaagtt gtttgctatc caaattttgt atttttataa taagttggag agacagagaa  47760
tcaaaaaatt attgatttgg aaccattaga catcagctag tccaattagt tcattttgtg  47820
gaaggaaaaa ggatacccag agatgttaca tgactttata gccatgcctc tagctagtat  47880
ctaacttggt ctagcccagg tctccatact gagactctcc tcctgctaat aaaaaaataa  47940
```

-continued

```
taaaaaagta ttagtggttt gtattttgct ggcttgcttg tggagaatag gattagaagg  48000
tttgacttgc ctgttagcac tctcttgtag ccatttttct aattaacata cacattttac  48060
cctttctcat gaaacagatc taacttgttt agaagcttca gtcttcttga tttaattaat  48120
cactttctcc cacctttagt cattgttgaa gtttcctgat ttacaatgtt atctttttat  48180
cttttcagta gtataaggag gaatgatatt tctactgttg tactattttt ctgtttatct  48240
ttcagaagaa aaatagcttt tcttattggc ccaaaaaacc atcaccctac aggaaataaa  48300
tcacactctt tgcttgattt tcctgatctg gctactgatt tctcttcaaa tttaagccaa  48360
tacttagact ttaagacttc attgttactt ccttacaggt cattcttatg aactaaaatc  48420
catagtcatt gttctagcaa gcctgagcag tttattcttt gagtcacagg attataaaag  48480
aaaaaataga ccttagagat cataatacag tgctcttcaa actgtactct tcaatttttc  48540
tactacttat cagttgtttt ttattctaat aaaatataat tacctagcaa gtgagcagac  48600
atgtatttac agtagcttta caattcttta tacacttctt tactctctcc attacacatg  48660
ccacatggta tgatacaagt cataactcaa ctatgtgaaa gcaaaaccac tcttatacat  48720
ggtgtcttgc atatatatta aggcccagag tggtatcagt agtctctgtg tcccaagaga  48780
ctgaattaaa caagactgtt gaccttcttg tggcatttat ctgacaacct tggcaatccc  48840
taaattcaca aatagctgta tagcattttt tgcatttaat gcatatccac atatgatgtg  48900
tcctttgatt ttagaacaag taaagcatgc taaaatagac tgcaccttat gaaagtcatt  48960
ttcactattc ttgtgtttca gtttcctcat caaaaggtga aatatcagct gcctctgttg  49020
atctcaggat cttttaagta gaaatggaag agtcttagtg aaaacagttt gtattctgaa  49080
agaaaattgc aatgtaaata caggcactaa aaacgtttat tcatctttac agatgttaat  49140
ctgaccagac atttttctca aaatgtgaaa atagtatgga ttttcttagc tcatttaata  49200
ttgaaagact agaaaaacaa gtaatgatgt tctagaagaa tctatgatca tataattaca  49260
gttgtccttc agtatctgtg ggagattggt tccaggaccc cccatggata tcaaaatctg  49320
tggatcctca agtctcttat ataaaatagt gcagtatttg cacatgattt acatataccc  49380
tcccatatac ttcgaatcat ctctcgatta tttataatac tacaatgtcc atgctatgta  49440
agtagttatt acactgtatt gtttagggaa tagtgacaag aaaattaatc tgtacatgtt  49500
cattacaaac acagcaatcc atttttttc tgagtatttt gatctgtgat tgattgaatc  49560
cacagatgct ggaatccatg aatacccatg gggggctgac tataatgttg tctatgtgcg  49620
tagcaatttt gtaattctca accaaggaca cgtatagtcc ttgaatcttg gtaggagtct  49680
tggggacttt tcttaaaata ttttgaccat cttctcaaga tcttgactcc tacccccact  49740
tgtacacgtg cacatacttg tgcacactca cacacaatac ccttccttaa gtcctgctca  49800
ccagcttgct tcctattgca ttgagagcat tcaacctgta gaccaagaac ttctaccata  49860
tttttccacc tctaccccaa aacacagttt agacatatcc attcttttca ttcttcagag  49920
tcatctcacc acttccataa attatttcct aattgttccc tctgcctctg ttcttttttt  49980
tttttctgat gatcagttca aagtacctct gtatgcccat tcttaagtgc aaatctgacc  50040
atctataccc cttcttaata tcctttcttt tatggatacc catttcagac tttattaaag  50100
gagtggaagc ttccccctcc ccacctcacc acttgaagtt tttgcaatta gaatggagtt  50160
tatttggtta atgcaaaaat agatgtgatg tagaattctt ggggacacct acttatcccc  50220
ttttcagagt ggccctgaat agctctgtga acccaggaat ctgaagaact cagtacagaa  50280
```

-continued

```
aaccatcagc ctacagaaag tagatcaaac tctatgcttg atattcctga tctggctcct  50340
ggttactctt caaattcctc cttactatat tgtcccttca gatttgtaaa tctttaccgt  50400
gacatcgtat tttacacact gaacctttgt accgctgttc ctctcctgat gaacttccct  50460
tttctcttaa ctacacagct cagatttctc ataagggaag cttcatattt gttgtggcac  50520
tgttgttcct caaacatcct acttactgta gtcatttgtt tatgcttgtc tcctttgcag  50580
attctgaaat tcctagggca aaggctgcat cttgtcttct tattactaat attttacaca  50640
gtatctggtt acatagtagg cattcaatca tacaatttaa aagaagaggt tgactttgtg  50700
atctttttca tatgttttat ttccctctcc ccctactggc aacttcttcc tacttcttaa  50760
aatagataca gcacttgccc actaagtgga gggaagaggt gtgggagtcg agtagttgga  50820
acttcaagtg tcaaaacatg ataatctcat ttgcaaagtt acattatatc ggagcttgaa  50880
cctcagagat acttaattat aagcaacact tgtggaacat ttgataccta catttttttc  50940
actaaagtat cctatcaaaa ttaaatgtgt tgcagttgag atttgtgagg ttttagctat  51000
ttagagactt tagggatatg tttagtgttc taattctaat agtattgatg aatataaatg  51060
tttcactgta gaaagagaag tttgagagct gttgtgaatg atatttgatg tctattaggt  51120
gataatttct gatgactaaa catgctcaag accttagtga gaaatacatg aatacagaaa  51180
atattttgaa aattatgaga agtttatcat tgattataga ttttcttatc cagcagtttt  51240
tggttgtgtt ctgtttttca ctgtcagaga agcagaaagt ggtcagtgga ctttagaatg  51300
taggctcttg taggaggcca tatgtttgag agtgctgtcc aggtgctttg tgatgtggct  51360
gagaatggat gcaggcttgc agggaaaaac taatactgta gatctctaga gagcatttta  51420
ggaaagactt ctaagcttta ggttccctga ccaaagagta aaaagtgatt cttaatatcc  51480
atagctatag aggaaagtaa atacacttcc cacatcaaat gtagaattaa atatttaggc  51540
atttcaagtg tatttcattt agaacaaaat aaaatcatat attcactaat gaaatataaa  51600
accagatggt ctctgaaagg tttttccctt tactcacttt cagagtaagg caaggaagag  51660
tagttttgtt ttttaattta tattttaatt gtccctttct gtttttccaa aagttttatt  51720
ttttgaaagt gagtcacctt ttagacattt gaaaaattag aattactatg atgtttattt  51780
tattagtaag tcttcctaga gtagcaacgt agaaaagcat ctctgaatgc ctacatagta  51840
agtatttaat aaatgttttt tgggccaggt gaggtagctc actcctgtaa tcccagcaat  51900
ttgggaggcc gaggcgggtg gatcacctga ggtcaagagt ttgagaccag cctgaccagt  51960
atggtgaaac cccatctcta ctaaaaatgc aaaattagct gggggtggtg gtgcatgcct  52020
ataataccag ctactcggga ggctgaggca ggggaatcgc ttgaactcag gaggtggagg  52080
ttgcagtgag ccgagatcgt gccgttgcac tccagcctga gcaacaagag tgaaactctg  52140
tctcaataaa taaataaata aataaaatac ataaataaat gctttttgat ttaacgaagg  52200
tgtcattgtc ctatgaaaag gaaaactatc aaaatatatt ttttaaaact tagcttttga  52260
taatgatatg gaagatattt ctcttaatta acctaagtca gaaactaaaa tatgttataa  52320
aatgctaaca tcaaatattt gagaccagtt aaaggagaca gaaggaagtt atggagaaag  52380
aagcagtagc cagaaaataa gggcaagaaa atgttttcta aatttatgag aatcagaatg  52440
tttacaaaat tgctattatt atcatctgga aaaaatatgc cttgtaggct gaaaaaatga  52500
acattccctt tccataccat gcaggaacct tctttactgc attcctaaga ggactagtct  52560
agcacctaat tggatacttg tggtaatatt tgggaactca ctgatctggt acatcagtgt  52620
gggagtcgag tagtcagaac ttcaagtgtc aaaacatgat agtctcattt gcgaagttac  52680
```

```
actatattag agcttgaacc tcagagatac ttaattataa ttaacacttg cagaacattt  52740
gatacttaca tttttttttc actaaagtgt cctaccaaaa ttaaatgtgt tgcagttgag  52800
agttgtgagg ttttagctat ttggaaactt tagggatatg tttagtgttc taattccaat  52860
agtattgatg aacataaatg ttttactgta gaaagagaag tttgagagca agttgagcaa  52920
gaatctgtca ctctaggtct tctactcttt attaaagaat gttggattca tttataactt  52980
actggtccct taaatattaa agtttggtgt ttggtatctt aaacatgatt acatccttat  53040
agggctctct tctaattgcc tggatactgc acatctatta atacagtctc aaagcacact  53100
tgctttttttg atagtaagag cgtacgattt aatcacattg aagttagtcc gcaaaggttt  53160
ttgtcttttt ttcaggcaag cagctgatga atgaatctct actatccttc actttgtgac  53220
tgtgattttc taaataaatg ttggagattt taacttacaa tttattaatt tccatcttgt  53280
ttcttcaagt ccctccttta aggaaattta tggaaatctt tttccatacc atcaagtggc  53340
ttatttcttt ttaacttttt tccttaagtt caggagtaca cgtgcaggtt tgttgcatag  53400
gcaaccttgg gtcatgggag tttgttgtac aggttatttc atcacccagg tattaagcct  53460
agtacccatt agttattttt cctgatcctc tccctcctcc caccctccac cctctgatag  53520
gccccggtgt gtgttgttcc cctctgtgtc catatgtcct catcatttag ctcccactta  53580
taagtgagaa catgcagtat ttggttttct gttcctatgt tagtttgcta tggataatgg  53640
cctccagctc catccatgtc catgcaaaaa acatgatctt attctcttat atggctgcat  53700
gttattccat ggtgtatata taacacagtt ttttttatc cagtctatta ttggtgggca  53760
tttaggttga ttccatgtct ttgctattgt gaataggact gcagtgaaaa tatgtgtgca  53820
tgtgtcttta taatagaata atttttttt cctttggtat atacccagta gtggggttgc  53880
tgggttgaat agtatttctg tcttgaggtc tttgaggaat cgctacactg tcttccacaa  53940
tggttgaact aatttacatt cccaccaata gcatataagt gttccttttt ctccgcaacc  54000
tcactaacgt gttatttttt gactttttaa taatagccgt cctgactggt gtgagatggt  54060
atctcattgt ggttttgatt tgcatttctc taatgatcag tgatgttgag ctttatttca  54120
tatgtttgtt ggccgcatgt atgtcttctt ttgtaaagtg tctgttcatg tcctttgccc  54180
actttttcaa tggggatgtt tgtttgtttg tttgttttc ctgtaaattt aagatcctta  54240
tagatgctgg atactattgt cagatacata aattgcaaaa tttttctccc attctgtagg  54300
ttgtctgttt tctctgttga tagtttattt tgctatgaag aatgtcttta gtttaattag  54360
atcccatttg tgaattttg ctatgaactg gatctgatat aagcatatgt ttaattttaa  54420
ctcccaggtc acactgtttt tttttgtttg ttttgttttt gtttttgttt ttgtttttgt  54480
ttttttggag atggagtctc acgctgtcac cagtctggag tgtggtgata caatcttggc  54540
tcattgcaac ctccacattc cgggttcaag caattcttct gcctcagcct cctgagtagc  54600
tgggactaca ggcacacacc accatgccca gctaattttt gtatttttag taaagatggg  54660
gtttcaccat gttggccagg atggtctcta tctcttgact tcatgatctg cccgcctcag  54720
cctcccaaag tgctgggatt acaggcttga gccaccacac ctggccccag gtcatacttt  54780
taatcaaaat gagaaaaaag attgacttca ctggagtgct tatgtcttgt tttatattca  54840
agttttaaat ttatgttctt gagattatta catcttgagt tacttgataa taccacggtt  54900
gaaatccatg ttgttgaatc cttcaacccc ttgaggactg agaattccct ttaattatct  54960
gtctgaatca ttaaatactt gtaaatcaag agttcaattt agaaatgtta tacttgatac  55020
```

-continued

```
atttttaaa gctggataaa ttaacctatt aaacaaaatt atctcttctt caaaaaaaag  55080
gcatcacttc cccacaaat gtgtaattta ggaattgttt tctattggag tggttcacgc  55140
ttatatattt tagttgctct aatgcaaggt gtttcctaaa aagtttaagg aaagtataac  55200
tttattttca tgtatgatag taaataatac aataggggt gcatttgtgc tatgcttgtt  55260
tttgttccca tttcagtgct caattactgt agcttctaat aaataaaatt atcagttgct  55320
aacatttaaa tcaaacagtt ccacaagtgg aagtattgct tatttgtgag agttgtgttt  55380
ttttaaactt aaccttactg aggggtttta aggactgcta attatagatt gtactaagca  55440
aagtataaag taatagaagg ttaccaagtt gaggctagaa ttcaattagt gccaatacag  55500
ttaaaatggt atcattaaca gaacatcttc atccaggacc ttttttttt ttttttttt  55560
tttttcaga cagggtttca ctcctgttgc ccagactgcg gtgcagtggc ctgattgagg  55620
ctcactgcag cctcaacttc ccaggctcag gtgatcctcc cacctcagct tccagagtag  55680
ctgagaccac aggggcatgc caccacccct ggctaatttt ttgtattttt tgtagagaca  55740
gggttttgcc atgttgccca ggctgttcgc aaactcctgg cctcaagcaa tccacctgcc  55800
tcggcttccc aaagtgctgg aattatggga atgagctgcc acacccagcc cctccggaat  55860
ctttagatta ccaacttctg tcttccaggt ttttatgtcc ttggaaattt atgcatattt  55920
ttagaggtaa gacccatcct catcttcttc ctaatccttg acatattgtg aacacagata  55980
tatatacaat taagtagttc cctgagttac aaatatactt aaatatactt taacttatta  56040
tagaaggctt acaaaaactg tggataaata acatatattt atcttagtta atgaataact  56100
gatgctgaaa ataatgtgaa tgtcaaatta gttctctttt tttctagccc tcacctttga  56160
aaagcctgag cctctgagat gtgagatgac tgctgtaaag tgaagcagcg aatttctaga  56220
ggctgggttc acgcttcagg tcctctaaat cctaggtcgc ttcccactac tacatactac  56280
cctaaaaaat ctgtaattcg caaatttatt ttttgatctt tttcataact tattaaattt  56340
ttattgaaca aatacaggaa acagttttaa attactcatt gctcttgaat acattggtga  56400
ttatttttct tctctgaaat tctgttttcc ttaaaggcag tcattttttg gtctcttcta  56460
aatgacactt agtattttta gtaacatcat aacttcagtg gccacagtga gccctcattt  56520
tgcaacatat gcctactttt catatctggc ttgcctttta ttatttataa tttaatgaaa  56580
agaaagtacc actctttcca tagttttgta atagaattgc tgtcaacaaa gtagtggatg  56640
cactatgtta taaagatttc attgtgaaaa catgaaatgg ctgttaacta tacatcaggc  56700
aaaataaaaa caggaaatat aaacatttcc tggaacaggg cagagtatga gtaataaggt  56760
atcaaatata attggatacc tgaccaaata tttttaaatg tcttaagaaa tgtcactgga  56820
aagactggag tacttggatt tgtctcttat tcttattttg attcctaaca ctgtgcttgg  56880
cacatggtag gtaattaata aatgtgtgat ggatgaataa tgattgtcat tcaattagtg  56940
actaagagag ttggaaaggg ctatcaattt caaattggtt cctttaagac atttttacgt  57000
aagatttggg agaaaagtaa aagagcacca tatgattatg ctttactaag agctgcttcc  57060
attcctacat tgaccatgtg gactcatatt tggcctatat aattacatta gaataaacaa  57120
agcaccaaaa gttggaaaag gaagtagtag taggagaggg ttttaagcta tgtatttact  57180
gggaaaaaaa gtcatgtttt cttttttaaa aatgttctaa acagtactgt aatcacttgg  57240
gaattgaatg tgctttgtgt cagacaaagg tctttgtata caatacatta cattttgtat  57300
accaatacat tacattacac agaagggagt gcctggcttt gtatacaata cattacattt  57360
tgtataccaa tacattacat tacacagaag ggagtgcctg gctttgtata caatacatta  57420
```

```
cgttttgtat accaatacat tacattacac agaagggagt gcctggcttt gggaaacaca  57480
tctacctaaa ctcttaacat agcacaatgc tgccatacgg taggtaatac caagacaaat  57540
cagggccgtt attaacaacc ttgaggaaat gtcttgggaa atatttaaat aatttttgtt  57600
taattataat aaggaatcta cagcctctgt gaagtcatcc caaactcttc gaggcaaatt  57660
tagtctcctc ccacccctgt tttttaatgt ttctaaagga tgttatgtat aatctattag  57720
aaaactggcc aagtgcagtg gctcatgcct gtaatcgcag cactttggga ggccaaggcg  57780
ggtagattac ctgaggtcag gagtttgaga ccagcctagc caatatggcg aaaccctctc  57840
tactaaaaat acaaaaatta gccaggcgta gtggcaagtg cctgtaatcc cagctactca  57900
ggaggctgag gcaggagaat ctcttgaacc cgggaggcga ggttgcagtg agttgagttc  57960
gcgtcactgc attccagcct gggcgacgga gtgagactcc gtctcaaaaa acaaaaacaa  58020
accaaaaaaa aaaaaaatat atacacacac acacacacac acacacacac acacacatac  58080
atacatacat tagaaaacta attacattgt tttcttaaaa tgttttaagc atctctcttc  58140
ctcaaggaca agaatcttga atccttagtg catatgaggt acttaataga tatttaaatg  58200
aatagtgagc tactattgcc taaaaatatt agacatcatg taatatcagg cctacagttg  58260
atagaaaaag tattctcaac taagaataat ttaccaatgg agaaaactgt tagttttccc  58320
ttctttttct ttgctttata aaatttaaat gacattaaga gttacgtttc ttggaaaatt  58380
gaaaagaata tctgtggcac aatgggctct gggtataatt gcaggataat ttgaaaagtt  58440
taaagaatat tttcaatagg tataagttta tttaggctct gtgtctcctc ttgagatgac  58500
tttagcagta tatatttccc tggaacacca tgcactctag gttttctaat ttattggttt  58560
aaaatacatg gcattttact acgtaaatat tctctgtatc tgtaggtaca gcacctctgt  58620
gtacactaag ttagtgtatg tattttttta aaattgcctt agttttgcta ttcactagat  58680
tattttccaa ggaacctact cttagattta ttaagcctac tatatatatt ttgttattaa  58740
ctaattctct tatttttaaa aattactttt cctttctttg cttaaatttg ctttgttttc  58800
ctaaattagt gatttggaat acttaattgt ttttattttg ttttgttttg tcaataaaag  58860
agttttaaga ctctagttat actatagcta tagccaatgc attttgagag gtgcttacat  58920
attacaatta ttttcagaaa ttccttattt caaagctttg ctttctttga acaaagagtt  58980
atttaggaaa agaaaggaat aaaaatctca acttattctc cacttgacta gctttattat  59040
ttgcagtatt ctgtttttta cttgttctaa tacttcttta tattttgttg tggaattatg  59100
tcacctaaca atattttcct taacttctta attttagcct gttttccaag ttaatcattt  59160
atctgttgtt tcaatgaata cctaagaaaa ttttctttgt caggataagg cacatgaggt  59220
ctaagattta tttctagaac agtaagcaaa tcatttctga aagtgtgttc ttctactatt  59280
aagtaacatg tttattttg tcttttagtt gaagtccccc ccaacccaat aggtactatt  59340
ctgatttgtt ctcctattca cacattcttg aaggagagct gatttatctg tacccacaaa  59400
attataatat aattttctca gagtattcaa aacattgtct tttttatttt tctttttttt  59460
gagtttttca ctcttgttgc ctaggctgga gtgcaatggc aggatctcag ctcactgcaa  59520
cctccgcctc ccggtttcaa gagattctcc tgcctcagcc tcccgagtag ctgggattat  59580
aggcatgcac caccactcct ggctaatttt tttctatttt tagtagagac ggagtttctc  59640
catgttggtc aggccggtct caaactccca acctcaggtg atccacctgc ttcagcctcc  59700
taaagtgcta ggattacagg cgtgagccac cacacccagc cgaaaacatt atcttaatgg  59760
```

agcatttaga acgttatcac tgacaaactt ttttctattg aaaatactgc ttaaaagatc 59820
aggtcatgcc caccccacaa cccacaccct ttgtatttct cttttacttg tcttggcctc 59880
tagttcagat ttatagtttg gtaatgtctg attttcttg ttagtgcttc agcccatctg 59940
gttggggaac agctctatcc cactgggacc tctccctttc ctcatgagtg acgccagggt 60000
cctgctgccc ataagcattc tgtttgctga gtttgtatat atttcctttc cccagcttcg 60060
ctgcctttgg ctgctttgtg attaagtaag acatacccat gtttcctaaa gcctccttcg 60120
cctttagtcc ttgatgctgg ggaccttttg gttgggaaga cagcttcctt atgtcagggt 60180
gagcctgcta cacaggtatg taactcagac agtgacctac tgttgagttt ctgtttagtg 60240
tttctttgtc tccctcaaat ggtacaaacg tggagggctt caactgcagt ctacctttgt 60300
cctgttagtt ttgtctatca cagcccatgc cctccaaata agagatgatg gagcagtctg 60360
cttattttct gtagcactcc acaactgact ttaaaagagg gactgggatt gggctcttag 60420
tgatgacttt taatgtggat tcatctgcat tttctctaga aattctttaa actctctgcc 60480
tctcagctgg cactattcca tggtatttta gtgctaatgg gggatctttt ctaatttttg 60540
tttttctttg actgtttaaa tcatttactg gaaagagggc ttagatatct gctcatatgc 60600
tcctgctagt ctacaagtcc tccagcctga ttttgttcat gaacatgatg gaaataagct 60660
tcttaaatgc ctttaatatt ggatactgct ttcaaggaaa tttaaaatag caagcaggct 60720
ttcaagaaga gagaataaat tatcagccag tctcgcaaga acaaaaataa gccaagtcat 60780
ataaaacaag tttggagtaa acttgttttt acatttcaaa ttcgagttga actcttcaag 60840
tgaagcttca gagatataaa aaactttaac tgataaagat tccaaacatt aatatatgga 60900
aatgtatgag ctcactgaaa attttacata aattttacta gaagaggtga ctgaccagtt 60960
gcttttataa gattctcaaa aagatctcaa atcttaggga ctaatattgt aagtatacgg 61020
ggaaattaag acaaagattt actatcttgt gagtttttag tttggataat gaacttaatt 61080
tcacaagaaa ttgctttagc acaaacatga aaaccttaag catgagaact ctccttttga 61140
agtacaaagg gagactaaag tgaataactc aaactggaaa tgtagaaaat tgaatttgct 61200
atgatttgaa gtcctttcag aatagccaac agattttaaa caagagtttt attgcatagt 61260
ttctttggga tatacattga aggagaaagg aggagggagt tttaaaagac aagtggaaag 61320
ccctttctgc ttgttttggc tatggcttcc atttcagtgt ctgtatttaa gggatcataa 61380
aaggaactgg aaagactggt cacaatggca gctctgtacc tgtatgattt cggatgtgaa 61440
aagagtttag cgatttcctt gttaacctat actgctgtgg aagtcattca ttatgcagtt 61500
aggcattagc agaacaaata aagttcacag ctctaggaac caaatttaac tttatcactc 61560
ttctgattta gaatattttc atatgctttc atatgtccta cagacgataa gaagatagaa 61620
tcaatacttg gtgattgata ggttattttt taaaagggaa gaaagaatta aacatccatg 61680
gtttcttctt aagtaactgg ggggatgata gtatccctca caccaatggg gagtatagat 61740
gacaggtttg gagtgaaaga cagtgaattc cattttggat aagttgaatt tgaagtgcct 61800
atgggacata caggtacaga tgactaggag acaattgaaa atccaaattg tgaactctgc 61860
tgaagattag aagtacagat ctgagattaa attgctactt gagttcatgg gaataaaata 61920
ggtcattctg caaatggtta tctcaatatc ttcctggcca tctcttgggt caccttgcca 61980
acttttcatt ctctttacaa tctctaaatt ctcatgtttt taaggctctc atcttaggcc 62040
aacttatctt gggtcacctt gctaactttt cattctcttt acagtctcta aatttgtgct 62100
tttaaggccc cattctcaag ctggcttctc tgttttggtg ggaactggta gcaaacattc 62160

```
atttgtaaac aacccaaatg gctagcattg agcaggactc cccaacatac tcctctgaat  62220
tacattttga gttatctgaa ggatcaatat ctcaaactag gaaactgtag ctttctcatt  62280
tattttcatc atctaattat ttttcttgcc tttaagtata agggatagag acttgattga  62340
tttttatgta caacaagtta aaaaatttaa ttaggcgtct ttgccattta atcagtttat  62400
acttcttgaa tcttttccag tcatcaaaaa gttgctgagc atgcgcagct ttacttacta  62460
gcttatagca tgaagaagag taaaatagga gtggataaag gcacagtggt gagtagtcag  62520
tgtttccaat taatctcaaa gtttaggatt aatttagcgt gaattctgtt cttttgtgtc  62580
ttcctgcttt ttgacgtggt aacctgccat aacaaaagga aacagcagga aacttggtac  62640
caattaaaac agtcttcttc cccaaagaa cgaactgtca gcaaacaatc tcaaattcaa  62700
agtgataagt gttttagagt gaaacaagga taaagagaca aggctattaa attttaacat  62760
ctgctggaac acaaagcgca tgccagtaga attaagtttg gcatttaata agatacaatt  62820
tgcacatcag aaatgaaata gatgcctcaa ggcatggtat atatatatat atatatatat  62880
atatatatat atatatatat atatatgttt gagcgagggg cacttctagc aaaactgaat  62940
acactggtat aaatgtctgc gtgaaaattt ttttatccat tcacttttgg tgtgtattcc  63000
agctgtgagt tattcaacca ggctcactaa gtttgagtct gattaataac gtttaaggtc  63060
acatctgatt aacagtattt gaagtttgaa tttgttctaa gatgactcaa gcgcaataac  63120
attttctata tcaaaatgaa tttccatcca aatagggagg aaatctgaaa tttcagttcc  63180
agtgttgact gagatgctct ggatgagcct ggactcagag ctcaccaact ttggatcttt  63240
atgttaagta gtcagtgggg ttgacttcta gactagagat caaaatgttc tacacctctt  63300
gatataggtc agtggctgat gtaatgtgct tccaacaact ttcttttaac taaaacagta  63360
catataccaa gttggtttgt cacaatggga acaaaacaga aatctgacaa cagatttctc  63420
taattttttg tgtgtatgtt tctgaatggg ctaaaataca taattttact cttccttggt  63480
gaagatgctt ttataagagg acgtgtttaa gaaaattaag aaatgttgta ggtagccatg  63540
aaagaattat tttaaacaga attagtatag aggtgtgaag atctactgaa gggtgataag  63600
taagtgtgga agagatggtg ttcagcattg ggcttcagta tgaataggta gaagatgagc  63660
aaggcttaga gacaagaagt tcattcaata ggctgttgcg gttatccagc aatgagatgg  63720
tgacagcatg agccatggta gtaaaagtaa ggacatggat aatttgtggg ttctacagac  63780
aataagaaca tagaaccgat aggttatttt ttaaacggga agaaagaatt aaacatccat  63840
ggtttcttct taagtaactg cgtggatgat agtacccctc acactgatgg ggaatgtaga  63900
tgacaggttt ggagtgaaag aatgaattcc attttggata agtagagttt gaagtgccta  63960
tgggacatac aggtacagat gactaggaga cgattgaaaa tccaaattgt gaactctgct  64020
gaaggttaga agtatagatc tgagattgaa ttgctacttg agttcatggg aataaaatag  64080
gtcattcagt aaattgttat ctcaatatct tcctggccat ctcttgggtc accttgttga  64140
cttttcattc tctttacaat gtcaaaattc tggtgttttt aaggccccaa tctcaggctg  64200
gcttctccaa ctgtactctt acttgggatg atcttatcta gtcatggggc attaaatacc  64260
attggtaggt taacacagtt cacaattttc tccagcttag accccttgct gatttcctga  64320
cttgtacact caactgcctg cctaatatac ccactttaat gataatgtac atctcaaact  64380
gagcttattc gaaatagaag ccttaatttt tctgtcagtc atattgttcc catttaccca  64440
tcctaacaaa tagcaccatc atcaaccttt tagctcaaga caaaactcta ggcattatct  64500
```

```
tgctttcatt cctttcatgt actttctcac atctaatcca ttaccaagtt gttctgtttc  64560
tgccttcaaa atgtgtccta aatttatcca tttctctgcc actgctattc tctagttcag  64620
gacattctat cctttctctt gtattactgc ggtctctaaa cttcatgtat ctatgtttta  64680
tacttttaat tcattgtcta tacagctacc agagtgatct tttaaaggtc taaatcagtt  64740
catgtcactg ctttatatat aatgcaccta tggcttccca ctggatttaa ataataatct  64800
taacacttta ctcctccatg gcctttacat acttctagcc gcacctcaaa acactcctct  64860
tgttcactga gaactaacta gaccagtttc tcttctcctc agctatatca tgctaattta  64920
tgcttcagtg ccttttgtac ttttgttccc tctagctgaa tcattcttcc aggtcattct  64980
atcattggct ttttcattca gttcagatag atatcagcaa atcaagagag tctttcctta  65040
cctgctctat ctaaatagtc ctgttttagt cctctttatc tcatcactca gatttatttc  65100
cctcatagca ctcatcagtc tgaaattgtt tgtttatttg gctacttgtt tgtctagata  65160
aacttcactg gtgaaggaat ccagactatc ttgttcatcc ctacatccct agaacctaga  65220
acaatatgtt aaagataaat aaataaatag atgaaagaat gttgaagaga agagggtcca  65280
gtccagcccc ctgaggtgac cagcatttag ggaataagcc gaggcagagg agggccatta  65340
agaaggagca atgagagata gaggaaaact aagaacaagg tgtccctaaa gtgagagtgt  65400
cctaacacag gtctaaatga aaggatagtt cagaagaggg cactgcagct ggctgaaaga  65460
gaacaagaaa ggctgtaagg tggaggtgaa tttttaattg agccgtgaaa gatagggaaa  65520
ttctgtatga aggagtaaat ggaggcatag aggcatagag gcagaagatg catgcctgtt  65580
tggggaatag tcatcccatt tgtctttcac atatctcatt taatacttct catttaatcc  65640
ttttagtgtt aatgttgtca ctagattaaa aaacaaaggc tccatcagga tcacacagta  65700
aacagaagaa tatggattta aatggagatc tatctgactg caaagactac ttactgtaac  65760
ttaagtcatt gagattcctt atggccacct catattcacc ctgcatataa cagtatgcca  65820
atgtaggaat gaggcgtgaa taagcagggt aacaatagaa acatattctc accttgatta  65880
ttcctttggt agcttcaagg gaaattgagt ttgaggataa agtaactctt cccatgtcag  65940
cactttatct gtcctgaaac atgagaaatt ccaaatgttc aagccatgca gtttttatct  66000
agtcagatgg ttgagaagtc caggttaccc atagttgtaa tgaatacctc ctctttatct  66060
tcttaatgtt ctgctttgcc aaatgatcta taaagattac tcagtgtacc tttcagattg  66120
aggtccagca gactttcaga acactacatt taattacaga aacccaacta ataaaataat  66180
aagctcatgt tagtttcagg tgttgatttg tttttaatgt agtcaataat atttacatat  66240
aatgactggc aacttaacag agttataata gattattcac ctgtatttgc ctttatttgt  66300
gggtatacac acatatatac atgccttaaa ctagagtaaa atcatttatg catactaaat  66360
caaatttgag agtcccaaaa ttttcaaatt gtgtatggct ggtctatatt ttctaggact  66420
gtcctttctg gtttaaatga aattaaaaat tgaattaatg atattagtct cttttaattt  66480
tctatttttt tcatgattaa aaaatattaa tttccagcca ggtgcggtag ctcacgcctg  66540
taatcccagc actttgggag gctgaggcgg gtggatcacc tgaagtcagg agttcaaaac  66600
cagcctggcc aacatggtga aaccctgtct ctactaaaaa tacaaaaact agccaggcat  66660
ggtggcacgt gcctgtagtc ccagatactt ggatggctga ggcaggagaa tcacttgaac  66720
ccaggaggcg gaggttgcag tgagctgaga ttgtgccact gcactctagc ctggtcgaca  66780
gagtgagaat ctgtctcaga ggaaaaaaaa aaattaattt tccccattcc cccacccacc  66840
caccaaaaga ctccattgga gttttatttt acaaatgcat ctgctcatct acttcttttt  66900
```

aagtgcataa actagtttta caagcttgag tttaaatctt aactcctcaa ttctttttct 66960
gacatagaaa tatacaggtg cattatgaaa tagctaatag tgactatttt ctagggctgt 67020
aactcaatat ttataagcat aatgatataa cctgctgaag tttgacacgt cagtatagtt 67080
cttttgttat tctaagtcat aaaggcagaa tttggaaaaa ttcacagctt ttcaaatatg 67140
cagaagagga aaaattgaga ggaagcatac taaaatttct ttagccaatt ttaatcaaat 67200
tgagtttgaa acttacagga ttatgcttca aagcttgtaa tgatcgtcaa aagtagcctt 67260
attcaaaatg acacactaat ttctaccaca tctgtattct tctcattgta agatgttaca 67320
tatacctatg cttgaccaaa tggacttcct gctattttaa gatatttttc tgtgttttaa 67380
gtctttctac aaattttctc aagcatttcc ctttacctag gatgttcttc tttcactgca 67440
agtgaagaca ttctaaaaat tcctaaagca cactaccaaa agcccttcat ttggatgacc 67500
caccttccta tgagtctcca tagttgcatg tctgatggca tttattttaa ctctatgatc 67560
tgcttctaaa ttagataaaa gctctcagag agaactatga ccaattgtca ttctgtttcc 67620
catggcacct agtacagtac tctgctcaca ggctcaataa gtaatgagtt gagctacgtt 67680
tttttaaggc agagtctccc tctgtcgccc agggtggagt acagtggtgc aatctctgct 67740
cactgcaacc tctgctgctg ggttcaagtg attctcctgt ctcagactcc cgagtagctg 67800
ggactatacc accatgccac catgcctggc taacttttag tagaaacaag gtttcaccat 67860
gttggccagg ctggtctcca actcctggcc tcaagtgatc cacctgcctt ggcctcataa 67920
agtgctagga caaaagtttg ccattgtcat gttacgatat atattggttt ttgtccatgg 67980
tttctggttc atagctccaa tatccctttt tacagtcttt tgttagaatg tggggtgtgt 68040
tggacctcgg ggcaggcctt agaaaacaga atctctcctg ccttcctttc acttgtcccc 68100
cgagggagat tttttttttt tttttttttt ttgagacaag acttccctgt gtcacccagg 68160
ctggagtgca gtggtgtgat catagctcac cgcagcctca gcctcctagg ttcaagcaat 68220
cctcccatct cagcctccca agtacctggg actacaggca catgccacca cacctggcat 68280
tttttttttt tttttttttt ttgtagagag gtttcgccat gttgcccagt ctggcctcca 68340
gctcctgggc tcaagtgatc cacccacctt ggctcaaacc accacaccca accctgaggg 68400
agattctaat cttccccacc cttctgattt tgagtcttaa aaccccagag aaggtcccac 68460
cctttgcact ggggaaagga atgctgatga tcatgaagcc tccataaaaa ctcaggagga 68520
ttgagtctgg ggagcttctg gatagctgaa ccagtggagg ttcctggaag gtggctcatc 68580
cagggaggac ttagaagctc cgtgcacttt ccttatactt caccctaagc atctcttcat 68640
ctgtatcctt tgataaacca gcaaatataa gtaagtgttt cttgagttat gtgagctgct 68700
tgaccaaacg tattgaaccc aaagagggtg ttgtgggaac cccaactcga agctggttgg 68760
tcagaagttc tggaggcctg gatttgtgac ttgtgtctgt ggcaggagca tcttgggaac 68820
tgagcgttta atctacgggg tctgacactg tctccgggaa ttaaattgga ggacacccag 68880
ctagtgtctg ctgcttgtta ttggggagaa accctcacac atttggtcac aagagagaag 68940
ttttctgttt tgaatattgt tgtgatgtga gagcagagga aaaatgcatt ttggagaggt 69000
tttttcctac acagccatag gcagtgataa gaatatgatg ctttttttcca gaaaatgcta 69060
catgagacct ttttataaaa tctaattttc ttcaactgag tagcatttaa actaaaaaga 69120
ataggttatt tcagtgtctc tctgtaataa catcttacaa tcacttgtca gaccatgaaa 69180
taatgttcta gaaaatcagt gaaagagctt tttaaacttt gtgacatttg acttatattt 69240
attaccaaaa agcctgaatt attattcagc acattataat tttatttaaa atttaaatta 69300
gagatgaaat acttgtaaat gtttataaga ttggtagctg tgtgggcttc cagagttaga 69360
aatgcctctg agaaaagatt tagagttttg aaagtatttt gaaaaaagaa acagaaagga 69420
atacaacatt tttcccagca ctgcttcaat aatgcagtct tcagcatcat ctcaaagcaa 69480
taactgcagt acagatgaga tcagccagtt ttttttccc ccttatctgc agtgatttta 69540
ccatctcttc atgctacatc ttaccacaaa gagaacattg aaacatggga aagagtttgc 69600
tttgatttca accagaatgc caactcattt ctggggttct aaaccataac ctttttagc 69660
agagcagtgt agaattttta tacgatacca taaatggtcg gcctgagtaa cattttaact 69720
gtaagtcaat acctttgaag agacatgtct gacaactcag agttctattt tctccatgtg 69780
tgactaaagt accttttcta ttaagagatc aaccaccatt tccttctact ctttgttctc 69840
cccttaaata aagttaattc agcttcaaaa tattttatga tcttgattac taactgtggg 69900
tctttagaag acaatgtaaa acatttccat gctgtgaata ttagagctag tatacttgga 69960
gtttggctag tatttctggg ggaggtagaa gaggagacat agagtacaaa tgagtatttt 70020
taaagccacg ctgactaaaa caaaaggaat gttttataca tgtttatttc atagtacttc 70080
tttgaaacag gtcgggggga ggagagttaa aatattgctt tgaattttaa tcaaagttct 70140
ttcatggaat tgttggtgct tctggtaata acagttctat aatctttgtg agttaatctg 70200
aaatgctctt tttcttcatc gtaattcagt gcttgtctta actggtggac ttattttatg 70260
gtattatgtt tataagatgg caactaaaat cagatttttt atactcctaa aagatggata 70320
cgatagaggg gaaagggggt aagctacaac ttttaggttg ttggtgatat ttgaagtgtt 70380
tattgcttct gatttacatt tatatattat attcaaatat aaactttaaa agtaatgatt 70440
tgccacaggt taaagcagaa catttatatg atatttccta gatgttttcc tctacaatcc 70500
tgtttttgtt ctatgaaaaa tgccataaac ttggatcatt cactaattaa tttgaagctg 70560
ttttcaaaca aaaagctaat tcatctttta gcggatttag ttataatcgt gataacagat 70620
gtatagctaa gtctgttgga caaactgttg gtcacatcaa tcttaaatgc atcatacagc 70680
gtgatgtgaa tttatgatat ttcctaggta atgttaaggt tatatggaaa tttctttgca 70740
ggtagttaag tcttattttg aattcaaatg ttattttcaa tacatacgtg gaagtgtatt 70800
ttttgtttgt cctaaatgtt tagattttt gagtttacaa tttttttgtg tgttctttct 70860
ttgttcttgc ccctccctgc attctctatg aagatacatg tcagcactat gcaacactaa 70920
aataacaatc aaccaaatta tatcctatga acagaccttt ctcttcattt caaaggcata 70980
acttggatgg tctgtttagc tcatggtgaa aaaaaaaagt tatgattttg tatttgggca 71040
aagtacaggt gaagagcgtg aatcattaga acagcaatat aactggaaga agatagttta 71100
gtttttacaa gttaaatttg aagctaaagc aaaacttgca taggtatgtg tcctttgctc 71160
ttgaaaatga actcagaact ctacatctga gtggttttat gaatttatac tctcctagtc 71220
cacaggttct catcagtgcc tcaagatcta tgcacagatt aaaattacat aagatatcat 71280
atactacatc tgaattaggg ttttccaaag tatgctattc catggaaata ctgtttattc 71340
agggtgctcc ataaacaatg atcctgtgtt tcattatgtc caggaaatgc cacacagcac 71400
ctttccagac atcctatcat catattaaag actttgaggc catgcattaa agaaagtttt 71460
aaattagaaa aaaaataagt tttcttgctt gagcacagaa ctttattttt tctcaggctg 71520
gttctccttt tttaaaatta cacgttaata tcccaaagaa ccagtcccat agatagatat 71580
cacatatgat aagaatctgt ttcaatggtg ttggtgtaca tgtgtgttca ggtacctaca 71640

```
cattaggaca catctctagt ttattaatac tgcacttata aagagacatg gtagagacat  71700
caagaagaca tcattttagg gtggacacca ttgcctagga cctgcttctt aatgtcaaaa  71760
attcagaaac ccaattttat ctctcccgca gagttgactc gagtgaagga aattgagttg  71820
ttttaattaa actcacatga gattgatgtt taaacaaaat tgtaagttta tcaattaata  71880
atcaagaatt ctgattttta attttcaaaa tattatttat gtccactgtc cagggtactt  71940
gctttaaggg cacccagtga ttcttgaaga tgaagagtct taggaatatt tattttctag  72000
acctcaatga agaaagcttt ttaatcatcc tgccccatag aagaatttat gttcctagtg  72060
atgtgatcat attggccaat ccagtgtttc ttttccaagg acagtactga taaggagcac  72120
caaatctacc tctttgtcct gaacagatca tctccatcta ttcatagttt ggctcagaag  72180
ttggacaagg ctgcatttta tatctacttc ttcctcatgt cggctatgcc atgccgtttc  72240
gttcttttag cttgtttact tatgtgtaaa atgaggtaaa aattacaccc ttcaaaccga  72300
aagtggtctt cgtgatgagt tatttaattg aagccccagt agatatttat cattgccagt  72360
tttagagaat catagcattt tagaacacaa gatgacctta gatgtaatca tgttcattcc  72420
cctcgtatta taaattttta aaaattgaga tgtggggtgg ttgtgacttg ctcacaaacc  72480
cacatttaga accaaaactc agcattcttg ttctgactgt gtctatgtcc tgtaggtata  72540
tgtcttgtct tctcagttaa ataattaaag attcttaaag atagagacca tattttatgc  72600
aacttctgga tcccataaat tatgtttcca gaagaacctt ttgtaatgaa aaaatatata  72660
taatgtctat attatatata tagtctatta ctattttgat aatctaaaac atgctatata  72720
attttaggcg atcttaacct atttatcaga gcttttcaga tcaaagaaaa ttagagtaat  72780
cttcatcatg tatgggaaca ttgatgtatt tttctgatga acacatggtt atatgatact  72840
cttttaaagc atctgtatta ctctttcttc tgatagactg gttattttgt ttatgttatg  72900
aaataatgtt ggcagctttt cattagaact gatacatatt gaaatttctt aaattgatag  72960
ctcatggatg tgcagttggt ttaatggcat ctccattatt aatctttaag aagatcttca  73020
tcttactctc aaaaataacc gtaatatcct acaaattaac taaaacatga tcattgctag  73080
ttgttccaaa ataggaagaa taaaaatgac cagattgtta tggtaaccag ttgattaaga  73140
ctagatcaat aggaaaacga atttattcaa gtctgtacaa aacttctcca aaacatagat  73200
ggcatgcctt ttgaggcaat ggtagggaac aaaatatttt tgagaaggag cagattttag  73260
ggatacagta cagtacataa ttgccaaaat gcttgtgtta caaggattcc tggtacagag  73320
tttttaaata aaatgctagg tatgtcatgt ttgtttcaca ttaatattgt agagtcccct  73380
ggggatgtga caatttagtt gaccaactct aatatagtta atttctacct tttgatagct  73440
ttgtggggtt ttgtttgttt gtttttgtt ttgccattct tgattttagg gctgaagata  73500
tgagacaatg tatcaaacag taaagaatta tgcattgatt aagatcatct tggtgaatta  73560
gatgtttatt atataactcg actttaagac tttgttcaga tctcactatc ttaatgagat  73620
ttaccctcat tatatagtat ttaatagggc aaccactccc cgatactctt gattcctcgt  73680
tagctgccct attatttctt tgtttttccc ttagcactca acattttctt accacaccac  73740
ataatttact ttcttattgt gtttattgtt tttctcctca ttagaatatc aggtccaaga  73800
agacaggagt atttatctct tttgttcagt ggtgtgttac tggtgactac tagagtgcct  73860
gacacataga atatgttcaa taaatattcg ttgcatgaaa gaatgaatac cttgacagat  73920
tatttttata actctaccag tgtcattata taactacact gaatgattat gagccctcct  73980
```

-continued

```
agaaattaca taaagttctt atatattatt agaacccatt tgttggcctt atgtaatggt  74040
tctattggaa aaatcatacc tccgtatata aaaatgaaag tatttttttt ctacaattgc  74100
ccctcatata tactattata gtctccttca ccccattcag ccattaatgt cttcttgacc  74160
aggtaacata atttttacag caccttttgg ttattagaac aattttattt gtctttcaaa  74220
ctcagtccta ttcattttaa aactcccaac tcaagcctga gtcagtgttc ttctcccagc  74280
acaaacttaa acactggctc caacccttgg agttgaaagt aggggagcct cactcctgat  74340
acctcccctc cccctctacc gtgagcacca gtgcctagga gattgggcag gactgaggaa  74400
ggatgaaaag gagctcaggg ctccttaagc acctgaacaa gactggagga ctttggatgt  74460
tgctattttt ctgcctggca ttgactggct attggacgcc ctctgtgagg caggcatccg  74520
aatactggct ttcttgacat atatggagcg ttctttagag aggcctacaa gggctctcac  74580
tgcacagtac cctgatagga gagatctgtc cttatttctt ctatcaccat agctacttca  74640
gctttgcctg ctgagtccac cccacagtct ctttctgctg gggcatcctt gccctggaca  74700
gattcttaga gcatgaccaa gcctaaacaa cttctgcaat tttctaagt acactttttat  74760
ttaattgaaa gtttcaagca ttggataata taaatgtatc ctagacagtg ttccagtaag  74820
gacaaccagc tcacaattat ccattctaat aatgggagtc aactgaaata gaaaaatata  74880
gatttttaaa ataatttatg agaaacaaat atttgtgaca cagtacattt ctaattatgt  74940
ttatctttat tattattatt atcgtttcct tcagtacaca ctagtttggt gagacttgga  75000
gaaaggccag gaataagccc aaattcaaaa aacaattcca ggattaacag ataagtggat  75060
aatagagaat tgacaaaaga tcatgctcat tttaccaata agaaactggt tggttaactt  75120
gggttgcaaa ctgaaagcag atttatacta aactggcagg tgtctccaga tcttaaatgc  75180
agatctctat ctctgagtta atctgcctct catcttcaat ggcattcctc tgaatttttc  75240
tccctcaaat aatctatata ttattaaatt ttgtttatac tgccatttta agaaacagat  75300
tttaaaactt taaacatggg aattaaatag gccctactga ggattatgaa aaacctgaca  75360
aaacctccta tgcacatgat ttagattagg agcagtgcac acgctgtatg tgtatgtgca  75420
gctacttgtc caattaacac cttttcagaa atggaggaac tttctctgag gactttgaca  75480
tatttgtgtg ttcagcagtc ctttttcttt tttttattt tttatttttt tattattata  75540
ctttaagttt tagggtacat gggcacaatg tgcaggttag ttacatatgt atacatgtgc  75600
catgctggtg cgctgcaccc actaactcgt catctagcat taggtgtatc tcccaatgct  75660
atccctcccc cgtcccccca ccccacaaca gtccccagag tgtgatgttc cccttcctgt  75720
gtccatgtgt tctcattgtt caattcccac ctatgagtga gaatatgcgg tgtttggttt  75780
tttgttcttg tgatagttta ctgagaatga tgatttccaa tttcatccat gtccctacaa  75840
aggacatgaa ctcatcattt tttatggctg catagtattc catggtgtat atgtgccaca  75900
ttttcttaat ccagtctatc attgttggac attagggttg gttccaagtc tttgctattg  75960
tgaatagtgc cgcaataaac atacgtgtgc atgtgtcttt atagcagcat gatttatagt  76020
cctttgggta taaacccagt aatgggatgg ctcagtcaaa tggtatttct agttctagat  76080
ccctgaggaa tcgccacact gacttccaca atggttgaac tagtttacag tcccaccaac  76140
agcgtaaaag tgttcctatt tctccacatc ctctccagca cttgttgtgt cctcactttt  76200
taatgatcgc cattctaact ggtgtgagat gatatctcat tgtggttttg attttcattt  76260
ctctgatggc cagtgatggt gagcattttt tcatgtgtct tttggctgca taaatgtctt  76320
cttttgagaa gtgtctgttc atgtgcttcg cccacttttt gatgggattg tttgtttttt  76380
```

tcttgtaaat ttgtttgagt tctttgtaga ttctggatat tagccctttg tcagatgagt 76440
aggttgcgaa aattttctgc cattttgtgg gttgcctgtt cactctgatg gtagttcctt 76500
ttgctgtgca gaagctcttt agtttaatta gatcccattt gtcaattttg gcttttgttg 76560
ccattgcttt tggtgtttta gacatgaagt ccttgcccgt gcctatgtcg tgaatggtgt 76620
tgcctaggtt ttcttctagg gtttttatgg ttttaggtct aacgtttaag tctttaatcc 76680
atcttgaatt gatttttgta taaggtgtaa ggaagggatc cagtttcagc tttccacata 76740
tggctagcca gttttcccag caccatttat taaataggga atcctttccc catttcttgt 76800
ttttctcagg tttgtcaaag atcagatagt tgtagatatg tggccttatt tctgagggct 76860
ctgttctgtt ccattgatct atatctctgt tttggtacca gcaccaggac catgctcagc 76920
agtccttttt caagagatgt gaagtacatc ttcacagatt tttaaatatt tagatagaaa 76980
gttcttacag aatgagaaat aaaaagttag ctttgcctta aaaatattaa ttcaccttat 77040
attctccata cttaatccat ataggaaaca ttatattcca ggtctaacat gtggcttgct 77100
tacattaatt ttgctgttga aaaatatatg ttttggatta tgtttttaaa attttagctt 77160
taatatttaa atattaaata atgttaactt taaattaacg aagaatagtt tttaatttta 77220
taagaaatgc cctataaaaa acactttctt tacctcaaga gtgagacttg gcaaccatac 77280
caatattaca tagtaatttt aaagtcaaac gaaatggaga gaacttaata gatacagaag 77340
ataagaattt aaactaacat tttgctcggg attttagaac actatacaga gggaaattta 77400
gtagacaata atgaagtcca tagcattgca cacatcttga aataagtgta taattgacac 77460
aagctatgtc ccatgttgat aggaagaatc caaaatagtt ttggagaata atgccatcta 77520
tgcaggaggt gtggccatat acatcatctt tactcagtgt ttttcatgtc aataaatatt 77580
taattcctaa cactctgaat tactaataga ggtgaagcct gtcagtggaa gtgacagaga 77640
gatacacagt gattcccgta agtttgatcc tgaaacacag tgcctttagc agatatagtt 77700
cccataagca agcagtctga agtatttacc ctcagtaatc tgaatgtata aataaacagg 77760
attcatgatg gtagagtaat ttatatatac ttgtagtatt aggacatgca aaacttattt 77820
tatggaaaaa aataatttac taccttatag tatggcaact atacaaatct ataaattgac 77880
tcttttgtcc ccttgaaaaa aagctgacat aaaatttaaa tgatgtgtat tttttcttag 77940
agcaataaaa gatatacccc cacctagaaa agcaataaac caaaaaataa aacaaaaaca 78000
aaatcaagcc ctcttcacaa atttgagcat atctacagct ttatgtggtg agagatacag 78060
ctaccattct tgagtaatcc gaagagtcaa atggtatgga gcaaaattac agtcctaaat 78120
gcatattggt gaaatgagat gctgatccat ttgcacacta atgtgctatt tttaagtcat 78180
gcatcatagc atcttcaaag aggcctgtca taattatgat ggattagact gcagagtcag 78240
tcctagatgc agtaattgtt tcacagatgc tgccaatgcg actagaattt ataataaatt 78300
attttcagag aggcgggaga aggaacaaaa tcaaaggaaa actgctgtgg ctaaaacctg 78360
ttttggtctt aggaaaccaa aatgttagct agtagtcaaa aggccagtat tttcaactga 78420
gataaacatg cttcattaat acatgcctct gacatagaag ataaaggtta acataattga 78480
catatcagcc agtctctctc tctctctctc tctctctctc tctctctctc tctctgtctc 78540
gtagcttatg aaaatttatt ctggggcatt agctgaaatt attgagtggc catataattg 78600
ttgcatgttt ctatttatgt taaattgcct ggttataatt tgacctttag aatttctgaa 78660
aaaaatggtg gtatttatag taaatagaaa tattcttttt ggttccttgg aagcccatgc 78720

```
attacaaaga acattagatt attggaataa aaggatagac atacataata tgactagtgg  78780
gatctaaatt ataacctttt aaaattgtaa tttaattagt ctgtcattta ggcaaatgat  78840
aatttctaaa actgcctttt tagacttaaa aaaataccaa agttcttata actttagcat  78900
tatgttttgt tcattcttaa agtttaattc actttgttgc ctttttggta aacctatgaa  78960
gaaatctcat gctgcaccat atagtaaaaa atcgtgtgtg tgtgtgtgtg tgtgtgtgat  79020
ttgaataatg agctatgtgt tatattttga taagcaaaga taagtttata gtgaagcaga  79080
taaacatgcc atgtattttc ctaggttaag ggttcaataa tcagaagagc ttctacaact  79140
catttgcctt ctcactagtt tttttgaaat tgcgctctat gagtttttta tgtggtgttc  79200
tctgtacttg ctgactactg atgcacattt ctccttaggt cactggttct cctccctcag  79260
caatgttgta ggtagctttg atgaacattc gttgtcagcc ttttaccttt gacttagtgt  79320
ttttctctca tactacggca agaagaaatg aagttaaatt ttacaagagt gacttgggtg  79380
gctgatatgc ccacattgac agggacaaga gctctagtct tcccctctcc tgtattccca  79440
tggcacttca gtagtctcat tgcctcaaca taaccacagt tcagggcagt agaggatgtt  79500
tgcatctttg tgttagctcc atgccatggc aactgcactg agtgaggatt caactcagtg  79560
cagcaggact gaaaaaataa atgaactaat gtgtcttgag ctccaattct ctgagtgaca  79620
ttatcagggg agattcataa atcatcctca aatattctag agaaaaatca tcagcagtcc  79680
agcattgcaa agataatctg ggaaggtggc aaagaaggga tcagaataac tctgtggcag  79740
cttcaaattc catgtcctaa aagtttacgt tttctttttt attctatccc aaaccacata  79800
aagaaatgat ttgttggcaa aagacatgca aaatgccctt aatcatctta ataattacag  79860
acctacagat acgtagccaa aatacttgtt ttttaatcct aaaccttaaa aaaaaagctt  79920
aaattgttgg ctaaatgtga atttaataac aaaacttact cctttaatta tgcacttgtc  79980
ttagtattgt gtggtgggaa gagctttaga gagctgccag agtgcttagg cctagtccct  80040
gtgggagcct ctgttttggt gcttcaccat gggcagattc ctcagttttc acatctttaa  80100
aatgagaaaa tggtactaga tccttgctgc tactctgaaa tgtttataca ttgttaggac  80160
cattgttaca tattattact tatatttgag tgtcacctta gaatttctta gccgtgtgat  80220
atggtttggt tgttggctcc tctaaatctc ctgttgaaat ataatcccca gtgttggagg  80280
tgggggcctg gtgggaagtg tttggattat tggggcagat ccctcatggc atggtgctgt  80340
cctcctgata gtgagttctc aagagatctg gttaagggtg tgtggcacgt ccccctccct  80400
gtctccttcc ctccctctct ccttccctcc ctctgtcctt ccctccctct tcctccctct  80460
tcctctctct ttttctccca ctccagccat gttagatgcc tgctcccctt ttgctttctg  80520
ccatgattat aagttttgta aggcctcacc caaagcagat gccagtgctt tgcctcctat  80580
acagcctgca gaaccatgag ccaattaaac ctattttctt ataaattacc cagacagcta  80640
tttctttata gcaactcaaa aacagcctaa catacctttc aaaaggttaa aatgctattt  80700
agtcattcca gaagcaagat ctctttgtcc agaattctgg aaataaagat gccaaaataa  80760
tatggcatgt atttgatctc agggaatttt catttttttca aaaggaggaa aaaagagtaa  80820
tataattttt taatattttg gtagctctaa cagtgcttag aaccagttct caagagcaca  80880
ttgtgaaact ttcaggaatt gcatgagctg taggttgata acatgatgcc agctataacc  80940
cataagagca tctcctgagg aatatgttaa aaactgtatt cattcttaaa ttttaactaa  81000
atgcaatgag tgaagtattg acatcatgaa aatcatccct gggtaaacaa ttagtcactc  81060
caggttttcc caaaggttct tctgtctctg ttcttgtata taaacttcgt aaccagttta  81120
```

acaaccccaa aaaaggcctt aattttgatt ggccagcatc ctcttaggaa agacattgcc 81180
atcctcttgt aaagttgctt ctcattctaa aataagaatt gtttccatct agggaatgat 81240
ttttataggt agaatcttat ttggcatgga ctcttttgca tacagtgaat tacaatgtgt 81300
agaccttcaa tagcaaggtg tttgaatatt tagttgcaca atagagcagt atcttaatat 81360
tgtataccat attaattttg tgttctctgg tgtaagaaaa aatagaagga tgtttaattt 81420
caactaaaaa atcaatcatg ataattcaaa atatttctga tgagtcattt ataagagcag 81480
atatgaatta aaattatatt tttgttctta gtctctgaga agcaaaaatc acacaaataa 81540
tctccatagc aaaaatttat atttatctga aaaacagttt aactttgaaa aacttttctt 81600
tgcaatcatt taaattcata aaaaaaattc attaactcta ctttcactga atagcaggtg 81660
aatagcaggt caatatctac aaaaattcat ctttgaagat ttttttatct tacgcaaaaa 81720
ttattgactt catgtagact ttttatgcaa gcttgaaaac actgtgtaaa tgaccccata 81780
aaaactacag catgaaagct ttttcagtat ttctacaatg agcaaaatgc ataggtctca 81840
tttccttctc ttttattaag caaaataata ctttatcaac atcagtatgc aagcactaag 81900
agcttgaaag agtactgtgc aagtgggtta ctggatcata atattccagg gtatgtatat 81960
aaaaagtgtg atttagcaca tattaaagta aaagaaaata ttgcattttt ctccttctaa 82020
aatggcagtt tattagttta aatttcctga aataagattt aaagaccaat aacaaatttt 82080
cctcattcta acatataact ttcctgccct tcttgtgaaa aagttaacca ttaaactttt 82140
cacacaaatg gttgtataaa ggacttgctg tcacagacaa aatagttctg tataatgttt 82200
aaaaatggcc attgtgttta aaactccata ttgaaataca tttctttttt agtcaccttc 82260
atttcttagt agctattatt atactcaaag gatttgccct tgacacttta aagaatgtcc 82320
aaaattatgt ggaatggatt ataataaaag ataatatatt aaatgcttaa aatattttat 82380
accttagaaa gtagaaaaac atgtattatg tacagatcct acaaatttta tataatttat 82440
cataaatgta cacatgtata tacatgtaaa taccttttga ttgctctgta tatgaattgg 82500
tgttttacag ttaccaaaag aaaagtgcct ttttttggta gtatctggac aggtaattga 82560
ctttctttct gcaggattta tttagattta tgtctatgct ccttaatttt tgaaaagtga 82620
tagtgtcctg attttggaga agcctctcat atcaaagact acaaatcaat tttcatgatt 82680
ttaaaaccta aagtttcttt attaggtgtt attgatgatt aaaagccatt gtctcaccca 82740
aattttctac ttgttcaata gaaacataat gtaagccaca tggaatttta cattttctag 82800
tactcacatt aaaacaagtg aaaaagaaac aaattgatga tacgtttgat ttaacccaat 82860
acatttaaaa tagttcaaca tgtattaaat attttttgag tatttttgtg tttttttaac 82920
actaaatctt tgaaatccaa actaaatgtt ttcatagata ccacatctca atttggacta 82980
gacacatttt aagggctcaa tagctatatg tgactagtca ctgttggatg atgtatatct 83040
agaccatctc ttaatgtatg gaaggaagta aatctagcag aaataaaaac atcactttgt 83100
tttctttgtc caatatgagt tataacttta tttttttgag acagagtctc gctctgttgc 83160
caggctggag tgcagtggcg cgatctcggc tcactgcaac ctccgcctcc tgggttcaaa 83220
tgattctcct gcctcagcct cccaagtaac tgggactaca ggcatgcgcc accatgccca 83280
gctacttttt gtatttttag tagtggcggt gtttgaccac gttggccaag atggtctcga 83340
tctcttgacc tcgtgatctg cctgcctcag cctcccaaag tgctgggact acaggcgtga 83400
gccaccgtgc ctggcctttt attttattta ttaagtaata cacatgcttg gaagttattt 83460

```
aaaaaaaaaa aaaaggaata gttaaaagta atccccctcc cagtgctttt ctccagctgc  83520
cccattcctt ttcctggagg caaattatta tggccagttc attatatatt ctccagagat  83580
gatttttttt tattttacaa aggtataggt tgtagcattc ttatataaac tgttgtgtag  83640
cttcctttat tccatttaat tactgggaga tacttccatc tgaaaatata gagatactaa  83700
ttttaatagc tacatggtat tatattgtgt ggctgtacca taaattattt aacataaccc  83760
ttattgatgt aggttgtttc taacctttta ttactgcaaa agattgtgcc tacatcattt  83820
aatgtatata tgagcatatt tgtcagatat atatatatat attttttgag acagtgtctc  83880
actctgtcac ccaggctgga gtgcagcatc acaatctcac ctcactgcag tgtccacctc  83940
ctgggttcag gtgattcttc ttcctcagcc tcccaagtaa ctgggattac aggtgcctac  84000
caccatgccc tgctaatttt tgtatctttt taggagagac gggatttcac catgttggcc  84060
aggttggtct agaactcctg gcctcaggtg atccactggc cttagcttcc caaagtgctg  84120
ggattatagg cgtgagctac cacacccagc ctgtcagata aattcttaaa agggtcaagg  84180
aaagtgtttc tgaaatttta tacatattgc caaattgtca tcctacatga tatttgtggc  84240
agttttgact ctcaaaagcc acatgagaga gtatctgttt tcccacatgc ttgccaaaca  84300
tagtatagta tcaagcttac tgatcttcac taattggaga agagaaaaaa actgtacctt  84360
gttgcagttt taatttgcat ttctttttat gagcaatagt agatatcttc ttaaatactt  84420
aagagccatt cacatttcat tttctatgaa ctgtccatgt cccttgtcca ttttttagta  84480
tgtggttatt catttatttg taggcgtcct atatgttaag aaaagtttta tacaactttt  84540
aactcttttt acatgtttat tttggcacat ataaatttta gcaaactttc ccatctttta  84600
tgacttctag attttgtttc acaaaaaaag agcttagcca gtcattagat ttttttaagt  84660
tttctcagat tgtttttaac ttttgggggg gttttatttc ctgtattcaa atattaaatt  84720
catctagaat ttatcttaaa gtgtaaggga atgatcccac tttatcattt tttcaggaga  84780
ttacccagtt gttctaatat caagtatgtc tttgaaatcc catccttatc ttgtagcata  84840
tttctgtggt ttgggtctat ttttgaacat tctgttttat tccattgatc atattaatat  84900
tatatgtgca aacacaaact attttaagta tagtagcttt gttgctttta aatatctttt  84960
aatttggcta ctaggcccca tacaattctt tttcagaata ttcctggcta cccaatttgt  85020
ttatttttcc aaatgaactt tggagtcaac ttccttaatt cctcaaaata ttctgcaagt  85080
acttttagta agagtatatt aagtgaataa tttgacaact atctaagaac atattatagc  85140
ttttcccttg ttttgttttt gtacttatat attagtatag ttttaaagtt atattaaaat  85200
aggtcttcca cattttaaaa acttattcct agtgtattaa tttcttctat tataactaca  85260
gtattttatt ccagtaaaac ttctgactgg ttgatgctct tataaatcaa ggctataaat  85320
ttttcttcag ctactttgct gaattctcac aaactgtaac catttttac ttgattctct  85380
aggttgacca gtatataatc tttttatctg taaacaataa ctttagcgtt gctttcaaca  85440
tctatattct tattctattt catttttctt gtttatcaag aaatagctgt tttaatagag  85500
ttgtttttcg cccaaaaaga aaatagtctt tctttttcta cttatatctt taaaataaat  85560
gtaatgagaa agactgtggg aaaataaagc agacacctta tacaatggat taattttttt  85620
agtgccattt cttctggctt tctctattat tgggactctg aaatcttcgt tagtactact  85680
ctcaaaaatg ttcgaatgaa tgcaatcaga ttcaagggta caagtgcagg ttatataggt  85740
gaattgcatg ccttgggggt ttggtgtaca gactattttg tcacccaggt aataagcgta  85800
gtacttaata ggtagttttt tgatcctctc ccttctccca tcctcaaagt atccctgctg  85860
```

tctgttgttc cccctctttg tgtccatgtg ttcttgctgt ttagctgcca cttaagagaa 85920
catgtggtat ttttctgttc ctttgttagt ttgtttagga taatggcctc cagctccatc 85980
catgttgctg cacagaacac gattttgtgt ttctttatgg ctgtgtagta ttccatggtg 86040
tatatgtaac actttcttta tccagtctac tacttacgga catttaggtt gattccatgt 86100
cttcgctatc attaatagtg ctgtgatgaa catacgtgtg caatatgcct ttatggtaga 86160
atgatttata tccctttggg taatatgccg aataatggga ttgctcggtc agatggcaat 86220
tctaagtcct ctgaaattac cgcactgctt tccacaacag ctgaactagt ttacattccc 86280
acaagcaata aggggataag tgttcccttt tctctgcagg aatgattaat tcttttagag 86340
agtcaaagat ggaatcctag ggaagatgat atctgaggca ggtttagagt cattgggcaa 86400
ataaggggat taagaaggca ttctaggcag acagaaaacc aaaggcatga agctctgaaa 86460
cagcttacta tgtttggata tttataagct gttgttattg ttggagtata aactgtaaga 86520
gagagtagga ggacagaaaa aacagcctgt atgcgggggg aagaaaacat ttaaacagaa 86580
attctcaaaa gatttgggca gccagcccct ctagagaaaa acatagaatc acctagaaag 86640
ggtttttcat aaagtacact tttcatcacc cctattctgt cacctggaat attgataaca 86700
ctgaagggag tgtgccttat ctctcaggtg tatttggatg aaatagtttg agaaccatgc 86760
aggcaagttt aagccagtgt gttaaagaga atatgacatc agatttgcat tttacaatct 86820
tccttttgat aacaaaggga accttaaagg gctggagggg aagggcagac ggggctaggg 86880
gaggagaacc cttttaaaaa gctactgcag gtggggtgcg gtggctcaca cctgtaatcc 86940
cagcactttg ggaggccaag gcaggcagat cacctgaggt caggagttca agaccagcct 87000
ggccaacata gtaaaacccc atctctacta aaaatacaaa aattagctag gcatggtagc 87060
aggcacctgt aatctcagct acttgggagg ctgaggcagg agaattgctt gaacctggga 87120
ggcagaggtt gcagtgagcc aagattgtgc cgctgcactc cagcctgggc aagagagtga 87180
gactccatct caaaaaaaaa aaaaaaaaag ctactgcagt agatcaggag gaggcacagt 87240
gataaagaga agatctgagc tatgaagtgg cagtcaagat gattaaagga atatatagga 87300
agtacagttg atagaactta gcaagtgatt aggtaaatga agtgctagag aaaataaagg 87360
ggatattttt caattgtttt tagcattttg gcaaaaaatt atttaggaat gaaattgatg 87420
ctagtaacta agagtatgaa cttcccacat tagctggtaa ttttgatcac ccttgttctc 87480
catgaccata aatattttag agttgctatg aagacaagaa tgtttatttc ctgagtagct 87540
gtcagttgtc actatgaaac atgaaaataa atatcagttt gctatgtcta ggtattccga 87600
tatttatcca caattattcc ttaagatata ttagtatttt tatagataga tagatagata 87660
gatagaaata aacacatttt aatttttgtt tccatgctct ttagaattca actagagggc 87720
agccttgtgg atggccccga agcaagcctg atggaacagg atagaaccaa ccatgttgag 87780
ggcaacagac taagtccatt cctgatacca tcacctccca tttgccagac agaacctctg 87840
gctacaaagc tccagaatgg aagcccactg cctgagagag ctcatccaga agtaaatgga 87900
gacaccaagt ggcactcttt caaaagttat tatggaatac cctgtatgaa gggaagccag 87960
aatagtcgtg tgagtcctga ctttacacaa gaaagtagag ggtattccaa gtgtttgcaa 88020
aatggaggaa taaaacgcac agttagtgaa ccttctctct ctgggctcct tcagatcaag 88080
aaattgaaac aagaccaaaa ggctaatgga gaaagacgta acttcggggt aagccaagaa 88140
agaaatccag gtgaaagcag tcaaccaaat gtctccgatt tgagtgataa gaaagaatct 88200

-continued

```
gtgagttctg tagcccaaga aaatgcagtt aaagatttca ccagtttttc aacacataac  88260
tgcagtgggc ctgaaaatcc agagcttcag attctgaatg agcaggaggg gaaaagtgct  88320
aattaccatg acaagaacat tgtattactt aaaaacaagg cagtgctaat gcctaatggt  88380
gctacagttt ctgcctcttc cgtggaacac acacatggtg aactcctgga aaaaacactg  88440
tctcaatatt atccagattg tgtttccatt gcggtgcaga aaaccacatc tcacataaat  88500
gccattaaca gtcaggctac taatgagttg tcctgtgaga tcactcaccc atcgcatacc  88560
tcagggcaga tcaattccgc acagacctct aactctgagc tgcctccaaa gccagctgca  88620
gtggtgagtg aggcctgtga tgctgatgat gctgataatg ccagtaaact agctgcaatg  88680
ctaaatacct gttcctttca gaaaccagaa caactacaac aacaaaaatc agtttttgag  88740
atatgcccat ctcctgcaga aaataacatc cagggaacca caaagctagc gtctggtgaa  88800
gaattctgtt caggttccag cagcaatttg caagctcctg gtggcagctc tgaacggtat  88860
ttaaaacaaa atgaaatgaa tggtgcttac ttcaagcaaa gctcagtgtt cactaaggat  88920
tccttttctg ccactaccac accaccacca ccatcacaat tgcttctttc tccccctcct  88980
cctcttccac aggttcctca gcttccttca gaaggaaaaa gcactctgaa tggtggagtt  89040
ttagaagaac accaccacta ccccaaccaa agtaacacaa cacttttaag ggaagtgaaa  89100
atagagggta aacctgaggc accaccttcc cagagtccta atccatctac acatgtatgc  89160
agcccttctc cgatgctttc tgaaaggcct cagaataatt gtgtgaacag gaatgacata  89220
cagactgcag ggacaatgac tgttccattg tgttctgaga aaacaagacc aatgtcagaa  89280
cacctcaagc ataacccacc aatttttggt agcagtggag agctacagga caactgccag  89340
cagttgatga gaaacaaaga gcaagagatt ctgaagggtc gagacaagga gcaaacacga  89400
gatcttgtgc ccccaacaca gcactatctg aaaccaggat ggattgaatt gaaggcccct  89460
cgttttcacc aagcggaatc ccatctaaaa cgtaatgagg catcactgcc atcaattctt  89520
cagtatcaac ccaatctctc caatcaaatg acctccaaac aatacactgg aaattccaac  89580
atgcctgggg ggctcccaag gcaagcttac acccagaaaa caacacagct ggagcacaag  89640
tcacaaatgt accaagttga aatgaatcaa gggcagtccc aaggtacagt ggaccaacat  89700
ctccagttcc aaaaaccctc acaccaggtg cacttctcca aaacagacca tttaccaaaa  89760
gctcatgtgc agtcactgtg tggcactaga tttcattttc aacaaagagc agattcccaa  89820
actgaaaaac ttatgtcccc agtgttgaaa cagcacttga atcaacaggc ttcagagact  89880
gagccatttt caaactcaca ccttttgcaa cataagcctc ataaacaggc agcacaaaca  89940
caaccatccc agagttcaca tctccctcaa aaccagcaac agcagcaaaa attacaaata  90000
aagaataaag aggaaatact ccagactttt cctcaccccc aaagcaacaa tgatcagcaa  90060
agagaaggat cattctttgg ccagactaaa gtggaagaat gttttcatgg tgaaaatcag  90120
tattcaaaat caagcgagtt cgagactcat aatgtccaaa tgggactgga ggaagtacag  90180
aatataaatc gtagaaattc cccttatagt cagaccatga aatcaagtgc atgcaaaata  90240
caggtttctt gttcaaacaa tacacaccta gtttcagaga ataaagaaca gactacacat  90300
cctgaacttt ttgcaggaaa caagacccaa aacttgcatc acatgcaata ttttccaaat  90360
aatgtgatcc caaagcaaga tcttcttcac aggtgctttc aagaacagga gcagaagtca  90420
caacaagctt cagttctaca gggatataaa aatagaaacc aagatatgtc tggtcaacaa  90480
gctgcgcaac ttgctcagca aaggtacttg atacataacc atgcaaatgt tttcctgtg  90540
cctgaccagg gaggaagtca cactcagacc cctccccaga aggacactca aaagcatgct  90600
```

gctctaaggt ggcatctctt acagaagcaa gaacagcagc aaacacagca accccaaact 90660
gagtcttgcc atagtcagat gcacaggcca attaaggtgg aacctggatg caagccacat 90720
gcctgtatgc acacagcacc accagaaaac aaaacatgga aaaaggtaac taagcaagag 90780
aatccacctg caagctgtga taatgtgcag caaaagagca tcattgagac catggagcag 90840
catctgaagc agtttcacgc caagtcgtta tttgaccata aggctcttac tctcaaatca 90900
cagaagcaag taaaagttga aatgtcaggg ccagtcacag ttttgactag acaaaccact 90960
gctgcagaac ttgatagcca caccccagct ttagagcagc aaacaacttc ttcagaaaag 91020
acaccaacca aaagaacagc tgcttctgtt ctcaataatt ttatagagtc accttccaaa 91080
ttactagata ctcctataaa aaatttattg gatacacctg tcaagactca atatgatttc 91140
ccatcttgca gatgtgtagg taagtgccag aaatgtactg agacacatgg cgtttatcca 91200
gaattagcaa atttatcttc agatatggga ttttccttct ttttttaaat cttgagtctg 91260
gcagcaattt gtaaaggctc ataaaaatct gaagcttaca ttttttgtca agttaccgat 91320
gcttgtgtct tgtgaaagag aacttcactt acatgcagtt tttccaaaag aattaaataa 91380
tcgtgcatgt ttatttttcc ctctcttcag atcctgtaaa atttgaatgt atctgtttta 91440
gatcaattcg cctatttagc tctttgtata ttatctcctg gagagacagc taggcagcaa 91500
aaaaacaatc tattaaaatg agaaaataac gaccataggc agtctaatgt acgaacttta 91560
aatatttttt aattcaaggt aaaatatatt agtttcacaa gatttctggc taatagggaa 91620
attattatct tcagtcttca tgagttgggg gaaatgataa tgctgacact cttagtgctc 91680
ctaaagtttc cttttctcca tttatacatt tggaatgttg tgatttatat tcattttgat 91740
tccctttct ctaaaatttc atctttttga ttaaaaaata tgatacaggc atacctcaga 91800
gatattgtgg gtttggctcc ataccacaat aaaatgaata ttacaataaa gcaagttgta 91860
aggactttt ggtttctcac tgtatgtaaa agttatttat atactatact gtaacatact 91920
aagtgtgcaa tagcattgtg tctaaaaaat atatacttta aaaataattt attgttaaaa 91980
aaatgccaac aattatctgg gcctttagtg agtgctaatc tttttgctgg tggagggtcg 92040
tgcttcagta ttgatcgctg tggactgatc atggtggtag ttgctgaagg ttgctgggat 92100
ggctgtgtgt gtggcaattt cttaaaataa gacaacagtg aagtgctgta tcaattgatt 92160
tttccattca caaaagattt ctctgtagca tgcaatgctg tttgatagca tttaacccac 92220
agcagaattt ctttgaaaat tggactcagt cctctcaaac tgtgctgctg ctttatcaac 92280
taagtttttg taattttctg aatcctttgt tgtcatttca gcagtttaca gcatcttcat 92340
tggaagtata ttccatctca aacattcttt gttcatccat aagaagcaac ttcttatcaa 92400
gtttttttcat gacattgcag taactcagcc ccatcttcag gctctacttc taattctggt 92460
tctcttgcta catctccctc atctgcagtg acctctccac ggaagtcttg aactcctcaa 92520
agtaatccat gagggttgga atcaacttct aaactcctgt taatgttgat atattgaccc 92580
cctcccatga attatgaatg ttcttaataa cttctaaatg gtgatacctt tccagaaggc 92640
tttcaatgta ctttgcccgg atccatcaga agactatctt ggcagctgta gactaacaat 92700
atatttctta aatgataaga cttgaaagtc aaaagtactc cttaatccat aggctgcaga 92760
atcaatgttg tattaacagg cacgaaaaca gcattaatct tgtgcatctc catcggagct 92820
cttgggtgac taggtgcctt gagcagtaat attttgaaag gaggttttgg ttttgttttt 92880
tgtttttttt ttttgttttt tagcagtaag tctcaacact gggcttaaaa tattcagtaa 92940

-continued

```
actatgttgt aaaaagatgt gttatcatcc agactttgtt gttccattac tctacacaag  93000
cagggtacac ttagcataat tcttaagggc cttggaattt tcagaatggt aaatgagtat  93060
gggcttcaac ttaaaatcat caactgcatt agcctgtaac aagagagtca gcctgtcctt  93120
tgaagcaagg cattgacttc tatctatgaa agtcttagat ggcaccttgt ttcaatagta  93180
ggctgtttag tacagccacc ttcatcagtg atcttagcta gatcttctgc ataacttgct  93240
gcagcttcta catcagcact tgctgcctca ccttgtcctt ttatgttata gagacagctg  93300
cgcttcttaa actttataaa ccaacttctg ctagcttcca acttctcttc tgcagcttcc  93360
tcattctctt catagaactg aagggagtca aggccttgct ctggattaag ctttggctta  93420
aggaatgttg tggctgacgt gatcttctat ccagaccact aaagcgctct ccatatcagc  93480
aataaggccg ttttgctttc ttacctttca tgtgttcact ggagtaattt ccttcaagaa  93540
tttttccttt acattcacaa cttggctaac tggcatgcaa ggcctagctt tcagcctgtc  93600
ttggcttttg acatgccttc ctcacttagc tcgtcatatc tagcttttga tttaaagtgg  93660
caggcataca actcttcctt tcacttgaac acttagaggc cactgtaggg ttattaattg  93720
gcctaatttc aatattgttg tgttttaggg aatagagagg cccagggaga gggagagagc  93780
ccaaacggct ggttgataga gcaggcagaa tgcacacaac atttatcaga ttatgtttgc  93840
accatttacc agattatggg tacggtttgt ggcacccccc aaaaattaga atagtaacat  93900
caaagatcac tgatcacaga tcgccataac ataaataata ataaacttta aaatactgtg  93960
agaattacca aaatgtgata cagagacatg aagtgagcac atgctgttga aaaaaatgac  94020
actgatagac atacttaaca cgtgggattg ccacaaacct tcagtttgta aaagtcacag  94080
taactgtgac tcacaaaaga acaaagcaca ataaaacgag gtatgcctgt atttttaaaa  94140
aaagcttttt gttaaaattc aggatatgta ataggtctgt aggaatagtg aaatattttt  94200
gctgatggat gtagatatat acgtggatag agatgaagat cttaattata gctatgcagc  94260
atagatttag tcaaagacat ttgaaaagac aaatgttaaa ttagtgtggc taatgaccta  94320
cccgtgccat gttttccctc ttgcaatgag ataccccaca ctgtgtagaa ggatggaggg  94380
aggactccta ctgtccctct ttgcgtgtgg ttattaagtt gcctcactgg gctaaaacac  94440
cacacatctc atagataata tttggtaagt tgtaatcgtc ttcactcttc tcttatcacc  94500
cacccctatc ttcccacttt tccatctttg ttggtttgca acagcccctt ctttttgcct  94560
gactctccag gattttctct catcataaat tgttctaaag tacatactaa tatgggtctg  94620
gattgactat tcttatttgc aaaacagcaa ttaaatgtta tagggaagta ggaagaaaaa  94680
ggggtatcct tgacaataaa ccaagcaata ttctgggggt gggatagagc aggaaatttt  94740
atttttaatc ttttaaaatc caagtaatag gtaggcttcc agttagcttt aaatgttttt  94800
tttttccagc tcaaaaaatt ggattgtagt tgatactaca tataatacat tctaattccc  94860
tcactgtatt ctttgtttag tttcatttat ttggtttaaa ataatttttt atcccatatc  94920
tgaaatgtaa tatattttta tccaacaacc agcatgtaca tatacttaat tatgtggcac  94980
attttctaat agatcagtcc atcaatctac tcattttaaa gaaaaaaaaa ttttaaagtc  95040
acttttagag cccttaatgt gtagttgggg gttaagcttt gtggatgtag cctttatatt  95100
tagtataatt gaggtctaaa ataataatct tctattatct caacagagca aattattgaa  95160
aaagatgaag gtccttttta tacccatcta ggagcaggtc ctaatgtggc agctattaga  95220
gaaatcatgg aagaaaggta attaacgcaa aggcacaggg cagattaacg tttatccttt  95280
tgtatatgtc agaatttttc cagccttcac acacaaagca gtaaacaatt gtaaattgag  95340
```

taattattag taggcttagc tattctaggg ttgccaacac tacacactgt gctattcacc 95400
agagagtcac aatatttgac aggactaata gtctgctagc tggcacaggc tgcccacttt 95460
gcgatggatg ccagaaaacc caggcatgaa caggaatcgg ccagccaggc tgccagccac 95520
aaggtactgg cacaggctcc aacgagaggt cccactctgg ctttcccacc tgataataaa 95580
gtgtcaaagc agaaagactg gtaaagtgtg gtataagaaa agaaccactg aattaaattc 95640
acctagtgtt gcaaatgagt acttatctct aagttttctt ttaccataaa aagagagcaa 95700
gtgtgatatg ttgaatagaa agagaaacat actatttaca gctgcctttt tttttttttt 95760
tcgctatcaa tcacaggtat acaagtactt gcctttactc ctgcatgtag aagactctta 95820
tgagcgagat aatgcagaga aggcctttca tataaattta tacagctctg agctgttctt 95880
cttctagggt gccttttcat taagaggtag gcagtattat tattaaagta cttaggatac 95940
attggggcag ctaggacata ttcagtatca ttcttgctcc atttccaaat tattcatttc 96000
taaattagca tgtagaagtt cactaaataa tcatctagtg gcctggcaga aatagtgaat 96060
ttccctaagt gccttttttt tgttgttttt ttgttttgtt ttttaaacaa gcagtaggtg 96120
gtgctttggt cataagggaa gatatagtct atttctagga ctattccata ttttccatgt 96180
ggctggatac taactatttg ccagcctcct tttctaaatt gtgagacatt cttggaggaa 96240
cagttctaac taaaatctat tatgactccc caagttttaa aatagctaaa tttagtaagg 96300
gaaaaaatag tttatgtttt agaagactga acttagcaaa ctaacctgaa ttttgtgctt 96360
tgtgaaattt tatatcgaaa tgagctttcc cattttcacc cacatgtaat ttacaaaata 96420
gttcattaca attatctgta cattttgata ttgaggaaaa acaaggctta aaaaccatta 96480
tccagtttgc ttggcgtaga cctgtttaaa aaataataaa ccgttcattt ctcaggatgt 96540
ggtcatagaa taaagttatg ctcaaatgtt caaatatttt gattgcctct tgaattcatt 96600
tgctaattgt atgtgtgtgt gtttctgtgg gtttctttaa ggtttggaca gaagggtaaa 96660
gctattagga ttgaaagagt catctatact ggtaaagaag gcaaaagttc tcagggatgt 96720
cctattgcta agtgggtaag tgtgacttga taaagccttt ggtcttaaat cttgggcatt 96780
ttgatttgta aatctgaccc tgagaattgg gttacccaga tcaaagactc atgccagtta 96840
aaaagaacat tacctgtatt ttttatcatg tgttatctct taagaagagg cagattagtt 96900
ctaaaatcaa caaattgtat ttaattgaaa taatttagtg atgaggaaga ggtccattct 96960
agtgcctgct aaatgtataa tccttcttag aatgtgaagt tgtccttaaa cttttaaata 97020
ccttcagtta atctttatat tgtcatttat gaaaaccttg aactaagact tatgtatctt 97080
tcatctagct ctggttttaa tgcaggtagc atttaattgt ccccactgta ctgggtatag 97140
tctgctaaac attaaggagt agttttgcat ctctccttgt tctgatacta gggtcaaagc 97200
ccacttttta tagatgggca gcaaaaggca cattggacat gctgataaat gttgccctaa 97260
ttgtgatcta aacatgataa aatatacata cataagtgcc cttatctgct gcaagtgacc 97320
cttgttttgt tttggttggg gtgggggtg tttgggatgg aatggtgatc cacgcaggtg 97380
gttcgcagaa gcagcagtga agagaagcta ctgtgtttgg tgcgggagcg agctggccac 97440
acctgtgagg ctgcagtgat tgtgattctc atcctggtgt gggaaggaat cccgctgtct 97500
ctggctgaca aactctactc ggagcttacc gagacgctga ggaaatacgg cacgctcacc 97560
aatcgccggt gtgccttgaa tgaagagtaa gtgaagccca gggcctctcc cctctttgcg 97620
gccactgata ggaaagccca atctttggtt gaaaggaaga gagttcagcg tgcactttta 97680
catttataaa atgggcatca aaatgcctgt ttggcagtca tgcgataaga agttgtattt 97740
gctaatgtga ataacttgag atgatttcat tatctgaatt gtacagttta gccattaatt 97800
aggagcagtc agagtgtctg taaccacatg gcctcagtta taccataaac ttgaaattgt 97860
ttatgtgctc acatgctaca agtgacggct cctgtgtgcc tggccactat attagtatgt 97920
attgactcca cttccatgtt gcagtatctg aaacagaaag taagtctaat gagaaacttt 97980
gggattccca ggtcaaatac cttccatatg tatgtagcaa aaacaaaata caaagcctag 98040
aagttctgta gaaatagaac tgatttttac tttcattcaa actattcatt atttccacaa 98100
tagtaatcaa aactgcttct acttttactg ctgctaaatg atcagcaaat tactggatat 98160
ggatatatat tattttccag gaatataaga atttagaata gaactgcaag agtatgcact 98220
taaatatatt tagtgcatcc agttgctaat gttttgtttt aaacaccatc cactttgcat 98280
gaagtctaaa ccttcagttg gaaaaagcct catttttaat attcctctac tgtgctgata 98340
atcctgtata acactaaaag aatagatgaa tgttcacggt gctacacaga aatgtttttt 98400 ttttttttt ttttttttt gagatggagt ttcgctcttg ttgcccaggc tggagtgcaa 98460
tggcgcgatc ttggttcacc gcgacctcca cctcccaggt tcaagagatt ctcctgcctc 98520
agcctcccta gtagctggga ttacaggcat gtgccaccac acccggctaa ttttgtattt 98580
ttagtagaga cagggtttct ccatgttggt caggctggtc tcgaactccc gacctcaggt 98640
gattgcccac ctcggcctcc caaagtgcct tacaggcatg agccgccgcg cctggccaga 98700
aatcttacaa gttattttgc ccacgattgg ttttaaaata attttaattt tgcactattt 98760
cctttagtgt ctttttctct gcatccacca aactatagaa tcatttgctg agcttataag 98820
aaatgctcat actgctcatt gcaacagcta gccaaatttg tcctttgctg tttaaaactc 98880
taactagcat ggttttacta aatttatgtt aacacagttt ctctctctgg gttgtgggga 98940
gacaaatcaa ttataaataa tctctttaga aaagttactc tttctatatg aaagtgtgac 99000
ttgactttct atgataatta tgatccaaaa attttatggt gtgtacctga ccacttttac 99060
aaatgattaa ttggaaggta gaaattgctg attcataaca tgtaacttat aaacttatga 99120
tggactactt taagcataaa ttttttttt tttttaaga cagagtttca ctctgtcacc 99180
caggctggag tgcaatggtg cgatctcggc tcactgcaac ctccatctcc tgggttcaag 99240
caattctcct gcctcagcct cccgaatagc tgggattaca ggcatgcact accacaccca 99300
gctaattttg tatttttagt agagacaggg tttctccatg ttgatcaggc tggtctggaa 99360
ctcctgacct cgggtgatcc gcccgcctcg gcctcccaga gtgctgggat tacaggcatg 99420
agccactgtg cccagcctga aatatttttt taatctaccc tgactcctct tgctctttct 99480
gaagaaaaat ttttaaaaat gtatgtaggt gcctttaatt agaaaaaaaa ttaaaaatta 99540
aggcaacttg tgctcatatt ggtaatagca tttctttcaa gaactcagta atactgcatt 99600
gtctttaaag cataatatct cttagacttg acggtttgag attctaaatc actgaagaac 99660
ctcttgtgaa aatgatagtt ttaaaatttc ttttcaaaaa tagtcctatt gcaaaatgtt 99720
tgattttctt gaagtttcct ggaaactata tttcattcat tgtaatgaat ttaattttca 99780
ttaacataga tctctaatat ttttctcagc tcaccacaac ctccacctcc cgggttcaag 99840
tgattctcat gccacagcct cccgagtagc tagaattaca ggcacccacc cggctcattt 99900
ttgtattttt agtagagaca gggtttcacc atgttggcca gattgatctc gaactcctgg 99960
cttcaggtaa cccacccacc ctggcctccc aaagtgctgg gattacaggt gtaggccacc 100020
atgcccagcc agcttttcca taattcttat aaatgccaat gcctgaaatg gaatctgaca 100080
tataaaaaat tacatgaaga acttttatta ttttgcattt gaaaaccatg aaaaatagtt 100140
ggaccagagt ctcagaaagc ttgtagtttg ttagtttaac tgctctaaat gtcaggcaga 100200
tacaaaacta ttaaaagaca tgcttcaaat atgaagacaa tttaaaagca cagctgtaca 100260
cttttgcttt ttgtctagtt tcaaggtaaa gatgaataat catttagata atgcttaagc 100320
tatgcttatg catacttaga gcaattctcc aaaataaaaa attttaatac ttaaatacat 100380
gattaaaata gacacgtatc caatgtcaat acagacttta ctcagaaata gcttttgaag 100440
tttcttctac cccataaata gattttattt tatggctggc agaaatgaaa attacaactt 100500
tttgccaaga acagagaata gaataatctc aaattggggc tgcggactca gttttatgtt 100560
caaagctgtg tgaacctcat cactgagttc ttacaaatcc ctgtgtccac atgctccaaa 100620
ccacccactg tgagttcaga aaagaactct gagtgcatct ttcagtagga aagtaaaaac 100680
tgatttttac atttcctttg agccaaacca gctgtttctt ctttaaagat ttccctttga 100740
gatttccatt ttatgactaa gtctaaccag tatttttttg gcaagtaaga gttgtgggag 100800
tgtatctgtc atcataagga aatcaaagcc agaaatgcct tctgccatgg tgggtgatgt 100860
taaacatttc aaggaacttt atattataaa aattgtcaaa cataaaagga aaagtgcaat 100920
ataatgaatt ccatggaccc atcacacagc atcaatattt atcaacattt tatcaatatt 100980
ttttcatata tttttcccac atccactccc actagtgttt gaaagcagaa gacagataac 101040
ttaccatctt acctgttaac atttcaggat gtatttctaa caggtaaaga ctttatcatt 101100
taatatttag actgtgtttg ttcaaattat ctgattagat tctatttcag aaaacacaca 101160
cataaacaaa aatgataatg agaaaaagaa agcccttcca catgattgac acttctgagt 101220
agtgtgatcc cagttcatgt ccattgtctg ggatagctat taaataaaac ttcctctcat 101280
aaaattctct ccatttagaa gataaattct gtgattcaca agcctctttt tatttataat 101340
agcccttccc ctttctttat gaatttgaat ttgtttttta aagaaactgt gatttttctct 101400 gtaaaattcc ccacattctg gatttggccg atttcatctt ggttcttttg tttactttaa 101460
cctattcctc tatccccagt atcttctgtg gactggtagt ttgactggtt ctttttcttt 101520
tctttttttt tttttttttt tttttttgag acaggctctc gctctgtcgc ttaggctgga 101580
gtgcagtggc ccaatctcag ctcactgcaa cctccacctc ccaggttcaa gctattctca 101640
tgcctcagcc tcctgagtaa ctgggactgc aagcatgtgc cacctcatcc tgctgatttt 101700
tgtactttta gtagagacgg ggtttcgcca tgttggccag gctggtctgg aactcctggc 101760
ctcaagtgat ccgcccacct tggcctccca aagtgctggg attacaggca tgagctatca 101820
cgcccagctg atttttaagt aatataagta tgtgtgcatg tatagtatac attggcaaaa 101880
acacttcata agtagtgcta aaatcatctt atttatatac atcaggagac acataatgtc 101940
tgtttgtttc ccattttagt gatattaaga gtgtttagca tgtttagttg tcagcctgat 102000
ccatcattat gttcttcatc aaactttcac cagatagttt cacatcaatt gatgatcatt 102060
gcctgtttct attattttgt tttcaagttg acagttttct ctcacttgat gttgtgtaaa 102120
tttagttata taaagttaaa ttattttgct attttttcta tgctgtatac atttgaataa 102180
ctgacctaat ttttacttta aaaatatttt acaattagaa gtccaaatag taaatcaaag 102240
gttaagaatt tttgcagaaa tctgttatat agatgacatt ttaatatttg ccctttatat 102300
catttaccat gagccaaatt tcaagtcata ttaaaatgac tgtcatgtgc taattctaac 102360
aatatttgaa agacccctat caaaataaat atacctttta gtagccactt tattagaaaa 102420

-continued

```
tcaactttaa gttattcccc catgtttttt tctaattgag atataattca cataccataa 102480
aatttaccct tttaaagtat acaattcagt tgtttcagta cattcacaaa gctatgcaaa 102540
tgtcacctct acctagtttc agaacgtttt catcattccc agaaggaaac cctgtattta 102600
ttaggcagtc acttcccctt ctccccttct tccttcctct aagtggcaac cacaaataaa 102660
cattcagttt ctctggattt acctattctg ggcattttgt attagtgaaa tcatgtattt 102720
ggcctttctc tctggcttct ttcatgtacc tcaatgtttt caagtctcat tcattttatt 102780
aaaaaaaaaa agtacctttt ttctttttct tttttttttt tttgtccacg tatatattca 102840
caccacattt tttgagacag agtctcgctc tgttgcccag gctagggtgc aatggtgcaa 102900
cctcagctca ctgcaacctc tgtctcccgg gttcaagtga ttctcatgcc tcagcccccca 102960
agtagttggg attacagttg tgcaccacca cacccagcta atttttgtat ttttagtaga 103020
gacagggttt caccatgttg gctaggctgg tctcaaactc agcctcaagt gatccttcta 103080
ccttagcctc ctaaagtgct gggattacaa gcatgagcca ctgtgcccag ccacattttc 103140
tttttccatt tattagttaa ttgacatttg gatcgttttct actttttggc gattataaat 103200
tatgctgcaa tgaacatcgg tgtacaagtt tttgtgtgaa catgttttca gttaccttgg 103260
gatatacacc taggagtgac attgttagta atatggtaac tttatgttta actttttgaa 103320
gaactgccaa actgttttcc aaagtagctt tatgctttta catttctgcc aacaatgtat 103380
gaaggttcca gtgtatctcc acatcctcaa gaaaatgtta ttgtcttttt aattgtaacc 103440
atccaagtgg gtatgaagtt tatctcgtga ttttgatttg cattttccta atggctgata 103500
ttgggcatct tttcacgtgt gtattgacca tgtatttttt tgagaaaagt ctacttatat 103560
gtttttaatt gtattatttt tagagttgta agaatatgtt atgttgatac ttgaactttg 103620
tcaaatgcct ggtttgcaga tattttctcc tatcccacag gttgtcgctt cactttgata 103680
atgtccttaa agtacaaaag ttttaaattg attttgatga aactcaattt ctttttaatt 103740
ggcagcttgt gcatttgggg tcatatttaa gaaatcattg cctcattcaa gatctgaaag 103800
atttacacct atgctttctt ctcagagtat tataacttta gttcttacat ttagattttt 103860
aattaatgtt gagttaattt gatggtgaga gataagagtc caacttcatt cctttgcaag 103920
tagctgtcca gttttctcag caccatttgt taaaagactg tttttttttca attaactgac 103980
caagatgtat gggtttattt ctggactctt aattctgtta atctgcatga cttttcttat 104040
gccagtacca cactgtgctg attcctgtag ttttgtagta aattttgaaa tcaagacagg 104100
taagtcttcc aactttgtac ttttgcctac catgtttctt gggtttccat atgcatttta 104160
agatcagctt ctccgtttcc tttctggatt tttttttttt tttttttttt ttttttttttg 104220
gtggagctgg agtcttacta tattacccaa gctggttttg aactcctggc taaagagatc 104280
ctccctccta ggcttcccag agagctgggg ttacaggcat gagccaccac atccaacccc 104340
cttctgggac tttgactggg gttctgttga atctgttggt caatttggag agtattgata 104400
tcttaacatt aaagcttcca atttatgaac acaggctatt tttccattta ttcttaaatt 104460
tctttcagta atgttttgga tgaaacatgt acaaagtcct gcacttttta ttttttttaa 104520
gacagagtct tgctctgctg cccagtccag agtgcagtgc tgccatctca gctcactgca 104580
acctccacct ccgggttcaa gtgattctcc tgcctcagct ggaactacag gtgcgcgcca 104640
ccatgcctgg ctaattgttt tgtgtttttg gtggagacag ggtttcacca tgttggccag 104700
gctggtctca aacacctggc ctcaagtgac ctgactgcct tggcctccca aagtactggg 104760
attacaggca tgagccacca cgcctggcct gtacttctgt taaaattttt tctatgtatt 104820
```

tttttatcc tattgcaaaa tcaaattttt tgttgataat atatggtcat aaatttcatt 104880
tttatatatt ggtctcatat cctaccaact tgctgaacta gcttattagc actaactttt 104940
tttggtagat tccttaggat ttgctgcata caagattatg tcatctacaa gtagagatag 105000
ttttgtttct tcacttccaa tctgggtggc tttatgtttt tttcttgcct gattacccag 105060
ttagaacttc cagaaaatgt caggtacaat taacaactgc aaacatcctt gtcttattca 105120
ttttagaaag aaatttttag tttttcacca ttaagtatga tactagttgt aggttttgtt 105180
taaaaaaaga ctgtgtcaag ttcagaagtt cccttctgtt gctagtttgt tgaataattt 105240
tatcacgaaa gggtgttgaa cttttctcaa atgctgtggc tacatctaat gaaatgatca 105300
tgcgttcttc tcctttattc tattaatatg gtatattata ttgattcatt tttatacatt 105360
agattaacat tatatttctg gaataaatcc cacttggcct cagtgtgtat tactttttat 105420
atattgctgg agtctgtttg caggtatttc attgaggact ttcgcatctc tgttgataag 105480
gtatactgat ctttagttct cttgtgatat ctttggtttt ggtgtcagag taattctgag 105540
ttcacaaaat gcattgggaa atgttccctt ctctatcttt tggaagagtt tacaaaggat 105600
tggtttaact ctttttttaaa tgtttgagga aattctctac ccctgggctt tcctttgtgg 105660
gaatttttaa acatttttaa aatagattat ttttaaagca attttagggt aaaagcacat 105720
tgaatgaaag gcacagagct tccttaagta catgctgccc ctgtatgtgc atagcctccc 105780
tcattatcaa catcctttac cagaatggta catttgttgc agtcaatgaa cctgcattga 105840
caattgtcga tgaaagttca tagtttagag ttcacctttg gtgttatgta ttctgtgagt 105900
ctggatccat gtttaatgat actcattcac cattacagta tcattcagag taatttcact 105960
gccttaaaag tcctctgtac cctacctatt tttctctcct accccactaa cccttagcaa 106020
ccaatgatct ttttatctca ataattttgc ctattccaga atgtcatata gttggaatga 106080
tacagtatat ggagcctttt cagactggtt tttgtcactt agtaataagc ttttaaattt 106140
tccaccatgt catgatcgtt catttctttt cagcattgaa taatattcca ttgtctggtt 106200
tatcacagtt gatttatcca ttcacatagt gaaagacatc ttagttgctt ccaagttttg 106260
acaattatga ataaagctgt tataaaagta tgtaggtttt tgtgtggaca aaagttttca 106320
gctcctttga gtaaataaca cagagcacag tagcttgatt gacagtaaga gtaagaaata 106380
tttttctca gtctgtgtct tattttttca ttcacttgac agtgccattt gcagaacaaa 106440
cagaaagttt taattttaat gaagtctagg ttatcagtta attcatgaat aatgtttttg 106500
gtattgtatc taaaaagtca acaccaaggt catctatatg ttctgtgtta tcttccagaa 106560
attttatagt tctgcatttt acatttaggg ctgtgaccca ttttgcatta attttgcaaa 106620
agctataaag actatgtata gattcacttg tttgcatgtg gagttgtcca gttgttcccg 106680
taccatttct taaagactat ctttgcttta ttgtattacc tttgctactt tgtcaaagat 106740
cagttgatta taattaagtg gtctgtttct ggactcttta ttctgttcca ttgatatatt 106800
tgtctagact ttcaccaata ccacactatc ttgttaactt aggctttaga gtaagtcttg 106860
caatcatgta gtgtcagtcc tctgacattg tttttctcct tcagtattga gttggctatt 106920
cttttgccta ttactaagta aaaaaagcag tctgaaaagg ctatatatac agtcatttat 106980
tggtcttttg cctcttgata taaactttaa aattactttg tcagtatcct caaaatcttg 107040
caggaatttt gatagattgc actgcatttc tagattgagt tagaaatact gccatcttga 107100
caatacacat cttcctatcc atgaacatgg aacatctctt tcttggatat ccttcattag 107160
aattttgcat tttccccata tagaccatgt acatattaga tttatacata aatatttcat 107220
ttgggggggt gctaatggta atgtattttt atctcagatt ctgcttgtac attgctggta 107280
tgcagaaaag tgatcaactt ttgtatatta aacttgtttc ctgcaaccat gttatataat 107340
cactttagat ccagtttttt ttttttggt cattctttca tattttctag gtgatcatgt 107400
catctagcaa agacaacttc tttctaatct gtataccttt tattttcttg tcttaatgta 107460
ttagctagca tttccagtat gatgttgaaa ggcattggtg agaggcaaca tacttgcctt 107520
gttcctgatc tcagcaggaa atcttcaatt ttatgttagc tctatggttt tgtagatatt 107580
ctttatttac attaaatatg ttagctgtat ggttttgtat atattcttta tcaggttcag 107640
gtagttcccc tcttttccta gtttactgag aggcttttga aaatcattaa tcagtgttgg 107700
attttgtaaa tactttttt ccacctattg atattaccat atgatttttc tttagcttat 107760
taacgaaatg gattacatta attgattttc aaattttgaa ctagactggc atacctggag 107820
caaatcccac atggttgtga tacattattt atgaatgcat tcatggtcat ggttgctatt 107880
agtctgtagt tatcttttat tgtaaagact ttggtgttgg tattaaggta atgctgccct 107940
catagaataa gttatgaagt attttctctg cttctgtctt aattgagatt gtagagaatt 108000
catataattt cttccttaaa actttggtag aaatcagaat gaaccatctg tgtctggtac 108060
tttgttttga aaagttattg ctgattcaat ttctttcata gatataggcc tatttagatt 108120
attattttgc ataaatattg gtagttgtgt ccttcaagga attggtccat ttcaccttga 108180
ttattaaatg tgtgggcaca tttgttcata atatttcttt attatccttt gtttttgaga 108240
cagggtctca ctctggttgc ccaggctgga gtgcagtagt atgatctcag ctcactgcag 108300
ccttgacttc ctgggctcaa gtgatttacc cacctcagcc tcccaagtag ctcggactac 108360
aggcacatgc caccatgcct ggctaatttt tttattatta ttagagatgg agttttccta 108420
tgttgcccag tgtggtcttg aactcctgga ctcaagcaat ctgcctgcct cagcctccaa 108480
agagtgatgg gattgcaggc atgagccatc acacctagcc tgatggcaga actttttagg 108540
aacaatagaa tggtatatgg cattttcaaa aattgttttc ccctcctcct atggaagcat 108600
gaagggattt ttctctagta ttcattgtga gaacctcatc tggctcctga atgtagaaaa 108660
ctcacaaaac tgtgaggaac ctattatgac tggatgcctt tggagttgtt cacactgaac 108720
ctccagcaat tcatcaatta tatttcagat tttcctatcc caacactggt tcctacagag 108780
gtttctgctc cagtaagctg taattctttt tatccatctg cttccttggt tgtgagggca 108840
gtgattttcc ctgtgacctc atttctctga cagatctaag tagtcttgat tacatctttt 108900
aacctgttgt aggtatattc agattttcta tttcttcttc agtcaatttt agtagtttgt 108960
gtttttctag aagtttgttc tctagctctg ctttagctcc atccaataaa atatgagtat 109020
gtcgagtttt catttacaac aaggtatttt ctaatttcta tcatgttttt ttgattcctg 109080
actgtatagg agtatatttt tacctattac ccaaatttgc ttgttattca tgtataattt 109140
tatcagaaaa cacactttgc acaatttttg cagtgttaca tttatttaga cttgttttat 109200
aacttgacat acagtccatc ctggagaatg tttcacgtgt gcttgagaag aatgtgtata 109260
ttcagctgtt ggtgggtggc atgttttata gatgtctgtt agacctagtt ggtttatagt 109320
gttttttaca acttctgttt tctttttaat cttctatcta cttttagcca ttattgaaag 109380
tggattagta aattatctat ttattccttt aattctgcca ttttttgctt catgtatttt 109440
ggtgctctgt tgcttattac atgtatgttt acatttgtta catcatttta atggcttgaa 109500
ctttttatta taaaatgtgt atatcttgta gatatcgtat agttaaatct ttttaaaaat 109560
tgatattgct agtctttgcc ttttaatttt tcaatttata tacatttaac ataattattg 109620
ataaggtagg atttgtctgc cattttgtct gtatcttgtc tttttttgtg ttcaatagat 109680
attttctagt gtactgtttt aattcccttg tcttttacta aattttttga tgttcttaat 109740
ggtttccctg ggattacaa ctaacttata acagctagtc tgaagtaata ccaatttcat 109800
tacaatataa ggaaactttg ttcccatata gctacattcc ctctttttac tctgtgctat 109860
tatacaaatt acattttatt ttatgcccat taacacagat tatgtttttt cttttaaatc 109920
agattgatat tgtcatttaa atcaaatatg agaaaaatag ttacaaaaaa atacatatat 109980
gatttcatat ttacctatgt aattatcttt actggtgctc tttaagttct taggtgtatt 110040
tgaggtactg tctagtgtcc tttcctttca gcctgaagta tacatttagt attttttgta 110100
ggacatgcct gaaaacaata aactcttatt tatcagagaa tgtcctaatt tattatataa 110160
tacatttctg aaagatagtt ttgcaaaata cagaattctt ggttggcagt ctttttcttg 110220
tggttctatg tcattctact gccttctggt cttcattgtt tctgatcaga gatcagctat 110280
taatcttatt gggaatcctg catacatgat aatcatacag ttttcatgat tttcttgtgt 110340
tggctttcag cagtttggtt atgatgttta tatgtatgca tatctttggg tttatgttac 110400
atggagttag ttgagcttct tggacatgta gattgatgtt gttcatcaaa tttgagaagt 110460
tttcggccat tatttttcaa atattcttcc tattctttat tcttcatcct ctactttggg 110520
gacctgcatt atgtctatgt tggtatgctt tatggtcttc cacagatctc tgaggttctg 110580
tttatgtttt catttttcag actgaataat ctcaattgac ttatcttcaa gtcccttttt 110640
cccctccttt tcaactctgc tattgaaccc ctctaatttt tactgcagtt attacacttt 110700
cagctttaga attctattta ataatatctt tttcttgagt ttatctcatg tatttaataa 110760
aatgctgtag tcttacttta gttatttaaa tacagttttc tttcattatt tgggcataca 110820
tgaaatagct gacttaaagt ctttgtccag tggcctaaca tctggacttt ttcaggaata 110880
gcctctattg actactttat aggggccata ctttgtttct gtttctctta attgtttaga 110940
cattttaaac taatgtaatg gctgagagca gtggctcgtg cctgtaatcc cagcacgttg 111000
agaggccaaa gcaggagcat cacttaagcc caggagttca agactagcct gggcagcata 111060
gtgagaccct gtctctacaa aaataaaaat aaataaaata atataatctg gtaaatctga 111120
aaatcagatt ctacccccctg cccagaatat gttactgttt ctggtggttg ttgtttattt 111180
ctttttaact actcctataa agtttgtatt gtttctcata gatagccatc gaagtctttg 111240
cttggttaac ttagaggtca gctaaggatt agacagaatt ccttaggtgc ctgagatcaa 111300
taagtcagtc tttgacaaag gggtctgtat gtgtgttggg gcatgcattc aacactcagc 111360
caggctattt gcagctctgg attagccttt attccctgct tgtgcagagt ctcaaggtta 111420
gactgtggtg agagtttagg gctttctgag gtcttttgtg ggccctacag ttgcatgtgg 111480
ctttctaaat tcccaggaat atattttcaa agcctcctgt ggatcatctc atttcccagg 111540
taatttactt ttaagctttt ttagttatct tatgttttgc tccagttatt agctacacct 111600
gagtcagtga caatattcaa cagctgccta tgattatttg acaaatgcct ctgtggaaaa 111660
ggtggttcac actaggtgaa ctccaagtta gataaagtaa agataacctt actagtggga 111720
tcttccagga aactaccaaa caggtcaaat aatgtaaggt ctctgtgaat gggactttag 111780
agtatatcca accagtctag agtatatcca accaatctgg cctcctctag tggcagcctg 111840
gctgctgctt ttcataataa atgtgggctg ttttgatttg aaggctacca tagagctgtg 111900

-continued gggaaagtta aaataccaca gagctcactc ttctcactga aatcctgtct ttttttccct 111960
tgaacaaatt ctccctatat tgctgcaagc tttttgctaa tttccagatc tgaaaaagct 112020
gattctgaca atatttatca gtacttttat tgcttttatg gaggataaaa ttttcagaga 112080
tccttattct gccatttttg ctgacatgtg taaagtgatc atttctaatt gtaaaattcc 112140
ttttgcattt attagctgga atactttaca ggacttttcc tcatcaaccg ttagttacca 112200
tttaatatag tttgtaagaa tgatagaata aatgcatggc aagaatcttt acttctcaaa 112260
tttcagagat tttgatggga aattatattt agagatcaca atcagtgtct agatgtgctc 112320
cctgctatgg aggtgtcatt acttttaggc ttttttaatg ggcaaataca tgaagtaatt 112380 atttttttaga aagaaaatct gagattaact caaatcatta attcatactg attttttccta 112440 ttcatagttg acagagtatt attatctttt gttctgcttc tcttgtacac tgaaattctt 112500
ggtttttgat attaacaatt atttacttat atcacaatat acatacatta atttaaaaat 112560
aatttacagt gctacctgaa tattttttct tgtaagttgt tttatctctc tttgcttact 112620
tgtatgtttg tttattgtca ttagaatgta tcaaactagg gctataaagc tgtaatacta 112680
tattttagcc agaaactagg acctagcact caaatgccca tcaatggtag aataattcat 112740
cacattttta taagatggaa tatggtactc aatgaaaatg aataaagtac aactacatgc 112800
agtgatttgg atggatatcc caaacataat ggaaaaagca cacacaaata agcttatatt 112860
atataattcc atatacctat gtatatatca agtataaaag taggcaaaac aagctactga 112920
tggtggcaca cacctatagt tccagctatt tgggaggctg aggcgggaag atcacttgag 112980
cccagaagtt caggttcaac ctgagcaaca tagcaagacc ccatctgtaa aaaagaaagc 113040
attattaaca taaaaatagg cagaactact atattcttag agaagttact gttagggaga 113100
cagacagtga gtgactgaaa ggcaaaatga ggggaaattc caggggatag taaatatttt 113160
gtttcttagt gtgggttcta cttaactggg tattttccat ttgtaaactg taaaattatg 113220
tgcacttttc tgtatgtgta ttacattgca ataaaattgt ttaaaagtca attgaaatag 113280
ttctgtgtgt ggttatgcca cagcttaata cagagttaga ttagacttct tttcaaactc 113340
attttgcata tagacaccta taatatcagc tgcacagcct atataatgct atccatagca 113400
atgaatttgg tcttttgatt tttcaggaga acttgcgcct gtcaggggct ggatccagaa 113460
acctgtggtg cctccttctc ttttggttgt tcatggagca tgtactacaa tggatgtaag 113520
tttgccagaa gcaagatccc aaggaagttt aagctgcttg gggatgaccc aaaagaggtt 113580
tgtttacttc ctgatgtata atcgctttat ttttcataga gaattcatta gcttagatga 113640
agtgaacaat atgacatatc ttggtaagct cttattaatc aaagtttttc ccaaactgta 113700
gatacacact attttttaag ttggcataat aatcatatta tgccaaaata atagataaaa 113760
tttgagcaac aaaaacttcc tctttggtct tttatgttaa ttccaaagtt ttaaaggggt 113820
gtcacttcat tgttaaaact aaatgagaat tggtgatgtt tttcatattt tgactctgaa 113880
ttatggaagt tacataagta ctacattcag aaaagaccat ttttagtcac atttatgtgc 113940
aatgagattc aaataattta aagtcactgt aatgaatgca tttaataaag tcactgtaat 114000
gaatgcattt aagtaactaa aacatttaga ttttaatata actctgtaat ggaaataaat 114060
ggacactaat ttctcactga agtcattggt ttttgtcttg tctgtagaat acgtatttct 114120
tataatttgc aaattgataa atttaacaac ttttgggtgg catgtagtct agagtataga 114180
tacttcttga cttatgagga gactacattc ctataaatcc gttgtaaaat gaaaatccat 114240 ttaataccc caataaaccc atcctaaagt aaaaaaaaaa cgaagccatt ataggtcagg 114300

-continued

```
gactgtctcc gtactaattg aatgatgaga aaacctcagt atatttagca tttagctatg 114360
accacatttt cagtcattct atacacttac aattatcttt tgaatttcga atacaattaa 114420
aatatttcca tactatagat attataacat tgatgagtcc ctttaaatga agaatttgtt 114480
aaccttatta agctttcact tactattata gtcacagtta ataaagcaag tgcaaaaact 114540
cctgaaatca cagtataagt tttttaaagg atgttttcaa taattaaagt ttacttaaat 114600
gtgcgagaca tcatttcata agacaagaat atgaatatta ataacttaat gaaaagtact 114660
gattttgctt gctgtcattt taattttcta cagataactt ttttttaac cactgtttta 114720
tcaagtgata aatgtttatc actttcacga ggtttcatgt aaaccaaatc cagaggatac 114780
caagtaactt attgcctctg ttgggtagga gagctctgtt cagaaacctc ctcaccttct 114840
aaaatttaca tctctgccag gtggttatgt ctcacaactt ttttttttta gagaaatatc 114900
aatctgaaat gaagacttct aagtataaat ggagcagcta aatatgatca cctaccattt 114960
tttaacagta tattacttgg aaaatctgtt cttcatgagc agggcaggtg ggggtgtaac 115020
tgagcatttc ccctttcaag taaattctgc aaaggttttc atgtatcctg cattctagtt 115080
ctgaagcatt ttatccatat ttgaagtgtc cagtaaattt tagttgctct atggagagat 115140
cattccaaat tatttaaata ctatctttat aaacataaaa tgtaaagatt agaaatagac 115200
aaattaagct aaagaagttc ttttaatagt tcatcttcct tggtagctaa aaaatgtgac 115260
ctctttaaga ccatacggct taattcccct aaccctactc ctggcacagg cttgtgtgta 115320
taaaatgcaa aatatctgca tgcagttaga aaatcaatct tatgaaaaaa acaaatagct 115380
agatatttac tagcacatat gaaattaaat gatagtcatg ttttaaagat gctttattta 115440
gtaataaagg caccatatat tgtgtttggg attcaaaatg taaggggaat aatctaactg 115500
atagtctctt ttacatagag aaaatggact tagaatttaa tatgtagaat tattcacttt 115560
atacaggaag agaaactgga gtctcatttg caaaacctgt ccactcttat ggcaccaaca 115620
tataagaaac ttgcacctga tgcatataat aatcaggtaa gtttaaataa tcattggcag 115680
caattgtaac aacttacttg ttactaatga cctatgtcca aaaatatttt tgaaacaatg 115740
atttttaaat attattctaa cttttcctct taattgttga aaccactgca gtgttcagtt 115800
tcgagtatat aaaaattata ccatacaaaa gtacattttt tttgtctttt agctgtaaag 115860
acatgcgctt ctaaaagtca caggctgttc tatctactaa tcttgttctc atatgaataa 115920
ttttgtttct gtaaacagac tatggagatt acatcaaaat tatgtggccc aagctatagg 115980
ttctaactac ctatttttac tgcaagtcta taagtataaa tgagtattca taagaattta 116040
tagacttaca aatattcaca taaagctatg catatactaa cattgtaagt atatatattt 116100
cggtccagat gtgtcagatt ttgctgatct tcctttttg tttgaccttg acttcataca 116160
ccaagcaaaa acattttttt tttctatttt acatgtgtat tctaaactat agctagttaa 116220
gacaggtaga tgatttggtc agaaatctct catcatgaag gcaaaaaact aaaatcttca 116280
ctgtttcagt aacatcaaca acaaaagcat taagtgaaag tctattacaa actaaacact 116340
gtgtttagtc actgggaaca taaaggtgag cagtgccatc tctgtctgtc tttaagaatt 116400
ccgtctttgc tgggtacggt ggctcacacc tttaatccca acactttggg aggccaaggc 116460
aggtggatca cctgaggtca ggagttctag accagcctga tcaacatgga gaaaccctgt 116520
ctctactaaa aatacaaaat tagctgggtg tggtggcagg cacctgtaat cccagctact 116580
cggaaggcta aggcaggaga atagcttgaa cctgggaggt ggaggttgca gtgagccgaa 116640
```

-continued

```
gtcaaaccat tgcactccag cctaggcaac aagagcgaaa ctccatctca aaaaaaaaaa 116700
aaaattcatc tttaactggg tgcggtagtt tatgcctgta atcccagcta cccaggagac 116760
caggagtctg aggctgcggt gagccatgat tgcatcactg tgctccatcc tgggtgacaa 116820
agatgaccca gattctaaaa aaaaagcaaa aaacaaaaga attccttctt tagtggagac 116880
agagacatat aaaataaata gcaattttag aattacacag ttccagctgg aatagaagaa 116940
tgtgcacatt tctaaaaaaa tttaaaaaca aaacccaaaa gtagactaga tgtcacaagc 117000
agccttagac gctaaataaa gatctttgaa ctttattctg taggtaacca ttgggctgtt 117060
tcaagtgtgt gttggggatg gaagggtaaa gtgatgtaat tcgtattttg aaaaatttac 117120
ttaaaagcca agtaagggaa atataactta aatctatgta agattagaga gagaagaaag 117180
ctattgcaat cattgggcaa gagattttaa ggacctaaag aaatggcagg aattaagtat 117240
gtacactaac taaggtggag cttagagaac ttggtgacta gatgtatgga tgagaaaaga 117300
atttggagat acaacaaatt tccagtttgg acaggtagtt ctattaacta gtatcagaaa 117360
ttggtaagaa atagtaagtt ttgggatggg gagaagatat caaaattttg gacatgctag 117420
gcttctaggt taattagatg gagaatcagg agaaaaattc aggctagcac tgtagatttg 117480
agagtcagaa tgctggcagg acttaaagtt gaatacatag gaatgaaagg aggttttcaa 117540
agtagagatt ataaagagga caaagggctg atgatgggat tctggagcca tcaatcattt 117600
taggcatgag tggaggaaga gaagccaatg aagtaagaac tgggggaggg agtagaagaa 117660
atgtagtagg aaaagtgaaa gagggagatg gatggatgga ggaaagctgg aatgatgaga 117720
agacacccag agcagagtat acaggagcaa taggtatggg gctctgggat gggtgctctg 117780
tcatttactt gataatatta aagactctcg tgggattaga ttagtttaca cagcagacat 117840
ggacaaggga ctaatcctaa aatgatttag ctactcttct tttccactgt ggactttaac 117900
gtcccaaaca tttttttttt tttttggttc gaacaataga ggcaaattaa acgatggtct 117960
atttgtaagt tattttatgt caaattatgt ttttagaaat gtgtatgaat atctatgaaa 118020
agtttttaaa cactattaat agttggatta atactgttat tttgtttagc tagtatcaca 118080
aagtataagg agtgctttga tactgtcgta aaagtttaat tctcagcaag aacttctgaa 118140
ataaatcaag ctataaaaat aaataaatga atgagtctat gttgctagat ttaaagttgg 118200
gtcattttct attaaatgaa tttttaatag gtgctgttaa tcaaatggct ttacttgagg 118260
cagaataaca aagcattgat gttctttttg ctcccttgat tcttattatg gaccgtctca 118320
tacttgaaac tattttatac atttcctaaa acttaagtac ccaaaatatg aagccatcaa 118380
atatgttcaa gttttaatat ttatatatga aaatgtgttg atgtaatgtc tagataaatt 118440
aagtcaatta atagttgtaa atggatgaga tgcttctgaa tggataaaat atttttatat 118500
tgcatggtag gtactattgg taatattcat ccatgtatgt taatatgctt tagagatcaa 118560
aataatagcc atgtgatgtt tccacacagt acacgggaag accatttgat gttatagatg 118620
ctgtcataaa acctactatt tgatctttac ctcctttccc caactgagtg tcgtatctct 118680
atttctcaca tctgaatatt cttccttgct ttattccttg atttcatgaa gtcttattgc 118740
taaagtttag ttggctctcc acagcatctc ttctgtcagt cccatggaat tagagcttca 118800
gttttctcaa cttaaatgtc ctttcttcgt gtctatccag tagacatata tttggctctg 118860
tcttttctat gcctgcctta caatttaaca gtagacctga aatagcaggt gtcaatctca 118920
aaatcgtgtg ctatttatca tacatgaaga tgacatttta gacaaatgct tctaagagag 118980
ctttctatga agatggaaat attctctatt tatgctgttc agtgtaatag gcactagcca 119040
```

catgtggtta ttatttaaca gttgatacgt ggctagtgta attgagttta aattaatgta 119100
aaaattaaca caaacagcca catgtggata atggttacca tagtgaacag cacaacctta 119160
gaccatgaga aagttatgca tttagaattg tcttccagac atttagatgg atttccagta 119220
attcattcac aaaatcctgc atggtatttt ttaggagatg gcataagtgt aatttctagc 119280
tgattgtata tctgtttttg ttcaagaaac agaataaagc taactagacc acagcatgaa 119340
ctgaacggcc acaaagcaca catctatgtt aaagagtagt tggtaccttc attttccttt 119400
ggccaaagtt ttatgaggtt agatagacaa atacatatat gaatccaaca gtaaataata 119460
tgaagccacc acaaactttt atcctaatgc aagttcatct tctagccatg atggagtaaa 119520
cagagactac atatgccgtt acacatttaa gaaaaaactg acaaaatata tgaaacaatg 119580
gtttttagac atagaataag aaattcaaga gacagtggca ccagagagaa aggaagtaaa 119640
aaggtgaacc tataaatacc ccagtttact tcctgaagag agtattaggc tccagtgtag 119700
ccagtaggaa cccaaacaca cccagcctta tctctgtatt aaggagacaa agttcaaaat 119760
ttggagaggc caaggtgacg agagttcact attcagaata tcagagagga gagagtgtta 119820
ttgagaaaag ctccagagac ctgcagaggg ttctgatcca gtcttcagct gagtattaaa 119880
cagcacatgc atgtgaaaaa actgccaagg ctaggtaggg aaagaaccat cagaagaagc 119940
aggcagaata atcccttgat ctcacacagg acctggaata gttcttgatc ataccagcca 120000
gacggagaag acttcataat actattcata attgtattgc cttggtagta gaagtaaatt 120060
tggcagttct gacctcatct aaaaatgctt aaaatgaaaa catagaaggg ccaaactgat 120120
tctaagtaat ttaactgcat cacagtacaa aaattaaaaa aaaaatctac caacaaggta 120180
aaatttatag tctagcattc catcagaaaa tacaaggcat acaaagaaaa aagaaaatat 120240
aacctttact ggggaacagg cagaaatcaa tcaataaaaa tagtcccaga actgacatat 120300
gtgatacaat atgtaaataa gttcattaaa atggctatca tatttcatat gttaaaatgc 120360
cagaggaaag catgagagtg ataaggaaag atcagaagat attaaaatac cctacaatga 120420
ccttctagaa gtgaaaaata tatatctaga ttaaaaatac actaggcgga attaacagat 120480
taaggaactt gaagacatag taatagaaat ttttcagtat aaagaaaaaa ctgaaaaaaa 120540
tgaatatata aaagacctat tagccaatat tgttacacta atatatgtgt aattggagta 120600
ccagaaggag gtgggagaca gaaaaatatt taaagaaaca atggccaaat ttttttcaga 120660
tttgttcaaa actgtgaacc cacagatctc agcagctcag caaaccccag attaaaaaac 120720
aaagacataa aaaaagacta tcaaaaattt ataatcaact tgcttacaat ctgtgataaa 120780
gagaaactca gaaaggcaaa tggagaaaaa aggacatatt acactaggtg ggaaaaaata 120840
agacaggaga cttcattcag aaaaaggcaa gagagaagat gtaagagaaa catctttaac 120900
atactaaaag aaaaaagact ctccacccag aaatatataa ccaatgaaaa caactctcaa 120960
aaaagacagc aaaataaaga atatttttc agacatacat acaaaagctg aaagaattca 121020
ccaccaacaa actagcactt taaaaatgtt aaacgaaatc cttcaggaag aaagaacatg 121080
ataccagaca gaaatccaga tcaacataat gaaatgaaca gtatcaaaaa tagtaaacat 121140
ggttaaaaga cttttaaaaa aatgataact tgctatctta aaaatatatt aacaatgtat 121200
tatgaggttt ataacacgta gaagtagcac agaggctgag gaattgaaag tatattattg 121260
taaagtactt atacgatatg tggactgggt atattacttg gctgtaaact gtgagacgtt 121320
agagtacact gtgtacctta aaccactaaa aaaaaaaaaa aaagtatata gctaatcagc 121380

-continued cagtaaagac agaaaaatga aatcaatcca aaaatgtttt taaaaatata taggaccaaa 121440
aaaagataaa tataaaaata aaacaaatag caagatggtt tatttaaacc caactgtatc 121500
aacaaccaca ttaaatgtaa atggttttaa cacccctaat tataaggcag agcttgtgat 121560
attgaaaaaa aagcaaaaac caagaaaacc actttaaata taaagataca aataaattaa 121620
aaagatattt ttaacataaa aaatgatgtt gaaaagacat aacaggaaaa aatatgatta 121680
ttgcagtagg tacagaaaaa ccatttgata atattcaaca ttcataaaag gaaactttct 121740
caacctatta aatacataaa tggaaagcca aaagctaatg ctatacttag tggtgaaaga 121800
ctaatacttg acccctaaga taaggaacaa gacaacaatg tccattttta accaactgct 121860
tctattcaac atcaaactgt aaattttaga aagtgcagta aggcaataaa taaagcagtc 121920
aagattgggt aggaaaaaat aaaactgtac ttatttgcag atgacatgtt tgtctacata 121980
agaagtctca aaaaatctac cagaaaatga aattaatata tgaatttagc aaagttgtga 122040
aatacaaaat tcaagtgtat ttttatatac tagcaataaa taaatcaaaa taaaccatta 122100
aaatagcatc aaaatataaa attcttagac atacatttga caaaaatgta taagattata 122160
tactggaaac taaaacattg ctgagataaa ttatagaaaa cttcagtaac tggagagata 122220
cactatgtta atggatcaaa agactaaata ttattaagat gtcagttctc cccaaactaa 122280
tcaatatgtt caatacatga tgtttcaaaa ccccagcagg ttttttgaaa gaattggaca 122340
agatggctgt aaaatatata tacttggaaa tgcaaaggac ttggaatagt caaataatat 122400
tttaaaataa gggcagaatt tgagactata tattgcatgg ttttcagatt tactgaaatc 122460
tataattgct actgtctgtc aagacagttt gatattgccc aggcgcagtg gctcacgcct 122520
gtaattccag cactttcgga ggccgaggtg ggtggatcac ttgaggccag gagttttgag 122580
accagcctgg ccaacatggc aaaactctat ctctaataaa aatacaaaaa attactgggg 122640
catggtggcg cgtgcttata gtcccagctg cttgggaggt tgaggcctga gaatcgcttg 122700
aatccaggag gcagaggttg cagtgagccc agatcgtgcc actgcactcc agcctgggtg 122760
acagagtggg actctgtctc aataaataaa taaaattttt aaaaagtttg atattgacat 122820
acctacatac acaccattat acacaagtgg atcagaatag agaatcctta agtagaccca 122880
acatatataa tatggtcaat tgatttttaa caaagatgat tcaattggga agggataacc 122940
attttatcca gtagtatctg aacagttgga aagccataag ggaaaaaagg taatcttgac 123000
ccttaatttc acaccattta taaaaattaa ctccaaataa atccatttat atgaaattct 123060
agaaaatgaa aatctgtagt gatagattag tagttgtctg agaacaaagc aggaagcatg 123120
aattatacag gggcatgagg aaatttttaa gagtaatgaa tatgtacttt attttggttg 123180
tgacaaatat atatcaaaac tcaaatagca tactttatgg cctcaataac actataaaat 123240
aaaaatttta ccatgtcaag atatttgctc tattttgtgt cattccattt tgtttctgga 123300
tatatattta agttcaaaac attttttaa agttctaaat ggtctaaata ctagtgagtt 123360
ttcggtgtaa gagtaaaact aactactttc gcattcacac acacttttat ttttcagatt 123420
gaatatgaac acagagcacc agagtgccgt ctgggtctga aggaaggccg tccattctca 123480
ggggtcactg catgtttgga cttctgtgct catgcccaca gagacttgca caacatgcag 123540
aatggcagca cattggtaag ttgggctgag gacagcttag cagctgttga gtctgttctc 123600
acactgctaa taaagacata tgcaagactg ggtaatttat aaaggaaaga gatttaattg 123660
actcacagtt ccacatggct gtggaggcct cacaatcata gctgaaggca aatgaggagc 123720
aaagtcacat cttacatggc ggcaggcaag agaacatgtg caggggaact cccctttata 123780
aaatcatcag atctcatgag acttactctc ctgagaacag catgggaaag atctgccccc 123840
atgattcaat tacctcccac tgggtccttc ccaaaacaca tgggaatttt gggagctaca 123900
attcaagatg agatttaggt agggacacag ccagaccata tcagcagcat ctcatgttga 123960
ggagcagaac actggaattt agtagcattc ggttagagta atatgttgtc tgcaggtttc 124020
actggacagc aatattttca tgaatgaatt cctgttgcaa agtgacctgc tttggcataa 124080
ctagcactct catgataggt tggcacatta gtttcctgtc aattgtgttg acaagcacat 124140
gagaatcatg gaaatccttg gtgttaatct aaaccagtga ctatgcattg ccagttacag 124200
ttaacttcca ggaaaatctc aaaattcagt gccagttacc tggtagattg taatcagtta 124260
agcaaaaagc caaatacaag ccattcacct tacagagaga gaagcatatt caccttacag 124320
agagagaagc ataaatgaga aacacatcat cattgtcaca gtaactgtgg taacctattg 124380
taaaagattc acagtgcaaa agagcctgac tacatattac agtgggtaaa atggatcggt 124440
cttgtaattg gaggcagtgg tgaggggaaa atagatacat gttatatata tatatatata 124500
tatatatgtt ctataccaac aaagggttca gggtataatt ttgcatgtaa aggggtgacc 124560
cagagtagag ataaagaaca aaatattctg ttgaaaaaac tatgaatcaa tcaacctaat 124620
gaattatcaa catggatgta ggtgtagttg aagaagatgg tcagtgagaa tatggaaaca 124680
gatatcagga attaaagtca tattctaggg cagaaaagca ttcatggagg tattagatga 124740
tagctgaagt aatttgaaga agctggtgtg aagtttttgt tgagaagcag agaagatatt 124800
aatttaatgt tctagatcag agattggaaa actcttctct ataaagggca agatggtaaa 124860
tattttaggg actgcaggcc acataggatt tctgtcacat tgtttggtgg ggtttttttg 124920
tttattttgt tttttaaaaa ctccttgaaa atgtaaaaac cattcttagt ttactggcca 124980
tacaaacaca agctgtgagg cacattagcc gtaggttctg gtttcctaac ttctgatcca 125040
gaagaacaaa cacaaggcct accaaccacc ccaacatcta aaatcatcac taatcatgta 125100
ctcagcacct gctcattatt aggaggctat gctagtttct gaaaagcaga agtagtaaat 125160
gataactggg gctatagtgc atcctaatat aaccatgttt cattccagga aggtgacaga 125220
gagtaagatg atgagaagga tgtttagaat caagaagaat ttgcctctga tagagcatgg 125280
gttctgtgaa gtaaaatgga aaggagcact agataagaac tgaatagggt taaatatgta 125340
tgggaaaagt aacaaggtgc tcagagacat gaatttgaag acttctgtgc agaaagtgac 125400
aggctcatta ataccatctc atgttgaagt tatttctaaa gtcagtccat tgtgatcaca 125460
tttctctcaa gaatatcttc taattttatt ttagatcaca ttagatcaca ttgtctccat 125520
tgatcaaaaa cactaaatac taaaaagtta gtatttaaaa accacaaata atcttttacc 125580
aaagctagtg taattgtagt aactaaagca aaaagtacca tttaattatc aaagcaacag 125640
aggtagcttt cctccctcca ccccttaccc ttttcagagt acccacttat atggtcatat 125700
ttcagaaaag aaatgaagaa aagagaaagt taggtttgac agagtacaaa ggaggagaga 125760
caagagagtg aaaatagtat taagttgcat attacctgta tcagccaaat ctttaccttt 125820 tcattttta tatttttact tcagttatct tatggaaatt tcttaaacag agagagttag 125880
gtgtcaggta tgtgaaaaga catgaaattt gtgttcagaa gtatgagatg aggcaaatgt 125940
gatactacca aaaacagagg aagtcatttc gtagaaaaaa cttttagcct gtttttgaag 126000
aggcttcaca tctagcacat ctatttttga agtgtgaaaa gcaagagagt gcttcatttt 126060
gggggagtgt tgcttcttcc catagacaga aacatatgtg aagaacaagg gtcaccacag 126120
ctaactgttc ctgatagact cagagaaagg gtgggtgggc aatgtcaatt tgtcttatct 126180
ccctgtacca ttttgttgct attttcatta ataacaggta ggatggtttt atggtaatat 126240
atatgtcact gatctggatc aactaggcca ccaacacaaa tctgaatact gagaggagaa 126300
agatacacac acacacacac gttttctttg ggacctgtag ttgaggctgt aatgtcttac 126360
ttccctacca ggtatgcact ctcactagag aagacaatcg agaatttgga ggaaaacctg 126420
aggatgagca gcttcacgtt ctgcctttat acaaagtctc tgacgtggat gagtttggga 126480
gtgtggaagc tcaggaggag aaaaaacgga gtggtgccat tcaggtactg agttcttttc 126540
ggcgaaaagt caggatgtta gcagagccag tcaagacttg ccgacaaagg aaactagaag 126600
ccaagaaagc tgcagctgaa aagctttcct ccctggagaa cagctcaaat aaaaatgaaa 126660
aggaaaagtc agccccatca cgtacaaaac aaactgaaaa cgcaagccag gctaaacagt 126720
tggcaggtaa atttaatgta aagcatttgt agataaatgt gttgtgtggt atattaaaaa 126780
tgaaaattat tttggttttg cccccatcaa cttgtaagtt ctggggtaca catgcaggat 126840
gtgcaggttt gttatacagg taaacatgtg ccatggtgat ttgctgcaca gatcaaccca 126900
ttacctaggt attaagccca gcatcttcct gatgcacccc taccaatagg cgccagtgtg 126960
tgttgtcccc actcccccac catgtgtcca tgtgctctta ttgtaaaatg aacattgtta 127020
attttggaaa gttatatcaa tcatggtctt agttctgtgc cagagtcttc tctaaagtag 127080
caagggccag gctttgttct cagagatggt aatgagatat tgcaccatca acatggaaaa 127140
catggaaaag tctggatttt attctataat aaacagcaac ttttttttaac aggtaagtga 127200
tacgatgaaa ttcattgtaa tttggcagta ggccaaatta gtagaggagc taatagtttg 127260
gagataaaca cagtaaacca gaactgaggt aacaagacct tgaattttgt tggttagtag 127320
caaagatata gcaaaatgat gcaaatgagc tcttccaaaa tgggaaaaag aaaatacatt 127380
ggtgacaaaa cactggaatg aaagagaaga aaagtttaaa gatgacccca aagttttaaa 127440
cctaaactta acctactgtt ttaggtttct aaaacagtac tatttattga aataagtaag 127500
tttgaaaata tgattgagag agagagaggg gagaatgaaa catttttcct tagacatgtt 127560
gagtctgtgg tttaggaggg gttctacatg tagattatgc tacaaaactt ttacccatca 127620
aaatagatta cagctgtagt aataacaata gaacattatt catgaatact aagttattgt 127680
ctttccatag cctcctgctt tatgtctgca gtttgtaaaa agaaaaaaaa tccaaaattt 127740
gggatggtat tggcctggcc attaacaaaa gcaaaccagt ttgcttaaaa ctagccatct 127800
ttgctgcttc atgaagtcaa atttctctac tgattcattt ccaagctcag aggaactaag 127860
ttaaataatt tagaatatgc taaagatgct tgataagtgt ttattgactg gttgacttaa 127920
cactaagtaa atactgttca cttaggttag ctgtgaaata taattagata gaaccttgtc 127980
tctgctccct tttaactggc ttctgcaggt aataatccct tctgttctca gaactgccat 128040
tgcagtttca tctatttgtt cttaactcat atgacttttt aaagtgaggt caaaacagaa 128100
gtatgacttt taaaagtttc atttacaaag ctgaaagttt ctttaaagtg ttatctacaa 128160
ctgtgttaac ttcctttctg gaaagcctgc ttataaagta gcacttgttg attatataag 128220
atgctttttg tgtttaaata cgtgtcattc tttttttttca caacattccc gaatcttaca 128280
taataaatct tattttaatt atttagcaaa ttccattgca tgccaggcaa tgaagaagta 128340
agtaaaataa aacattttcc ttcccattta ggaatttact taccagtggg ggtgaagaga 128400
gggctaaaaa cataactata atacattgtg agtattgctt tatcagatct atctttgcag 128460
ttgagtatta caaaagcact agaagatgag gtcaaagcgg tcccttgagg aagggatgac 128520
tacaccaagg aaggataggg agagagggag gaaaagggag gcacttcaag cagaggcatg 128580
ttcagaagtt ccaaagaaca ttttgctctc aatggaatgg ctttggatgt ttattacatt 128640
tttttttca ctaagttttg tatttctaat gccttagaca aaaaattgtg ctggacaatg 128700
atcagaaccc tgactttgct cttatctttg cttaatgggt gtcgtatatc actagtggag 128760
tttcttacct acatttaagt atcctcacta gccttcataa aataatcatc aacatcaaag 128820
atacctgttt ctgttctctc ttaccctgtc cacagaactt ttgcgacttt caggaccagt 128880
catgcagcag tcccagcagc cccagcctct acagaagcag ccaccacagc cccagcagca 128940
gcagagaccc cagcagcagc agccacatca ccctcagaca gagtctgtca actcttattc 129000
tgcttctgga tccaccaatc catacatgag acggcccaat ccagttagtc cttatccaaa 129060
ctcttcacac acttcagata tctatggaag caccagccct atgaacttct attccacctc 129120
atctcaagct gcaggttcat atttgaattc ttctaatccc atgaaccctt accctgggct 129180
tttgaatcag aatacccaat atccatcata tcaatgcaat ggaaacctat cagtggacaa 129240
ctgctcccca tatctgggtt cctattctcc ccagtctcag ccgatggatc tgtataggta 129300
tccaagccaa gaccctctgt ctaagctcag tctaccaccc atccatacac tttaccagcc 129360
aaggtttgga aatagccaga gttttacatc taaatactta ggttatggaa accaaaatat 129420
gcagggagat ggtttcagca gttgtaccat tagaccaaat gtacatcatg tagggaaatt 129480
gcctccttat cccactcatg agatggatgg ccacttcatg ggagccacct ctagattacc 129540
acccaatctg agcaatccaa acatggacta taaaaatggt gaacatcatt caccttctca 129600
cataatccat aactacagtg cagctccggg catgttcaac agctctcttc atgccctgca 129660
tctccaaaac aaggagaatg acatgctttc ccacacagct aatgggttat caaagatgct 129720
tccagctctt aaccatgata gaactgcttg tgtccaagga ggcttacaca aattaagtga 129780
tgctaatggt caggaaaagc agccattggc actagtccag ggtgtggctt ctggtgcaga 129840
ggacaacgat gaggtctggt cagacagcga gcagagcttt ctggatcctg acattggggg 129900
agtggccgtg gctccaactc atgggtcaat tctcattgag tgtgcaaagc gtgagctgca 129960
tgccacaacc cctttaaaga atcccaatag gaatcacccc accaggatct ccctcgtctt 130020
ttaccagcat aagagcatga atgagccaaa acatggcttg gctctttggg aagccaaaat 130080
ggctgaaaaa gcccgtgaga aagaggaaga gtgtgaaaag tatggcccag actatgtgcc 130140
tcagaaatcc catggcaaaa aagtgaaacg ggagcctgct gagccacatg aaacttcaga 130200
gcccacttac ctgcgtttca tcaagtctct tgccgaaagg accatgtccg tgaccacaga 130260
ctccacagta actacatctc catatgcctt cactcgggtc acagggcctt acaacagata 130320
tatatgatat caccccccttt tgttggttac ctcacttgaa aagaccacaa ccaacctgtc 130380
agtagtatag ttctcatgac gtgggcagtg gggaaaggtc acagtattca tgacaaatgt 130440
ggtgggaaaa acctcagctc accagcaaca aaagaggtta tcttaccata gcacttaatt 130500
ttcactggct cccaagtggt cacagatggc atctaggaaa agaccaaagc attctatgca 130560
aaaagaaggt ggggaagaaa gtgttccgca atttacattt ttaaacactg gttctattat 130620
tggacgagat gatatgtaaa tgtgatcccc cccccccgct tacaactcta cacatctgtg 130680
accactttta ataatatcaa gtttgcatag tcatggaaca caaatcaaac aagtactgta 130740
gtattacagt gacaggaatc ttaaaatacc atctggtgct gaatatatga tgtactgaaa 130800
tactggaatt atggcttttt gaaatgcagt ttttactgta atcttaactt ttatttatca 130860
aaatagctac aggaaacatg aatagcagga aaacactgaa tttgtttgga tgttctaaga 130920
aatggtgcta agaaaatggt gtctttaata gctaaaaatt taatgccttt atatcatcaa 130980
gatgctatca gtgtactcca gtgcccttga ataatagggg taccttttca ttcaagtttt 131040
tatcataatt acctattctt acacaagctt agtttttaaa atgtggacat tttaaaggcc 131100
tctggatttt gctcatccag tgaagtcctt gtaggacaat aaacgtatat atgtacatat 131160
atacacaaac atgtatatgt gcacacacat gtatatgtat aaatatttta aatggtgttt 131220
tagaagcact ttgtctacct aagctttgac aacttgaaca atgctaaggt actgagatgt 131280
ttaaaaaaca agtttacttt cattttagaa tgcaaagttg attttttaa ggaaacaaag 131340 aaagctttta aaatattttt gcttttagcc atgcatctgc tgatgagcaa ttgtgtccat 131400
ttttaacaca gccagttaaa tccaccatgg ggcttactgg attcaaggga atacgttagt 131460
ccacaaaaca tgttttctgg tgctcatctc acatgctata ctgtaaaaca gttttataca 131520
aaattgtatg acaagttcat tgctcaaaaa tgtacagttt taagaatttt ctattaactg 131580
caggtaataa ttagctgcat gctgcagact caacaaagct agttcactga agcctatgct 131640
attttatgga tcataggctc ttcagagaac tgaatggcag tctgcctttg tgttgataat 131700
tatgtacatt gtgacgttgt catttcttag cttaagtgtc ctctttaaca agaggattga 131760
gcagactgat gcctgcataa gatgaataaa cagggttagt tccatgtgaa tctgtcagtt 131820
aaaaagaaac aaaaacaggc agctggtttg ctgtggtggt tttaaatcat taatttgtat 131880
aaagaagtga aagagttgta tagtaaatta aattgtaaac aaaacttttt taatgcaatg 131940
ctttagtatt ttagtactgt aaaaaaatta aatatataca tatatatata tatatatata 132000
tatatatata tgagtttgaa gcagaattca catcatgatg gtgctactca gcctgctaca 132060
aatatatcat aatgtgagct aagaattcat taaatgtttg agtgatgttc ctacttgtca 132120
tatacctcaa cactagtttg gcaataggat attgaactga gagtgaaagc attgtgtacc 132180
atcatttttt tccaagtcct ttttttattt gttaaaaaaa aaagcatacc ttttttcaat 132240
acttgatttc ttagcaagta taacttgaac ttcaaccttt ttgttctaaa aattcaggga 132300
tatttcagct catgctctcc ctatgccaac atgtcacctg tgtttatgta aaattgttgt 132360
aggttaataa atatattctt tgtcagggat ttaacccttt tattttgaat cccttctatt 132420
ttacttgt 132428

<210> SEQ ID NO 2
<211> LENGTH: 2002
<212> TYPE: PRT
<213> ORGANISM: Homo sapiens

<400> SEQUENCE: 2

Met Glu Gln Asp Arg Thr Asn His Val Glu Gly Asn Arg Leu Ser Pro
1 5 10 15

Phe Leu Ile Pro Ser Pro Pro Ile Cys Gln Thr Glu Pro Leu Ala Thr
20 25 30

Lys Leu Gln Asn Gly Ser Pro Leu Pro Glu Arg Ala His Pro Glu Val
35 40 45

Asn Gly Asp Thr Lys Trp His Ser Phe Lys Ser Tyr Tyr Gly Ile Pro
50 55 60

Cys Met Lys Gly Ser Gln Asn Ser Arg Val Ser Pro Asp Phe Thr Gln
65 70 75 80

Glu Ser Arg Gly Tyr Ser Lys Cys Leu Gln Asn Gly Gly Ile Lys Arg
85 90 95

-continued

```
Thr Val Ser Glu Pro Ser Leu Ser Gly Leu Leu Gln Ile Lys Lys Leu
            100                 105                 110

Lys Gln Asp Gln Lys Ala Asn Gly Glu Arg Arg Asn Phe Gly Val Ser
        115                 120                 125

Gln Glu Arg Asn Pro Gly Glu Ser Ser Gln Pro Asn Val Ser Asp Leu
    130                 135                 140

Ser Asp Lys Lys Glu Ser Val Ser Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
            180                 185                 190

His Asp Lys Asn Ile Val Leu Leu Lys Asn Lys Ala Val Leu Met Pro
        195                 200                 205

Asn Gly Ala Thr Val Ser Ala Ser Ser Val Glu His Thr His Gly Glu
    210                 215                 220

Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
                245                 250                 255

Thr Asn Glu Leu Ser Cys Glu Ile Thr His Pro Ser His Thr Ser Gly
            260                 265                 270

Gln Ile Asn Ser Ala Gln Thr Ser Asn Ser Glu Leu Pro Pro Lys Pro
        275                 280                 285

Ala Ala Val Val Ser Glu Ala Cys Asp Ala Asp Asp Ala Asp Asn Ala
    290                 295                 300

Ser Lys Leu Ala Ala Met Leu Asn Thr Cys Ser Phe Gln Lys Pro Glu
305                 310                 315                 320

Gln Leu Gln Gln Gln Lys Ser Val Phe Glu Ile Cys Pro Ser Pro Ala
                325                 330                 335

Glu Asn Asn Ile Gln Gly Thr Thr Lys Leu Ala Ser Gly Glu Glu Phe
            340                 345                 350

Cys Ser Gly Ser Ser Ser Asn Leu Gln Ala Pro Gly Gly Ser Ser Glu
        355                 360                 365

Arg Tyr Leu Lys Gln Asn Glu Met Asn Gly Ala Tyr Phe Lys Gln Ser
    370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Pro Leu Pro Gln Val Pro
                405                 410                 415

Gln Leu Pro Ser Glu Gly Lys Ser Thr Leu Asn Gly Gly Val Leu Glu
            420                 425                 430

Glu His His His Tyr Pro Asn Gln Ser Asn Thr Thr Leu Leu Arg Glu
        435                 440                 445

Val Lys Ile Glu Gly Lys Pro Glu Ala Pro Pro Ser Gln Ser Pro Asn
    450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
            500                 505                 510
```

-continued

```
Lys His Asn Pro Pro Ile Phe Gly Ser Ser Gly Glu Leu Gln Asp Asn
        515                 520                 525

Cys Gln Gln Leu Met Arg Asn Lys Glu Gln Glu Ile Leu Lys Gly Arg
    530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
                565                 570                 575

Ser His Leu Lys Arg Asn Glu Ala Ser Leu Pro Ser Ile Leu Gln Tyr
            580                 585                 590

Gln Pro Asn Leu Ser Asn Gln Met Thr Ser Lys Gln Tyr Thr Gly Asn
        595                 600                 605

Ser Asn Met Pro Gly Gly Leu Pro Arg Gln Ala Tyr Thr Gln Lys Thr
    610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
                645                 650                 655

Ser His Gln Val His Phe Ser Lys Thr Asp His Leu Pro Lys Ala His
            660                 665                 670

Val Gln Ser Leu Cys Gly Thr Arg Phe His Phe Gln Gln Arg Ala Asp
        675                 680                 685

Ser Gln Thr Glu Lys Leu Met Ser Pro Val Leu Lys Gln His Leu Asn
    690                 695                 700

Gln Gln Ala Ser Glu Thr Glu Pro Phe Ser Asn Ser His Leu Leu Gln
705                 710                 715                 720

His Lys Pro His Lys Gln Ala Ala Gln Thr Gln Pro Ser Gln Ser Ser
                725                 730                 735

His Leu Pro Gln Asn Gln Gln Gln Gln Gln Lys Leu Gln Ile Lys Asn
            740                 745                 750

Lys Glu Glu Ile Leu Gln Thr Phe Pro His Pro Gln Ser Asn Asn Asp
        755                 760                 765

Gln Gln Arg Glu Gly Ser Phe Phe Gly Gln Thr Lys Val Glu Glu Cys
    770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                805                 810                 815

Ser Pro Tyr Ser Gln Thr Met Lys Ser Ser Ala Cys Lys Ile Gln Val
            820                 825                 830

Ser Cys Ser Asn Asn Thr His Leu Val Ser Glu Asn Lys Glu Gln Thr
        835                 840                 845

Thr His Pro Glu Leu Phe Ala Gly Asn Lys Thr Gln Asn Leu His His
    850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
            900                 905                 910

Gln Leu Ala Gln Gln Arg Tyr Leu Ile His Asn His Ala Asn Val Phe
        915                 920                 925

Pro Val Pro Asp Gln Gly Gly Ser His Thr Gln Thr Pro Pro Gln Lys
```

-continued

```
    930                 935                 940

Asp Thr Gln Lys His Ala Ala Leu Arg Trp His Leu Leu Gln Lys Gln
945                 950                 955                 960

Glu Gln Gln Gln Thr Gln Gln Pro Gln Thr Glu Ser Cys His Ser Gln
                965                 970                 975

Met His Arg Pro Ile Lys Val Glu Pro Gly Cys Lys Pro His Ala Cys
            980                 985                 990

Met His Thr Ala Pro Pro Glu Asn  Lys Thr Trp Lys Lys  Val Thr Lys
        995                 1000                 1005

Gln Glu  Asn Pro Pro Ala Ser  Cys Asp Asn Val Gln  Gln Lys Ser
    1010                 1015                 1020

Ile Ile  Glu Thr Met Glu Gln  His Leu Lys Gln Phe  His Ala Lys
    1025                 1030                 1035

Ser Leu  Phe Asp His Lys Ala  Leu Thr Leu Lys Ser  Gln Lys Gln
    1040                 1045                 1050

Val Lys  Val Glu Met Ser Gly  Pro Val Thr Val Leu  Thr Arg Gln
    1055                 1060                 1065

Thr Thr  Ala Ala Glu Leu Asp  Ser His Thr Pro Ala  Leu Glu Gln
    1070                 1075                 1080

Gln Thr  Thr Ser Ser Glu Lys  Thr Pro Thr Lys Arg  Thr Ala Ala
    1085                 1090                 1095

Ser Val  Leu Asn Asn Phe Ile  Glu Ser Pro Ser Lys  Leu Leu Asp
    1100                 1105                 1110

Thr Pro  Ile Lys Asn Leu Leu  Asp Thr Pro Val Lys  Thr Gln Tyr
    1115                 1120                 1125

Asp Phe  Pro Ser Cys Arg Cys  Val Glu Gln Ile Ile  Glu Lys Asp
    1130                 1135                 1140

Glu Gly  Pro Phe Tyr Thr His  Leu Gly Ala Gly Pro  Asn Val Ala
    1145                 1150                 1155

Ala Ile  Arg Glu Ile Met Glu  Glu Arg Phe Gly Gln  Lys Gly Lys
    1160                 1165                 1170

Ala Ile  Arg Ile Glu Arg Val  Ile Tyr Thr Gly Lys  Glu Gly Lys
    1175                 1180                 1185

Ser Ser  Gln Gly Cys Pro Ile  Ala Lys Trp Val Val  Arg Arg Ser
    1190                 1195                 1200

Ser Ser  Glu Glu Lys Leu Leu  Cys Leu Val Arg Glu  Arg Ala Gly
    1205                 1210                 1215

His Thr  Cys Glu Ala Ala Val  Ile Val Ile Leu Ile  Leu Val Trp
    1220                 1225                 1230

Glu Gly  Ile Pro Leu Ser Leu  Ala Asp Lys Leu Tyr  Ser Glu Leu
    1235                 1240                 1245

Thr Glu  Thr Leu Arg Lys Tyr  Gly Thr Leu Thr Asn  Arg Arg Cys
    1250                 1255                 1260

Ala Leu  Asn Glu Glu Arg Thr  Cys Ala Cys Gln Gly  Leu Asp Pro
    1265                 1270                 1275

Glu Thr  Cys Gly Ala Ser Phe  Ser Phe Gly Cys Ser  Trp Ser Met
    1280                 1285                 1290

Tyr Tyr  Asn Gly Cys Lys Phe  Ala Arg Ser Lys Ile  Pro Arg Lys
    1295                 1300                 1305

Phe Lys  Leu Leu Gly Asp Asp  Pro Lys Glu Glu Glu  Lys Leu Glu
    1310                 1315                 1320

Ser His  Leu Gln Asn Leu Ser  Thr Leu Met Ala Pro  Thr Tyr Lys
    1325                 1330                 1335
```

```
Lys Leu  Ala Pro Asp Ala Tyr  Asn Asn Gln Ile Glu  Tyr Glu His
    1340                 1345                 1350

Arg Ala  Pro Glu Cys Arg Leu  Gly Leu Lys Glu Gly  Arg Pro Phe
    1355                 1360                 1365

Ser Gly  Val Thr Ala Cys Leu  Asp Phe Cys Ala His  Ala His Arg
    1370                 1375                 1380

Asp Leu  His Asn Met Gln Asn  Gly Ser Thr Leu Val  Cys Thr Leu
    1385                 1390                 1395

Thr Arg  Glu Asp Asn Arg Glu  Phe Gly Gly Lys Pro  Glu Asp Glu
    1400                 1405                 1410

Gln Leu  His Val Leu Pro Leu  Tyr Lys Val Ser Asp  Val Asp Glu
    1415                 1420                 1425

Phe Gly  Ser Val Glu Ala Gln  Glu Glu Lys Lys Arg  Ser Gly Ala
    1430                 1435                 1440

Ile Gln  Val Leu Ser Ser Phe  Arg Arg Lys Val Arg  Met Leu Ala
    1445                 1450                 1455

Glu Pro  Val Lys Thr Cys Arg  Gln Arg Lys Leu Glu  Ala Lys Lys
    1460                 1465                 1470

Ala Ala  Ala Glu Lys Leu Ser  Ser Leu Glu Asn Ser  Ser Asn Lys
    1475                 1480                 1485

Asn Glu  Lys Glu Lys Ser Ala  Pro Ser Arg Thr Lys  Gln Thr Glu
    1490                 1495                 1500

Asn Ala  Ser Gln Ala Lys Gln  Leu Ala Glu Leu Leu  Arg Leu Ser
    1505                 1510                 1515

Gly Pro  Val Met Gln Gln Ser  Gln Gln Pro Gln Pro  Leu Gln Lys
    1520                 1525                 1530

Gln Pro  Pro Gln Pro Gln Gln  Gln Gln Arg Pro Gln  Gln Gln Gln
    1535                 1540                 1545

Pro His  His Pro Gln Thr Glu  Ser Val Asn Ser Tyr  Ser Ala Ser
    1550                 1555                 1560

Gly Ser  Thr Asn Pro Tyr Met  Arg Arg Pro Asn Pro  Val Ser Pro
    1565                 1570                 1575

Tyr Pro  Asn Ser Ser His Thr  Ser Asp Ile Tyr Gly  Ser Thr Ser
    1580                 1585                 1590

Pro Met  Asn Phe Tyr Ser Thr  Ser Ser Gln Ala Ala  Gly Ser Tyr
    1595                 1600                 1605

Leu Asn  Ser Ser Asn Pro Met  Asn Pro Tyr Pro Gly  Leu Leu Asn
    1610                 1615                 1620

Gln Asn  Thr Gln Tyr Pro Ser  Tyr Gln Cys Asn Gly  Asn Leu Ser
    1625                 1630                 1635

Val Asp  Asn Cys Ser Pro Tyr  Leu Gly Ser Tyr Ser  Pro Gln Ser
    1640                 1645                 1650

Gln Pro  Met Asp Leu Tyr Arg  Tyr Pro Ser Gln Asp  Pro Leu Ser
    1655                 1660                 1665

Lys Leu  Ser Leu Pro Pro Ile  His Thr Leu Tyr Gln  Pro Arg Phe
    1670                 1675                 1680

Gly Asn  Ser Gln Ser Phe Thr  Ser Lys Tyr Leu Gly  Tyr Gly Asn
    1685                 1690                 1695

Gln Asn  Met Gln Gly Asp Gly  Phe Ser Ser Cys Thr  Ile Arg Pro
    1700                 1705                 1710

Asn Val  His His Val Gly Lys  Leu Pro Pro Tyr Pro  Thr His Glu
    1715                 1720                 1725
```

-continued

```
Met Asp  Gly His Phe Met Gly  Ala Thr Ser Arg Leu  Pro Pro Asn
    1730                 1735                 1740

Leu Ser  Asn Pro Asn Met Asp  Tyr Lys Asn Gly Glu  His His Ser
    1745                 1750                 1755

Pro Ser  His Ile Ile His Asn  Tyr Ser Ala Ala Pro  Gly Met Phe
    1760                 1765                 1770

Asn Ser  Ser Leu His Ala Leu  His Leu Gln Asn Lys  Glu Asn Asp
    1775                 1780                 1785

Met Leu  Ser His Thr Ala Asn  Gly Leu Ser Lys Met  Leu Pro Ala
    1790                 1795                 1800

Leu Asn  His Asp Arg Thr Ala  Cys Val Gln Gly Gly  Leu His Lys
    1805                 1810                 1815

Leu Ser  Asp Ala Asn Gly Gln  Glu Lys Gln Pro Leu  Ala Leu Val
    1820                 1825                 1830

Gln Gly  Val Ala Ser Gly Ala  Glu Asp Asn Asp Glu  Val Trp Ser
    1835                 1840                 1845

Asp Ser  Glu Gln Ser Phe Leu  Asp Pro Asp Ile Gly  Gly Val Ala
    1850                 1855                 1860

Val Ala  Pro Thr His Gly Ser  Ile Leu Ile Glu Cys  Ala Lys Arg
    1865                 1870                 1875

Glu Leu  His Ala Thr Thr Pro  Leu Lys Asn Pro Asn  Arg Asn His
    1880                 1885                 1890

Pro Thr  Arg Ile Ser Leu Val  Phe Tyr Gln His Lys  Ser Met Asn
    1895                 1900                 1905

Glu Pro  Lys His Gly Leu Ala  Leu Trp Glu Ala Lys  Met Ala Glu
    1910                 1915                 1920

Lys Ala  Arg Glu Lys Glu Glu  Glu Cys Glu Lys Tyr  Gly Pro Asp
    1925                 1930                 1935

Tyr Val  Pro Gln Lys Ser His  Gly Lys Lys Val Lys  Arg Glu Pro
    1940                 1945                 1950

Ala Glu  Pro His Glu Thr Ser  Glu Pro Thr Tyr Leu  Arg Phe Ile
    1955                 1960                 1965

Lys Ser  Leu Ala Glu Arg Thr  Met Ser Val Thr Thr  Asp Ser Thr
    1970                 1975                 1980

Val Thr  Thr Ser Pro Tyr Ala  Phe Thr Arg Val Thr  Gly Pro Tyr
    1985                 1990                 1995

Asn Arg  Tyr Ile
    2000


<210> SEQ ID NO 3
<211> LENGTH: 311
<212> TYPE: PRT
<213> ORGANISM: Homo sapiens

<400> SEQUENCE: 3

Arg Cys Val Glu Gln Ile Ile Glu Lys Asp Glu Gly Pro Phe Tyr Thr
1               5                   10                  15

His Leu Gly Ala Gly Pro Asn Val Ala Ala Ile Arg Glu Ile Met Glu
            20                  25                  30

Glu Arg Phe Gly Gln Lys Gly Lys Ala Ile Arg Ile Glu Arg Val Ile
        35                  40                  45

Tyr Thr Gly Lys Glu Gly Lys Ser Ser Gln Gly Cys Pro Ile Ala Lys
    50                  55                  60

Trp Val Val Arg Arg Ser Ser Ser Glu Glu Lys Leu Leu Cys Leu Val
65                  70                  75                  80
```

```
Arg Glu Arg Ala Gly His Thr Cys Glu Ala Ala Val Ile Val Ile Leu
                85                  90                  95

Ile Leu Val Trp Glu Gly Ile Pro Leu Ser Leu Ala Asp Lys Leu Tyr
            100                 105                 110

Ser Glu Leu Thr Glu Thr Leu Arg Lys Tyr Gly Thr Leu Thr Asn Arg
        115                 120                 125

Arg Cys Ala Leu Asn Glu Glu Arg Thr Cys Ala Cys Gln Gly Leu Asp
    130                 135                 140

Pro Glu Thr Cys Gly Ala Ser Phe Ser Phe Gly Cys Ser Trp Ser Met
145                 150                 155                 160

Tyr Tyr Asn Gly Cys Lys Phe Ala Arg Ser Lys Ile Pro Arg Lys Phe
                165                 170                 175

Lys Leu Leu Gly Asp Asp Pro Lys Glu Glu Glu Lys Leu Glu Ser His
            180                 185                 190

Leu Gln Asn Leu Ser Thr Leu Met Ala Pro Thr Tyr Lys Lys Leu Ala
        195                 200                 205

Pro Asp Ala Tyr Asn Asn Gln Ile Glu Tyr Glu His Arg Ala Pro Glu
    210                 215                 220

Cys Arg Leu Gly Leu Lys Glu Gly Arg Pro Phe Ser Gly Val Thr Ala
225                 230                 235                 240

Cys Leu Asp Phe Cys Ala His Ala His Arg Asp Leu His Asn Met Gln
                245                 250                 255

Asn Gly Ser Thr Leu Val Cys Thr Leu Thr Arg Glu Asp Asn Arg Glu
            260                 265                 270

Phe Gly Gly Lys Pro Glu Asp Glu Gln Leu His Val Leu Pro Leu Tyr
        275                 280                 285

Lys Val Ser Asp Val Asp Glu Phe Gly Ser Val Glu Ala Gln Glu Glu
    290                 295                 300

Lys Lys Arg Ser Gly Ala Ile
305                 310
```

<210> SEQ ID NO 4
<211> LENGTH: 80
<212> TYPE: PRT
<213> ORGANISM: Homo sapiens

<400> SEQUENCE: 4

```
Asn Asp Glu Val Trp Ser Asp Ser Glu Gln Ser Phe Leu Asp Pro Asp
1               5                   10                  15

Ile Gly Gly Val Ala Val Ala Pro Thr His Gly Ser Ile Leu Ile Glu
            20                  25                  30

Cys Ala Lys Arg Glu Leu His Ala Thr Thr Pro Leu Lys Asn Pro Asn
        35                  40                  45

Arg Asn His Pro Thr Arg Ile Ser Leu Val Phe Tyr Gln His Lys Ser
    50                  55                  60

Met Asn Glu Pro Lys His Gly Leu Ala Leu Trp Glu Ala Lys Met Ala
65                  70                  75                  80
```

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5

-continued tgaacttccc acattagctg gt 22

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
gaaactgtag caccattagg catt 24

<210> SEQ ID NO 7
<211> LENGTH: 25
<212> TYPE: DNA
<213> ORGANISM: Artificial sequence
<220> FEATURE:
<223> OTHER INFORMATION: Primer

<400> SEQUENCE: 7
caaaaggcta atggagaaag acgta 25

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
gcagaaaagg aatccttagt gaaca 25

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
gccagtaaac tagctgcaat gctaa 25

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
tgcctcatta cgttttagat ggg 23

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
gaccaatgtc agaacacctc aa 22

<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
ttgattttga atactgattt tcacca 26

<210> SEQ ID NO 13
<211> LENGTH: 24
<212> TYPE: DNA
<213> ORGANISM: Artificial sequence
<220> FEATURE:
<223> OTHER INFORMATION: Primer

<400> SEQUENCE: 13
ttgcaacata agcctcataa acag 24

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
attggcctgt gcatctgact at 22

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
gcaacttgct cagcaaaggt act 23

<210> SEQ ID NO 16
<211> LENGTH: 24
<212> TYPE: DNA
<213> ORGANISM: Artificial sequence
<220> FEATURE:
<223> OTHER INFORMATION: Primer

<400> SEQUENCE: 16
tgctgccaga ctcaagattt aaaa 24

<210> SEQ ID NO 17
<211> LENGTH: 34
<212> TYPE: DNA
<213> ORGANISM: Artificial sequence
<220> FEATURE:
<223> OTHER INFORMATION: Primer

<400> SEQUENCE: 17
atactacata taatacattc taattccctc actg 34

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
tgtttactgc tttgtgtgtg aagg 24

<210> SEQ ID NO 19
<211> LENGTH: 26
<212> TYPE: DNA
<213> ORGANISM: Artificial sequence
<220> FEATURE:
<223> OTHER INFORMATION: Primer

<400> SEQUENCE: 19
catttctcag gatgtggtca tagaat 26

<210> SEQ ID NO 20
<211> LENGTH: 23
<212> TYPE: DNA
<213> ORGANISM: Artificial sequence
<220> FEATURE:
<223> OTHER INFORMATION: Primer

<400> SEQUENCE: 20
cccaattctc agggtcagat tta 23

<210> SEQ ID NO 21
<211> LENGTH: 29
<212> TYPE: DNA
<213> ORGANISM: Artificial sequence
<220> FEATURE:
<223> OTHER INFORMATION: Primer

<400> SEQUENCE: 21
agacttatgt atctttcatc tagctctgg 29

<210> SEQ ID NO 22
<211> LENGTH: 25
<212> TYPE: DNA
<213> ORGANISM: Artificial sequence
<220> FEATURE:
<223> OTHER INFORMATION: Primer

<400> SEQUENCE: 22
actctcttcc tttcaaccaa agatt 25

<210> SEQ ID NO 23
<211> LENGTH: 27
<212> TYPE: DNA
<213> ORGANISM: Artificial sequence
<220> FEATURE:
<223> OTHER INFORMATION: Primer

<400> SEQUENCE: 23
atgccacagc ttaatacaga gttagat 27

<210> SEQ ID NO 24
<211> LENGTH: 30
<212> TYPE: DNA
<213> ORGANISM: Artificial sequence
<220> FEATURE:
<223> OTHER INFORMATION: Primer

<400> SEQUENCE: 24
tgtcatattg ttcacttcat ctaagctaat 30

<210> SEQ ID NO 25
<211> LENGTH: 28
<212> TYPE: DNA
<213> ORGANISM: Artificial sequence
<220> FEATURE:
<223> OTHER INFORMATION: Primer

<400> SEQUENCE: 25
gatgctttat ttagtaataa aggcacca 28

<210> SEQ ID NO 26
<211> LENGTH: 35
<212> TYPE: DNA
<213> ORGANISM: Artificial sequence
<220> FEATURE:
<223> OTHER INFORMATION: Primer

<400> SEQUENCE: 26
ttcaacaatt aagaggaaaa gttagaataa tattt 35

<210> SEQ ID NO 27
<211> LENGTH: 25
<212> TYPE: DNA
<213> ORGANISM: Artificial sequence
<220> FEATURE:
<223> OTHER INFORMATION: Primer

<400> SEQUENCE: 27
tgtcattcca ttttgtttct ggata 25

<210> SEQ ID NO 28
<211> LENGTH: 26
<212> TYPE: DNA
<213> ORGANISM: Artificial sequence
<220> FEATURE:
<223> OTHER INFORMATION: Primer

<400> SEQUENCE: 28
aaattaccca gtcttgcata tgtctt 26

<210> SEQ ID NO 29
<211> LENGTH: 22
<212> TYPE: DNA
<213> ORGANISM: Artificial sequence
<220> FEATURE:
<223> OTHER INFORMATION: Primer

<400> SEQUENCE: 29
ctggatcaac taggccacca ac 22

<210> SEQ ID NO 30
<211> LENGTH: 33
<212> TYPE: DNA
<213> ORGANISM: Artificial sequence
<220> FEATURE:
<223> OTHER INFORMATION: Primer

<400> SEQUENCE: 30
ccaaaattaa caatgttcat tttacaataa gag 33

<210> SEQ ID NO 31
<211> LENGTH: 25
<212> TYPE: DNA
<213> ORGANISM: Artificial sequence
<220> FEATURE:
<223> OTHER INFORMATION: Primer

<400> SEQUENCE: 31
gctcttatct ttgcttaatg ggtgt 25

<210> SEQ ID NO 32

<211> LENGTH: 27
<212> TYPE: DNA
<213> ORGANISM: Artificial sequence
<220> FEATURE:
<223> OTHER INFORMATION: Primer

<400> SEQUENCE: 32
tgtacatttg gtctaatggt acaactg 27

<210> SEQ ID NO 33
<211> LENGTH: 24
<212> TYPE: DNA
<213> ORGANISM: Artificial sequence
<220> FEATURE:
<223> OTHER INFORMATION: Primer

<400> SEQUENCE: 33
aatggaaacc tatcagtgga caac 24

<210> SEQ ID NO 34
<211> LENGTH: 26
<212> TYPE: DNA
<213> ORGANISM: Artificial sequence
<220> FEATURE:
<223> OTHER INFORMATION: Primer

<400> SEQUENCE: 34
tatatatctg ttgtaaggcc ctgtga 26

<210> SEQ ID NO 35
<211> LENGTH: 23
<212> TYPE: DNA
<213> ORGANISM: Artificial sequence
<220> FEATURE:
<223> OTHER INFORMATION: Primer

<400> SEQUENCE: 35
cagagctttc tggatcctga cat 23

<210> SEQ ID NO 36
<211> LENGTH: 25
<212> TYPE: DNA
<213> ORGANISM: Artificial sequence
<220> FEATURE:
<223> OTHER INFORMATION: Primer

<400> SEQUENCE: 36
gcccacgtca tgagaactat actac 25

<210> SEQ ID NO 37
<211> LENGTH: 28
<212> TYPE: DNA
<213> ORGANISM: Artificial sequence
<220> FEATURE:
<223> OTHER INFORMATION: Primer

<400> SEQUENCE: 37
tctaagctca gtctaccacc catccata 28

<210> SEQ ID NO 38
<211> LENGTH: 25
<212> TYPE: DNA
<213> ORGANISM: Artificial sequence
<220> FEATURE:
<223> OTHER INFORMATION: Primer

<400> SEQUENCE: 38

```
tgctcgctgt ctgaccagac ctcat                                          25


<210> SEQ ID NO 39
<211> LENGTH: 6869
<212> TYPE: DNA
<213> ORGANISM: Homo sapiens

<400> SEQUENCE: 39

ccgtgccatc ccaacctccc acctcgcccc caaccttcgc gcttgctctg cttcttctcc     60

caggggtgga gacccgccga ggtccccggg gttcccgagg gctgcaccct tccccgcgct    120

cgccagccct ggcccctact ccgcgctggt ccgggcgcac cactcccccc gcgccactgc    180

acggcgtgag ggcagcccag gtctccactg cgcgccccgc tgtacggccc caggtgccgc    240

cggcctttgt gctggacgcc cggtgcgggg ggctaattcc ctgggagccg gggctgaggg    300

ccccagggcg gcggcgcagg ccggggcgga gcgggaggag gccggggcgg agcaggagga    360

ggcccgggcg gaggaggaga gccggcggta gcggcagtgg cagcggcgag agcttgggcg    420

gccgccgccg cctcctcgcg agcgccgcgc gcccgggtcc cgctcgcatg caagtcacgt    480

ccgccccctc ggcgcggccg ccccgagacg ccggccccgc tgagtgatga gaacagacgt    540

caaactgcct tatgaatatt gatgcggagg ctaggctgct ttcgtagaga agcagaagga    600

agcaagatgg ctgcccttta ggatttgtta gaaaggagac ccgactgcaa ctgctggatt    660

gctgcaaggc tgagggacga gaacgaggct ggcaaacatt cagcagcaca ccctctcaag    720

attgtttact tgcctttgct cctgttgagt tacaacgctt ggaagcagga gatgggctca    780

gcagcagcca ataggacatg atccaggaag agcaaattca actagagggc agccttgtgg    840

atggccccga agcaagcctg atggaacagg atagaaccaa ccatgttgag ggcaacagac    900

taagtccatt cctgatacca tcacctccca tttgccagac agaacctctg gctacaaagc    960

tccagaatgg aagcccactg cctgagagag ctcatccaga agtaaatgga gacaccaagt   1020

ggcactcttt caaaagttat tatggaatac cctgtatgaa gggaagccag aatagtcgtg   1080

tgagtcctga ctttacacaa gaaagtagag ggtattccaa gtgtttgcaa aatggaggaa   1140

taaaacgcac agttagtgaa ccttctctct ctgggctcct tcagatcaag aaattgaaac   1200

aagaccaaaa ggctaatgga gaaagacgta acttcggggt aagccaagaa agaaatccag   1260

gtgaaagcag tcaaccaaat gtctccgatt tgagtgataa gaaagaatct gtgagttctg   1320

tagcccaaga aaatgcagtt aaagatttca ccagtttttc aacacataac tgcagtgggc   1380

ctgaaaatcc agagcttcag attctgaatg agcaggaggg gaaaagtgct aattaccatg   1440

acaagaacat tgtattactt aaaaacaagg cagtgctaat gcctaatggt gctacagttt   1500

ctgcctcttc cgtggaacac acacatggtg aactcctgga aaaaacactg tctcaatatt   1560

atccagattg tgtttccatt gcggtgcaga aaaccacatc tcacataaat gccattaaca   1620

gtcaggctac taatgagttg tcctgtgaga tcactcaccc atcgcatacc tcagggcaga   1680

tcaattccgc acagacctct aactctgagc tgcctccaaa gccagctgca gtggtgagtg   1740

aggcctgtga tgctgatgat gctgataatg ccagtaaact agctgcaatg ctaaatacct   1800

gttcctttca gaaaccagaa caactacaac aacaaaaatc agtttttgag atatgcccat   1860

ctcctgcaga aaataacatc cagggaacca caaagctagc gtctggtgaa gaattctgtt   1920

caggttccag cagcaatttg caagctcctg gtggcagctc tgaacggtat ttaaaacaaa   1980

atgaaatgaa tggtgcttac ttcaagcaaa gctcagtgtt cactaaggat tccttttctg   2040
```

```
ccactaccac accaccacca ccatcacaat tgcttctttc tccccctcct cctcttccac   2100
aggttcctca gcttccttca gaaggaaaaa gcactctgaa tggtggagtt ttagaagaac   2160
accaccacta ccccaaccaa agtaacacaa cacttttaag ggaagtgaaa atagagggta   2220
aacctgaggc accaccttcc cagagtccta atccatctac acatgtatgc agcccttctc   2280
cgatgctttc tgaaaggcct cagaataatt gtgtgaacag gaatgacata cagactgcag   2340
ggacaatgac tgttccattg tgttctgaga aaacaagacc aatgtcagaa cacctcaagc   2400
ataacccacc aatttttggt agcagtggag agctacagga caactgccag cagttgatga   2460
gaaacaaaga gcaagagatt ctgaagggtc gagacaagga gcaaacacga gatcttgtgc   2520
ccccaacaca gcactatctg aaaccaggat ggattgaatt gaaggcccct cgttttcacc   2580
aagcggaatc ccatctaaaa cgtaatgagg catcactgcc atcaattctt cagtatcaac   2640
ccaatctctc caatcaaatg acctccaaac aatacactgg aaattccaac atgcctgggg   2700
ggctcccaag gcaagcttac acccagaaaa caacacagct ggagcacaag tcacaaatgt   2760
accaagttga aatgaatcaa gggcagtccc aaggtacagt ggaccaacat ctccagttcc   2820
aaaaaccctc acaccaggtg cacttctcca aaacagacca tttaccaaaa gctcatgtgc   2880
agtcactgtg tggcactaga tttcattttc aacaaagagc agattcccaa actgaaaaac   2940
ttatgtcccc agtgttgaaa cagcacttga atcaacaggc ttcagagact gagccatttt   3000
caaactcaca ccttttgcaa cataagcctc ataaacaggc agcacaaaca caaccatccc   3060
agagttcaca tctccctcaa aaccagcaac agcagcaaaa attacaaata aagaataaag   3120
aggaaatact ccagactttt cctcaccccc aaagcaacaa tgatcagcaa agagaaggat   3180
cattctttgg ccagactaaa gtggaagaat gttttcatgg tgaaaatcag tattcaaaat   3240
caagcgagtt cgagactcat aatgtccaaa tgggactgga ggaagtacag aatataaatc   3300
gtagaaattc cccttatagt cagaccatga aatcaagtgc atgcaaaata caggtttctt   3360
gttcaaacaa tacacaccta gtttcagaga ataaagaaca gactacacat cctgaacttt   3420
ttgcaggaaa caagacccaa aacttgcatc acatgcaata ttttccaaat aatgtgatcc   3480
caaagcaaga tcttcttcac aggtgctttc aagaacagga gcagaagtca caacaagctt   3540
cagttctaca gggatataaa aatagaaacc aagatatgtc tggtcaacaa gctgcgcaac   3600
ttgctcagca aaggtacttg atacataacc atgcaaatgt tttcctgtg cctgaccagg    3660
gaggaagtca cactcagacc cctccccaga aggacactca aaagcatgct gctctaaggt   3720
ggcatctctt acagaagcaa gaacagcagc aaacacagca accccaaact gagtcttgcc   3780
atagtcagat gcacaggcca attaaggtgg aacctggatg caagccacat gcctgtatgc   3840
acacagcacc accagaaaac aaaacatgga aaaaggtaac taagcaagag aatccacctg   3900
caagctgtga taatgtgcag caaaagagca tcattgagac catggagcag catctgaagc   3960
agtttcacgc caagtcgtta tttgaccata aggctcttac tctcaaatca cagaagcaag   4020
taaaagttga aatgtcaggg ccagtcacag ttttgactag acaaaccact gctgcagaac   4080
ttgatagcca caccccagct ttagagcagc aaacaacttc ttcagaaaag acaccaacca   4140
aaagaacagc tgcttctgtt ctcaataatt ttatagagtc accttccaaa ttactagata   4200
ctcctataaa aaatttattg gatacacctg tcaagactca atatgatttc ccatcttgca   4260
gatgtgtaga gcaaattatt gaaaaagatg aaggtccttt ttatacccat ctaggagcag   4320
gtcctaatgt ggcagctatt agagaaatca tggaagaaag gtttggacag aagggtaaag   4380
ctattaggat tgaaagagtc atctatactg gtaaagaagg caaaagttct cagggatgtc   4440
```

-continued

```
ctattgctaa gtgggtggtt cgcagaagca gcagtgaaga gaagctactg tgtttggtgc   4500
gggagcgagc tggccacacc tgtgaggctg cagtgattgt gattctcatc ctggtgtggg   4560
aaggaatccc gctgtctctg gctgacaaac tctactcgga gcttaccgag acgctgagga   4620
aatacggcac gctcaccaat cgccggtgtg ccttgaatga agagagaact tgcgcctgtc   4680
aggggctgga tccagaaacc tgtggtgcct ccttctcttt tggttgttca tggagcatgt   4740
actacaatgg atgtaagttt gccagaagca agatcccaag gaagtttaag ctgcttgggg   4800
atgacccaaa agaggaagag aaactggagt ctcatttgca aaacctgtcc actcttatgg   4860
caccaacata taagaaactt gcacctgatg catataataa tcagattgaa tatgaacaca   4920
gagcaccaga gtgccgtctg ggtctgaagg aaggccgtcc attctcaggg gtcactgcat   4980
gtttggactt ctgtgctcat gcccacagag acttgcacaa catgcagaat ggcagcacat   5040
tggtatgcac tctcactaga gaagacaatc gagaatttgg aggaaaacct gaggatgagc   5100
agcttcacgt tctgccttta tacaaagtct ctgacgtgga tgagtttggg agtgtggaag   5160
ctcaggagga gaaaaaacgg agtggtgcca ttcaggtact gagttctttt cggcgaaaag   5220
tcaggatgtt agcagagcca gtcaagactt gccgacaaag gaaactagaa gccaagaaag   5280
ctgcagctga aaagctttcc tccctggaga acagctcaaa taaaaatgaa aaggaaaagt   5340
cagccccatc acgtacaaaa caaactgaaa acgcaagcca ggctaaacag ttggcagaac   5400
ttttgcgact ttcaggacca gtcatgcagc agtcccagca gccccagcct ctacagaagc   5460
agccaccaca gccccagcag cagcagagac cccagcagca gcagccacat caccctcaga   5520
cagagtctgt caactcttat tctgcttctg gatccaccaa tccatacatg agacggccca   5580
atccagttag tccttatcca aactcttcac acacttcaga tatctatgga agcaccagcc   5640
ctatgaactt ctattccacc tcatctcaag ctgcaggttc atatttgaat tcttctaatc   5700
ccatgaaccc ttaccctggg cttttgaatc agaataccca atatccatca tatcaatgca   5760
atggaaacct atcagtggac aactgctccc catatctggg ttcctattct ccccagtctc   5820
agccgatgga tctgtatagg tatccaagcc aagaccctct gtctaagctc agtctaccac   5880
ccatccatac actttaccag ccaaggtttg gaaatagcca gagttttaca tctaaatact   5940
taggttatgg aaaccaaaat atgcagggag atggtttcag cagttgtacc attagaccaa   6000
atgtacatca tgtagggaaa ttgcctcctt atcccactca tgagatggat ggccacttca   6060
tgggagccac ctctagatta ccacccaatc tgagcaatcc aaacatggac tataaaaatg   6120
gtgaacatca ttcaccttct cacataatcc ataactacag tgcagctccg ggcatgttca   6180
acagctctct tcatgccctg catctccaaa acaaggagaa tgacatgctt tcccacacag   6240
ctaatgggtt atcaaagatg cttccagctc ttaaccatga tagaactgct tgtgtccaag   6300
gaggcttaca caaattaagt gatgctaatg gtcaggaaaa gcagccattg gcactagtcc   6360
agggtgtggc ttctggtgca gaggacaacg atgaggtctg gtcagacagc gagcagagct   6420
ttctggatcc tgacattggg ggagtggccg tggctccaac tcatgggtca attctcattg   6480
agtgtgcaaa gcgtgagctg catgccacaa ccccttttaa gaatcccaat aggaatcacc   6540
ccaccaggat ctccctcgtc ttttaccagc ataagagcat gaatgagcca aaacatggct   6600
tggctctttg ggaagccaaa atggctgaaa aagcccgtga gaaagaggaa gagtgtgaaa   6660
agtatggccc agactatgtg cctcagaaat cccatggcaa aaaagtgaaa cgggagcctg   6720
ctgagccaca tgaaacttca gagcccactt acctgcgttt catcaagtct cttgccgaaa   6780
```

-continued

| | |
|---|---|
| ggaccatgtc cgtgaccaca gactccacag taactacatc tccatatgcc ttcactcggg | 6840 |
| tcacagggcc ttacaacaga tatatatga | 6869 |

TET2 AS A DIAGNOSTIC AND PRONOSTIC MARKER IN HEMATOPOIETIC NEOPLASMS

This application claims the priority of European patent applications EP 08305255.5 and EP 09155169.7 filed on Jun. 12, 2008 and on Mar. 13, 2009 respectively, which are incorporated herein by reference.

FIELD OF THE INVENTION

The present invention relates to genetic markers to diagnose myeloid neoplasms, more particularly to a new identified tumour suppressor gene, the Ten Eleven Translocation protein family member 2 gene (TET2). Genetic alterations of TET2 are useful to diagnose myeloid tumours, such as myelodysplastic/myeloproliferative syndromes, MDS, AML or MPD, and lymphoid tumours.

BACKGROUND OF THE INVENTION

Hematopoiesis is maintained by a hierarchical system where hematopoietic stem cells (HSCs) give rise to multipotent progenitors, which in turn differentiate into all types of mature blood cells. The molecular mechanisms controlling multipotentiality, self-renewal, quiescence and HSC commitment have been extensively studied. However, numerous issues remain to be addressed and important genes regulating these processes remain to be identified.

Myeloid malignancies include Acute Myeloid leukaemia (AML), Myeloproliferative disorders (MPDs), myelodysplastic syndromes (MDS) and myelodysplastic/myeloproliferative syndromes that are all clonal stem-cell (HSC) or progenitor malignant disorders (TIU et al., *Leukemia*, vol. 21(8), p: 1648-57, 2007).

Several genetic mutations have been correlated to AML, and four groups are recognized: (i) the AML with recurrent genetic abnormalities AML t(8;21)(q22;q22) with RUNX1-ETO fusion gene; AML with abnormal bone marrow eosinophils and inv(16)(p13;q22) or t(16;16)(p13;q22) with CBFB/MYH11 rearrangement; acute promyelocytic leukaemia APL with t(15;17)(q22;q12) PML/RARA; AML with 11q23 (MLL) abnormalities); (ii) AML with multilineage dysplasia following MDS or MDS/MPD or without antecedent of MDS or MPD; (iii) AML or MDS therapy related and (iv) other unclassified AML among that comprises the group of AML with normal karyotype which prognosis is based on molecular analysis of oncogenes such as mutations of FLT3-ITD or NPM1.

Myelodysplastic/myeloproliferative syndromes include four myeloid diseases grouped in 1999 by the WHO: chronic myelomonocytic leukemia (CMML), juvenile myelomonocytic leukemia (JMML), atypical chronic myeloid leukemia (aCML) and unclassified myelodysplastic/myeloproliferative syndromes (U-MDS/MPS).

MDS include refractory anemia (RA), and refractory cytopenia with multilineage dysplasia (RCMD). MDS are characterized by ineffective hematopoiesis in one or more of the lineage of the bone marrow. Early MDS mostly demonstrate excessive apoptosis and hematopoietic cell dysplasia (CLAESSENS et al., *Blood*, vol. 99, p: 1594-601, 2002; CLASESSENS et al., *Blood*, vol. 105, p: 4035-42, 2005). In about a third of MDS patients, this ineffective hematopoiesis precedes progression to secondary AML (sAML). Although some molecular events associated with specific MDS subtypes (ELBERT et al., *Nature*, vol. 451(7176), p: 335-9, 2008) or disease transformation (BRAUN et al., *Blood*, vol.

107(3), p: 1156-65, 2006) have been identified, the underlying molecular defects are still poorly understood. No biological markers, except morphological features, are currently available for early diagnosis and prognosis.

MPDs, referred now as myeloproliferative neoplasms (MPN; TEFFERI & VARDIMAN, *Leukemia*, vol. 22, p: 14-22, 2008), are chronic myeloid diseases including chronic myelogenous leukaemia (CML), polycythemia vera (PV), essential thrombocythemia (ET), primary myelofibrosis (PMF) and idiopathic myelofibrosis (IMF). MPDs are characterized by an increased proliferation of one or several myeloid lineages. If most MPDs are sporadic diseases, familial cases of MPDs, for which the exact prevalence is unknown, have been reported (GILBERT, *Baillieres Clin. Haematol*., vol. 11, p: 849-858, 1998; KRALOVICS et al., *Blood*, vol. 102, p: 3793-3796, 2003; BELLANNE-CHANTELOT et al., *Blood*, vol. 108, p: 346-352, 2006). The clinical analysis of these familial cases has shown that they are phenotypically identical to sporadic cases. Nevertheless, MPD families are characterized by a clinical and genetic heterogeneity. First, MPD cases from a single family can either display the same subtype or different types of MPD (GILBERT, abovementioned, 1998; BELLANNE-CHANTELOT et al., abovementioned, 2006; RUMI et al., *Cancer*, vol. 107, p: 2206-2211, 2006). Second, about 6-15% of patients with PV and 3-5% of patients with ET are at risk of developing hematological complication after 15 years of evolution (FINAZZI & HARRISON, *Semin. Hematol*., vol. 42, p: 230-238, 2005; KILADJIAN et al., *Blood*, vol. 112, p: 1746, 2008; PASSAMONTI et al., *Blood*, vol. 111, p: 3383-3387, 2008; PASSAMONTI et al., *Haematologica*, vol. 93, p: 1645-1651, 2008).

MPDs, in both sporadic and familial cases, are commonly associated with an acquired constitutive kinase activity, as exemplified by the JAK2$^{V617F}$ mutation in Polycythemia Vera, in most PV cases and in half of ET and PMF cases (MORGAN & GILLIGAND, *Anna. Rev. Med*., vol. 59, p: 213-22, 2008; DELHOMMEAU et al., *Cell Mol. Life Sci*., vol. 63(24), p: 2939-53, 2006, CAMPBELL & GREEN, *N. Engl. J. Med*., vol. 355(23), p: 2452-66, 2006; BELLANNE-CHANTELOT et al., abovementioned, 2006; JAMES et al., *Nature*, vol. 434, p: 1144-1148, 2005; BAXTER et al., *Lancet*, vol. 365, p: 1054-1061, 2005; LEVINE et al., *Blood*, vol. 106, p: 3377-3379, 2005; KRALOVICS et al., *N. Engl. J. Med*., vol. 352, p: 1779-1790, 2005). MPDs frequently result from the expression of a constitutive tyrosine kinase protein:

- Through a fusion like BCR-ABL in CML, FIP1L1-PDGFRA in HES, TEL-PDGFRB in CMML with hypereosinophilia, ZNF198-FGFR1 in rare MPD coupled to lymphoid proliferation and PCM1-JAK2 in rare MPDs, AML and T cell lymphomas
- A limited or single nucleotide mutation i.e. JAK2 V617F (1849G>T), which recent discovery of in PV (98%), ET (75%), IMF (50%) and a few percent of CMML, MDS/MPD and U-MPD allows for a new MPD classification and diagnosis criteria and perspectives for treatment. In addition, KIT mutations are recurrent in systemic mast cell proliferation.
- Through activating mutations in the receptor for thrombopoietin receptor (MPL), especially of the tryptophan 515 (MPLW515$^{K/L/A}$) (PIKMAN et al., *PLoS Med*, vol. 3 (e270), 2006; CHALIGNÉ et al., *Leukemia*, vol. 22, p 1557-66, 2008).
- Marginal cases of CML presented with BCR/JAK2 rearrangement due to t(9;22)(p24;q11).

The JAK2 gene on chromosome 9p encodes a tyrosine kinase that associates with type 1 cytokine receptors. The V617F mutation is predicted to disrupt the auto-inhibitory effect of the JH2 domain to constitutive activation of the kinase. Wild type JAK2 exerts a dominant negative effect on the activity of the mutated protein. Therefore the loss of WT JAK2 associated to the duplication of the mutated gene by mitotic recombination observed in most of MPD samples allows for a higher expression and activity of the mutated kinase.

However, several observations, such as the Polycythemia Vera co expressing the WT and mutated JAK2 and the characterization of secondary AML emerging from mutated MPD but lacking of JAK2 mutation in the blast phases indicate ontogenetic events earlier occurring before JAK2 mutation. Moreover, and as discussed previously, the MPD disease evolution is indeed highly variable within and between families. Thus, there is some evidence that there is at least one other mutation than JAK2 implicated in MPDs and, more specifically, their progression.

Lymphoid tumours consist of expansion, of cells with lymphoid features, Acute lymphoblastic leukaemia/lymphoma are proliferation of cells blocked in lymphoid differentiation, from either T (T-cell acute lymphoblastic leukaemia; T-ALL) or B (B-cell precursor acute lymphoblastic leukaemia; BCP-ALL) origin. Some leukaemia lymphoma are from Natural Killer (NK) origin. Lymphoma involve expansion of more mature lymphoid cells (B or T). Some neoplasms are chronic, and can involve T cell (prolymphocytic leukaemia) or B cells (Chronic Lymphocytic Leukaemia). The classification of lymphoid neoplasm is based on anatomopathological analyses, differentiation markers and pathogenesis data (Swerdllow S. H., Campo E., Harris N. L., Jaffe E. S., Pileri S. A., Stein H., Thiele J. W., Vardiman J. W. (Eds): WHO classification of tumors of haematopoietc and lymphoid tissues. IARC: Lyon 2008). For example, Anaplasic large T-cell lymphoma are associated with NPM-ALK fusion oncogene (and variant thereof), follicular lymphoma are associated with BCL2 activation following t(14;18)(q32;q21) chromosomal translocation, mantle cell lymphoma are associated with CCND1 activation following t(11;14)(q13;q32) chromosomal translocation. Many lymphoma however lack any reliable molecular marker suggesting a pathophysiological mechanism. This is the case, In particular, for more than 50% of diffuse large B cell lymphomas (DLBCL), for most peripheral T-cell lymphomas (PTCL) and for a majority of non-follicular low grade lymphomas.

Therefore, there was an urgent need of a reliable diagnostic marker that allows to identify lymphoid and myeloid neoplasms, in particular MDS and MPD, and eventually to prognosticate their progression.

The Ten Eleven Translocation protein family contains three recently identified members, with unknown functions, characterized in that they share two highly conserved domains at their C-terminal end. As used herein, the expression "gene of the TET family" refers to members of the Ten Eleven Translocation family, TET1, TET2 or TET3, which have been recently identified (Lorsbach et al, *Leukemia* 2003).

Among them, TET1 is the only studied member, because it has been identified as a fusion partner with the protein mixed lineage leukemia (MLL) in two different and independent studies (ONO et al., *Cancer Research*, vol. 62(14), p: 4075-80, 2002 and LORSBACH et al., *Leukemia*, vol. 17(3), p: 637-41, 2003). This protein, also called LCX, or "leukemia associated protein with a CXXC domain in N-terminal region", contains an α-helical coiled-coil region in its C-terminal region, region which is retained in the fusion MLL-TET1. On the contrary, the N-terminus CXXC domain of TET1 is not present in this protein fusion (Ono R, Cancer Research 2002). The two highly conserved carboxy terminal regions are included in the MILL-TET1 fusion (Lorsbach et al, Leukemia 2003). One conserved region is disrupted by the translocation; the other one is fused to MLL. Despite its description as an MLL fusion partner 7 years ago, functional and sequence analysis of the TET1 gene have been reported recently, after the priority date of the present application.

The MLL gene is located at human chromosome 11q23 and is found to be rearranged in a heterogenous group of lymphoid, myeloid and mixed lineage human leukemias. More than 70 loci have been described to be rearranged with the 11q23 chromosomal hand and at least 50 of these have been cloned and characterized on a molecular level. Most of the MLL rearrangements map to a 8.3 kb base of the genes. The partners genes are always fused in frame to the 5' part MLL and may include itself. Amplifications of MLL have also been reported. The partner genes code for proteins with disparate functions. In the MLL fusion, they may provide transcriptional activation domains, chromatin modifier complex recruitment or dimerization/oligomerization motif. Indeed, the expression of an MLL-Beta-galactosidase (a bacterial protein able to tetramerize) or to dimerization domain is sufficient to induce leukemia in mouse models. Therefore, it is not possible to infer the function of a protein or its independent involvement in cellular transformation from its fusion to MLL (The versatile mixed lineage leukaemia gene MLL and its many associations in leukaemogenesis. Daser A, Rabbitts T H. Semin Cancer Biol. 2005 June; 15(3):175-88. Review. Chromosomal rearrangements leading to MLL gene fusions: clinical and biological aspects. Harper D P, Aplan P D, Cancer Res. 2008 Dec. 15; 68(24): 10024-7.)

On the contrary, little is known about the TET2 protein, which is encoded by a gene located on the 4q24 chromosomal region, and the TET3 protein, which is encoded by a gene located on the 2p12 chromosomal region.

More specifically, the Ten Eleven Translocation oncogene number 2 (TET2) has been designated recently (Lorsbach et al, *Leukemia* 2003). The TET2 gene located on the chromosomal region 4q24, comprises 11 exons spread over >130 Kb and is normally widely expressed. This gene is referenced with the accession number ID 57790, and its cDNA (Accession number NM_001127208, SEQ ID NO:1) is encoding a protein of 2002 amino acids (Accession number NP_001120680, SEQ ID NO:2).

The TET2 protein shares two highly conserved regions with a single orthologous *Drosophila* predicted protein. These regions are i) a 310 amino acid region located near the center of the protein TET2 (amino acids 1134 to amino acid 1444), and ii) a second 80 amino acid region located near the carboxyterminal end of the protein TET2 (corresponding to amino acid 1843 until amino acid 1922) (these regions are highlighted in FIG. 1). The predicted sequence of TET2 did not reveal any motif corresponding to an identified function.

Applicants report herein that one or both copies of the Ten Eleven Translocation 2 (TET2) gene are often inactivated/modified by acquired mutations in MPD, MDS and CMML, but also in lymphoma. These events target the hematopoietic stem cell and indicate an important function for TET2 as a tumor suppressor gene in myeloid or lymphoid neoplasms.

SUMMARY OF THE INVENTION

In a first aspect, the present invention provides an in vitro method for diagnosing a myeloid tumour or a lymphoid tumour in a subject, which comprises the step of analyzing a biological sample from said subject by:

(i) detecting the presence of a mutation in the Ten Eleven Translocation protein family member 2 gene (TET2) coding for the polypeptide having the sequence SEQ ID NO:2, and/or (ii) analyzing the expression of the TET 2 gene;

wherein the detection of such a TET2 mutation, of the absence of expression of TET2 or of the expression of a truncated TET2 is indicative of a subject developing or predisposed to develop a myeloid tumour or a lymphoid tumour.

In a preferred embodiment, said subject is a mammal, preferably a human.

In another preferred embodiment, said myeloid cancer is selected in the group consisting of myelodysplastic syndrome (MDS), acute myeloid leukemia (AML), myeloproliferative disease (MPD) and myelodysplatic/myeloproliferative syndrome.

In still another preferred embodiment, said lymphoid tumour is selected in the group consisting of lymphoma and more preferentially of T cell lymphoma Preferably, said mutation is detected on each copy of the TET2 gene coding for the polypeptide having the sequence SEQ ID NO :2 (encoded by the cDNA having the sequence SEQ ID NO:39) and is included in the group consisting of deletions, insertions and point mutations such as mutations affecting splice sites, missense mutation and nonsense mutations, preferably missense mutation and nonsense mutations.

In a more preferred aspect of the invention, the mutation is a deletion or an insertion which results in the absence of expression of the TET2 protein or in the expression of a truncated TET2 protein.

Even more preferably, this truncated TET2 protein does not comprise at least one of the two highly conserved regions shared by the other TET proteins and corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4), preferably the 80 amino acid region located near the carboxyterminal end of the protein TET2 (corresponding to amino acid 1843 until amino acid 1922, SEQ ID NO:4).

For example, these deletions or insertions can be selected in the group comprising or consisting of those disclosed, in Table I in reference to SEQ ID NO:39 for nucleic acid position and to SEQ ID NO:2 for amino acid position.

TABLE I

| Nucleotide Change | Consequence |
|---|---|
| del1264_1666 | p.Glu135 FS |
| delC 1642 | p.Ser261 FS |
| del1893_1896 | p.Lys345FS |
| delC 2448 | p.Gln530 FS |
| delA 2505 | p.Thr549 FS |
| delC 2524 | p. Pro555 FS |
| Ins 2540_2544 | p.Leu560FS |
| delT 2685 | p.Ser609 FS |
| delA 2815 | p.Gln652FS |
| del 2834_2835 | p.His658 FS |
| delA 2935 | p.Glu692 FS |
| delT 2944 | p.Leu699 STOP |
| delG 2994 | p.Glu711 FS |
| delC 3009 | p.His717 FS |
| insA 3009 | p.His717 FS |
| del 3131_3137 | p. Leu757 FS |
| insC 3151 | p.Gln764 FS |
| delA 3166 | p.Gln769 FS |
| delT3215 | p.Phe785 FS |
| insA3350 | p.Gln831FS |
| insT3995 | p.Glu846 FS |
| delA3430 | p.Asn857FS |
| insT 3465 | p.Pro869 FS |
| insA 5757 | p.Gln891 STOP |
| insCT 3581 | pGly 908 FS |
| del CA 3756_3757 | p.Gln966 FS |
| dupT 3914 | p.Glu1026 STOP |
| delT 3998 | p.Leu1046FS |
| delA 4130 | p.Lys1090 FS |
| delG 4271 | p.Glu1137 FS |
| delA4327 | p.Asn1156 FS |
| delG 4527 | p.Ala1223 FS |
| — | p.del 1237-1239 |
| delG 4932 | p.Glu1357 FS |
| insG 5119 | p.Leu 1420 FS |
| delG 5133 | p.Asp 1425 FS |
| insA 5177 | p.Arg1440FS |
| dupA 5177 | p.Arg1440FS |
| delC 5222 | p.Leu1457 STOP |
| del5521_5524 | pThr1554 FS |
| insA 5540 | p.Tyr1560 FS |
| del 5583_5605 | p.Pro1575FS |
| delT 5570 | p.Leu1637 FS |
| del5828_5843 | p.Met1656 FS |
| del6049_6050 | p.Asp1830 FS |
| delC 6360 | p.Gln1834 FS |
| del6396_6531 | p.Val1846 FS |
| delA 6507 | p.Thr1883 FS |
| insC 6507 | p.Thr1883 FS |
| del6511_6512 | p.Pro1885FS |
| DelC 6555 | p.Leu1889FS |
| insC splice site | mutation of splice site exon 8 |

Del: deletion;
ins: insertion;
FS: frame shift

In another more preferred aspect of the invention, the mutation is a missense mutation, which is located in the open reading frame of the TET2 protein, preferably in at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), and more preferably in the 80 amino acid region located near the carboxyterminal end of the protein TET2 (corresponding to amino acid 1843 until amino acid 1922, SEQ ID NO:4). For example, these missense mutations can be selected in the group comprising or consisting of I1175V, L1197N, H1219Y, E1235V, C1271W, K1299E, L1340P, R1302G, G1370E, A1344E, N1387S, V1417F, H1868R, G1869W, L1872P, I183T, R1896M, and S1898E, preferably can be selected in the group comprising or consisting of L1197N, H1219Y, E1235V, C1271W, K1299E, L1340P, R1302G, G1370E, A1344E, N1387S, H1868R, G1869W, L1872P, I1873 T, R1896M, and S1898F, and more preferably in the group comprising or consisting of H11868R, G1869W, L1872P, I1873T, R1896M, and S1898E.

In another more preferred aspect of the invention, the mutation is a nonsense mutation, which is located in the open reading frame of the TET2 protein, preferably before or inside at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), and more preferably before or inside the 80 amino acid region located near the carboxyterminal end of the protein TET2 (corresponding to amino acid 1843 until amino acid 1922, SEQ ID NO:4). For example, said nonsense mutations can be selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751 Stop, L1819Stop, Q1834Stop and W1847Stop.

In another aspect of the invention, the mutation in the TET2 gene induces absence of expression or under-expression of the polypeptide having the sequence SEQ ID NO:2 and more preferably the absence of expression or under-expression of at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), more preferably of the 80 amino acid region located near the carboxyterminal end of the protein TET2 (corresponding to amino acid 1843 until amino acid 1922, SEQ ID NO:4).

In a second aspect, the present invention provides a kit for diagnosing myeloid cancer in a subject comprising at least one nucleic acid probe or oligonucleotide or at least one antibody, which can be used in a method as defined previously for detecting the presence of a mutation in the TET2 gene and/or analysing the expression of the TET2 gene.

In a preferred embodiment of the invention, said oligonucleotide is at least one PCR primer, and preferably a set of PCR primers.

More preferably, said set of primers is selected in the group comprising SEQ ID NO: 5 to SEQ ID NO: 38 (see examples).

In a third aspect, the present invention provides the use of a hypomethylating agent for treating a patient suffering from a myeloid or a lymphoid tumour, for which tumour, a TET2 mutation, an absence of TET2 expression or an expression of a truncated TET2 has been detected.

In a final aspect, the present invention provides a method for treating a subject suffering a myeloid or a lymphoid tumour, for which tumour, a TET2 mutation, an absence of TET2 expression or an expression of a truncated TET2 has been detected, said method comprising the step of administrating to said subject a therapeutically efficient amount of a hypomethylating agent.

BRIEF DESCRIPTION OF THE DRAWINGS

The FIG. 1 shows the protein sequence of TET2 (SEQ ID NO: 2), highlighting the conserved regions between species (bold).

The FIG. 2 shows the sequence traces obtained by sequencing the PCR products obtained for samples obtained from two patients A and E, showing that the mutation only occurs in the tumoral and not in non-tumoral samples (NT), and Peripheral Blood Lymphocytes (PBL). R corresponds to the sequence obtained with the Reverse primer, and F corresponds to the one obtained with the Forward primer. WT corresponds to the sequence obtained in healthy individuals.

The FIGS. 3A-3D show that in MOS samples, mutated TET2 is observed in immature CD34+ cells and is associated with in vivo expansion of the mutated clone.

Figure 4B:
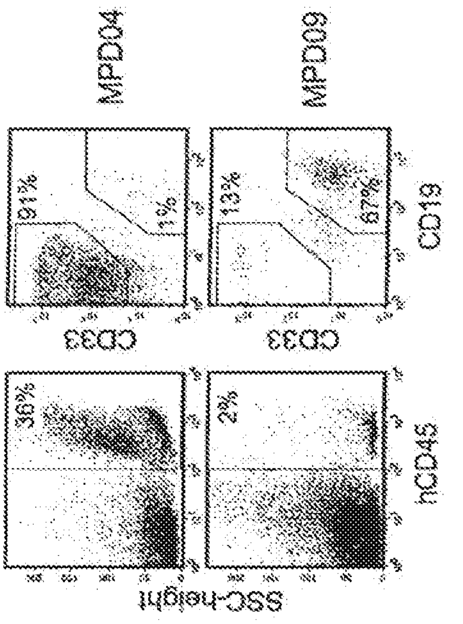
Figure 4A:
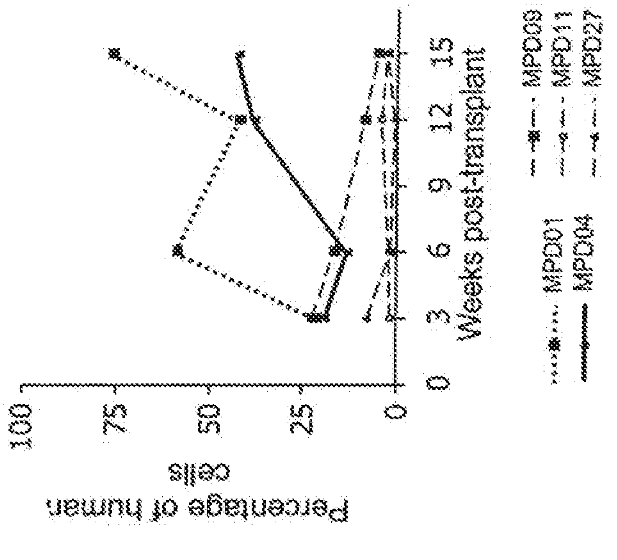

The FIGS. 4A-4B show that $JAK2^{V617F}$-positive MPD hematopoietic stem cells with TET2 defects display enhanced NOD/SCID repopulating capacities.

Figure 5:
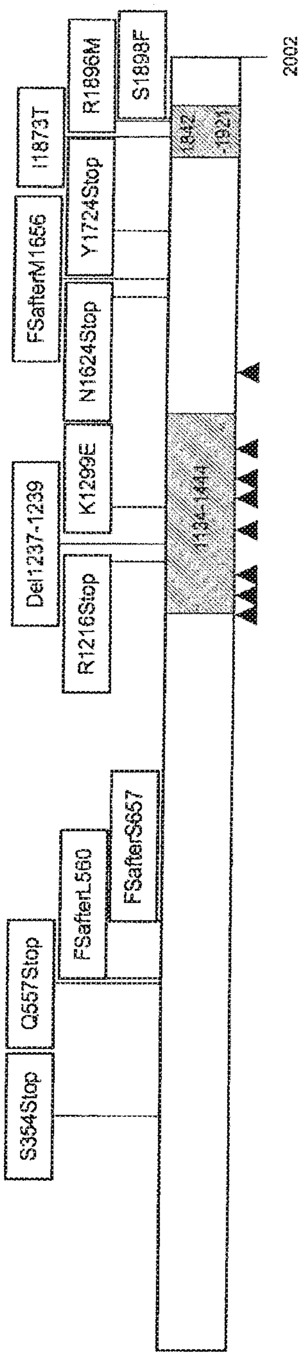

The FIG. 5 shows the locations of some of the identified mutations of the TET2 gene distributed along the protein sequence. Conserved regions are marked with gray stripes. Arrowheads indicate the location of exon boundaries. FS: Frame shift.

Figure 6:
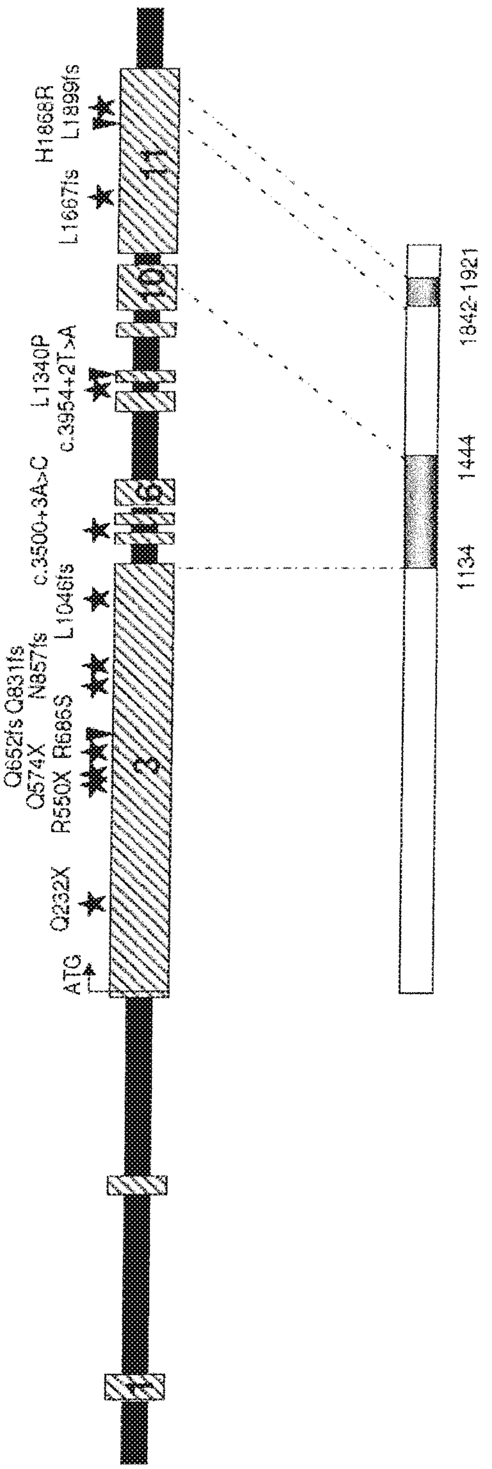

The FIG. 6 shows a schematic representation of the TET2 gene and protein showing the mutations identified in familial myeloproliferative neoplasms. Hatched boxes indicate exons. Truncating mutations are depicted as stars, missense mutations as inverted triangles. Conserved functional domains are depicted as boxes on the protein scheme. fs: frameshift.

Figure 7:
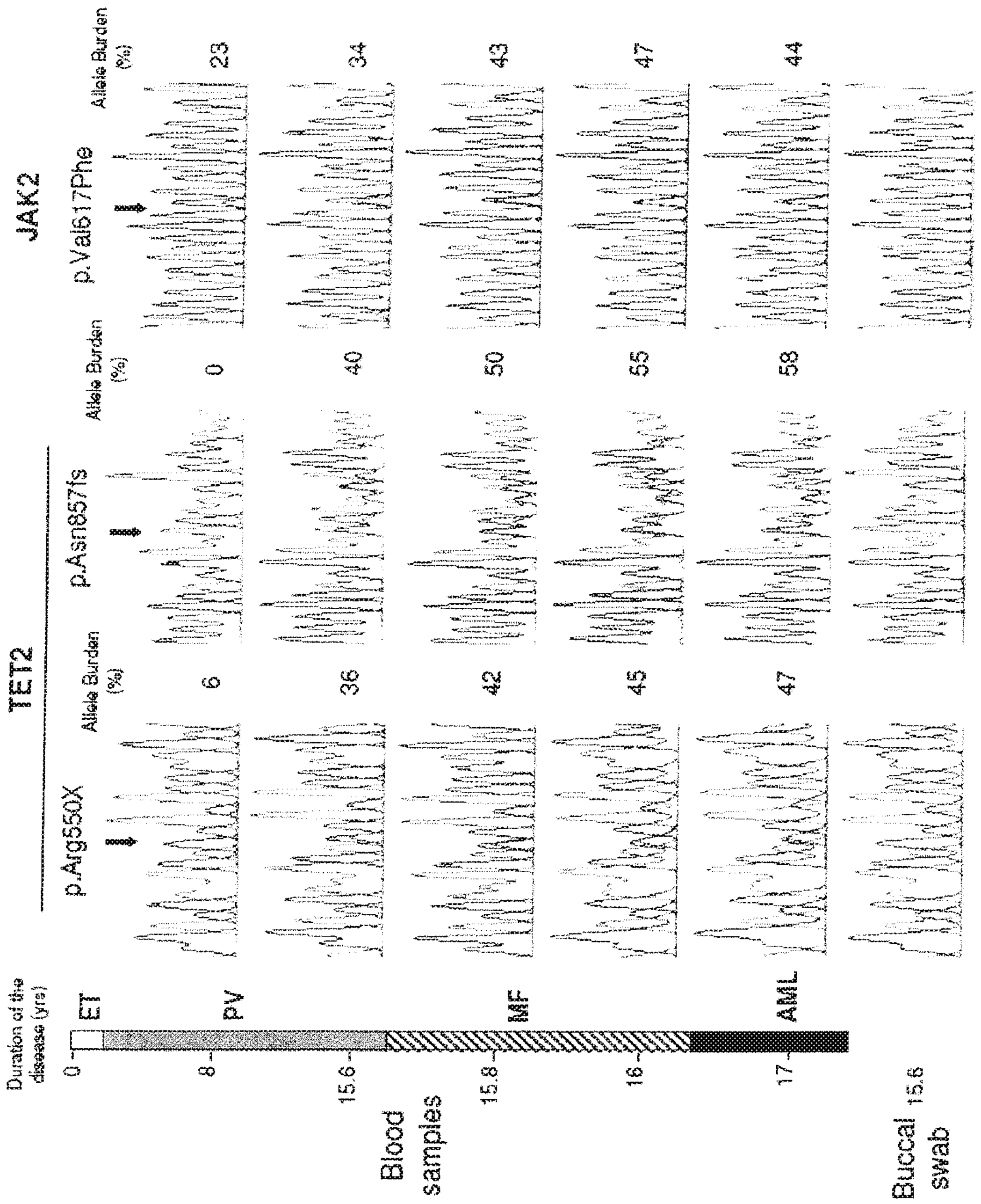

The FIG. 7 shows the sequential study of TET2 and JAK2 in patient P4 (F3). Sequence electrophoregrams are shown for each TET2 mutation and for JAKV617F. The diagram on the left indicates time lapse from diagnosis (in years) and corresponding phenotype for each sample (white: ET; grey: PV; hatched: post-ET MF; black: AML).

Figure 8:
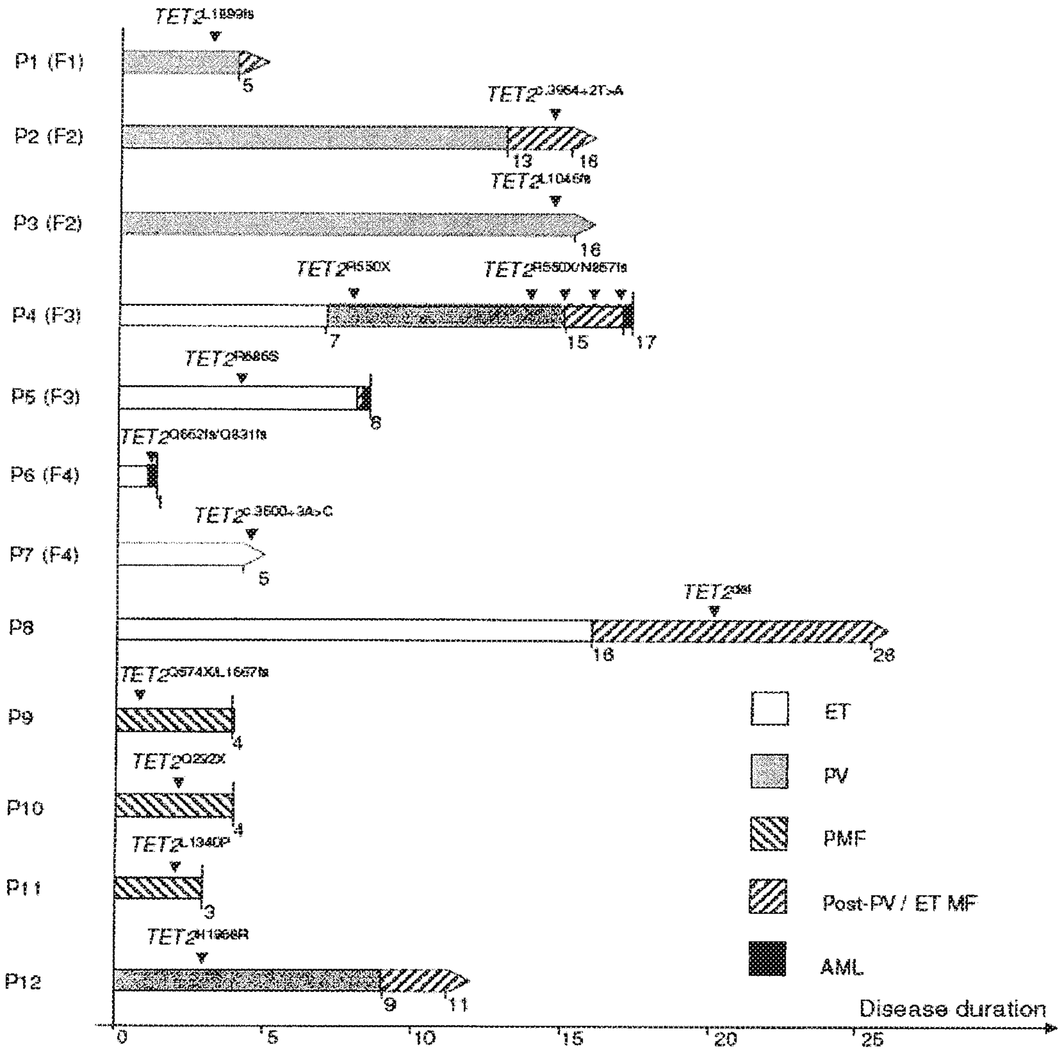

The FIG. 8 shows the schematic representation of the clinical status of the twelve patients with at least one TET2 mutation. White boxes depict ET stages, grey, PV, crosswised hatching indicates myelofibrosis, either primary (left-slanting) or post-PV/ET (right-slanting) and AML are symbolized as black boxes. Above each arrowhead indicating a molecular analysis is annotated the TET2 corresponding mutation. Disease duration (in years) is indicated below the bars, the “zero” point indicating time of diagnosis. Time of death is symbolized as a vertical line, when appropriate, at the right end.

Figure 9:
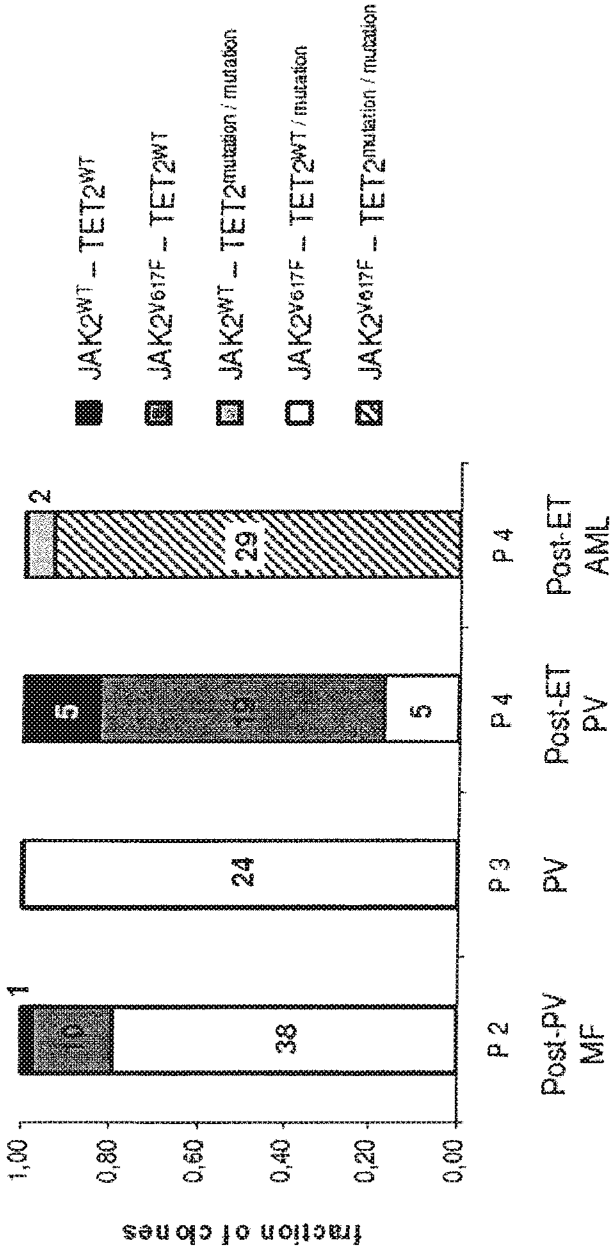

The FIG. 9 shows the TET2 and JAK2 genotypes in committed progenitors of patients P2, P3 and P4. Histograms show the fraction of clones harboring JAKV617F and two TET2 mutations (crosswised hatching), JAK2V617F and one TET2 mutation (white), wild type JAK2 and two TET2 mutations (light grey), JAK2V617F and wild type TET2 (grey) and no mutation in any of the two genes (black). Two samples were analyzed for patient P4, the corresponding stage is indicated below each bar. The numbers of analyzed clones are indicated.

Figure 10:
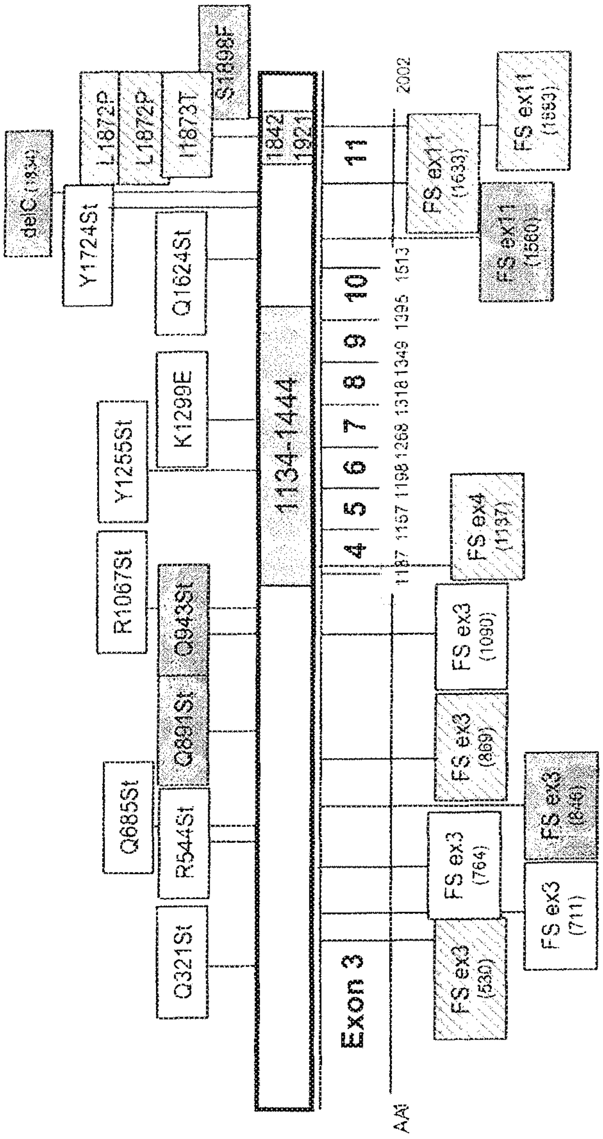

The FIG. 10 shows the clinical status and TET2 genotypes in MDS patients. Whites boxes represent low/int-1 grade MDS, hatched boxes represent int-2/high grade MDS and grey boxes represent secondary AML.

DETAILED DESCRIPTION OF THE INVENTION

The present invention is based on the discovery by the present inventors that the TET2 alleles are often genetically targeted by mutations and/or deletions in tumoral cells in patients suffering from lymphoid tumour or from myeloid tumour such as MPD, AML or MDS and can be considered as a bona fide tumor suppressor gene of human myeloid malignancies.

In a first aspect, the inventors report that, for sporadic cancer, the frequencies of TET2 mutation in unselected patient series were 12% in MPD, 18.5% in MDS, 24% in sAML until 50% in CMML patients. Also, applicants demonstrated that TET2 is a tumor suppressor gene in myeloid malignant disorders, because mutated hematopoietic stem cells are endowed with a growth advantage leading to enhanced proliferation.

In a second aspect, the inventors demonstrated by an analysis of 61 familial MPD cases (i.e. PV, ET, and PMF) that anomalies of TET2 gene are found in 20% of the three major MPD phenotypes (PV, ET and PMF) with a higher prevalence in PMF (42%).

Among the TET2-positive patients diagnosed with PV or ET, 77% developed myelofibrosis (MF) suggesting that the presence of acquired events of TET2 influence the evolution of the disease. In four patients (3 PV and 1 ET), we were able to show that the TET2 defect preceded from one to 7 years the hematological complication. The patients with a defect in TET2 are prone to progress to MF. This highly suggested a possible link between the TET2 acquired mutations and the severity of the disease, more specifically between TET2 and the development of MF.

In a third aspect, the inventors report that, for sporadic cancer, the frequencies of TET2 mutation in patients suffering from T-cell lymphoid tumour was ~20%. Finally, the TET2 rearrangements were observed in patients suffering from B-cell lymphoid tumour.

Thus, in a first aspect of the invention, there is provided an in vitro method for diagnosing a myeloid tumour or a lymphoid tumour in a subject, which comprises the step of analyzing a biological sample from said subject by:

(i) detecting the presence of a mutation in the Ten Eleven Translocation protein family member 2 gene (TET2) coding for the polypeptide having the sequence SEQ ID NO:2, and/or (ii) analyzing the expression of the TET2 gene;

wherein, the detection of a TET2 mutation, of the absence of expression of TET2 or of the expression of a truncated TET2 is indicative of a subject developing or predisposed to develop a myeloid tumour or a lymphoid tumour.

Recent evidence indicate that proteins of the TET family encode enzymes responsible for the conversion of 5-methylcytosine to 5-hydroxymethylcytosine (TAHILIANI et al., *Sciencexpress,* 2009), thus have potential roles in CpG demethylation and epigenetic regulation. Moreover, this reference established that the conserved TET domains, where most TET2 mutations are observed, are implicated in this activity.

Concomitantly, several works have established, in the last years, a role for hypomethylating agents in MDS (ITZYKSON & FENAUX, *Current Opinion in Hematology*, vol. 16, p: 77-83, 2009).

The results of the inventors now suggest that the observed efficiency of hypomethylating agent in some MDS potentially results from a demethylation defect in MDS with TET2 mutations.

Thus, the results of the inventors further suggest the use of hypomethylating agent on subjects suffering from lymphoid or myeloid tumour, such as MDS, for which tumour, a TET2 mutation, an absence of TET2 expression or an expression of a truncated TET2 has been detected.

Consequently and according to a preferred embodiment, the detection of a TET2 mutation, of the absence of expression of TET2 or of the expression of a truncated TET2 is indicative of a subject developing a myeloid tumour or a lymphoid tumour suffering from a demethylation defect, which subject can be advantageously treated with a hypomethylating agent, such as azacytidine (AZA).

Preferably, the method of the invention is dedicated to diagnose myeloid tumours.

In fact, the inventors have established that the frequency of TET2 mutations in patients suffering from myeloid tumor or from lymphoid tumour is greater than 10%.

The present invention furthermore provides a method for detection of the presence or absence of cells that have the potential to evolve to invasive myeloid neoplasms or to invasive lymphoid tumours, although those cells are not detectable as a lesion or precursor by conventional means.

As used herein, the term “subject” refers to a mammal, preferably a human.

Said subject may be a healthy, but the method of the invention is particularly useful for testing a subject thought to develop or to be predisposed to developing a myeloid cancer (i.e., myeloid tumour) or a lymphoid tumour. In that case, the method of the invention enables to confirm that said subject develops or is predisposed for developing a myeloid cancer a myeloid tumour) or a lymphoid tumour.

More preferably, said lymphoid tumour is selected in the group consisting of lymphoma such as T- or B-cell lymphoma, and more preferentially of T cell lymphoma.

Still more preferably, said myeloid cancer (i.e., myeloid tumour) is selected in the group consisting of myelodysplastic syndrome (MDS), acute myeloid leukemia (AML), myeloproliferative disorders (MPD) and myelodysplatic/myeloproliferative syndrome. Advantageously, said myeloid cancer is a myelodysplatic/myeloproliferative syndrome, and preferably a chronic myelomonocytic leukemia (CMML).

According to a preferred embodiment, the method of the invention is for diagnosing a myelofibrosis (MF) in a subject, wherein said subject is suffering from polycythemia vera (PV) or from thrombocythemia (ET), and wherein the detection of a TET2 mutation or TET2 under-expression is indicative of a subject developing or predisposed to develop a myelofibrosis (MF).

According to still another preferred embodiment, the subject is suffering from myelodysplastic syndrome (MDS), and the detection of a TET2 mutation or TET2 under-expression is indicative of a subject with a good prognosis.

As used herein a good prognosis corresponds to a patient suffering from MDS and having a reduced risk of developing an AML.

In fact, the inventors have established that five-year survival was significantly increased in TET2 mutated patients suffering from MDS compared to unmutated patients ($p<0.05$).

As used herein, the expression “biological sample” refers to solid tissues such as, for example, a lung biopsy; buccal swab, fluids and excretions such as for example, sputum, induced sputum, blood, serum, plasma, urine. Preferably, said biological sample is a bone marrow sample.

In this aspect of the invention, the method comprises the step of detecting the presence of a mutation in the TET2 gene coding for the polypeptide having the sequence SEQ ID NO:2.

As used herein, the term “mutations” correspond to any modification in the sequence of the original nucleic acid sequence. These mutations comprise small-scale mutations, or large scale mutations. Small scale mutations are those affecting a gene in one or a few nucleotides, including point mutations, insertions or deletions of one or more extra nucleotides in the DNA. Point mutations can be silent, missense and nonsense mutation. Large scale mutation in the genomic structure, such as gene duplications, deletions, or mutations whose effect is to juxtapose previously separate pieces of DNA, potentially bringing together separate genes to form functionally distinct fusion genes. These last mutations include chromosomal translocations, interstitial deletions, chromosomal inversions and loss of heterezygosity.

Preferably, only a biological sample containing cells including genomic DNA (or optionally RNA) from the subject to be tested is required.

Preferably, this detecting step is realized on each allele of the TET2 gene. In fact, the diagnosis is more reliable when the mutation is detected on each allele of the TET2 coding for the polypeptide having the sequence SEQ ID NO:2.

In a particular embodiment, the in vitro method of the invention aims to detect mutation included in the group consisting of deletions, insertions and point mutations such as mutations affecting splice sites, missense mutation and nonsense mutations, preferably missense mutation and nonsense mutations.

The inventors have established that the existence of such mutations is associated with myeloid or lymphoid cancer. Moreover, the inventors observed that the polypeptidic C-terminal domain of the TET2 protein is preferentially targeted by the deleterious mutations in the studied patients (see examples).

For deletion or insertion, said deletion or insertion preferably results in the absence of expression of the TET2 protein or in the expression of a truncated TET2 protein, which truncated TET2 protein does not comprise at least one of the two highly conserved regions shared by the other TET proteins and corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4). More preferably, said truncated TET2 protein does not comprise the 80 amino acid region located near the carboxyterminal end of the protein TET2 (corresponding to amino acid 1843 until amino acid 1922, SEQ ID NO:4).

For example, these deletions or insertions can be selected in those disclosed in table 1.

For missense mutation, said missense mutation is preferably located in the open reading frame of the TET2 protein, and preferably in at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4).

As an example, said missense mutations are selected in the group comprising or consisting of I1175V, L1197N, H1219Y, E1235V, C1271W, K1299E, L1340P, R1302G, G1370E, A1344E, N1387S, V1417F, H1868R, G1869W, L1872P, I1873T, R1896M, and S1898F; preferably in the group comprising or consisting of I1175V, L1197N, H1219Y, E1235V, C1271W, K1299E, L1340P, R1302G, G1370E, A1344E, N1387S, H1868R, G1869W, L1872P, I1873T, R1896M, and S1898F.

More preferably, said missense mutation is located in the 80 amino acid region located near the carboxyterminal end of the protein TET2 (corresponding to amino acid 1843 until amino acid 1922, SEQ ID NO:4). Even more preferably, said missense mutations are selected in the group comprising or consisting of H1868R, G1869W, L1872P, I1873T, R1896M, and S1898F, as an example I1873T, R1896M, and S1898F.

For non sense mutation, said nonsense mutation preferably results in the introduction of a stop mutation in the open reading frame of the TET2 protein, and preferably before at least one of the two highly conserved regions shared by the TET2 protein corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4).

As an example, said nonsense mutations are selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891 Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751Stop, L1819Stop, Q1834Stop and W1847Stop; preferably in the group comprising or consisting of Q321Stop, S354Stop, R544Stop, Q557Stop, R1216Stop, and Y1724Stop.

Also, said nonsense mutation can result in the introduction of a stop mutation inside at least one of the two highly conserved regions shared by the TET2 protein corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4).

More preferably, said nonsense mutation results in the introduction of a stop mutation in the open reading frame of the TET2 protein before the 80 amino acid region located near the carboxyterminal end of the protein TET2 (corresponding to amino acid 1843 until amino acid 1922, SEQ ID NO:4). As an example, said nonsense mutation is selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751Stop, L1819Stop, and Q1834Stop.

Also, said nonsense mutation can result in the introduction of a stop mutation in the open reading frame of the TET2 protein inside the 80 amino acid region located near the carboxyterminal end of the protein TET2 (corresponding to amino acid 1843 until amino acid 1922, SEQ ID NO:4). As an example, said nonsense mutation is W1847Stop.

Typical techniques for detecting the presence of a mutation may include restriction fragment length polymorphism, hybridization techniques, DNA sequencing, exonuclease resistance, microsequencing, solid phase extension using ddNTPs, extension in solution using ddNTPs, oligonucleotide ligation assays, methods for detecting single nucleotide polymorphisms such as dynamic allele-specific hybridization, ligation chain reaction, mini-sequencing, DNA "chips", allele-specific oligonucleotide hybridization with single or dual-labelled probes merged with PCR or with molecular beacons, and others.

Advantageously, the alteration is detected on the cDNA or DNA of the TET2 gene by either PCR and sequencing, SNP-array or CGH, all of them being well known for the skilled person.

In molecular biology and bioinformatics, a SNP array is a type of DNA microarray which is used to detect polymorphisms within a population. The basic principles of SNP array are the same as the DNA microarray. These are the convergence of DNA hybridization, fluorescence microscopy, and solid surface DNA capture. The three mandatory components of the SNP arrays are: i) the array that contains immobilized nucleic acid sequences or target; ii) one or more labeled Allele specific oligonucleotide (ASO) probes; and iii) a detection system that records and interprets the hybridization signal (see in Sheils, O., Finn, S. and O'Leary J. (2003) "Nucleic acid microarray: an overview." Current Diagnostic Pathology. 9:155-158).

Comparative genomic hybridization (CGH) is a molecular cytogenetic method of screening a tumor for genetic changes. The alterations are classified as DNA gains and losses and reveal a characteristic pattern that includes mutations at chromosomal and subchromosomal levels. The method is based on the hybridization of fluorescently labeled tumor DNA (frequently fluorescein (FITC)) and normal DNA (frequently rhodamine or Texas Red) to normal human metaphase preparations. Using epifluorescence microscopy and quantitative image analysis, regional differences in the fluorescence ratio of gains/losses vs. control DNA can be detected and used for identifying abnormal regions in the genome. CGH will detect only unbalanced chromosomes changes. Structural chromosome aberrations such as balanced reciprocal translocations or inversions can usually not be detected, as they do not systematically change the copy number (Emanuel B S, Saitta S C. From microscopes to microarrays: dissecting recurrent chromosomal rearrangements, *Nat Rev Genet.* 2007 November; 8(11):869-83. *Review*).

In another preferred embodiment of the invention, the method comprises the step of analyzing the expression of the TET family member 2 gene (TET2).

According to the results obtained by the inventors, the absence of expression or the under-expression of the TET2 protein or the expression of a truncated TET2 protein as disclosed previously is associated with myeloid cancer.

Methods for analyzing the expression of a gene are well known for the man skilled in the art.

In a particular embodiment of the invention, the expression of the TET2 gene is assessed by analyzing the expression of mRNA transcript or mRNA precursors, such as nascent RNA, of said gene.

Such analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TAQMAN), and probes arrays such as GENECHIP™ NA Arrays (AFFYMETRIX).

Advantageously, the analysis of the expression level of mRNA transcribed from the TET2 gene involves the process of nucleic acid amplification, e. g., by RT-PCR (the experimental embodiment set forth in U.S. Pat. No. 4,683,202), ligase chain reaction (BARANY, *Proc. Natl. Acad. Sci. USA*, vol. 88, p: 189-193, 1991), self sustained sequence replication (GUATELLI et al., *Proc. Natl. Acad. Sci. USA*, vol. 87, p: 1874-1878, 1990), transcriptional amplification system (KWOH et al., 1989, *Proc. Natl. Acad. Sci. USA*, vol. 86, p: 1173-1177, 1989), Q-Beta Replicase (LIZARDI et al., *Biol. Technology*, vol. 6, p: 1197, 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3'regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another particular embodiment, the expression of the TET2 gene is assessed by analyzing the expression of the TET2 protein translated from said gene.

Such analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the TET2 protein. Said analysis can be assessed by a variety of techniques well known by one of skill in the art including, but not limited to, enzyme immunoassay (EIA), radioimmunoassay (RIA), Western blot analysis and enzyme linked immunoabsorbant assay (ELISA).

Polyclonal antibodies can be prepared by immunizing a suitable animal, such as mouse, rabbit or goat, with the TET2 protein (SEQ ID NO:2) or a fragment thereof (e.g., at least 10 or 15 amino acids). The antibody titer in the immunized animal can be monitored over time by standard techniques, such as with an ELISA using immobilized polypeptide. At an appropriate time after immunization, e.g., when the specific antibody titers are highest, antibody producing cells can be obtained from the animal and used to prepare monoclonal antibodies (mAb) by standard techniques, such as the hybridoma technique originally described by KOHLER and MILSTEIN (*Nature*, vol. 256, p: 495-497, 1975), the human B cell hybridoma technique (KOZBOR et al., *Immunol.*, vol. 4, p: 72, 1983), the EBV-hybridoma technique (COLE et al., *In Monoclonal Antibodies and Cancer Therapy*, Alan R. Liss, Inc., p: 77-96, 1985) or trioma techniques. The technology for producing hybridomas is well known (see generally Current Protocols in Immunology, COLIGAN et al. ed., John Wiley & Sons, New York, 1994). Hybridoma cells producing the desired monoclonal antibody are detected by screening the hybridoma culture supernatants for antibodies that bind the polypeptide of interest, e.g., using a standard ELISA.

As previously mentioned, mutations in the TET2 gene may trigger the absence of expression or the under-expression of the TET2 protein.

As used herein, the "under-expression" of a polypeptide occurs when the transcription and/or the translation of the gene is affected by the mutation, leading to an expression level in a biological sample that is lower than the standard error of the assay employed to assess expression, and is preferably at least 20% inferior to the normal level of expression of said gene, preferably at least 50% inferior to the normal level of expression of said gene, and most preferably at least 100% inferior to the normal level of expression of said gene.

Therefore, the method of the invention may comprise comparing the level of expression of the TET2 gene in a biological sample from a subject with its expression level in a control (i.e., normal expression level). A significantly lower level of expression of said gene in the biological sample of a subject as compared to the normal expression level is an indication that the patient may develop a myeloid neoplasm.

As used herein, a "control" corresponds preferably to a control sample comprising non-tumoral cells. Preferably, said control corresponds to peripheral blood leukocytes (PBL), and most preferably to a peripheral blood leukocyte immortalized with Epstein Barr Virus.

Thus, the "normal" level of expression of the TET2 gene is the level of expression of said gene in a biological sample of non-tumoral cell. Preferably, said normal level of expression is assessed in a control sample and preferably, the average expression level of said gene in several control samples.

Analyzing the normal expression of the TET2 gene may be assessed by any of a wide variety of well-known methods for detecting expression of a transcribed nucleic acid or translated protein as previously described.

In a preferred embodiment of the invention, said mutation in the TET2 gene induces absence of expression or under-expression of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxy-terminal end of the protein TET2 (corresponding to amino acid 1843 until amino acid 1922, SEQ ID NO:4), and more preferably of the 80 amino acid region located near the carboxy-terminal end of the protein TET2 (corresponding to amino acid 1843 until amino acid 1922, SEQ ID NO:4).

In a second aspect, the present invention refers to a kit for diagnosing myeloid cancer or lymphoid cancer in a subject comprising at least one nucleic acid probe or oligonucleotide or at least one antibody, which can be used in a method as defined in the present in invention, for detecting the presence of a mutation in the TET2 gene and/or analysing the expression of the TET2 gene.

Preferably, the oligonucleotide is at least one PCR primer, preferably a set of PCR primers is provided, which allows to amplify the TET2 gene or a fragment thereof. The skilled person readily provides such an oligonucleotide or set of PCR primers which allows to amplify a region of the TET2 gene, provided that the nucleic acid sequence of TET2 is well known (Accession number NM_001127208, SEQ ID NO:1) (Current Protocols in Molecular Biology; edited by Fred M. Ausubel et al., supra).

In a preferred embodiment, the kit comprises at least one PCR primer selected in the group comprising SEQ ID NO:5 to SEQ ID NO: 38 (see examples and sequence listing) for detecting the presence of a mutation in the TET2 gene and/or analysing the expression of said gene.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The present kits can also include one or more reagents, buffers, hybridization media, nucleic acids, primers, nucleotides, probes, molecular weight markers, enzymes, solid supports, databases, computer programs for calculating dispensation orders and/or disposable lab equipment, such as multi-well plates, in order to readily facilitate implementation of the present methods. Enzymes that can be included in the present kits include nucleotide polymerases and the like. Solid supports can include beads and the like whereas molecular weight markers can include conjugatable markers, for example biotin and streptavidin or the like.

In one embodiment, the kit is made up of instructions for carrying out the method described herein for diagnosing a myeloid cancer or a lymphoid cancer in a subject. The instructions can be provided in any intelligible form through a tangible medium, such as printed on paper, computer readable media, or the like.

Still a further aspect of the present invention refers to the use, for diagnosing myeloid or lymphoid cancer, of the abovementioned kit comprising at least one nucleic acid probe or oligonucleotide or at least one antibody, which can be used in a method as defined for detecting the presence of a mutation in the TET2 gene and/or analysing the expression of the TET2 gene.

Advantageously, myeloid cancer is selected in the group consisting of myelodysplastic syndrome, acute myeloid leukemia, myeloproliferative disease and myelodysplatic/myeloproliferative syndrome.

Still advantageously, said lymphoid cancer is selected in the group consisting of lymphoma such as T- or B-cell lymphoma, and more preferentially of T-cell lymphoma.

In still another aspect, the invention relates to the use of a hypomethylating agent for treating a patient suffering from a myeloid or a lymphoid tumour, for which tumour, a TET2 mutation, an absence of TET2 expression or an expression of a truncated TET2 has been detected.

Preferably, said myeloid tumour is not a MDS.

Hypomethylating agent are well known from the skilled person and include, as an example, azacytidine.

In a final aspect, the invention relates to a method for treating a subject suffering a myeloid or a lymphoid tumour, for which tumour, a TET2 mutation, an absence of TET2 expression or an expression of a truncated TET2 has been detected, said method comprising the step of administrating to said subject a therapeutically efficient amount of hypomethylating agent.

Preferably, said myeloid tumour is not a MDS.

Preferably said hypomethylating agent is azacytidine.

A therapeutically efficient amount of hypomethylating agent can be simply determined by the skilled person. As an example of therapeutically efficient amount of azacytidine for treating lymphoid or myeloid tumour, one can cite the regimen which is disclosed in FENAUX et al. (*Blood*, vol. 110, 817, 2007) which is incorporated herein by reference.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

EXAMPLES

1. Identification of TET2 Gene Mutation in MDS, MPD and in AML.

We identified 6 patients suffering from myeloid cancer (AML (nAML1, nAML2, nAML3) or MDS (MDS01, MDS02, and MDS03)) and harboring an acquired chromosomal translocation associated with a genomic deletion in the vicinity of the chromosome 4 breakpoint at 4q24. These deletions were homozygous in one instance and heterozygous in the other cases and could indicate the location of a tumor suppressor gene in that region.

FISH analyses first permit to narrow the commonly deleted region in these patients to a ~500 kb interval (data not shown). Computer and RT-PCR assisted analyses uncovered the structure of a single gene, Ten Eleven Translocation (TET2) lying in this region (FIG. 1).

TET72 gene comprises 11 exons spread over 150 Kb. The predicted TET2 protein, encoded by exons 3 to 11, belongs to a three-member family (TET family) in human and mouse. Proteins of the TET family share two highly conserved regions with a single orthologous *Drosophila* protein in their central and carboxy-terminal part (FIG. 1).

The FIG. 1 shows the protein sequence of TET2 (SEQ ID NO:2), highlighting the conserved regions between species (bold).

For TET2, a translational initiation codon situated at the 5' end of exon 3 (Nucleotides 862-864 of the cDNA or 27-29 or Exon 3) was predicted to allow for the synthesis of a 2002 amino acids protein (FIG. 1). An alternative ATG situated in exon 2 (nucleotides 798-800 of the cDNA or 111-113 of Exon 2) will direct the synthesis of 21 more amino acids. Additional starts are not excluded.

TET2 transcript is widely expressed (ONO et al., abovementioned, 2002; LORSBACH et al., abovementioned, 2003), and as suggested by available data, the expression of TET2 was confirmed in human bone marrow and blood tissues by RT-PCR (data not shown). More specifically, TET2 transcripts were detected in umbilical cord blood $CD34^+$ cells, in granulocytes from healthy controls, and in hematopoietic cell lines.

Finally, of these six patients, five harbored a deletion on one chromosome 4 whereas both copies were deleted in MDS01.

The involvement of the same 4q24 region was also found by using a different approach in MPD. Analysis of $CD34^+$ $CD38^-$ multipotent progenitors, $CD34^+CD38^+$ committed progenitors, and mature cells, led us to identify two subsets of JAK2 V617F MPD at diagnosis with distinct kinetics of hematopoietic expansion (DUPONT et al., *Blood*, vol. 110 (3), p: 1013-21, 2007). The first subset is characterized by a late expansion of the malignant clone; i.e. downstream of the committed progenitor. In contrast, the second subset of patients had an early expansion of the clone, upstream of the committed progenitor. We hypothesized that the second subset of patients had a molecular defect able to promote the early expansion of the malignant clone. Five patients from this second subset (MPD01 to MPD05) were analyzed using high-resolution CGH and SNP arrays to compare presumed clonal cells (granulocytes) versus polyclonal cells (peripheral blood mononuclear cells or lymphocytes) DNA. One primary myelofibrosis (PMF) patient (MPD01) and one polycythemia vera (PV) patient (MPD04) exhibited a large acquired loss-of-heterozygosity (LOH) without copy number modification (uniparental disomy; LTD (20)) ranging from q22 to qter of chromosome 4. The third patient (MPD05) demonstrated an acquired deletion located in the 4q24 region. This 325 kb deletion in MPD05 was included in the 4q24 LOH region of patients MPD01 and MPD04 and contained TET2 as a single candidate gene. This region was normal in the two other studied MPD samples (MPD02 and MPD03).

As the 4q24 region is affected in patients suffering from myeloid neoplasms, and as TET2 localized in this region, the integrity of the TET2 gene might be affected in these patients. Moreover, loss of the two copies of TET2 in patient MDS01 and recurrent loss of one copy in 8 other patients with MDS, MPD or AML designated TET2 as a candidate tumor suppressor gene.

PCR on the TET2 gene was thus performed in order to detect alterations of the TET2 gene in these patients. Importantly, both alleles were analysed in order to detect bi-allelic modifications.

2. Experimental Procedure to Detect Alterations of the TET2 Gene 2.1. Primers Used for the Identification of TET2 Mutations or Deletions (Table 2)

TABLE 2

| SEQ ID NO | TM (° C.) | Sequences | Amplified region | Length of amplicon |
|---|---|---|---|---|
| 5 | 60.9 | TGAACTTCCCACATTAGCTGGT | 106374235- | 955 |
| 6 | 60.7 | GAAACTGTAGCACCATTAGGCATT | 106375189 | |
| 7 | 62.0 | CAAAAGGCTAATGGAGAAAGACGTA | 106374894- | 836 |
| 8 | 62.0 | GCAGAAAAGGAATCCTTAGTGAACA | 106375729 | |
| 9 | 63.0 | GCCAGTAAACTAGCTGCAATGCTAA | 106375458- | 843 |
| 10 | 62.3 | TGCCTCATTACGTTTTAGATGGG | 106376300 | |
| 11 | 60.0 | GACCAATGTCAGAACACCTCAA | 106376065- | 867 |
| 12 | 60.9 | TTGATTTTGAATACTGATTTTCACCA | 106376931 | |
| 13 | 60.5 | TTGCAACATAAGCCTCATAAACAG | 106376703- | 788 |
| 14 | 60.9 | ATTGGCCTGTGCATCTGACTAT | 106377490 | |
| 15 | 62.1 | GCAACTTGCTCAGCAAAGGTACT | 106377284- | 781 |

TABLE 2-continued

| SEQ ID NO | TM (° C.) | Sequences | Amplified region | Length of amplicon |
|---|---|---|---|---|
| 16 | 62.3 | TGCTGCCAGACTCAAGATTTAAAA | 106378064 | |
| 17 | 60.1 | ATACTACATATAATACATTCTAATTCCCTCACTG | 106381631- | 495 |
| 18 | 61.5 | TGTTTACTGCTTTGTGTGTGAAGG | 106382125 | |
| 19 | 61.7 | CATTTCTCAGGATGTGGTCATAGAAT | 106383324- | 286 |
| 20 | 61.5 | CCCAATTCTCAGGGTCAGATTTA | 106383609 | |
| 21 | 60.1 | AGACTTATGTATCTTTCATCTAGCTCTGG | 106383864- | 599 |
| 22 | 60.1 | ACTCTCTTCCTTTCAACCAAAGATT | 106384462 | |
| 23 | 60.0 | ATGCCACAGCTTAATACAGAGTTAGAT | 106400093- | 362 |
| 24 | 60.9 | TGTCATATTGTTCACTTCATCTAAGCTAAT | 106400454 | |
| 25 | 61.1 | GATGCTTTATTTAGTAATAAAGGCACCA | 106402226- | 354 |
| 26 | 61.5 | TTCAACAATTAAGAGGAAAAGTTAGAATAATATTT | 106402579 | |
| 27 | 61.7 | TGTCATTCCATTTTGTTTCTGGATA | 106410076- | 361 |
| 28 | 60.5 | AAATTACCCAGTCTTGCATATGTCTT | 106410436 | |
| 29 | 63.0 | CTGGATCAACTAGGCCACCAAC | 106413052- | 774 |
| 30 | 63.0 | CCAAAATTAACAATGTTCATTTTACAATAAGAG | 106413825 | |
| 31 | 61.1 | GCTCTTATCTTTGCTTAATGGGTGT | 106415516- | 748 |
| 32 | 60.5 | TGTACATTTGGTCTAATGGTACAACTG | 106416263 | |
| 33 | 60.5 | AATGGAAACCTATCAGTGGACAAC | 106416016- | 1107 |
| 34 | 60.2 | TATATATCTGTTGTAAGGCCCTGTGA | 106417122 | |
| 35 | 62.0 | CAGAGCTTTCTGGATCCTGACAT | 106416670- | 535 |
| 36 | 60.3 | GCCCACGTCATGAGAACTATACTAC | 106417204 | |
| 37 | 66 | TCTAAGCTCAGTCTACCACCCATCCATA | 106416118- | 570 |
| 38 | 66.7 | TGCTCGCTGTCTGACCAGACCTCAT | 106416571 | |

2.2. PCR

PCR were performed in 20 μL starting from 25-50 ng of DNA on APPLIED BIOSYSTEM PCR 9700.

For each sample: 17 PCR were used to detect the mutations/deletions localized on the TET2 gene. The mix was prepared as below:

| | mix *1 |
|---|---|
| 10X | 2 |
| dNTP 25 mM | 0.15 |
| O1 100 pmol/μl | 0.1 |
| O2 100 pmol/μl | 0.1 |
| hot star (5 U/μl) | 0.2 |
| Water | 15.5-16.5 |
| DNA sample (25 ng/μl) | 1-2 |

We use the following PCR cycles conditions:

| | | |
|---|---|---|
| 15' | 94° C. | 1 cycle |
| 20s | 94° C. | 2 cycles |
| 20s | 56° C. | |
| 30s | 72° C. | |
| 20s | 94° C. | 2 cycles |
| 20s | 54° C. | |
| 30s | 72° C. | |
| 20s | 94° C. | 2 cycles |
| 20s | 52° C. | |
| 30s | 72° C. | |
| 20s | 94° C. | 37 cycles |
| 20s | 50° C. | |
| 30s | 72° C. | |
| 10' | 72° C. | 1 cycle |

2.3. Sequencing the PCR Products

Finally, the PCR products sequencing was realized by EUROFINS MWG Biotech (France, 9, rue de la Laponic, 91967 Les Ulis cedex) or by "Département des services commun de l'Institut Cochin" (Plate forme transcriptomique, Hôpital Cochin/Bat G. Roussy/3ème étage, 27 rue du Fg St Jacques, 75014 Paris) with the kit Big Dye terminator V1.1 and 3130 XL sequencing machines (both from APPLIED BIOSYSTEMS).

3. Mutations of the TET2 Gene in Patients Suffering from MDS or AML with Heterozygous 4q24 Deletion 3.1. In Tumoral Cells TET2 gene integrity was checked on the 4q24 "intact" copy of the 8 abovementioned patients harboring the heterozygous acquired chromosomal translocation associated with a genomic deletion in the vicinity of the chromosome 4 breakpoint at 4q24.

To identify potential mutations of the TET2 gene in these alleles, the sequence of the eight coding exons and of their splice sites in the DNA extracted from bone marrow samples of 8 patients having a 4q24 rearrangement was investigated by PCR as described previously.

Table 3 discloses the status of both alleles of the TET2 genes in patients suffering from MPD, MDS or AML and having a 4q24 deletion on one allele:

| Patient | Copy 1 | Copy2 | Disease |
|---|---|---|---|
| nAML1 | R1896M | Deletion | AML |
| nAML2 | I1873T | Deletion | AML |
| nAML3 | Deletion | Unknown | AML |
| MDS01 | Deletion | Deletion | RA |

-continued

| Patient | Copy 1 | Copy2 | Disease |
|---|---|---|---|
| MDS02 | FS after L560 (Exon 3) | Deletion | RA |
| MDS03 | N1624Stop (Exon 11) | Deletion | RA |
| MPD01 | Q557Stop | Q557Stop | PMF |
| MPD04 | Deletion (1237 to 1239) | Deletion (1237 to 1239) | PV |
| MPD05 | Deletion | Wild type | PV |

Comparison of the sequence obtained from the patients with the wild type counterpart identified nucleotide changes in 6 patients (Table 3). Changes were not attributable to identified polymorphisms. Patient nAML1 and nAML2 harbored single nucleotide changes, leading to an I1873T in patient nAML2 and to R1896M in patient nAML1. Patient MDS03 exhibited a CAG to TAG changes, introducing a stop codon instead of N1624. Patient MPD01 exhibited a single nucleotide change, introducing a stop codon instead of NQ557. Patient MDS02 had a 4 base pair insertion, leading to a stop codon 6 amino acids after L560. Patient MPD04 had an in frame 9-nucleotide deletion. No notable nucleotide changes were observed in DNA of patient nAML3. Patient MDS01 harbors a bi-allelic deletion of the TET2 gene.

3.2. In Non-Tumoral Cells of the Patients

To confirm that the observed changes were somatically acquired, we analyzed DNA from non-tumoral samples when available.

Figure 2:
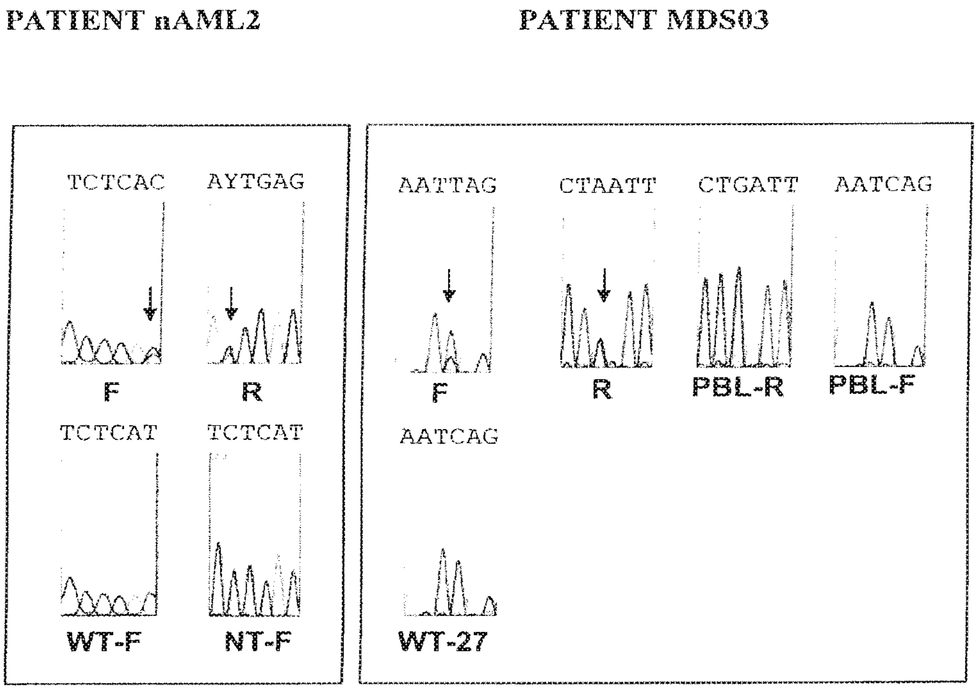

In patient nAML2, the T to C change was not observed in DNA from EBV-transformed B cell population (FIG. 2). In patient nAML1, the analyses of a sample obtained after auto-bone marrow transplantation demonstrated an inversed ratio between the wild type G and the mutated T, when compared to the diagnosis sample (data not shown). Similarly, the signal corresponding to the mutated T is almost absent in DNA extracted from stimulated PBL from patient MDS03 (FIG. 2). This analysis has also shown the absence of mutation for MPD04 or of deletion for MPD05 in non-tumoral cells (data not shown). This analysis has further shown that a small amount of residual wild-type sequence is detected in peripheral mononuclear cells from patient MPD01 (data not shown).

The FIG. 2 shows the sequence traces obtained by sequencing of PCR on samples obtained from the two patients nAML2 and MDS03, and showing that the mutation only occurs in the tumoral (R: reverse primer and F: forward primer) and in non-tumoral samples (NT or PBL).

Taken together, these results demonstrate that the two copies of the TET2 gene is targeted in patients suffering from diverse myeloid neoplasm, and this through two different events, a chromosomal translocation associated with a deletion and point mutations, establishing TET2 as a tumor suppressor gene.

4. Alteration of the TET2 Gene in Patients Suffering from MDS or AML without Cytogentically Detectable 4q24 Deletion To establish whether mutation of TET2 could also occurs independently of a chromosomal abnormality, DNA from bone marrow samples of 309 additional patients with different subtypes of MDS (n=81), sAML (n=21), CMML (n=9), $JAK2^{V617F}$ positive MPD (n=181), and $JAK2^{V617F}$ negative MPD (n=17) without known 4q24 abnormality was analyzed by PCR as previously described.

Table 4 discloses the status of the identified TET2 defect in patients suffering from MDS or AML:

| Patient | TET2 defect | Disease |
|---|---|---|
| sAML2 | S1898F | sAMLII |
| sAML4 | FS (Exon3) | sAMLII |
| sAML5 | FS (Exon11) | sAMLII |
| sAML6 | FS (Exon11)/Q891stop | sAMLII |
| sAML7 | Q943Stop | sAMLII |
| MDS04 | K1299E/R544Stop | RA |
| MDS07 | No amplification Ex11 | RA |
| MDS30 | FS (Exon3) | RA |
| MDS09 | FS (Exon3) | RARS |
| MDS35 | Y1225Stop Exon6 | RARS |
| MDS10 | Y1724Stop/Q321Stop | RCMD-RS |
| MDS28 | FS (Exon3) | RCMD-RS |
| MDS18 | FS (Exon11) | RAEB1 |
| MDS27 | FS (Exon3)/FS (Exon3) | RAEB1 |
| MDS33 | FS (Exon4) | RAEB1 |
| MDS39 | L1872P | RAEB1 |
| MDS40 | FS (Exon11) | RAEB1 |
| MDS42 | L1872P/I1873T | RAEB1 |
| | Mutation of splice acceptor | |
| MDS34 | Site Exon5 | RAEB2 |
| MDS41 | FS (Exon11) | RAEB2 |
| CMML01 | Q585Stop | CMML |
| CMML02 | FS (Exon3)/R1067Stop | CMML |

RA, refractory anemia; RARS, refractory anemia with ringed sideroblasts; RARS-T, RARS with thrombocytosis; RAEB, refractory anemia with excess blasts; RAEB1: blasts 5-9%; RAEB2: blasts 10-19%; AML, acute myeloid leukemia; FAB, French American British classification; del, deletion; FS, frame shift; ND, not done. All MDS/AML tested (22/27) were negative for $JAK2^{V617F}$. MDS03 was studied at the RAEB1 and RAEB2 phases. Two successive samples of patient MDS34 were analyzed. Selected patients analyzed during the initial part of the study appear in bold.

Table 5 discloses the status of the identified TET2 defect in patients suffering from MPD:

| Patient | TET2 defect | Disease | JACK2 and MPL status |
|---|---|---|---|
| MPD18 | R1216stop | PV | $JAK2^{V617F}$ |
| MPD20 | FS Ex11 | PV | $JAK2^{V617F}$ |
| MPD35 | S354stop | ET | $JAK2^{V617F}$ |
| MPD43 | FS Ex3/R550stop | post ET MF | $JAK2^{V617F}$ |
| MPD45 | FS Ex3 | PV | $JAK2^{V617F}$ |
| MPD69 | FS Ex7/FS Ex11 | PV | $JAK2^{V617F}$ |
| MPD74 | FS Ex3 | PMF | WT |
| MPD81 | FS Ex6 | ET | $JAK2^{V617F}$ |
| MPD86 | FS Ex5/R1404stop | PV | $JAK2^{V617F}$ |
| MPD89 | FS Ex10 | PV | $JAK2^{V617F}$ |
| MPD92 | R1302G | PMF | $JAK2^{V617F}$ |
| MPD96 | W1847stop | ET | $JAK2^{V617F}$ |
| MPD99 | FS Ex3 | ET | $JAK2^{V617F}$ |
| MPD120 | FS Ex3 | PV | $JAK2^{V617F}$ |
| MPD130 | FS Ex3 | ET | $JAK2^{V617F}$ |
| MPD132 | FS Ex3 | PV | $JAK2^{V617F}$ |
| MPD133 | G1869W | ET | $JAK2^{V617F}$ |
| MPD142 | FS Ex3 | PV | $JAK2^{V617F}$ |
| MPD149 | FS Ex6 | ET | $JAK2^{V617F}$ |
| MPD158 | FS Ex3 | PV | $JAK2^{V617F}$ |
| MPD163 | Q1542stop | ET | $MPL^{W515L}$ |
| MPD164 | FS Ex3 | PMF | $JAK2^{V617F}$ |
| MPD183 | FS Ex7/Q635stop | PV | $JAK2^{V617F}$ |
| MPD200 | FS Ex3/FS Ex11 | ET | WT |

PMF, primary myelofibrosis, PV, polycythemia vera, ET, essential thrombocythemia, WT: negative for $JAK2^{V617F}$ and $MPL^{515}$ mutations, FS, frame shift.

Obvious abnormalities of TET2 coding sequence were observed in 45 patients, resulting in conserved amino acid substitution, generation of in frame stop codons, or frame shifts (Tables 4 and 5. In one additional patient (MDS07), amplification of the 5' part of exon 11 only resulted in trace amounts of PCR fragment despite the use of several conditions and primers pairs (data not shown), which was attributed to an uncharacterized structural genomic rearrangement affecting this region. Defects of TET2 were observed in all types of MDS (22/111) and BCR-ABL negative MPDs associated with JAK2 V617F (21/181), or MPL W515L/K (1/6) or devoid of these mutations (2/11).

The results demonstrate that TET2 defects can be identified in unselected diverse myeloid disorders with a high prevalence (46/309=17%). As an example, patient MDS04 showed two changes leading to K1299D and R544Stop. Patient MDS10 had two stop mutations, Y1724Stop and Q321Stop. Patient sAML2 had a point mutation leading to S1898F. These observed mutations may result in a partial or total loss of function of the TET2 protein. It can be anticipated that other defects such as deletions of the TET2 gene might have been missed and thus the estimated the frequency of TET2 defects in these malignancies would be underestimated.

Overall, in 19/55 of the patients with TET2 defects, two different mutations were detected, likely targeting both copies of TET2. This point was confirmed by sequencing individual molecules after subcloning of the PCR fragments obtained from patient MDS42. A single defect was observed in 35/55 samples suggesting that TET2 haploinsufficiency may play a role in these malignancies.

5. TET2 Mutations Target Early Progenitors in MDS.

MDS are myeloid malignancies originating from a HSC. If the mutations observed in TET2 are causative, they should also be observed in the HSC. To investigate this, we first analyzed the presence of the TET2 defects in $CD34^+$ which include HSC and hematopoietic progenitors, from 4 MDS patients (MDS03, MDS09, MDS28, MDS35).

The FIG. 3_a_ shows the sequencing histograms of sorted $CD34^+$ cells from patient MDS03 at RAEB1 and RAEB2 phases. Sequences observed in unsorted bone marrow sample and of wild-type control are shown for comparison purposes. Asterisks indicate the mutated nucleotide.

The FIG. 3_b_ shows the PCR-RFLP analysis of DNA isolated from sorted MDS03 $CD34^+CD38^+$ and $CD34^+$ $CD38^+$ cells at RAEB1 phase. Amplified fragments were digested using Tas1 and size-fractionated by agarose migration. The proportion of mutated TET2 mutated was evaluated by measuring the intensities of the mutated (mut) or wild-type (wt) signals relative to that of the signal generated by both alleles (wt+mut). Undigested (−) and digested (+). (ctl) correspond to PCR products from control DNA. MW: molecular weight.

The FIG. 3_c_ shows the PCR-RFLP analysis of TET2 directly performed from sorted $CD34^+CD38^+$ and $CD34^+$ $CD38^+$ cells from MDS09 patient using BseL1 endonuclease.

The FIG. 3_d_ shows the genotyping by PCR-RFLP using BseL1 of sorted $CD34^+CD38^+$ and $CD34^+CD38^+$ cells from patient MDS09 grown at one cell per well. Annotations are as in b. The histograms represent the fraction of clones with wild-type (gray) or mutated (black) TET2. Note the absence of wild-type fragment in $CD34^+CD38^+$ clones indicated by asterisks.

In all cases, the mutated TET2 sequence could be detected (FIG. 3). In one of these patients (MDS03), $CD34^+$ cells could be analyzed at refractory anemia with excess of blasts 1 (RAEB1) and RAEB2 phases. Interestingly, the wild-type sequence was detected at the RAEB1 phase, but not at the RAEB2 phase (FIG. 3_a_), suggesting expansion of TET2 mutated progenitors with the disease progression.

We next fractionated the $CD34^+$ from these four patients into $CD34^+CD38^+$ (corresponding to HSC and multipotent progenitors) and $CD34^+CD38^+$ (corresponding to more mature progenitors) cell populations using CD34-PeCy5 and CD38-FITC antibodies (IMMUNOTECH) using a FACS-Diva cell sorter (BECTON DICKINSON). In two patients (MDS03 and MDS09), PCR-RFLP analysis was used to distinguish mutated and wild-type TET2 sequences. The mutated TET2 burden increased in both patients from $CD34^+CD38^-$ to $CD34^+CD38^+$ cells (16% to 54% in MDS03, and 26% to 48% in MDS09) (FIG. 3_b, c_). Further analysis was performed at the cellular level, by seeding single hematopoietic progenitors from MDS09.

Sorted $CD34^+CD38^-$ cells from MDS09 bone marrow were seeded at one cell per well on a confluent layer of the MS5 cell line in MEM alpha medium supplemented with 10% FBS (STEM CELL TECHNOLOGIES), and a cocktail of early cytokines (thrombopoietin (Tpo) interleukin-3 (IL3), FLT3-L, Stem Cell factor (SCF) and interleukin-6 (IL6)). $CD34^+CD38^+$ cells were also seeded at one cell per well using the same combination of "late" cytokines (SCF, IL3, erythropoietin (Epo) and granulocyte-colony stimulating factor (G-CSF)) as used in methylcellulose cultures (DUPONT et al., abovementioned, 2007). After three weeks ($CD34^+CD38^+$) or 10 days ($CD34^+CD38^+$), individual clones were collected for further genotyping.

The results show that TET2 mutation was identified in 8 out of 32 (25%) and 18 out of 30 (60%) clones derived from $CD34^+CD38^-$ and $CD34^+CD38^+$ cells, respectively (FIG. 3_d_). Interestingly, the wild-type copy of TET2 was not always amplified from clones bearing a mutated TET2, suggesting its loss in a minority of the cells.

For the two other patients (MDS28, MDS35), the increase in TET2 mutation burden from $CD34^+CD38^-$ to $CD34^+$ $CD38^+$ samples was evaluated with the sequence graphs. To be more accurate, the amplified fragments from MDS28 samples were subcloned and individual bacterial clones were sequenced. The mutated copy was barely detectable in the $CD34^+CD38^-$ population of MDS28 whereas it represented 32% of TET2 sequences in the $CD34^+CD38^+$ population (data not shown). These data indicate that TET2 mutations target a $CD34^+CD38^-$ cell and that in MDS TET2 mutated burden increases from immature to mature progenitors, suggesting a selective advantage of the mutated cells during early phases of hematopoietic differentiation.

In three sAML samples (sAML2, sAML4, sAML5), TET2 mutations were also found in $CD34^+$ cells (data not shown). When analyzed, in sAML4, sAML5 sorted cells, no marked changes in the mutated TET2 burden were observed between $CD34^+CD38^-$ and $CD34^+CD38^+$ populations.

6. Prevalence and Prognosis Impact of TET2 Mutations in MDS.

So as to establish the prevalence and prognosis impact of TET2 mutations in MDS, we retrospectively analyzed TET 2 mutations and their prognosis value, in 204 MDS and AML post MDS enrolled in GEM multicenter trials (41 RA/RCMD/MDS-U/5q-, 18 RCMD, 28 RARS/RCMD-RS/RARS-T, 43 RAEB 1, 32 RAEB 2, 44 AML post MDS). TET2 mutations analysis was realized as described previously and the results are presented in table 6.

Table 6 discloses the status of the identified TET2 defect in patients suffering from MDS or AML:

| Disease | Nucleotide change | Consequence |
|---|---|---|
| MDS02 G04 | delA 3166 | p.Gln769 FS |
| MDS 04 | c.4755A > G + c.2490C > T | p.[Lys1299Glu] + [Arg544X] |
| MDS01 A08 | insT 3465 | p.Pro869 FS |
| MDS01 A11 | c.5071 C > T | p.Arg1404 STOP |
| MDS02 C01 | delT 2685 + insA 3009 | p.Ser609 FS + p.His717 FS |
| MDS01 B03 | insA 5540 | p.Tyr1560 FS |
| MDS01 B11 | c.2913 C > T | p.Gln685 STOP |
| sAML1 | | del/wt |
| MDS 07 | | No amplification of 5' Exon 11 |
| MDS01 C08 | delC 6360 | p.Gln1834 FS |
| MDS01 C09 | c.3532C > T + insA 5757 | p.Cys1633 FS + p.Gln891 STOP |
| MDS01 D01 | c.6475T > C | p.Leu1872Pro |
| MDS02 H02 | c.4384A > G + c.4625C > G | p.Ile1175Val + p.Tyr1255 STOP |
| sAML2 | | Ser1898Phe |
| MDS01 D06 | del 2834_2835 | p.His658 FS |
| MDS 10 | | p.Gln530 FS + p.Tyr1724 STOP |
| MDS02 C12 | delT 2685 + c.6316T > G | p.Ser609 FS + p.Leu1819 STOP |
| MDS02 D01 | delC 3009 | p.His717 FS |
| MDS 01 | | del/del |
| MDS 02 | | del/p.Arg581 FS |
| MDS01 E02 | c.5730C > T | del/Gln1624 STOP |
| MDS02 D04 | delT 2944 | p.Leu699 STOP |
| MDS01 E06 | insC 3151 + p.5406C > T | p.Gln764 FS + Arg1516 STOP |
| MDS01 E07 | c.6475T > C + c.6478T > C | p.Leu1872Pro + p.Ile1873Thr |
| MDS01 E08 | delC 2448 + delA 4130 | p.Gln530 FS + p.Lys1090 FS |
| MDS01 F02 | p.6360C > T | p.Gln1834 STOP |
| MDS01 F04 | delG 2994 | p.Glu711 FS |
| MDS02 E01 | c.6114T > G + insT splice site | p.Tyr1751 STOP + mutation of splice site exon 8 |
| MDS01 F06 | p.3688C > T + delA 6507 | p.Gln943 STOP + p.Thr1883 FS |
| MDS01 G01 | delG 4271 + c.6478T > C | p.Glu1137 FS + p.Ile1873Thr |
| MDS01 G03 | p.3688C > T | p.Gln943 STOP |
| nAML2 | c.6478T > C | del/p.Ile1873Thr |
| MDS01 G05 | delC 5222 | p.Leu1457 STOP |
| MDS02 F11 | dupT 3914 | p.Glu1026 STOP |
| MDS01 G06 | delA 2935 + del5828_5843 | p.Glu692 FS + p.Met1656 FS |
| MDS02 A12 | p.4969G > A + del6396_6531 | p.Gly 1370 Glu + p.Val1846 FS |
| MDS01 G7/8 | g.4366-1G > T | mutation of splice acceptor site exon5 |
| MDS02 E10 | insCT 3581 | pGly 908 FS |
| MDS02 H12 | delG 4932 + del5521_5524 | p.Glu1357 FS + pThr1554 FS |
| MDS02 G03 | insC 3151 + insC 6507 | p.Gln764 FS + p.Thr1883 FS |
| MDS02 G01 | delG 5133 + del6511_6512 | p.Asp 1425 FS + p.Pro1885FS |
| MDS02 G07 | p.5253C > T | p.Arg1465 STOP |
| MDS02 C07 | c.4561A > T | p.Glu1234Val |
| MDS02 B07 | c.2109C > T | p.Gln417 STOP |
| nAML1 | c.6547G > T | del/p.Arg1896Met |
| MDS02 E11 | c.2784C > T + p.5253C > T | p.Gln642 STOP + p.Arg1465 STOP |
| MDS01 H05 | c.4515C > T | p.His1219 Tyr |
| MDS02 H06 | del1264_1666 | p.Glu135 FS |
| MDS02 B08 | delA4327 + c.5020A > G | p.Asn1156 FS + Asn 1387Ser |
| MDS02 D10 | insC 3151 + c.4891C > A | p.Gln764 FS + p.Ala1344 Glu |
| MDS02 B02 | delT 5570 + insC splice site | p.Leu1637 FS + mutation of splice site exon 8 |

-continued

| Disease | Nucleotide change | Consequence |
|---|---|---|
| MDS01 F01 | insT3995 + c.4059A > T | p.Glu846 FS + p.Arg1067 STOP |
| MDS02 B11 | c.4673C > G + Del6049_6050 | p.Cys1271 Trp + p.Asp1830 FS |
| MDS01 E09 | insG 5119 | p.Leu 1420 FS |
| MDS | c.5430C > T | p.Gln1524STOP |
| MDS | c.5177dupA | p.Arg1440FS |
| MDS | c.5583_5605 del | p.Pro1575FS |
| MDS | c.5310 A > G | p.Lys1197Arg |
| MDS | c.2375C > A | p.Ser792STOP |

We found 59 mutations of the TET2 gene by direct sequencing of exons 3 to 11 (27 frameshifts, 21 nonsense and 11 missense mutations in conserved domains) 43/204 pts (Table 6). The frequencies according to the WHO subtypes were 21.8% in RA, 5.2% in RCMD, 21.4% in RARS/RARS-T/RCMD-RS, 34.9% in RAEB 1, 15.6% in RAEB 2, 19% in AML post MDS. Other anomalies of the 4q24 region were found including a deletion in 1/46 pts analyzed by CGH and 3 LOH in 3/22 patients analyzed by SNP arrays and 2 deletions in 5/23 pts analyzed SNP arrays. Thus, the overall prevalence of 4q24 anomalies was 21.6% patients (44/204). 20 patients had two anomalies of TET2 identified by direct sequencing (17 patients), or sequencing plus SNP array (3 patients), indicating that the two copies of the gene were targeted in 43.5% of mutated patients.

Then, univariate and multivariate survival analyses were conducted with Cox hazard proportional model so as to establish the prognosis impact of TET2 mutations. Comparison between the 43 patients with TET2 coding sequence mutations and unmutated patients found no significant differences in initial characteristics for sex, age, previous exposure to chemo or radiotherapy, Hb level, WBC count, ANC, plt count, % bone marrow blasts, multilineage dysplasia, WHO and FAB subtypes, karyotype and IPSS.

The analysis revealed that five-year survival (Kaplan-Meier curve) was significantly increased in TET2 mutated patients compared to unmutated patients ($p<0.05$).

7. Rearrangement of the TET2 Gene in Patients Suffering from MPD with 4q24 Abnormality Detected by SNP or CGH Arrays Analyses.

Among 35 MPD samples, 4 patients had a LOH by SNP arrays and were analyzed for mutations within TET2 gene on both alleles. In 3 of the 4 samples a clear mutation or deletion was observed.

Table 7 discloses the status of both alleles of the TET2 genes in patients suffering from MPD:

| Patient | Copy 1 | Copy2 | Disease |
|---|---|---|---|
| IGR-1 | Q557Stop | LOH | PMF |
| IGR-2 | Deletion 1237-1239 | LOH | PV |
| IGR-3 | whole gene deletion | No abnormality | PV |
| IGR-4 | unknown | LOH | ET |

In table 7, "PMF" stands for Primitive Myelofibrosis, "PV" for polycythemia Vera, "EV" for Essential Thrombocytosis. All these diseases are Class II MPDs.

Patient IGR-2 harbored a 9 base pair in frame deletion lead to the loss of three amino acids, P1237, L1238, S1239. As shown by SNP analyses and by the analyses of the sequence traces, patients IGR-1 and IGR-2 had lost the other TET2 copy. None of the mutations were observed in non-tumoral cells of the patients. These data establish that inactivation TET2 participates to the development of MPD.

Systematic sequencing of TET2 genes in 17 other patients revealed two patients with a stop codon on one allele (IGR17: S354Stop, IGR-18:R1216Stop) and one patient with one nucleotide deletion leading to a frameshift in exon 11.

8. Analysis of the Acquisition of the TET2 Rearrangement

Recent evidence indicate that $JAK2^{V167F}$ may not be the initiating event in some MPDs. Therefore we used MPD samples to evaluate the relative roles of TET2 detects and $JAK2^{V167F}$ mutation in these diseases and to gain insight into the sequence of the acquisition of the mutations. We first analyzed hematopoietic progenitors from five MPD patients with mutations in both genes, like the patient IGR2.

For MPD samples, Immature $CD34^+CD38^-$ cells were seeded at one cell per well for four to six weeks in conditions permitting simultaneous B, NK and granulocytic differentiations (lympho-myeloid differentiation) as described (DUPONT et al., abovementioned, 2007), whereas more mature $CD34^+CD38^+$ cells were grown in erythroid/granulocytic methylcellulose assays. Individual clones were collected for analysis of B, NK, and granulocytic differentiation by flow cytometry, and genotyping. $CD34^+CD38^+$ cells were seeded at 1,500 to 3,000 cells per culture dish in 2% standard methylcellulose supplemented with 37% FBS (STEM CELL TECHNOLOGIES), and a cocktail of cytokines as described (DUPONT et al., abovementioned, 2007)). Individual colonies grown from burst-forming units-erythroid (BFU-E) and colony-forming units-granulocyte/macrophage (CFU-GM) were picked on day 14. The obtained clones were analyzed for the presence of both molecular defects.

The results have shown that in all patients tested, sequence analyses revealed that both TET2 and JAK2 defects were present in clones derived from lympho-myeloid progenitors (data not shown). Interestingly the $JAK2^{V617F}$ mutation was not observed in the absence of TET2 defect whereas TET2 mutation could be observed in the absence of $JAK2^{V617F}$. These results demonstrate that, as in MDS, the TET2 mutation is present in immature progenitors of MPD patients and indicate that TET2 defects precede JAK2 mutation during the evolution of the disease.

To further define the role of the TET2 mutations in the amplification of the malignant clone, we compared the genotype of colonies derived from immature ($CD34^+$ $CD38^-$) progenitors to that of erythroid and granulocytic colonies derived from committed ($CD34^+CD38^+$) progenitors.

The results shown that in three MPD patients (MPD01, MPD04, MPD35), almost all the colonies at different stages of hematopoietic differentiation harbored a TET2 mutation, suggesting that the TET2 mutated clone expanded at early steps of hematopoiesis (data not shown). In 2 other patients (MPD05, MPD20), most immature progenitors were wild-type whereas most committed progenitors were mutated for TET2. Within JAK2 wild-type progenitors from these two patients, we observed an increase in the proportion of clones with TET2 defects from the immature (2/37 and 0/34, respectively) to the committed (10/23 and 9/54, respectively) progenitor stage. Taken together, our results indicate that the selective advantage of the TET2 mutated clone at early differentiation steps is independent of the $JAK2^{V617F}$ mutation.

Overall, these data front MPD samples demonstrate that TET2 defects (i) occur at early steps of hematopoietic differentiation and that (ii) they may precede the occurrence of the $JAK2^{V167F}$ mutation and (iii) they give a selective advantage to the clone as it proceeds to myeloid differentiation.

9. Engraftment and Proliferation of TET2 Mutated Cells In Vivo

We reasoned that loss of function of TET2 could confer a growth advantage to the hematopoietic stem cells. To demonstrate that the TET2 mutations occur in a HSCs with NOD-SCID repopulating capacity, we used a xenotransplantation assay by injecting, into NOD-SCID mice, $CD34^+$ cells isolated from $JAK2^{V617F}$ MPD patients with TET2 mutations.

$CD34^+$ cells (1 to $10\times10^5$ cells) from $JAK2^{V167F}$ MPD patients with TET2 mutations were injected intravenously into sub-lethally irradiated (3.5 Gy) NOD-SCID mice, previously treated with 200 μg of anti-CD122 antibody (JAMES et al., *Blood*, vol. 112(6), p: 2429-36, 2008). Bone marrow was obtained with heparinized syringue from the right femur at 3, 6 and 12 weeks after transplantation and mice were sacrificed at week 15. Human cell engraftment was evaluated by the sum of human leukocytes ($CD45^+$) and erythroid populations ($CD45^-CD36^+$ and $CD45^-CD36^-$ $GlycophorinA^+$), as assessed by flow cytometry. Bone marrow cells were seeded in culture dish and 96-well plates for methylcellulose and long-term culture-initiating cell (LTC-IC) assays, respectively allowing the selective growth of human cells as described in JAMES et al. (abovementioned, 2008). Individual colonies were subsequently picked and genotyped.

We first compared the kinetics of chimerism after transplantation of $CD34^+$ cells from these $JAK2^{V167F}$ MPD patients with TET2 mutations and from three $JAK2^{V617F}$ MPD devoid of TET2 defects (MPD09, MPD11, MPD27).

The FIG. 4*a* shows the percentage of human CD45-positive cells in mouse bone marrow monitored at 3, 6, 12, and 15 weeks post-transplant. MPD01 and MPD04 are patients with TET2 defects whereas MPD09, MPD11, and MPD27 are control patients devoid of identified TET2 defect.

The FIG. 4*b* shows the flow cytometric analysis of human cells present in NOD-SCID bone marrow 15 weeks after transplantation with $3\times10^5$ $CD34^+$ cells from patients MPD04 and MPD09. The percentages of human CD45 (hCD45)-positive myeloid and lymphoid cells were determined using anti-CD45-PC7, anti-CD33-APC, and anti-CD19-PE antibodies.

The results show that human cells from the three patients devoid of TET2 mutation disappeared with time (FIG. 4*a*).

In contrast, the percentage of human cells in the bone marrow of mice engrafted with cells from the two TET2 mutated patients increased with time (FIG. 4*a*). In these mice, differentiation was skewed toward myeloid progenitor expansion, at the expense of lymphoid progenitors, as judged from CD33 and CD19 antigen flow cytometry analyses (FIG. 4*b*) unlike what is observed with normal HSCs wherein lymphoid differentiation is favored (ROBERT-RICHARD et al., *Haematologica*, vol. 17(3), p: 637-41, 2003).

Human cells present in the mouse bone marrow 15 weeks after transplantation (W15) were tested in in vitro progenitor and LTC-IC assays, and analyzed for the presence of TET2 and JAK2 mutations. The TET2 defects were found in pooled W15 CFU-derived colonies from both MPD01 and MPD04 samples, and in all individual human LTC-IC and progenitors present in the mice (data not shown). The results were compared with progenitor assays performed immediately before engraftment (D0). All colonies arising from patients' committed progenitor cells (0 CFU) harbored TET2 mutation.

These results demonstrate that TET2 mutation occurs in a HSC. Interestingly, the results have further shown that the proportion of progenitor cells carrying only the TET2 mutation increased upon transplantation at the expense of cells carrying both TET2 and JAK2$^{V167F}$ mutations. These cells are thought to reflect the original HSC population. Therefore, these observations indicate that TET2 mutated HSCs with a wild-type JAK2 are more numerous than the TET2/JAK2 double mutant HSCs, further establishing the mutation of TET2 as a "pre-JAK2$^{V167F}$" event in these patients.

Therefore our data are compatible with the hypothesis that TET2 defects endow the HSC with a selective engraftment advantage independently of JAK2$^{V617F}$.

10. Positions of the Identified Mutations on the TET2 Gene

We report that the inactivation of TET2 is a common early event in human MDS, MPD and sAML and that the frequencies of TET2 mutation in unselected patient series were 15/81=18.5% in MDS, 2/9=22% in CMML, 24/198=12% in MPD and 5/21=24% in sAML. It must be noticed that in these analyses we did not consider amino acid changes occurring outside of the conserved domains. Sequencing of the TET2 gene using the couples of primers identified in table I permits to identify a number of mutations in the TET2 gene (FIG. 5).

The FIG. 5 shows the locations of some of the identified mutations of the TET2 gene distributed along the protein sequence.

Mapping of the identified TET2 mutations on the TET2 sequence suggest an essential role for the carboxy terminal conserved region (amino acids in position 1860 to the position 1950) in the function of the protein.

Finally, the detection of acquired genetic defects targeting the two TET2 copies in 19 of the 55 patients with TET2 alteration establishes this gene as a bona fide tumor suppressor gene of human myeloid malignancies. TET2 defects are observed in both MDS and MPD, which are two distinct myeloid diseases. It is therefore likely that their characteristic clinical and biological phenotypes require at least another additional cooperating event. In MPD samples with both TET2 and JAK2 mutations, TET2 mutations likely occur first in the natural history of the disease, preceding the occurrence of JAK2$^{V167F}$ mutation.

11. Identification of TET2 Gene Mutations in Familial MPD

Families with at least 2 affected patients with MPD were collected through a national network as previously described (BELANNE-CHANTELOT et al., abovementioned, 2006). The diagnoses of MPD were reviewed based on the 2008 World Health Organization criteria.1 All participants gave their written informed consent.

In a first step, we analyzed 15 probands of families compatible with an autosomal dominant inheritance, in search for a constitutional event that would account for these familial cases. Elected probands mostly suffered from PV or ET. In a second step, the analysis was extended to patients with hematological complications and to relatives of patients with TET2 variants.

Altogether, we analyzed 61 patients for mutations in the 6009 bp coding sequence of the TET2 gene from 42 MPD families (40 European, 2 African: families F3 and F4) including at least two available affected patients with MPDs. Thirty-four patients displayed a simple phenotype consisting of either PV (15), ET (12) or PMF (7) with no observed hematological evolution of the disease after a follow-up period of 12 years. Twenty-seven other patients had experienced an evolution in their MPD phenotype: PV evolving into myelofibrosis (post PV MF, 5) or into AML (12); ET evolving into MF (4) or AML (5), or PMF turning into AML (1).

The analysis was performed by polymerase chain reaction (PCR) on genomic DNA extracted from buccal swabs after heating at 95° C. for 10 minutes to release genomic DNA. Purified PCR products were sequenced using the BIGDYE TERMINATOR chemistry (APPLIED BIOSYSTEMS) and run on an APPLIED BIOSYSTEMS 3100 capillary sequencer.

The JAK2V617F mutational status was determined as previously reported in BELANNE-CHANTELOT et al. (abovementioned, 2006).

The whole coding region of the TET2 gene was sequenced as described previously. Two multiplex PCRs were set up to estimate the copy number of each TET2 exon using the quantitative multiplex PCR of short fluorescent fragments (QMPSF) method (CHARBONNIER et al., *Cancer Res*., vol. 60, p: 2760-2763, 2000). Two additional primer pairs amplifying short sequences of either the F9 or the DSCR1 gene were used as internal controls. PCR products were separated by capillary electrophoresis using a DNA genetic analyzer (ABI 3100). The analysis is based on the comparison of the peak heights generated from the tested DNA sample and the control DNA. The quantitative estimation of the height of peaks was determined using commercially available analysis software (GENEMAPPER VERSION 4.0, APPLIED BIOSYSTEMS).

Table 8 shows the TET2 mutations identified in 12 MPD patients.

| | | | | TET2 | | |
|---|---|---|---|---|---|---|
| Patients | Phenotype | Evolution | JAK2 | Location | Nucleotide change | Proteic change |
| P1 (F1) | PV | MF | 95 | Exon 11 | c.5695delC | p.Leu1899fs |
| P2 (F2) | PV | MF | 63 | Intron 7 | c.3954 + 2T > A | p.? |
| P3 (F2) | PV | | 49-82 | Exon 3 | c.3138delT | pLeu1046fs |
| P4 (F3) | ET | PV > MF > AML | 23-47 | Exon 3 | c.1648C > T | p.Arg550X |
| | | | | Exon 3 | c.2570delA | p.Asn857fs |
| P5 (F3) | ET | MF > AML | 0 | Exon 3 | C2058A > T | p.Arg686Ser |
| P6 (F4) | ET | AML | 0 | Exon 3 | C1955delA | p.Gln652fs |
| | | | | Exon 3 | c.2490dupA | p.Gln1831fs |
| P7 (F4) | ET | | 39 | Intron 4 | c.3500 + 3A > C | p.? |
| P8 | ET | MF | 90 | All exons | c.1.4999_5014del16 | p.0 |
| P9 | PMF | | 36 | Exon 3 | c.694C < T | p.Gln574X |
| | | | | Exon 11 | | p.Leu1667fs |

-continued

| | | | | TET2 | | |
|---|---|---|---|---|---|---|
| Patients | Phenotype | Evolution | JAK2 | Location | Nucleotide change | Proteic change |
| P10 | PMF | | 33 | Exon 3 | c.4019T < C | p.Gln232X |
| P11 | PMF | | 66 | Exon 8 | c.5603A < G | p.Leu1340Pro |
| P12 | PV | MF | 78-96 | Exon 11 | | p.His1868Arg |

Patients were initially diagnosed with the phenotype indicated in the second column and subsequently had a hematological evolution shown in the third column. When measured in several samples, the JAK2V167F allele burden is indicated as a range.

The FIG. 6 is a schematic representation of the TET2 gene and protein showing the mutations identified in this study. Hatched boxes indicate exons. Truncating mutations are depicted as stars, missense mutations as inverted triangles. Conserved functional domains are depicted as boxes on the protein scheme. fs: frameshift.

Following this analysis, we identified a complete deletion of TET2 in one patient and a total of 39 point variants. Examination of these variants showed that 15 of them, identified in 12 patients, were deleterious heterozygous mutations. They were distributed as one deletion of the entire gene, 11 truncating (3 nonsense mutations, 6 out-of-frame insertions/deletions and 2 splice site mutations) and 3 missense mutations (FIG. 6, Table 8).

Furthermore, all three missense mutations were absent from 165 control individuals of ethnically matched populations, thus confirming their deleterious effect. Two, p.Leu1340Pro and p.His1868Arg, were located in the highly conserved TET2 functional domains (1134-1444 and 1842-1921). Truncating mutations seemed to be randomly distributed along the coding sequence (FIG. 6).

In patients P4, P6 and P9 two TET2 mutations were identified. For the former, multiple allele specific amplifications of the two mutations located in exon 3 showed that these two molecular events occurred on different alleles leading to the biallelic inactivation of TET2 (data not shown). The observation of such a biallelic inactivation of TET2 in these patients meets the criteria of the classical two-hit recessive model of carcinogenesis and supports the hypothesis that TET2 acts as a tumor suppressor gene.

Twenty-five other variants identified on the coding sequence of TET2 and the short nearby intronic regions were polymorphisms. Seven were substitutions in non-coding regions (intronic or 3'UTR), one was a variation in an intronic short tandem repeat, 4 were silent variations in the coding sequence and 13 were missense polymorphisms. They were all classified as polymorphisms on the basis of their presence in public databases, the fact that they were found in asymptomatic family members, or their identification in control populations. It is of interest to note that none of the missense polymorphisms were located in either one of the functional domains.

12. TET2 Mutations were Sequentially Acquired in a Patient with Two Mutations

Seven blood samples were available for patient P4 from family F3, throughout the last three steps of her evolution: PV, MF and AML. Sequencing these samples allowed us to determine the temporality of the clinical and molecular events.

The FIG. 7 shows the sequential study of TET2 and JAK12 in patient P4 (F3). Sequence electrophoregrams are shown for each TET2 mutation and for JAKV617F. The diagram on the left indicates time lapse from diagnosis (in years) and corresponding henotype for each sample (white: ET; grey: PV; hatched: post-ET MF; black: AML).

The results show that JAK2V617F and the TET2 p.Arg550X mutation were already present in the first sample, when the patient suffered from PV. The second mutation, p.Asn857fs was detectable in the second sample, 7 years later and 5 months before the diagnosis of MF. This sequential analysis has shown that the burden of each of these mutations grew in time, concomitantly with the development of the disease.

Finally, TET2 mutations were found in similar proportions in JAK2V617F positive and negative patients suggesting that molecular events in both genes may arise independently of each other.

13. TET2 Molecular Events were Mainly Observed in Patients with PMF or Patients with PV or ET Who Secondarily Evolved Towards a Hematological Transformation Altogether, 12 patients were found carrying at least one TET2 mutation. They account for 20% of all MPD patients tested.

The FIG. 8 shows the schematic representation of the clinical status of these twelve patients with at least one TET2 mutation. White boxes depict ET stages, grey, PV, cross-wised hatching indicates myelofibrosis, either primary (left-slanting) or post-PV/ET (right-slanting) and AML are symbolized as black boxes. Above each arrowhead indicating a molecular analysis is annotated the TET2 corresponding mutation. Disease duration (in years) is indicated below the bars, the "zero" point indicating time of diagnosis. Time of death is symbolized as a vertical line, when appropriate, at the right end.

This analysis shows that these TET2 defects were identified in patients diagnosed with the three main MPD phenotypes: PV (4/32), ET (5/21) and PMF (3/8). No TET2 mutation was observed in relatives with rare hematological phenotypes, including de novo AML and systemic mastocytosis (data not shown). All patients with a TET2 defect but two were positive for the JAK2V617F mutation. The allele burden varied from 33 to 95% (Table 6). The negative cases were ET patients who developed very active AML and died rapidly (P5 and P6, data not shown). We should note that the two patients, P3 and P7, who had not developed post-PV or post-ET MF at the time of examination, were characterized by a high level of JAK2V617F allele burden (82 and 39% respectively, Table 6).

Altogether, our results established that 20% of the JAK2V617F positive patients were found mutated for TET2 (10/49) vs. 17% among the JAK2V617F negative patients (2/12).

All patients carrying a TET2 mutation but two had either a myelofibrosis that occurred at onset or was acquired secondarily after PV or ET, or a secondary AML. Hence 29% (10/34) of patients with PMF or hematological complication after PV or ET were found mutated in TET2 compared to 7.4% (2/27) of patients without any diagnosed haematological complications after a mean time of disease duration of 12 years. Both patients with TET2 mutations and presenting PV or ET without hematological transformations had nevertheless an active course of the disease.

No correlation can be done between the clinical presentation, the hematological data or even the course of the disease in patients and the type and location of mutations or between patients with a single heterozygous TET2 mutation and patients with two. As shown on FIG. 8, TET2 mutations were found at different times in the evolution of the disease for each patient from the time of diagnosis (P9) to 20 years later (P8); the time to progression was also variable [1-16 years].

14. TET2 Mutations were Present in Early Hematopoietic Progenitors and were Acquired Independently from JAK2V617F Three patients were available for analysis of their progenitor cells, patient P4 from family F3 and patients P2 and P3 from F2. Blood progenitor cells were available for the former at two different steps of her disease during the PV stage and the blast phase after MF.

The FIG. 9 disclosed TET2 and JAK2 genotypes in committed progenitors of patients P2, P3 and P4. Histograms show the fraction of clones harboring JAKV617F and two TET2 mutations (crosswised hatching), JAK2V617F and one TET2 mutation (white), wild type JAK2 and two TET2 mutations (light grey), JAK2V617F and wild type TET2 (grey) and no mutation in any of the two genes (black). Two samples were analyzed for patient P4, the corresponding stage is indicated below each bar. The numbers of analyzed clones are indicated.

The results show that eight years after diagnosis, during the PV stage, endogenous erythroid colonies already carried the p.Arg550X mutation (5/29) but p.Asn857fs was never observed (0/29, FIG. 9).

Nine years later, after leukemic transformation, all genotyped Burst forming unit-erythroid (BFU-E) and all colony forming unit-granulocyte macrophage (CFU-GM), but 2, carried JAK2V617F and both TET2 mutations (FIG. 9). The progenitor analysis therefore confirmed the temporality of these events: in patient P4, p.Arg550X was first acquired in the earliest stages of the disease; and the latest stages were characterized by the presence of both p.Arg550X and p.Asn857fs. Interestingly, two CFU-GM carried both TET2 mutations in the absence of JAK2V617F. For patient P2, colonies were found with either both JAK2 and TET2 mutations, the sole JAK2V617F or none (FIG. 9). This was an indication that for this patient the TET2 mutation occurred in clones already mutated for JAK2. All BFU-E and CFU-GM from patient P3 diagnosed with PV carried both JAK2 and TET2 mutations and did not allow concluding on the temporality of JAK2 and TET2 events.

15. TET2 Molecular Events were Mainly Observed in Patients with CMML

The nature and frequency of somatic mutations in TET2 was also studied in bone-marrow or peripheral blood collected from 88 patients with CMML1 (n=70) or CMML2 (n=18) according to the WHO criteria and 14 acute blastic transformation of a previously identified CMML. Patients signed their informed consent according to current ethical regulations. Patients with CMML in chronic phase were newly diagnosed (n=43) or known for hematopoietic disease and followed up every 3 months for therapeutic abstention, supportive cares or cytotoxic treatment, in most cases with Hydroxyurea (n=45).

Blood and bone-marrow samples were collected on EDTA and mononuclear cells were selected by Fycoll Hypaque. DNA was extracted using commercial kits (QIAGEN). Polymerase chain reaction (PCR) and direct sequencing reaction were performed using standard conditions with gene-specific primers designed to amplify coding sequences spanning from exon 3 to exon 11 of TET2 gene as described previously. For each PCR reaction, 20 ng of genomic DNA was used for PCR amplification followed by magnetic bead purification and bidirectional sequencing using ABI 3300 capillary sequencers (AGENCOURT BIOSCIENCE). Mutation Surveyor (SOFTGENETICS) was used to detect nonsense and missense mutations located in conserved regions spanning from 1134-1444 and 1842-1921 and sequences were reviewed manually to detect frameshift mutations. TET2 abnormalities were numbered according to FM 992369 EMBL nucleotide sequence database.

The mutations identified in TET2 are listed in table 10.

TABLE 10

| Patient | WHO | Nucleotide change in TET2 | Exon | Consequence |
|---|---|---|---|---|
| 2 | CMML1 | c.4453G > A | 5 | W1198STOP |
| 4 | CMML1 | c.5214C > T; Ins 5537 (A) | 10 & 11 | R1452 STOP; Y1560FS |
| 5 | CMML1 | c.4942G > A | 9 | G1361S |
| 15 | CMML1 | c.4500C > A; Del 5118_21 (TTAT) | 6 & 10 | R1214W; L1420FS |
| 18 | CMML1 | delT 4172; c.5011A > T | 3 & 9 | F1104FS, D1384V |
| 19 | CMML1 | del 5362_5365; c.6441G > A | 10 & 11 | G1501FS; G1860R |
| 20 | CMML1 | c.2631C > T | 3 | Q591 STOP |
| 21 | CMML1 | Del 6507 (A) | 11 | T1883FS |
| 22 | CMML1 | c.2961C > T | 3 | Q701 STOP |
| 23 | CMMLI | c.1818G > T; c.4936G > A | 3 & 9 | E320 STOP; R1359H |
| 24 | CMML1 | c.4515C > T | 6 | H1219Y |
| 25 | CMML1 | c.4663n + 1 G > A; Del 6424_33 | 6 & 11 | Mutation splice donor site exon 6 + L1855FS |
| 26 | CMML1 | ins 2468_9 (AA) | 3 | K536FS |
| 28 | CMML1 | c.1272C > A; c.4814n-1 G > A | 3 & 8 | Q138 STOP, Mutation splice receptor site exon 8 |
| 31 | CMML1 | Ins 3151 (C); c.4390T > G | 3 & 5 | Q764F3; I1175S |
| 32 | CMML1 | c.3675C > T | 3 | Q939 STOP |
| 35 | CMML1 | delG 4754; dup 6569_6573 (GAGA) | 7 & 11 | K1298F3; M1570F3 |
| 39 | CMML1 | delA 3874; del 4830_31 (TC) | 3 & 8 | K1008FS; S1324FS |
| 40 | CMML1 | c.2208A > T; del 4347 (A) | 3 & 4 | K450 STOP; I1163F3 |
| 41 | CMML1 | c.6478T > C | 11 | I1873T |
| 42 | CMML1 | ins 1921 (A); ins 2703 (G) | 3 & 3 | S354FS; L615FS |
| 44 | CMML1 | ins 3995 (T); c.4059 A > T | 3 & 3 | E846FS; R1067 STOP |
| 17 | CMML2 | c.2814C > T | 3 | Q652 STOP |
| 30 | CMML2 | Ins 4293 (A); c.6510A > G | 4 & 11 | G1145FS; T1884A |
| 34 | CMML2 | delT 4277; c.6598G > T | 4 & 11 | I1139FS; G1913V |
| 38 | CMML2 | c.4936G > C | 9 | R1359S |
| 14 | TA | c.3235C > A | 3 | S792 STOP |
| 29 | TA | c.2490C > T; Del 5334 (G) | 3 & 10 | R544 STOP; E1492FS |
| 1 | CMML1 | c.5043n-1G > A; Dup 6575_6579 (GAGCA) | 10 & 11 | Mutation splice receptor site exon ex10; M1907FS |

TABLE 10-continued

| Patient | WHO | Nucleotide change in TET2 | Exon | Consequence |
|---|---|---|---|---|
| 7 | CMML1 | c.4439T > G | 5 | C1193W |
| 8 | CMML1 | c.4726G > T | 7 | C1289F |
| 9 | CMML1 | c.5100C > T | 10 | Q1414 STOP |
| 11 | CMML1 | Del 6023 (G) | 11 | L1721FS |
| 12 | CMML1 | Del 1921 (C) | 3 | S354 STOP |
| 16 | CMMLI | c.4827G > T; Ins 5178 (A) | 8 & 10 | E1323 STOP; R1440FS |
| 27 | CMML1 | insG 2703; ins 5125_26 (AA) | 3 & 10 | L615F3S; K1422FS |
| 33 | CMML1 | Ins of 2950_85 (dup) | 3 | L718FS |
| 36 | CMML1 | c.4638G > A; c.4825T > C | 5 & 8 | C1193Y; L1322P |
| 37 | CMML1 | c.6414C > T; c.6496A > C | 11 & 11 | Q1852 STOP; E1879A |
| 43 | CMML1 | del 3859 (A) | 3 | N1000FS |
| 46 | CMML1 | del 1264_66 (AAA) | 3 | E135FS |
| 3 | CMML2 | c.4431C > T | 5 | Q1191 STOP |
| 6 | CMML2 | c.5070C > T | 10 | R1404 STOP |
| 10 | CMML2 | Del 2655_2658 (CAAA) | 5 | N598FS |
| 13 | CMML2 | Ins 5602_5606 (TCCAA) | 11 | S1582FS |
| 45 | CMML2 | c.2784 C > T; c.5253 C > T | 3 & 10 | Q642 STOP; R1465 STOP |

The results revealed that a mutated status of TET2 gene was detected in 44 out of the 88 (50%) patients. Among the 43 patients studied at diagnostic, a mutated status of TET2 gene was identified in 18 cases (42%). Such a mutated status was identified in 26 of the 45 patients (58%) studies along the course of the disease. These results thus suggest that TET2 mutation prevalence is higher in CMML than in any other studied myeloid disease.

Moreover, it must be noticed that two distinct mutations in TET2 sequence, suggesting a bi-allelic alteration of the gene, were identified in 18 out of the 44 (40%) mutated patients with a chronic phase CMML, including 5 out of the 18 (27%) patients whose mutations was identified at diagnosis, and 13 out of the 26 (50%) mutated patients studied along the course of the disease. Altogether, 69 mutations in TET2 were identified, including 33 frameshift mutations, 19 nonsense mutations, 14 missense mutations and 3 mutations in a splice site. These mutations most frequently involved exon 3 (22 events), exon 10 (9 events) and exon 11(10 events).

An analysis of overall survival was performed in 40 of the 43 patients whose TET2 status was determined at diagnosis with an at least two months follow-up and indicated a lower 1-year overall survival in patients with the 16 patients of this cohort with TET2 mutation, but the difference did not reach significance. When overall survival analysis was limited to the 29 patients with a CMML1 according to the WHO classification and an at least two months follow-up, the difference was then significant ($p<0.01$). None of the other tested parameters includes age, sex and FAB classification did affect survival. Finally, the results established that TET2 mutation was associated in the 29 patients with CMML1 with a trend to significantly lower survival.

16. Alteration of the TET2 Gene in Patients Suffering from Lymphoid Cancer

CGH analyses of 157 patients suffering from B-cell lymphoma showed the loss of a whole chromosome 4 in 2 cases, a partial deletion of chromosome 4q sequences deleting the TET2 gene in 4 cases and loss of the upstream side of TET2 associated with duplication of the downstream side of TET2 in one case. These rearrangements were found in diffuse large B-cell lymphomas (107 cases), whereas no rearrangement could be found in follicular lymphomas (50 cases).

We have analyzed 93 patients for variation within the coding sequence of TET2. They were 33 T cell lymphoma and 60 B cell lymphoma.

14 mutations were observed in 10 samples from T-cell lymphomas, including 10 frame shifts and 2 non-sense and 2 missense mutations.

Table 9 shows the TET2 mutations identified in 10 T-cell lymphomas patients.

| disease | Nucleotide changes | Amino acid consequences |
|---|---|---|
| T-lymphoma | c.3215delT | p.Phe785FS |
| T-lymphoma | c.[1893_1896delAAGC] + [4527delG] | p.[Lys345FS] + [Ala1223FS] |
| T-lymphoma | c.[2505delA] + [2524delC] | p.[Thr549FS] + [Pro555FS] |
| T-lymphoma | c.6564C > T | p.Tyr1902 |
| T-lymphoma | c.6745C > T | p.Pro1962Leu |
| T-lyrnphoma | c.5523_5524insA | p.Glu1555fs |
| T-lymphoma | c.[3131_3137delCCAGACT] + [5109G > T] | p.[Leu757FS] + [Val1417Phe] |
| T-lymphoma | c.[3747C > T] + [5331A > T] | p.[Gln963STOP] + [Lys1491STOP] |
| T-lymphoma | c.3756_3757del CA | p.Gln966 FS |
| T-lymphoma (LAI) | c.1642delC | p.Ser261 FS |

Thus, these results established that the frequencies of TET2 mutation in patients suffering from T-cell lymphoid tumour is 30%.

The invention claimed is:

1. A method for detecting a mutated TET2 gene comprising:

(i) obtaining a blood or bone marrow sample of a subject having a myeloid tumour or a lymphoid tumour; and (ii) detecting that Hematopoietic Stem Cells (HSC) or CD34+/CD38− progenitor cells in said blood or bone marrow sample have a mutation in the Ten Eleven Translocation protein family member 2 gene (TET2) coding for the polypeptide having the sequence SEQ ID NO:2, wherein the mutation is a deletion, insertion, or point mutation, by:

a) sequencing a region of the TET2 nucleic acid contained in said cells, or b) hybridizing the nucleic acid contained in said cells with at least one probe or primer comprising at least 10 consecutive nucleotides of the nucleic acid that encodes the TET2 polypeptide having the sequence SEQ ID NO:2.

2. The method of claim 1, wherein the mutation is a missense or nonsense mutation.

3. The method of claim 2, wherein the mutation is a nonsense mutation.

* * * * *